US011464932B2

(12) United States Patent
Barlow et al.

(10) Patent No.: US 11,464,932 B2
(45) Date of Patent: Oct. 11, 2022

(54) HEADGEAR TUBING FOR A PATIENT INTERFACE

(71) Applicant: RESMED PTY LTD, Bella Vista (AU)

(72) Inventors: Adam Francis Barlow, Sydney (AU); David James Braund, Sydney (AU); Andrew Chan, Sydney (AU); Justin John Formica, Sydney (AU); Gerard Michael Rummery, Woodford (AU); Matthew Robin Wells, Sydney (AU); Paul Derrick Watson, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/426,362

(22) PCT Filed: Dec. 4, 2019

(86) PCT No.: PCT/IB2019/060432
§ 371 (c)(1),
(2) Date: Jul. 28, 2021

(87) PCT Pub. No.: WO2020/157559
PCT Pub. Date: Aug. 6, 2020

(65) Prior Publication Data
US 2022/0096774 A1 Mar. 31, 2022

Related U.S. Application Data

(60) Provisional application No. 62/821,878, filed on Mar. 21, 2019.

(30) Foreign Application Priority Data

Jan. 29, 2019 (AU) .............................. 2019900260
Mar. 28, 2019 (AU) .............................. 2019901040

(Continued)

(51) Int. Cl.
A61M 16/06 (2006.01)
A61M 16/08 (2006.01)
A61M 16/10 (2006.01)

(52) U.S. Cl.
CPC .... A61M 16/0683 (2013.01); A61M 16/0622 (2014.02); A61M 16/0816 (2013.01);
(Continued)

(58) Field of Classification Search
CPC .......... A61M 16/0066; A61M 16/0069; A61M 16/06; A61M 16/0605; A61M 16/0611;
(Continued)

(56) References Cited

U.S. PATENT DOCUMENTS 2,452,047 A 10/1948 Hamblin
4,782,832 A 11/1988 Trimble et al.
(Continued)

FOREIGN PATENT DOCUMENTS

JP 2014-514035 A 6/2014
WO WO 98/004310 A1 2/1998
(Continued)

OTHER PUBLICATIONS

International Search Report dated Feb. 27, 2020 in corresponding PCT Application PCT/IB2019/060432 (18 pages).
(Continued)

Primary Examiner — Annette Dixon
(74) Attorney, Agent, or Firm — Nixon & Vanderhye P.C.

(57) ABSTRACT

A patient interface for treating sleep disorder breathing includes a headgear tube that provides support for the seal forming structure. The headgear tube includes a patient-contacting portion and a non-patient contacting portion that are joined along seams to form a gas passageway. The headgear tube may comprise a textile material and/or a foam
(Continued)

material. Portions of the headgear tube may be imparted with greater rigidity than other portions.

33 Claims, 91 Drawing Sheets

(30) Foreign Application Priority Data

| Mar. 28, 2019 | (AU) | 2019901041 |
|---|---|---|
| Mar. 28, 2019 | (AU) | 2019901043 |
| Apr. 30, 2019 | (AU) | 2019901459 |
| May 29, 2019 | (AU) | 2019901847 |
| Jun. 25, 2019 | (WO) | PCT/AU2019/050655 |

(52) U.S. Cl.
CPC ....... *A61M 16/0875* (2013.01); *A61M 16/109* (2014.02); *A61M 2205/0216* (2013.01)

(58) Field of Classification Search
CPC .......... A61M 16/0616; A61M 16/0622; A61M 16/0633; A61M 16/0666; A61M 16/0672; A61M 16/0683; A61M 16/0694; A61M 16/08; A61M 16/0816; A61M 16/0825; A61M 16/0833; A61M 16/0875; A61M 16/10; A61M 16/1045; A61M 16/1055; A61M 16/107; A61M 16/16; A61M 16/20; A61M 2016/0027; A61M 2016/0039; A61M 2202/0208; A61M 2205/02; A61M 2205/0216; A61M 2205/0238; A61M 2205/0266; A61M 2205/273; A61M 2205/42; A61M 2205/583; A61M 2205/588; A61M 2205/59; A61M 2207/00; A61M 2209/06; A61M 2209/082; A61M 2209/088; A61M 2210/0618; A61M 2210/0625; A61M 39/08; A62B 18/025; A62B 18/084; Y10T 29/49826
See application file for complete search history.

(56) References Cited

U.S. PATENT DOCUMENTS

| 4,944,310 | A | 7/1990 | Sullivan |
|---|---|---|---|
| 5,687,715 | A | 11/1997 | Landis |
| 6,105,575 | A | 8/2000 | Estes |
| 6,135,108 | A | 10/2000 | Hoenig |
| 6,418,928 | B1 | 7/2002 | Bordewick |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,731,090 | B2* | 8/2017 | Ovzinsky .......... A61M 16/0672 |
| 10,118,008 | B2 | 11/2018 | Grashow |
| 2004/0025885 | A1 | 2/2004 | Payne, Jr. |
| 2005/0284481 | A1 | 12/2005 | Meyer |
| 2008/0011305 | A1 | 1/2008 | Chandran et al. |
| 2008/0047560 | A1 | 2/2008 | Veliss |
| 2008/0060649 | A1* | 3/2008 | Veliss .................. A61M 39/08 128/207.18 |
| 2008/0097350 | A1 | 4/2008 | Bell et al. |
| 2009/0044808 | A1 | 2/2009 | Guney et al. |
| 2009/0050156 | A1 | 2/2009 | Ng et al. |
| 2009/0211579 | A1 | 8/2009 | Smith et al. |
| 2010/0000534 | A1 | 1/2010 | Kooij et al. |
| 2011/0247619 | A1 | 10/2011 | Formica et al. |
| 2012/0037162 | A1 | 2/2012 | Boussignac |
| 2012/0152255 | A1 | 6/2012 | Barlow et al. |
| 2012/0325219 | A1 | 12/2012 | Smith |
| 2014/0076311 | A1 | 3/2014 | Darab |
| 2015/0083136 | A1 | 3/2015 | Grashow et al. |
| 2015/0128949 | A1 | 5/2015 | Jablonski |
| 2015/0352306 | A1* | 12/2015 | Scheiner ........... A61M 16/0875 128/205.25 |
| 2016/0008564 | A1 | 1/2016 | Grashow |
| 2016/0317776 | A1 | 11/2016 | Cikkazi et al. |
| 2017/0082223 | A1 | 3/2017 | Garrett et al. |
| 2017/0333662 | A1 | 11/2017 | Ovzinsky et al. |

FOREIGN PATENT DOCUMENTS

| WO | WO 98/034665 A1 | 8/1998 |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2005/099801 A1 | 10/2005 |
| WO | WO 2006/074513 A1 | 7/2006 |
| WO | WO 2006/130903 A1 | 12/2006 |
| WO | WO 2008/011682 A1 | 1/2008 |
| WO | WO 2008/011683 A1 | 1/2008 |
| WO | WO 2009/052560 A1 | 4/2009 |
| WO | WO 2010/135785 A1 | 12/2010 |
| WO | WO 2012/167327 A1 | 12/2012 |
| WO | WO 2012/171072 A1 | 12/2012 |
| WO | WO 2013/020167 A1 | 2/2013 |
| WO | WO 2017/124152 A1 | 7/2017 |
| WO | WO 2017/124155 A1 | 7/2017 |
| WO | WO 2018/029638 A1 | 2/2018 |
| WO | WO 2019/122133 A1 | 6/2019 |
| WO | WO 2019/185474 A1 | 10/2019 |
| WO | WO 2020/037360 A1 | 2/2020 |

OTHER PUBLICATIONS

Written Opinion dated Feb. 27, 2020 in corresponding PCT Application PCT/IB2019/060432 (12 pages).
Written Opinion dated Jan. 20, 2021 in corresponding PCT Application PCT/IB2019/060432 (8 pages).
International Preliminary Report on Patentability dated May 18, 2021 in corresponding PCT Application PCT/IB2019/060432 (62 pages).
"*Respiratory Physiology*", by John B. West, Lippincott Williams & Wilkins, 9th edition published 2012 (8 pages).
Final Office Action dated Sep. 24, 2021 in related U.S. Appl. No. 17/255,615 (29 pages).
Office Action dated Jun. 21, 2021 in related U.S. Appl. No. 17/255,615 (31 pages).
EP Communication pursuant to Article 94(3) dated Apr. 8, 2022 in corresponding EP Application 19912954.5 (7 pages).
Supplementary European Search Report dated Feb. 3, 2022 in corresponding EP Application 19912954.5 (4 pages).
Office Action dated Jan. 27, 2022 in related U.S. Appl. No. 17/255,615 (22 pages).
Examination Report dated Mar. 8, 2022 in corresponding AU Application 2019426678 (3 pages).
Supplementary European Search Report dated Mar. 31, 2022 in related EP Application 19825205.8 (9 pages).
Notice of Reasons for Rejection and English translation thereof dated Apr. 4, 2022 in corresponding JP application P2021-544387 (13 pages).

\* cited by examiner

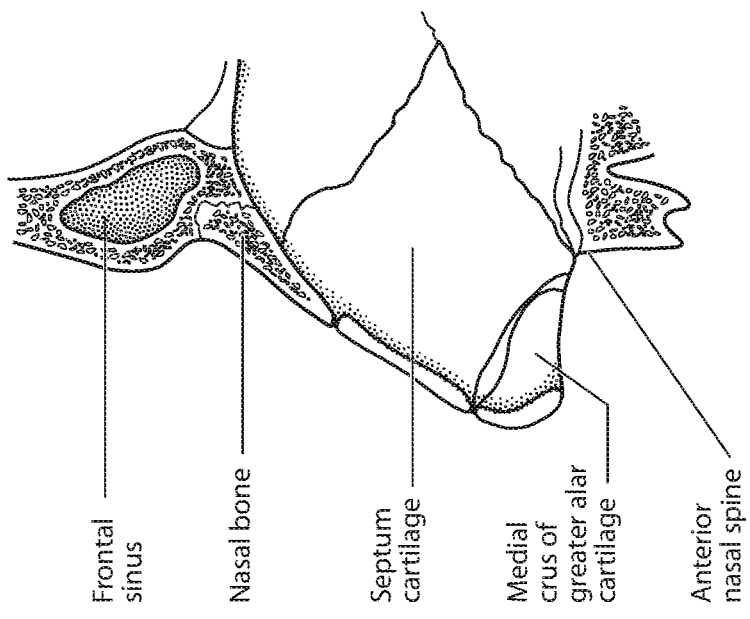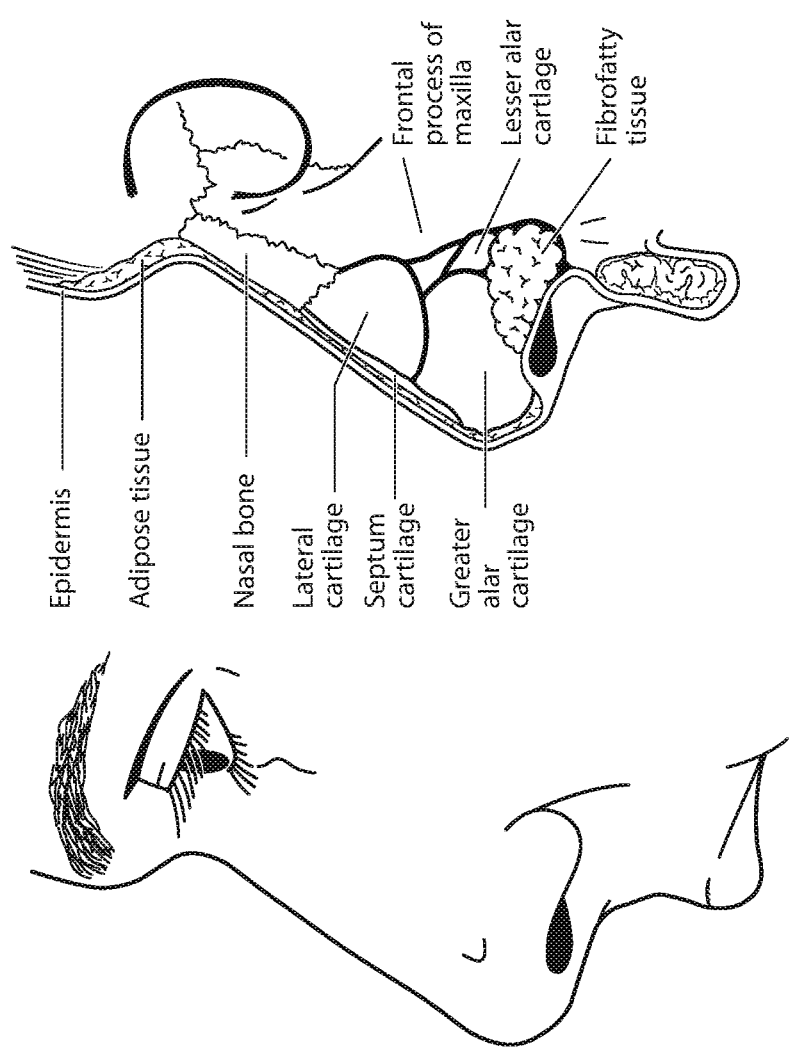
FIG. 2G  FIG. 2H  FIG. 2I

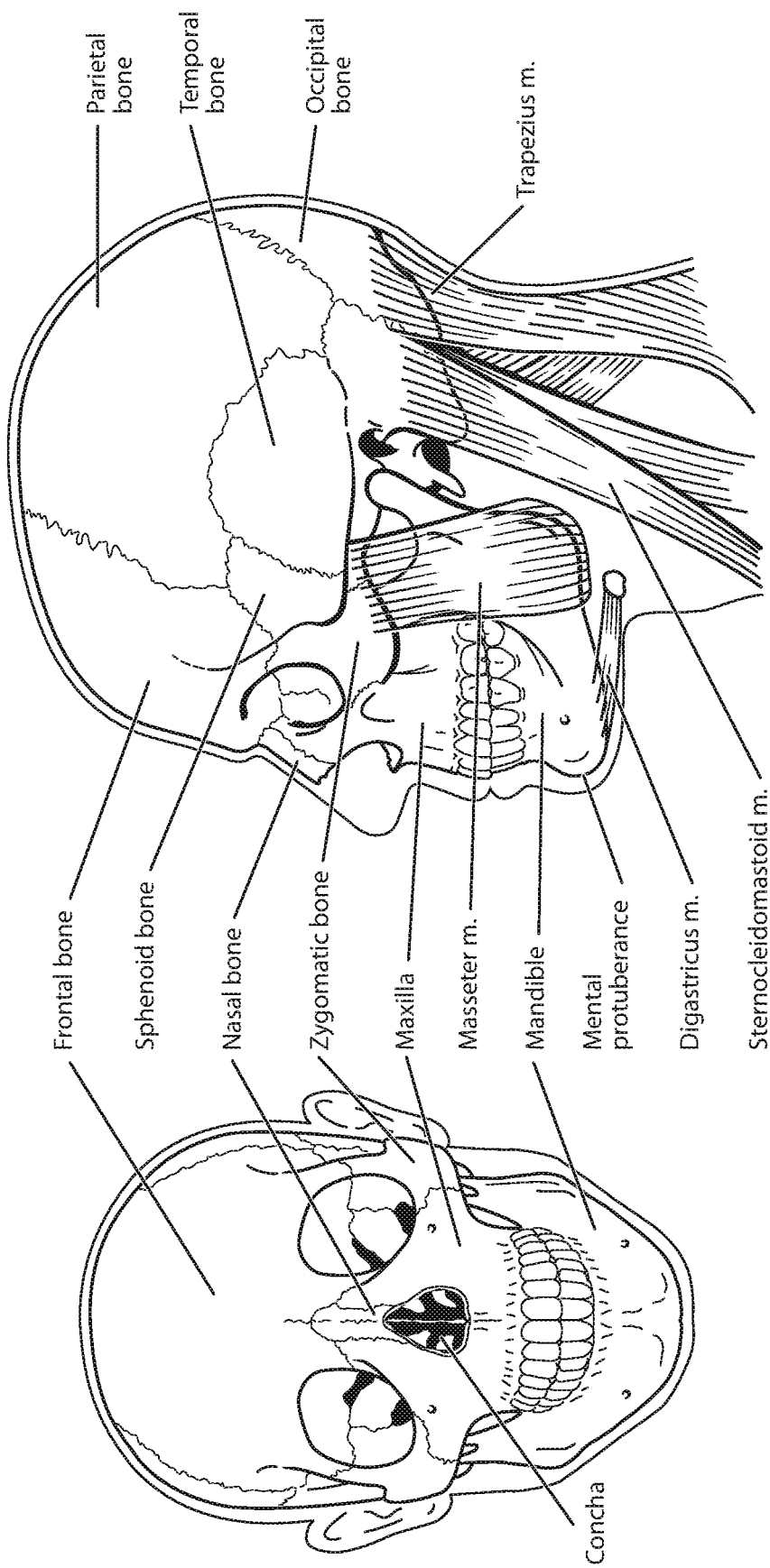

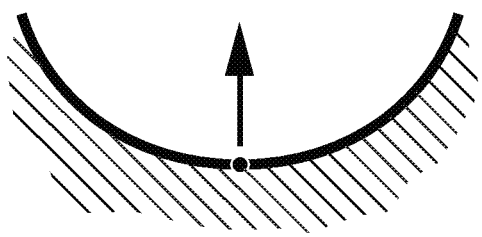
FIG. 3B — Relatively Large Positive Curvature
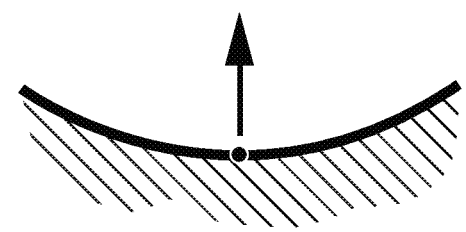
FIG. 3C — Relatively Small Positive Curvature
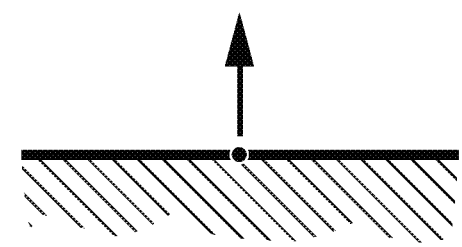
FIG. 3D — Zero Curvature
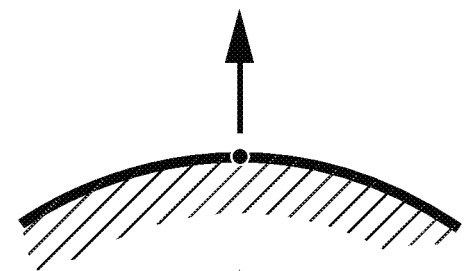
FIG. 3E — Relatively Small Negative Curvature
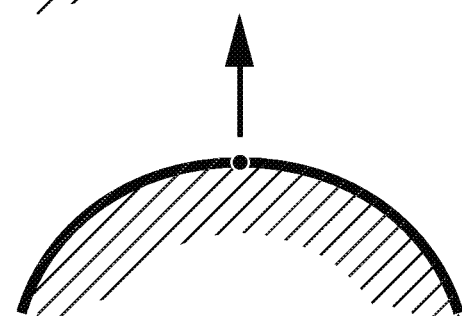
FIG. 3F — Relatively Large Negative Curvature

Left-hand rule
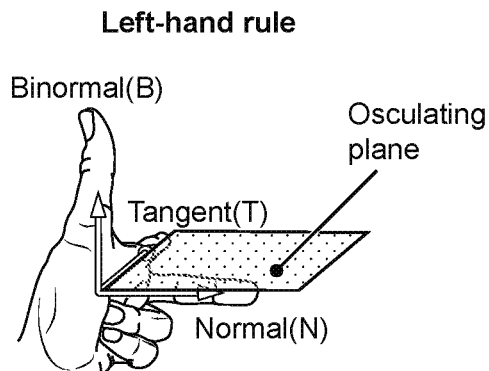
FIG. 3O
Right-hand rule
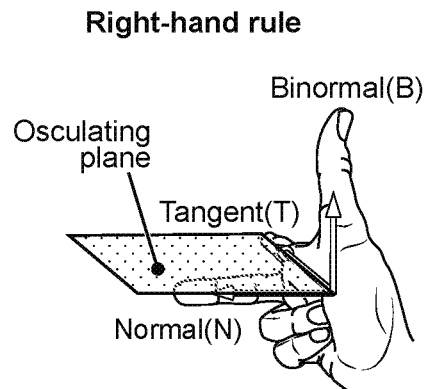
FIG. 3P
Left ear helix
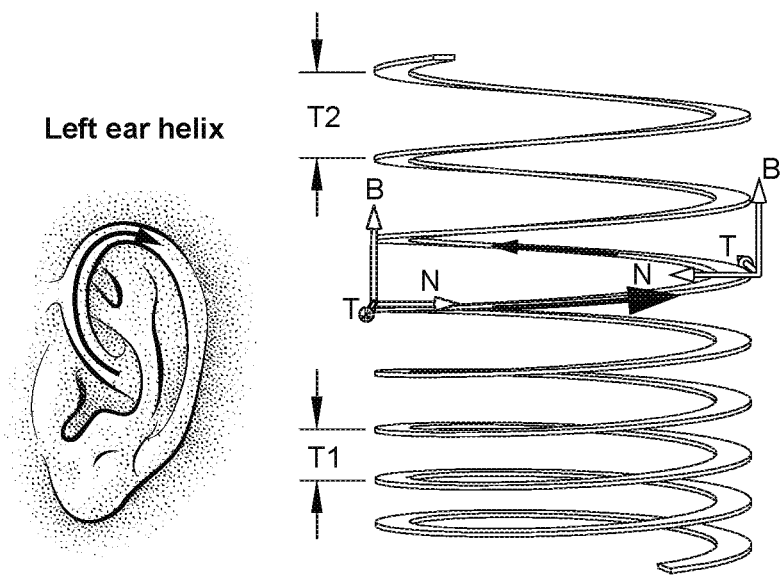
FIG. 3Q
Right ear helix
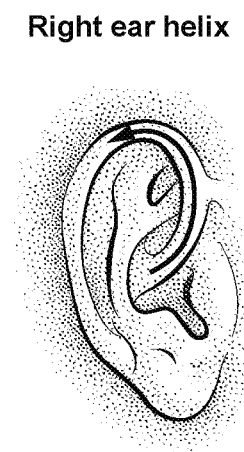
FIG. 3R
Right-hand helix
Right-hand positive
FIG. 3S
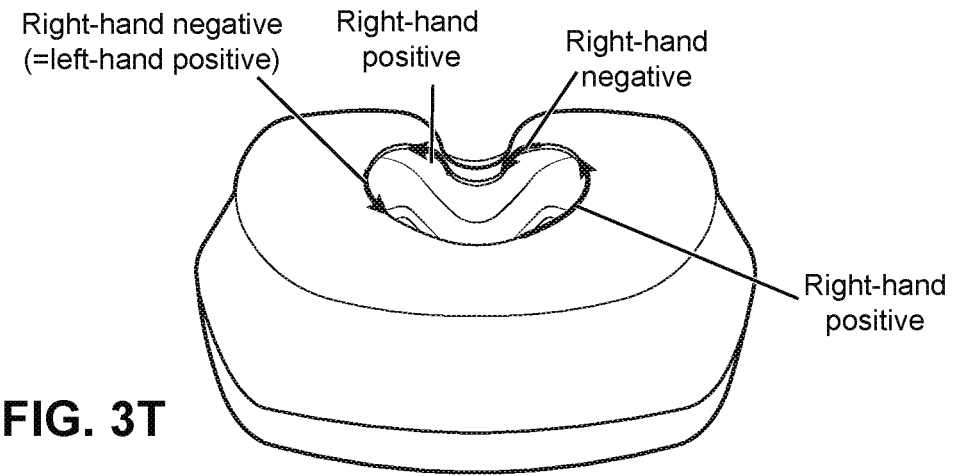
FIG. 3T

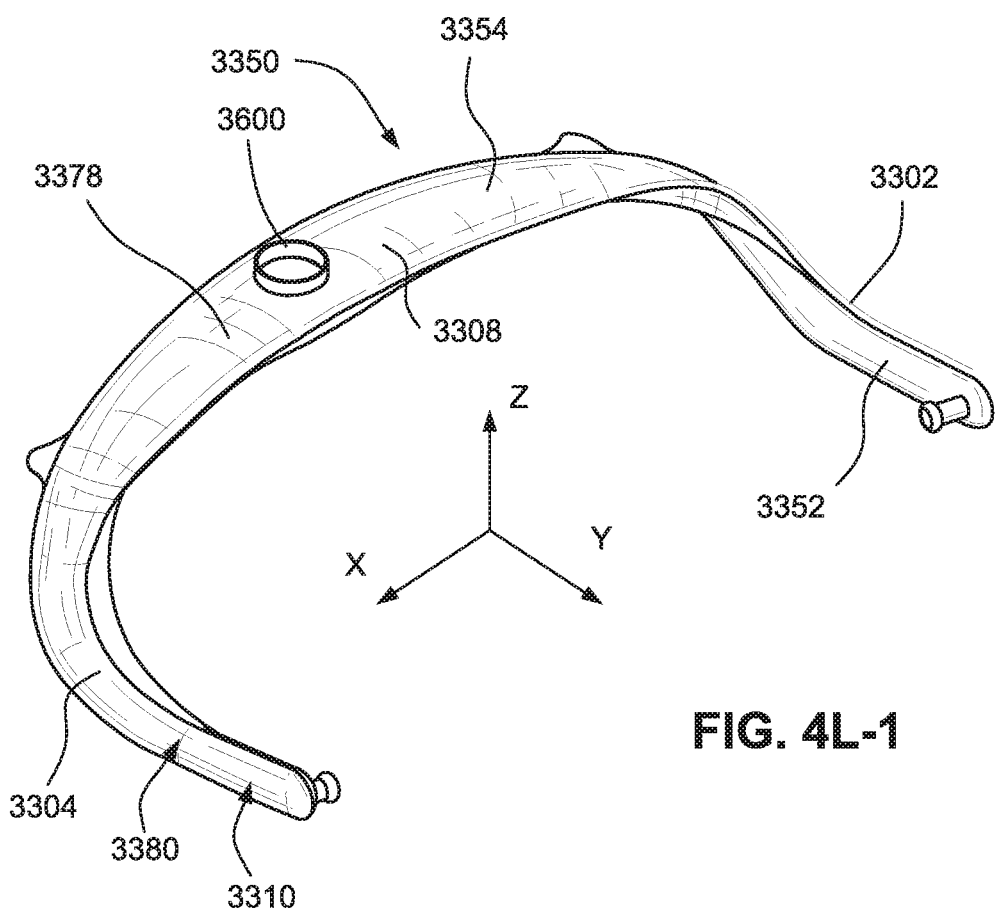
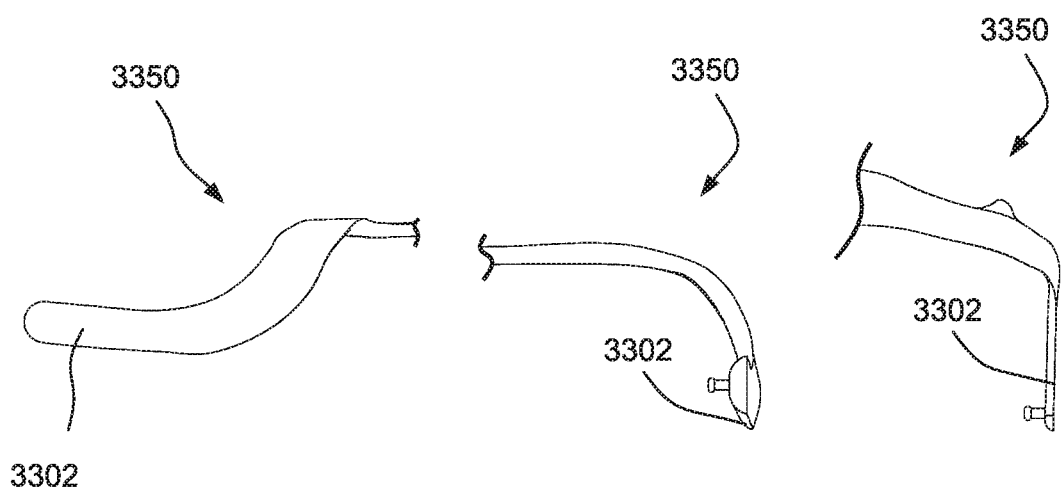
FIG. 4L-1
FIG. 4L-2   FIG. 4L-3   FIG. 4L-4

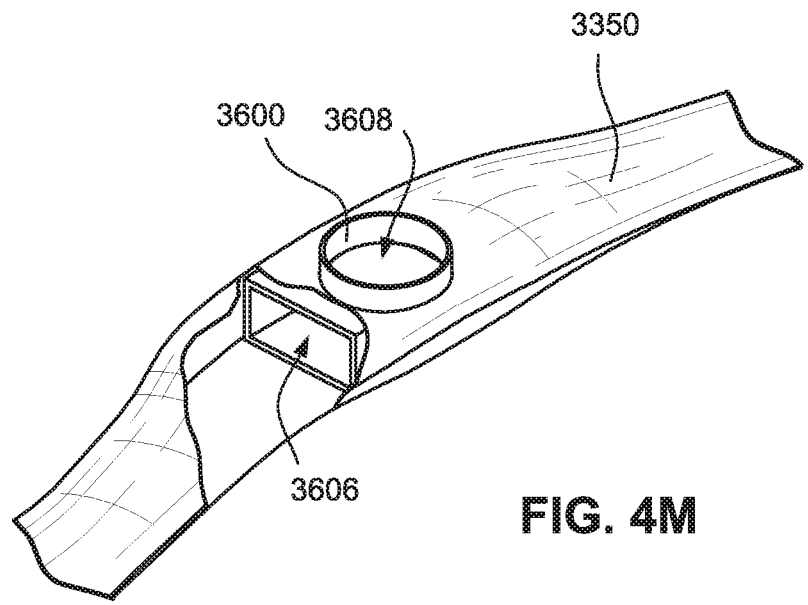
FIG. 4M
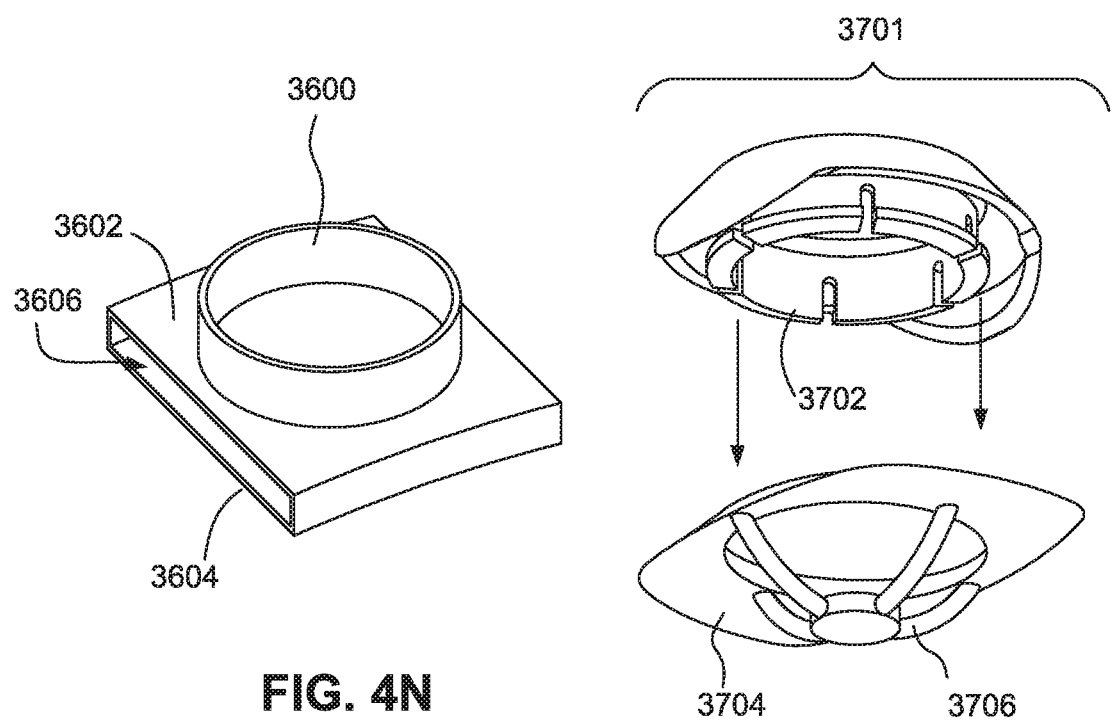
FIG. 4N
FIG. 4O

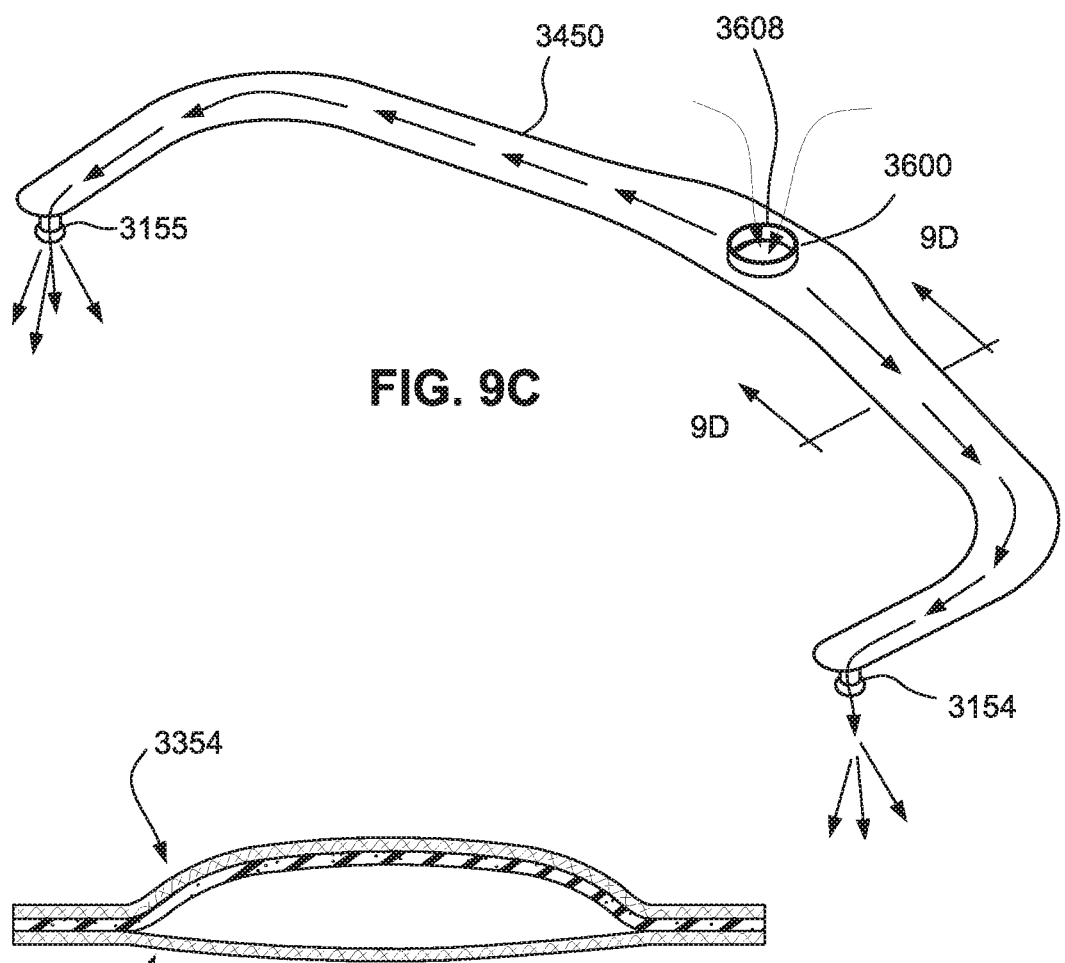
FIG. 9C
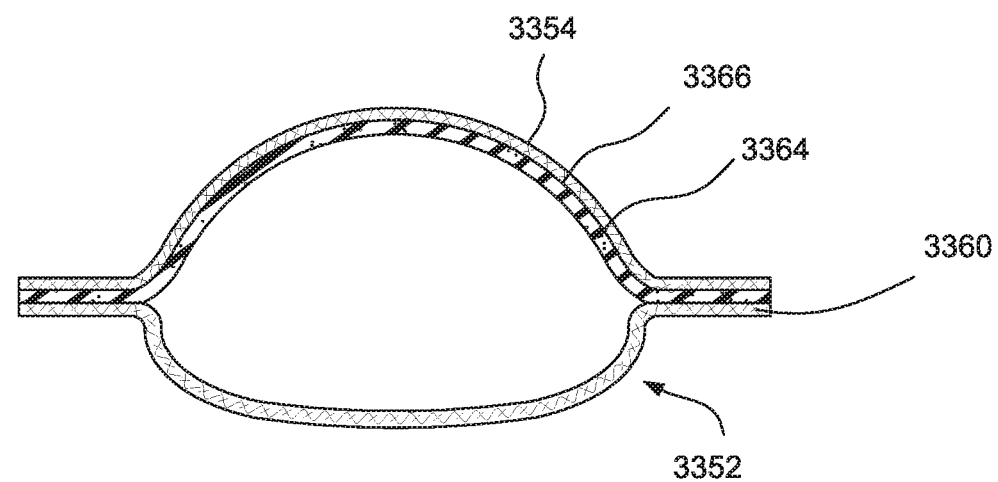
FIG. 9D
FIG. 9E

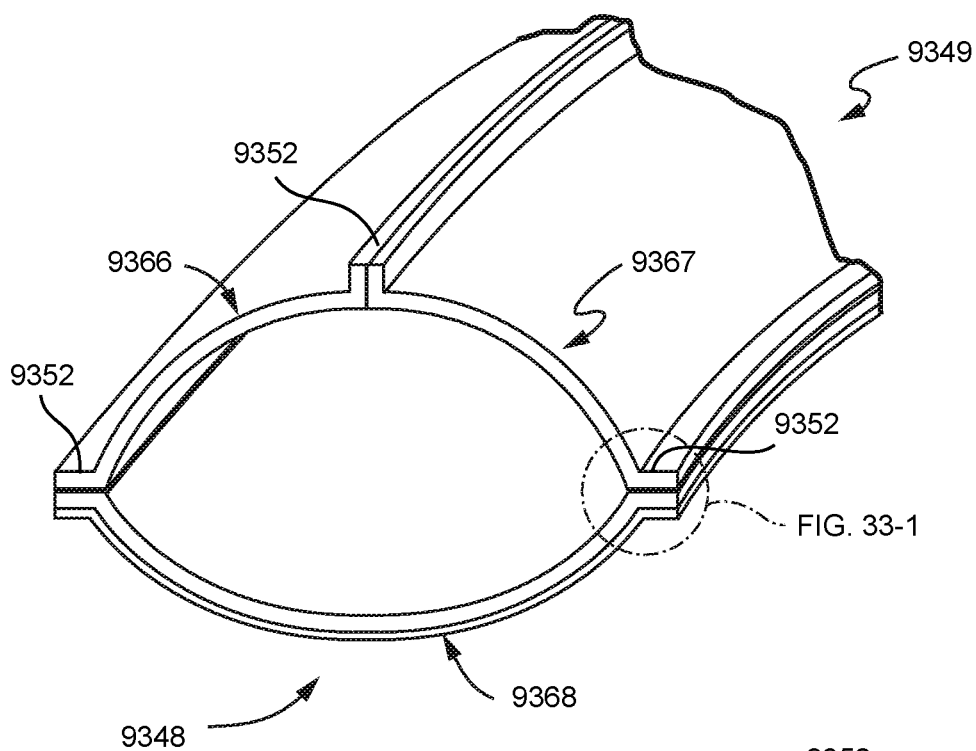
FIG. 33
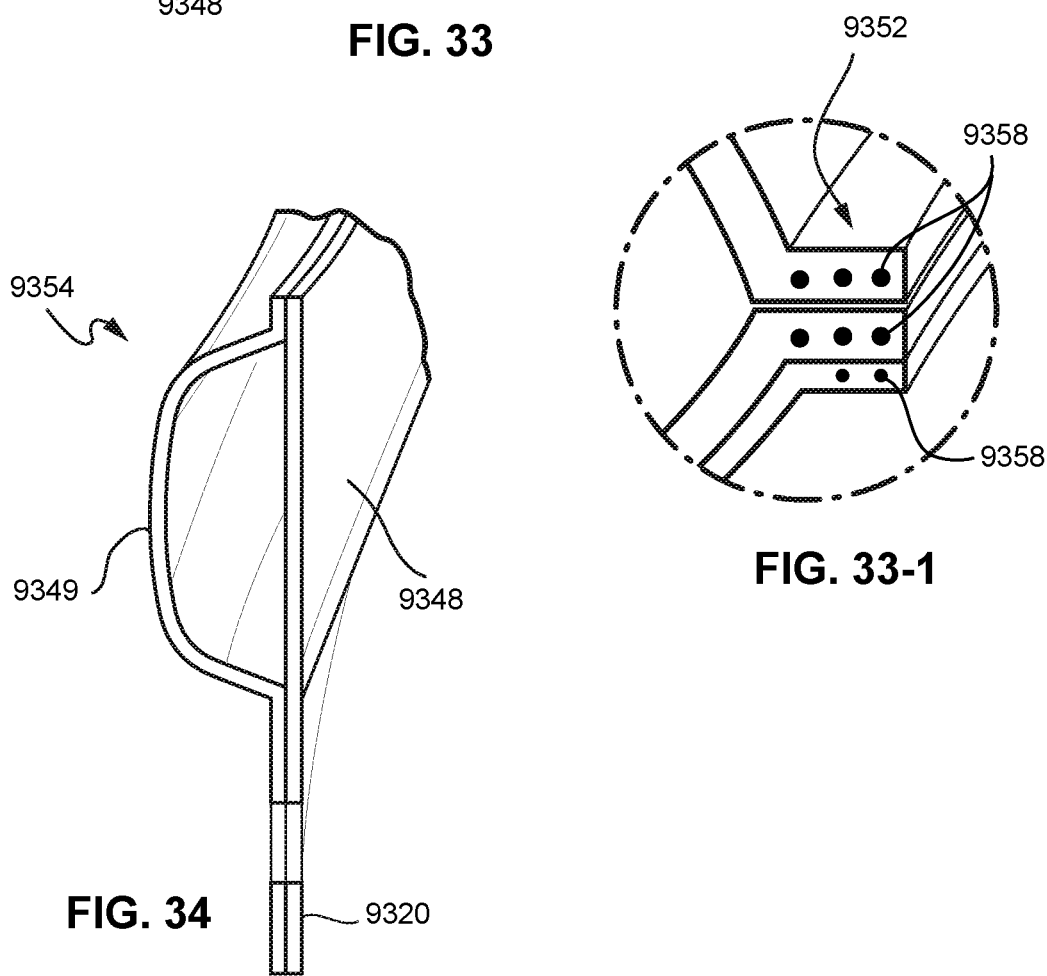
FIG. 34
FIG. 33-1

HEADGEAR TUBING FOR A PATIENT INTERFACE

1 CROSS-REFERENCE TO RELATED APPLICATIONS

This application is the U.S. national phase of International Application No. PCT/IB2019/060432 filed Dec. 4, 2019 which designated the U.S. and claims priority to U.S. Provisional Application No. 62/821,878, filed Mar. 21, 2019, and also claims the benefit of Australian Provisional Application Nos. AU2019900260, filed Jan. 29, 2019, AU2019901040, filed Mar. 28, 2019, AU2019901041, filed Mar. 28, 2019, AU2019901043, filed Mar. 28, 2019, AU2019901459, filed Apr. 30, 2019, AU2019901847, filed May 29, 2019, and PCT/AU2019/050655, filed Jun. 25, 2019, each of which is hereby incorporated herein by reference in its entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

Certain forms of the present technology relate to patient interfaces used in the treatment of respiratory, prevention and amelioration of respiratory-related disorders.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of a seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use. When designed to be worn on the patient's head such harnesses may be referred to as headgear.

2.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface to the appropriate part of the patient's face. This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. US 2007/0246043, the contents of which are incorporated herein by reference, in which the conduit connects to a tube in the patient interface through a port positioned in use on top of the patient's head.

The Philips DreamWear™ nasal mask includes such headgear tubing. One problem with this mask is that the headgear tubes are silicone. The silicone conduit may cause discomfort to a patient when against the face of a patient. Further, the weight of the headgear may cause some patients to be uncomfortable during use.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cm H$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface for delivery of a supply of pressurised breathable gas to an entrance of a patient's airways.

Another aspect of the present technology relates to at least one gas delivery tube having an inner textile layer and an outer textile layer, wherein the inner textile layer and the outer textile layer have different cross-sectional shapes.

Another aspect of the present technology relates to at least one gas delivery tube that includes an inner textile layer and an outer textile layer. The inner textile layer has a substantially planar cross-sectional shape and the outer textile layer has a pre-determined non-planar cross-sectional shape. The outer textile layer is resilient such that when subjected to external force the cross-sectional shape of the outer textile layer is altered, and when the external force is released the outer layer returns to the pre-determined non-planar cross-sectional shape.

Another aspect of the present technology relates to a gas delivery tube having an inner textile layer and an outer textile layer, wherein the outer textile layer is thermoformed to have a predetermined shape and the inner textile layer is not thermoformed.

Another aspect of the present technology relates to at least one gas delivery tube having an inner textile layer and an outer textile layer. The inner textile layer and the outer textile layer are joined along a first longitudinal edge at a first joint and along a second longitudinal edge at a second joint, wherein between the first joint and the second joint the outer textile layer is spaced from the inner textile layer, wherein the outer textile layer is thermoformed to have a predetermined shape and the inner textile layer is not thermoformed, and wherein the outer textile layer supports its own weight between the first joint and the second joint such that the outer textile layer remains spaced from the inner textile layer when not supported by pressurized air.

Another aspect of the present technology relates to at least one gas delivery tube having an inner textile layer and an outer textile layer, wherein the outer textile layer is more rigid than the inner textile layer, wherein the inner textile layer and the outer textile layer are joined along a first longitudinal edge and a second longitudinal edge, and wherein an air passageway is formed between the inner textile layer and the outer textile layer.

Another aspect of one form of the present technology comprises a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include at least one gas delivery tube to deliver the flow of air to the entrance of the patient's airways via the seal-forming structure, the at least one gas delivery tube being constructed and arranged to contact, in use, at least a region of the patient's head superior to an otobasion superior of the patient's head. The at least one gas delivery tube may include an inner textile layer and an outer textile layer. The outer textile layer may have a pre-determined non-planar cross-sectional shape. The outer textile layer may be resilient such that when subjected to external force the cross-sectional shape of the outer textile layer is altered, and when the external force is released the outer layer returns to the pre-determined non-planar cross-sectional shape.

In examples, (a) the inner textile layer may have different material properties than the outer textile layer, (b) the inner textile layer may comprise an interior textile membrane, wherein during use when pressurized with air, the interior textile membrane is configured to permit air transfer through the interior textile membrane, (c) the inner textile layer may comprise a conformable inner textile membrane, and the outer textile layer may comprise a conformable outer textile membrane, wherein the outer textile layer is thicker than the inner textile layer, (d) the inner textile layer may have a substantially planar cross-section, (e) the inner textile layer may be floppy, (f) the inner textile layer may be secured to the outer textile layer, wherein the outer textile layer imparts tension onto the inner textile layer, (g) the inner textile layer may comprise an exterior textile sheet and an interior textile membrane, wherein the interior textile membrane is configured to resist the transfer of air through the exterior textile sheet, (h) the at least one gas delivery tube may be configured to extend continuously from a right side of the patient, along the parietal bone, to a left side of the patient, (i) the at least one gas delivery tube may include an air supply conduit, wherein when the patient interface is worn by the patient the air supply conduit is located adjacent the parietal bone, (j) the outer textile layer may comprise an exterior textile sheet and an interior textile membrane, wherein a conformable sheet is sandwiched between the exterior textile sheet and the interior textile membrane, (k) the inner textile layer may be joined to the outer textile layer at a joint, wherein a width of the joint is varied along a length of the at least one gas delivery tube, (l) the outer textile layer has an interior surface, wherein the interior surface of the outer textile layer may have a positive curvature, (m) the inner textile layer may have a zero curvature, (n) the inner textile layer and the outer textile layer may be joined together without stitching, (o) the inner textile layer may comprise an inner interior textile membrane, wherein the outer textile layer may include an outer interior textile membrane, wherein the outer interior textile membrane of the outer textile layer and the inner interior textile membrane of the inner textile layer are joined together along edges of the at least one gas delivery tube, wherein the inner interior textile membrane and the outer interior textile membrane join the inner textile layer to the outer textile layer and form an air impermeable membrane between the inner textile layer and the outer textile layer, (p) the inner textile layer and the outer textile layer are may be joined at a first edge by a first joint and at a second edge by a second joint, and spaced from each other between the first joint and the second joint, wherein rigidizers are not utilized along the inner textile layer between the first joint and the second joint, (q) during use and pressurized by air the inner textile layer may expand away from the outer textile layer, (r) the outer textile layer may include a conformable material, wherein the conformable material is thermoformed to the non-planar cross-sectional shape, (s) the at least one gas delivery tube may be thermoformed in a predetermined shape such that a first arm extends along a first plane, and an upper portion extends along a second plane that is substantially orthogonal to the first plane without external force or pressure.

Another aspect of one form of the present technology comprises a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include at least one gas delivery tube to deliver the flow of air to the entrance of the patient's airways via the seal-forming structure, the at least one gas delivery tube being constructed and arranged to contact, in use, at least a region of the patient's head superior to an otobasion superior of the patient's head. The at least one gas delivery tube may include an inner textile layer and an outer textile layer, wherein the inner textile layer and the outer textile layer may be joined along a first longitudinal edge at a first joint and along a second longitudinal edge at a second joint. Between the first joint and the second joint the outer textile layer may be spaced from the inner textile layer. The outer textile layer may support its own weight between the first joint and the second joint such that the outer textile layer remains spaced from the inner textile layer when not supported by pressurized air.

In examples according to the preceding paragraph, (a) the inner textile layer may have different material properties than the outer textile layer, (b) the inner textile layer may comprise an interior textile membrane, wherein during use when pressurized with air, the interior textile membrane is configured to permit air transfer through the interior textile membrane, (c) the inner textile layer may comprise a conformable inner textile membrane, and the outer textile layer may comprise a conformable outer textile membrane, wherein the outer textile layer is thicker than the inner textile layer, (d) the inner textile layer may have a substantially planar cross-section, (e) the inner textile layer may be floppy, (f) the inner textile layer may be secured to the outer textile layer, wherein the outer textile layer imparts tension onto the inner textile layer, (g) the inner textile layer may comprise an exterior textile sheet and an interior textile membrane, wherein the interior textile membrane is configured to resist the transfer of air through the exterior textile sheet, (h) the at least one gas delivery tube may be configured to extend continuously from a right side of the patient, along the parietal bone, to a left side of the patient, (i) the at least one gas delivery tube may include an air supply conduit, wherein when the patient interface is worn by the patient the air supply conduit is located adjacent the parietal bone, (j) the outer textile layer may comprise an exterior textile sheet and an interior textile membrane, wherein a conformable sheet is sandwiched between the exterior textile sheet and the interior textile membrane, (k) the inner textile layer may be joined to the outer textile layer at a joint, wherein a width of the joint is varied along a length of the at least one gas delivery tube, (l) the outer textile layer has an interior surface, wherein the interior surface of the outer textile layer has a positive curvature between the first joint and the second joint, (m) the inner textile layer may have a zero curvature between the first joint and the second joint, (n) the inner textile layer and the outer textile layer may be joined together without stitching, (o) the inner textile layer may comprise an inner interior textile membrane, wherein the outer textile layer may include an outer interior textile membrane, wherein the outer interior textile membrane of the outer textile layer and the inner interior textile membrane of the inner textile layer are joined together along edges of the at least one gas delivery tube, wherein the inner interior textile membrane and the outer interior textile membrane join the inner textile layer to the outer textile layer and form an air impermeable membrane between the inner textile layer and the outer textile layer, (p) the inner textile layer and the outer textile layer are may be joined at a first edge by a first joint and at a second edge by a second joint, and spaced from each other between the first joint and the second joint, wherein rigidizers are not utilized along the inner textile layer between the first joint and the second joint, (q) during use and pressurized by air the inner textile layer may expand away from the outer textile layer, (r) the outer textile layer may include a conformable material, wherein the conformable material is thermoformed to the non-planar cross-sectional shape, (s) the at least one gas delivery tube may be thermoformed in a predetermined shape such that a first arm extends along a first plane, and an upper portion extends along a second plane that is substantially orthogonal to the first plane without external force or pressure.

Another aspect of one form of the present technology comprises a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include at least one gas delivery tube to deliver the flow of air to the entrance of the patient's airways via the seal-forming structure, the at least one gas delivery tube being constructed and arranged to contact, in use, at least a region of the patient's head superior to an otobasion superior of the patient's head. The at least one gas delivery tube may include an inner textile layer and an outer textile layer, wherein the outer textile layer is more rigid than the inner textile layer. The inner textile layer and the outer textile layer may be joined along a first longitudinal edge and a second longitudinal edge. An air passageway may be formed between the inner textile layer and the outer textile layer.

In examples according to the preceding paragraph, (a) the outer textile layer may have a pre-determined non-planar cross-sectional shape, and wherein the outer textile layer may be resilient such that when subjected to external force the shape of the outer textile layer is altered, and when the external force is released the outer layer returns to the pre-determined non-planar cross-sectional shape, (b) between the first longitudinal edge and the second longitudinal edge the outer textile layer may be spaced from the inner textile layer; and wherein the outer textile layer may support its own weight between the first longitudinal edge and the second longitudinal edge such that the outer textile layer remains spaced from the inner textile layer when not supported by pressurized air, (c) the inner textile layer may comprise an interior textile membrane, wherein during use when pressurized with air, the interior textile membrane is configured to permit air transfer through the interior textile membrane, (d) the inner textile layer may comprise a conformable inner textile membrane, and the outer textile layer may comprise a conformable outer textile membrane, wherein the outer textile layer may be thicker than the inner textile layer, (e) the inner textile layer may have a substantially planar cross-section, (f) the inner textile layer may be floppy, (g) the inner textile layer may be secured to the outer textile layer, wherein the outer textile layer may impart tension onto the inner textile layer, (h) the inner textile layer may comprise an exterior textile sheet and an interior textile membrane, wherein the interior textile membrane may be configured to resist the transfer of air through the exterior textile sheet, (i) the at least one gas delivery tube may be configured to extend continuously from a right side of the patient, along the parietal bone, to a left side of the patient, (j) the at least one gas delivery tube may include an air supply conduit, wherein when the patient interface is worn by the patient the air supply conduit is located adjacent the parietal bone, (k) the outer textile layer may comprise an exterior textile sheet and an interior textile membrane, wherein a conformable sheet may be sandwiched between the exterior textile sheet and the interior textile membrane, (l) the inner textile layer may be joined to the outer textile layer at a joint, wherein a width of the joint is varied along a length of the at least one gas delivery tube, (m) the outer textile layer has an interior surface, wherein the interior surface of the outer textile layer may have a positive curvature between the first longitudinal edge and the second longitudinal edge, (n) the inner textile layer may have a zero curvature between the first longitudinal edge and the second longitudinal edge, (o) the inner textile layer and the outer textile layer may be joined together without stitching, (p) the inner textile layer may comprise an inner interior textile membrane, wherein the outer textile layer may include an outer interior textile membrane, wherein the outer interior textile membrane of the outer textile layer and the inner interior textile membrane of the inner textile layer may be joined together along edges of the at least one gas delivery tube, wherein the inner interior textile membrane and the outer interior textile membrane may join the inner textile layer to the outer textile layer and form an air impermeable membrane between the inner textile layer and the outer textile layer, (q) the inner textile layer and the outer textile layer are joined at a first edge by a first joint and at a second edge by a second joint, and spaced from each other between the first joint and the second joint, wherein rigidizers are not utilized along the inner textile layer between the first joint and the second joint, (r) during use and pressurized by air the inner textile layer may expand away from the outer textile layer, (s) the patient interface may be configured to allow the patient to breath from ambient through their mouth in the absence of a flow of pressurised air through the plenum chamber inlet port, or the patient interface is configured to leave the patient's mouth uncovered, (t) the plenum chamber may be constructed from a transparent material, (u) the patient interface may be configured so that no part of the patient interface enters the mouth in use, (v) the patient interface may be configured so that the seal-forming structure does not extend below a mental protuberance region in use, (w) the patient interface may be constructed and arranged so that the plenum chamber does not cover the eyes in use, (x) the patient interface may be configured so that the positioning and stabilizing structure provides a retention force of at least (6 (g–f/cm2)×mask footprint area (cm2)) in use, (y) the patient interface may be configured so that the positioning and stabilizing structure provides a force of less than (30 (g–f/cm2)×mask footprint area (cm2)) in use, (z) a portion of the positioning and stabilizing structure may be constructed to be breathable to allow moisture vapour to escape and/or be transmitted therethrough.

Another aspect of the present technology is directed to a patient interface that includes: a plenum chamber; a seal-forming structure; a vent structure; and a positioning and stabilising structure to provide a force to hold a seal-forming structure in a therapeutically effective position on a patient's head. The positioning and stabilising structure including at least one gas delivery tube to receive the flow of air from a connection port and to deliver the flow of air to the entrance of the patient's airways via the seal-forming structure, the gas delivery tube being constructed and arranged to contact, in use, at least a region of the patient's head superior to an otobasion superior of the patient's head.

Another aspect of the present technology is directed to a positioning and stabilising structure comprising at least one gas delivery tube. The at least one gas delivery tube may comprise a non-patient contacting portion comprising a first outer layer, and a first inner layer comprising air impermeable material. The at least one gas delivery tube may comprise a patient contacting portion comprising a second outer layer configured to lie against the patient's head in use on an opposing side of the gas delivery tube to the first outer layer, and a second inner layer comprising air impermeable material.

Another aspect of the present technology is directed to a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use. The positioning and stabilising structure may comprise at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure. The tube wall may comprise 1) a non-patient contacting portion comprising a first outer layer and a first inner layer comprising air impermeable material; and 2) a patient contacting portion comprising a second outer layer configured to lie against the patient's head in use on an opposing side of the gas delivery tube to the first outer layer and a second inner layer comprising air impermeable material.

In examples: (a) the first outer layer comprises textile material; (b) the second outer layer comprises textile material; (c) the first inner layer comprises thermoplastic material; (d) the second inner layer comprises thermoplastic material; (e) the non-patient contacting portion comprises a first intermediate layer between the first outer layer and the first inner layer; (f) the non-patient contacting portion comprises a first adhesive layer bonding the first outer layer to the first intermediate layer; (g) the non-patient contacting portion comprises a second adhesive layer bonding the first intermediate layer to the first inner layer; (h) the first intermediate layer comprises a foam material; (i) the first intermediate layer comprises a spacer fabric; (j) the first intermediate layer is thicker than the first outer layer; (k) the patient contacting portion comprises a second intermediate layer between the second outer layer and the second inner layer; (l) the patient contacting portion comprises a first adhesive layer bonding the second outer layer to the second intermediate layer; (m) the patient contacting portion comprises a second adhesive layer bonding the second intermediate layer to the second inner layer; (n) the second intermediate layer comprises a foam material; (o) the second intermediate layer comprises a spacer fabric; and/or (p) the second intermediate layer is thicker than the second outer layer.

In further examples: (a) the non-patient contacting portion comprises a first adhesive layer bonding the first outer layer to the first inner layer; (b) the patient contacting portion comprises a first adhesive layer bonding the second outer layer to the second inner layer; (c) the patient contacting portion and/or the non-patient contacting portion are thermoformed to shape; (d) the gas delivery tube comprises one of a dome-shaped, trapezoidal or rectangular cross section; (e) the gas delivery tube varies in width from 24 mm to 18 mm along a length of the gas delivery tube; (f) the gas delivery tube varies in height from 8 mm to 6 mm along a length of the gas delivery tube; and/or (g) the patient contacting portion and the non-patient contacting portion are each elongate and each comprise an anterior edge and a posterior edge, the anterior edges being joined along the length of the gas delivery tube and the posterior edges being joined along the length of the gas delivery tube.

In further examples: (a) the anterior edges are joined to form an anterior seam of the gas delivery tube and the posterior edges are joined to form a posterior seam of the gas delivery tube; (b) the anterior seam and/or posterior seam are thermoformed; (c) the gas delivery tube comprises an eyelet configured to connect to a backstrap of the positioning and stabilising structure; (d) the eyelet is formed by the patient-contacting portion and/or the non-patient contacting portion; and/or (e) the eyelet is formed by a seam connecting posterior edges of the patient contacting portion and the non-patient contacting portion.

According to another aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use. The positioning and stabilising structure may comprise at least one gas delivery tube to receive the flow of air from on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure. The tube wall may comprise 1) an elongate patient contacting portion configured to lie against the patient's head in use; and 2) an elongate non-patient contacting portion on an opposing side of the gas delivery tube to the patient contacting portion, wherein the non-patient contacting portion is pulled by the patient contacting portion into a predetermined shape creating the hollow interior of the gas delivery tube.

In examples: (a) the gas delivery tube is biased towards an open configuration (b) the non-patient contacting portion is biased towards a flat shape; (c) the non-patient contacting portion is biased by elasticity in one or more materials forming the non-patient contacting portion; (d) the predetermined shape is a non-flat shape; (e) the gas delivery tube comprises a trapezoidal cross section; (f) the patient contacting portion comprises a non-flat shape; (g) the patient contacting portion comprises a flatter shape than the non-patient contacting portion; (h) the patient contacting portion is under tension across a width of the patient contacting portion; (i) the non-patient contacting portion is pulled by the patient contacting portion at edges along a length of the non-patient contacting portion; (j) the non-patient contacting portion and the patient-contacting portion are joined at a pair of seams; (k) the patient contacting portion and the non-patient contacting portion each comprise an anterior edge and a posterior edge, the anterior edges being joined along the length of the gas delivery tube and the posterior edges being joined along the length of the gas delivery tube; (l) the anterior edges are joined to form an anterior seam of the gas delivery tube and the posterior edges are joined to form a posterior seam of the gas delivery tube; (m) the anterior seam and/or posterior seam are thermoformed; (n) the patient contacting portion and the non-patient contacting portion are thermoformed.

In examples: (a) the patient contacting portion and/or the non-patient contacting portion comprise a plurality of layers; (b) the patient contacting portion comprises a first outer later comprising a textile or foam material; (c) the non-patient contacting portion comprises a second outer layer comprising a textile or foam material; (d) the patient contacting portion and/or the non-patient contacting portion comprises an intermediate layer comprising a foam material or spacer fabric material.

In further examples: (a) the patient contacting portion may be stiffer than the non-patient contacting portion; (b) the non-patient contacting portion may be more stretchable than the patient-contacting portion; (c) the patient contacting portion may comprise a greater thickness than the non-patient contacting portion; (d) the patient contacting portion may comprise a medially-facing surface configured to lie against the patient's head having a higher coefficient of friction with respect to the patient's skin than a laterally-facing surface of the non-patient contacting portion.

In some examples, the positioning and stabilising structure comprises a pair of gas delivery tubes.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use. The positioning and stabilising structure may comprise at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure. The tube wall may comprise 1) a patient contacting portion comprising a first outer layer comprising a textile or foam material configured to lie against the patient's head in use; and 2) a non-patient contacting portion comprising a second outer layer comprising a textile or foam material on an opposing side of the gas delivery tube to the first outer layer.

In examples: (a) the patient contacting portion comprises a greater stiffness than the non-patient contacting portion; (b) the patient contacting portion comprises a greater thickness than the non-patient contacting portion; (c) the patient contacting portion is thermoformed by a first thermoforming process and the non-patient contacting portion is thermoformed by a second thermoforming process, wherein the first thermoforming process provides a greater stiffness to the patient contacting portion than the second thermoforming process provides to the non-patient contacting portion; (d) the patient contacting portion and the non-patient contacting portion are each formed by layers, the patient contacting portion comprising a greater number of layers than the non-patient contacting portion; (e) the patient contacting portion comprises a rigidising layer; (f) the patient contacting portion comprises a rigidising member.

In further examples, (a) the patient contacting portion and/or the non-patient contacting portion may comprise a plurality of layers; (b) the patient contacting portion may comprise a first thermoplastic inner layer defining at least a portion of an air path within the gas delivery tube; (c) the patient contacting portion may comprise a first intermediate layer between the first outer layer and the first thermoplastic inner layer; (d) the patient contacting portion may comprise a first adhesive layer bonding the first outer layer to the first intermediate layer; (e) the patient contacting portion may comprise a second adhesive layer bonding the first intermediate layer to the first thermoplastic inner layer; and/or (f) the first intermediate layer may be formed from a foam material or a spacer fabric material.

In further examples: (a) the non-patient contacting portion may comprise a second thermoplastic inner layer defining at least a portion of the air path within the gas delivery tube; (b) the non-patient contacting portion may comprise a first adhesive layer bonding the second outer layer to the second thermoplastic inner layer; (c) alternatively, the non-patient contacting portion may comprise a second intermediate layer between the second outer layer and the second thermoplastic inner layer; (d) the patient contacting portion may comprise a first adhesive layer bonding the second outer layer to the second intermediate layer; (e) the patient contacting portion may comprise a second adhesive layer bonding the second intermediate layer to the second thermoplastic inner layer; and/or (f) the second intermediate layer may be formed from a foam material.

In further examples: (a) the patient contacting portion and/or the non-patient contacting portion may be thermoformed to shape; (b) the gas delivery tube may comprise a dome-shaped cross section; (c) the gas delivery tube may vary in width from 34 mm to 18 mm along a length of the gas delivery tube; and/or (d) the gas delivery tube may vary in height from 8 mm to 6 mm along a length of the gas delivery tube.

According to another aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use. The positioning and stabilising structure may comprise at least one gas delivery tube to receive the flow of air from on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure. The tube wall may comprise 1) a patient contacting portion configured to lie against the patient's head in use; and 2) a non-patient contacting portion on an opposing side of the gas delivery tube to the patient contacting portion.

In examples: (a) the patient contacting portion and/or the non-patient contacting portion may comprise a plurality of layers; (b) the patient contacting portion may comprise a first outer later comprising a textile or foam material; (c) the non-patient contacting portion may comprise a second outer layer comprising a textile or foam material; (d) the patient contacting portion and/or the non-patient contacting portion may comprise an intermediate layer comprising a foam material or spacer fabric material.

In further examples: (a) the gas delivery tube may comprise a dome shaped cross section; (b) the gas delivery tube may comprise a rectangular cross section with two or more rounded corners; (c) the patient contacting portion may be stiffer than the non-patient contacting portion; (d) the non-patient contacting portion may be more stretchable than the patient-contacting portion; (e) the patient contacting portion may comprise a greater thickness than the non-patient contacting portion; (f) the patient contacting portion may comprise a medially-facing surface configured to lie against the patient's head having a higher coefficient of friction with respect to the patient's skin than a laterally-facing surface of the non-patient contacting portion.

In further examples: (a) the gas delivery tube may be biased into an open configuration; (b) the non-patient contacting portion may be biased towards a flat shape and the patient contacting portion may pull the non-patient contacting portion into a curved shape to produce the hollow interior of the gas delivery tube; (c) the patient contacting portion and the non-patient contacting portion may each be elongate and each comprising an anterior edge and a posterior edge, the anterior edges being joined along the length of the gas delivery tube and the posterior edges being joined along the length of the gas delivery tube; (d) after the anterior edges and posterior edges are joined, the patient contacting portion and/or the non-patient contacting portion may be under tension; (e) the anterior edges may be joined to form an anterior seam of the gas delivery tube and the posterior edges may be joined to form a posterior seam of the gas delivery tube; (f) the anterior seam and/or posterior seam may be thermoformed; (g) the anterior seam may have a different rigidity to the posterior seam; (h) the anterior seam may comprise a greater rigidity than the posterior seam; (i) the anterior seam and/or the posterior seam may have a rigidity which varies along the length of the gas delivery tube; (j) the rigidity of the anterior seam and/or the posterior seam may be greater at an inferior portion of the gas delivery tube than at a superior portion of the gas delivery tube; (k) the gas delivery tube may comprise an eyelet configured to connect to a backstrap of the positioning and stabilising structure; (l) the eyelet may be formed by the patient-contacting portion and/or the non-patient contacting portion; (m) the eyelet may be formed by a seam connecting posterior edges of the patient contacting portion and the non-patient contacting portion.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use. The positioning and stabilising structure may comprise at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising a tube wall defining a hollow interior through which air is able to flow to the seal-forming structure. The tube wall may comprise 1) a patient contacting portion comprising a first outer layer comprising a textile or foam material configured to lie against the patient's head in use; and 2) a non-patient contacting portion comprising a second outer layer comprising a textile or foam material on an opposing side of the gas delivery tube to the first outer layer, wherein at least one seam is formed by an edge of the non-patient contacting portion being joined to a respective edge of the patient contacting portion.

In examples: (a) the at least one seam provides rigidity to the at least one gas delivery tube; (b) the at least one seam is formed by a thermoforming process; (c) the at least one seam comprises rigidity provided by compression of the edges forming the seam during the thermoforming process; (d) the at least one seam is welded.

In examples: (a) the at least one gas delivery tube comprises a superior tube portion and an inferior tube portion; (b) the at least one seam comprises a greater stiffness in the inferior tube portion of the gas delivery tube than in the superior tube portion; (c) the greater stiffness of the at least one seam in the inferior tube portion is provided by a greater compression of the edges forming the seam in the inferior tube portion during a thermoforming process than of the edges forming the seam in the superior tube portion; (d) the at least one seam comprises a greater thickness in the inferior tube portion of the gas delivery tube; (e) the at least one seam comprises a greater width in the inferior tube portion of the gas delivery tube than in the superior tube portion.

In examples: (a) the at least one seam comprises an anterior seam, wherein the patient contacting portion and the non-patient contacting portion of the gas delivery tube each comprises an anterior edge, the anterior edges of the patient contacting portion and the non-patient contacting portion being joined to form the anterior seam; (b) the at least one seam comprises a posterior seam, wherein the patient contacting portion and the non-patient contacting portion of the gas delivery tube each comprises a posterior edge, the posterior edges of the patient contacting portion and the non-patient contacting portion being joined to form the posterior seam; (c) the at least one seam comprises an anterior seam and a posterior seam, wherein the patient contacting portion and the non-patient contacting portion of the gas delivery tube each comprises an anterior edge and a posterior edge, the respective anterior edges being joined to form an anterior seam and the respective posterior edges being joined to form a posterior seam.

In examples: (a) the anterior seam comprises a greater stiffness than the posterior seam; (b) the greater stiffness of the anterior seam is provided by a greater compression of the edges forming the anterior seam during a thermoforming process than of the edges forming the posterior seam; (c) the anterior seam comprises a greater thickness than the posterior seam; (d) the anterior seam comprises a greater width than the posterior seam.

In examples: (a) the at least one seam comprises a posterior seam, wherein the patient contacting portion and the non-patient contacting portion of the gas delivery tube each comprises a posterior edge, the posterior edges of the patient contacting portion and the non-patient contacting portion being joined to form the posterior seam; (b) the posterior seam comprises a widened portion, the widened portion configured to connect with a strap of the positioning and stabilising structure; (c) the posterior seam comprises an eyelet configured to connect with the strap; (d) the posterior seam comprises a hole configured to receive the strap, the hole allowing the strap to be passed therethrough and looped back and secured onto itself; (e) the eyelet in the posterior seam comprises a slit; (f) the positioning and stabilising structure comprises an eyelet rigidising portion configured to reinforce the eyelet; (g) the eyelet rigidising portion is provided within the hole in the posterior seam and is configured to reinforce the shape of the hole; (h) the eyelet rigidising portion is substantially rigid.

According to one aspect of the present technology there is provided a positioning and stabilising structure to provide a force to hold a seal-forming structure in a therapeutically effective position on a patient's head for positive pressure airway treatment of sleep disordered breathing. The positioning and stabilising structure may comprise at least one gas delivery tube to deliver a flow of air to an entrance of the patient's airways via a seal-forming structure, each gas delivery tube being constructed and arranged to contact, in use, at least a region of the patient's head superior to an otobasion superior of the patient's head, each gas delivery tube comprising a tube wall defining a hollow interior through which air is able to flow to the seal-forming structure.

In examples: (a): each gas delivery tube may comprise a superior tube portion configured to extend in use from a position on top of the patient's head to a position along the side of the patient's head or face, the superior tube portion comprising a textile material and/or a foam material; (b) each gas delivery tube may comprise an inferior tube portion configured to extend from the position along the side of the patient's head or face to a position adjacent the entrance to the patient's airways, the inferior tube portion comprising a textile material and/or a foam material; (c) one of the inferior tube portion and superior tube portion has a greater rigidity than the other of the inferior tube portion and superior tube portion.

In further examples: (a) the superior tube portion comprises a first end configured to lie against a superiorly-facing surface of the patient's head in use and a second end configured to lie against a laterally-facing surface of the patient's head in use; (b) the inferior tube portion comprises a first end configured to lie against a laterally-facing surface of the patient's head in use and a second end configured to connect with the seal-forming structure; (c) the inferior tube portion is configured to fluidly connect the superior tube portion with the seal-forming structure in use; (d) the superior tube portion is adapted to receive the flow of air from a source via a crown connector arranged to be positioned on top of the patient's head in use; (e) the positioning and stabilising structure further comprises a crown connector, the at least one gas delivery tube comprises a pair of gas delivery tubes, the crown connector is configured to lie on top of the patient's head in use to fluidly connect between the pair of gas delivery tubes, and the crown connector comprises a hollow interior and a fluid connection opening configured to receive the flow of air into the hollow interior.

In further examples: (a): one of the inferior tube portion or the superior tube portion is configured with a first layer of material and a second layer of material, the first layer of material being more rigid than the second layer of material; (b) the inferior tube portion and/or the superior tube portion is configured with a rigidising element to provide rigidity to the inferior tube portion and/or the superior tube portion; (c) the inferior tube portion and/or the superior tube portion is configured with a seam; (d) the inferior tube portion is formed as a first tube and the superior tube portion is formed as a second tube, the first tube being joined to the second tube; (e) the first tube is joined to the second tube by thermoforming, ultrasonic welding, stitching, gluing or removably connectable connectors; (f) each gas delivery tube has a patient contacting portion configured to contact the patient in use and a non-patient contacting portion positioned away from the patient in use, the patient contacting portion and/or the non-patient contacting portion comprising a plurality of layers; (g) the patient contacting portion includes a first outer later comprising a textile material or a foam material; (h) the non-patient contacting portion includes a second outer layer comprising a textile material or a foam material; (i) the patient contacting portion and/or the non-patient contacting portion includes an intermediate layer comprising a foam material or a spacer fabric material.

In further examples: (a) the inferior tube portion has greater rigidity than the superior tube portion; (b) the inferior tube portion has a wall thickness that is greater than a wall thickness of the superior tube portion to provide greater rigidity to the inferior tube portion; (c) the inferior tube portion has at least one additional layer not provided to the superior tube portion to provide greater rigidity to the inferior tube portion; (d) the inferior tube portion comprises materials that are less extendible in length than materials of the superior tube portion, thereby providing greater rigidity to the inferior tube portion; (e) the inferior tube portion comprises a plurality of layers, and a rigidising element is provided to one of the plurality of layers to provide greater rigidity to the inferior tube portion; (f) the inferior tube portion comprises a greater number of layers than the superior tube portion, thereby providing greater rigidity to the inferior tube portion; (g) the superior tube portion and inferior tube portion each comprises a textile layer, the textile layer in the inferior tube portion having a woven structure that is different than a woven structure of the textile layer in the superior tube portion, and the woven structure of the inferior tube portion provides greater rigidity to the inferior tube portion as compared to the superior tube portion; (h) the inferior tube portion comprises a greater resistance to bending towards an inferior direction than towards a medial direction, in use; (i) the superior tube portion comprises a greater resistance to bending towards an anterior direction and/or a posterior direction than towards an inferior direction in use; (j) the superior tube portion has greater rigidity than the inferior tube portion.

According to one aspect of the present technology there is provided a positioning and stabilising structure to provide a force to hold a seal-forming structure in a therapeutically effective position on a patient's head for positive pressure airway treatment of sleep disordered breathing. The positioning and stabilising structure may comprise at least one gas delivery tube to deliver a flow of air to an entrance of the patient's airways via a seal-forming structure, each gas delivery tube being constructed and arranged to contact, in use, at least a region of the patient's head superior to an otobasion superior of the patient's head, each gas delivery tube comprising a tube wall defining a hollow interior through which air is able to flow to the seal-forming structure.

In examples: (a) each gas delivery tube may comprise a first elongate length of material having opposing first and second edges along its length; (b) each gas delivery tube may comprise a second elongate length of material having opposing first and second edges along its length; (c) each gas delivery tube may comprise a third elongate length of material having opposing first and second edges along its length; (d) the first elongate length of material is joined to the second elongate length of material along the first edge of the first elongate length of material and the second edge of the second elongate length of material, and the second elongate length of material is joined to the third elongate length of material along the first edge of the second elongate length of material and the second edge of the third elongate length of material, to form the tube wall of the gas delivery tube; (e) an outer layer of the gas delivery tube comprises a textile material and/or a foam material.

In further examples: (a) each gas delivery tube is configured to extend in use from a position on top of the patient's head, along a side of the patient's face, to a position adjacent the entrance to the patient's airways; (b) the first elongate length of material, the second elongate length of material and the third elongate length of material each comprises a plurality of layers; (c) the first elongate length of material has a rigidity that is different than a rigidity of the second elongate length of material and/or the third elongate length of material; (d) the first elongate length of material has a wall thickness that is greater than a wall thickness of the second elongate length of material and/or the third elongate length of material to provide greater rigidity to the first elongate length of material; (e) the first elongate length of material has at least one additional layer not provided to the second elongate length of material and/or the third elongate length of material to provide greater rigidity to the first elongate length of material; (f) the first elongate length of material comprises materials that are less extendible in length than materials of the second elongate length of material and/or the third elongate length of material, thereby providing greater rigidity to the first elongate length of material; (g) the first elongate length of material comprises a greater number of layers than the second elongate length of material and/or the third elongate length of material, thereby providing greater rigidity to the first elongate length of material; (h) each gas delivery tube includes a patient-contacting portion configured to contact the patient's body and a non-patient contacting portion configured to be oriented away from the patient's body in use, the patient-contacting portion includes the first elongate length of material, and the non-patient contacting portion includes the second elongate length of material and the third elongate length of material.

In further examples: (a) each gas delivery tube further comprises an inner portion covered by said outer layer, said inner portion comprising a foam material and/or spacer fabric; (b) the outer layer of the gas delivery tube comprises a sleeve configured to enclose the first elongate length of material, the second elongate length of material and the third elongate length of material; (c) the outer layer of the gas delivery tube includes three elongate lengths of material corresponding respectively to the first elongate length of material, the second elongate length of material and the third elongate length of material.

In further examples: (a) the positioning and stabilising structure further comprises 1) a first seam along the first edge of the first elongate length of material and the second edge of the second elongate length of material, to join the first elongate length of material and the second elongate length of material; and 2) a second seam along the first edge of the second elongate length of material and the second edge of the third elongate length of material, to join the second elongate length of material and the third elongate length of material; (b) the first elongate length of material has a concave shape to position the first seam away from the patient's face, in use; (c) the first seam and/or the second seam impart rigidity to the gas delivery tube; (d) the first seam imparts greater rigidity to the gas delivery tube than the second seam; (e) the gas delivery tube comprising rigidising elements embedded within or layered on the first seam and/or the second seam to provide rigidity to the gas delivery tube; (f) the rigidising elements comprise metal or plastic materials; (g) the at least one gas delivery tube comprises a pair of gas delivery tubes; (h) the positioning and stabilizing structure further comprising a crown connector that is configured to be positioned on top of the patient's head in use to fluidly connect between the pair of gas delivery tubes.

According to one aspect of the present technology there is provided a positioning and stabilising structure to provide a force to hold a seal-forming structure in a therapeutically effective position on a patient's head for positive pressure airway treatment of sleep disordered breathing. The positioning and stabilising structure may comprise at least one gas delivery tube to deliver a flow of air to an entrance of the patient's airways via a seal-forming structure, each gas delivery tube being constructed and arranged to contact, in use, at least a region of the patient's head superior to an otobasion superior of the patient's head, each gas delivery tube comprising a tube wall defining a hollow interior through which air is able to flow to the seal-forming structure.

In examples: (a) each gas delivery tube may comprise 1) a patient-contacting portion configured to contact the patient's body; 2) a non-patient contacting portion configured to be oriented away from the patient's body in use; and 3) at least one seam to join the patient-contacting portion and the non-patient contacting portion; (b) the at least one seam comprises rigidising elements embedded within or layered on the seam to provide rigidity to the gas delivery tube.

In further examples: (a) the at least one seam comprises a first seam and a second seam; (b) the first seam provides greater or lesser rigidity to the gas delivery tube than the second seam; (c) in use, each gas delivery tube is configured to extend along a side of the patient's face, and the first seam is configured to be positioned anteriorly and the second seam is configured to be positioned posteriorly with respect to the patient's face; (d) the rigidising elements comprise metal or plastic materials; (e) the rigidising elements comprise a yarn having a lower melt temperature than surrounding yarn; (f) the patient-contacting portion includes a first elongate length of material, and the non-patient contacting portion includes at least a second elongate length of material; (g) the non-patient contacting portion includes a third elongate length of material; (h) the patient-contacting portion and the non-patient contacting portion each comprises a plurality of layers; (i) each gas delivery tube is configured to extend in use from a position on top of the patient's head, along a side of the patient's face, to a position adjacent the entrance to the patient's airways; (j) each gas delivery tube comprises a textile material and/or a foam material; (k) the at least one gas delivery tube includes a pair of gas delivery tubes; (l) the at least one seam is thermoformed or ultrasonically welded to join the patient-contacting portion and the non-patient contacting portion.

According to one aspect of the present technology there is provided a positioning and stabilising structure to provide a force to hold a seal-forming structure in a therapeutically effective position on a patient's head for positive pressure airway treatment of sleep disordered breathing. The positioning and stabilising structure may comprise a pair of gas delivery tubes to deliver a flow of air to an entrance of the patient's airways via a seal-forming structure, each gas delivery tube being constructed and arranged to extend in use from a position on top of the patient's head to a position adjacent the entrance to the patient's airways, each gas delivery tube comprising a tube wall defining a hollow interior of the gas delivery tube through which air is able to flow.

In examples: (a) the positioning and stabilising structure may further comprise a crown connector comprising a hollow interior forming a conduit structure including a fluid connection opening configured to receive the flow of air into the hollow interior and a pair of crown connector tube portions to deliver the flow of air to the pair of gas delivery tubes, the crown connector tube portions being respectively removably connectable to the pair of gas delivery tubes, the crown connector configured to be positioned, in use, at a position on top of the patient's head; (b) each crown connector tube portion includes a crown piece connector and each gas delivery tube includes a corresponding headgear tube connector configured to engage a respective crown piece connector to removably connect the crown connector and the gas delivery tubes; (c) each crown piece connector is disposed along an inner surface of the corresponding crown connector tube portion; (d) the crown connector comprises a flexible material; (e) each crown piece connector comprises a material that is more rigid than the flexible material of the crown connector.

In further examples: (a) the crown connector comprises silicone; (b) each crown piece connector comprises polycarbonate, polypropylene, a semi-rigid or rigid plastic material, and/or nylon; (c) each crown connector tube portion includes a crown connector port through which the flow of air is delivered to a respective one of the gas delivery tubes; (d) each crown piece connector is a rigid female connector insert disposed proximate a corresponding crown connector port; (e) each crown piece connector has a ring or loop shape that corresponds to a cross-sectional shape of a respective crown connector tube portion; (f) each crown piece connector provides rigidity to the respective crown connector tube portion; (g) each crown connector tube portion is overmolded onto the corresponding crown piece connector; (h) each crown piece connector is configured to form a removable snap fit connection with a corresponding one of the headgear tube connectors; (i) each headgear tube connector is a male connector configured to engage with a corresponding one of the crown piece connectors; (j) the crown connector includes a sealing flange disposed around the fluid connection opening; (k) the positioning and stabilizing structure may further comprise a swivel ring configured to form a seal with the sealing flange, the swivel ring being removably connectable to the rigid conduit and permitting the rigid conduit to rotate relative to the swivel ring while connected.

In further examples: (a) each gas delivery tube is constructed and arranged to extend in use along a respective side of the patient's face between the patient's eye and ear; (b) each gas delivery tube has a patient contacting portion configured to contact the patient in use and a non-patient contacting portion positioned away from the patient in use, and the patient contacting portion and/or the non-patient contacting portion comprises a plurality of layers; (c) each gas delivery tube comprises a textile material and/or a foam material; (d) the patient contacting portion includes a first outer later comprising a textile material or a foam material; (e) the non-patient contacting portion includes a second outer layer comprising a textile material or a foam material.

According to one aspect of the present technology there is provided a positioning and stabilising structure to provide a force to hold a seal-forming structure in a therapeutically effective position on a patient's head for positive pressure airway treatment of sleep disordered breathing. The positioning and stabilising structure may comprise a pair of gas delivery tubes to deliver a flow of air to an entrance of the patient's airways via a seal-forming structure, each gas delivery tube being constructed and arranged to extend in use from a position on top of the patient's head to a position adjacent the entrance to the patient's airways, each gas delivery tube may comprise a tube wall defining a hollow interior of the gas delivery tube through which air is able to flow.

In examples: (a) the positioning and stabilising structure may further comprise a crown connector comprising a hollow interior forming a conduit structure including a fluid connection opening configured to receive the flow of air into the hollow interior and a pair of crown connector tube portions to deliver the flow of air to the pair of gas delivery tubes, the crown connector tube portions being respectively removably connectable to the pair of gas delivery tubes, the crown connector configured to be positioned, in use, at a position on top of the patient's head; (b) the fluid connection opening is adapted to receive the flow of air from a rigid conduit adapted to be removably connected to the crown connector at the fluid connection openin; (c) a lower wall of the crown connector includes an occlusion-preventer disposed thereon at a central location thereof below the fluid connection opening to prevent the rigid conduit from contacting the lower wall and thereby reducing or cutting off the flow of air through the hollow interior; (d) the lower wall of the crown connector includes at least one ramp along an inner surface thereof sloping downwardly toward the occlusion-preventer.

In further examples: (a) the crown connector comprises silicone; (b) the at least one ramp includes a first ramp and a second ramp disposed respectively on opposite sides of the occlusion-preventer, each of the first ramp and the second ramp sloping downwardly toward the occlusion-preventer; (c) the lower wall of the crown connector includes a reinforcement along opposing anterior and posterior sides of the crown connector, and anterior and posterior ends portions of the occlusion-preventer are disposed in the reinforcement to provide stability to the occlusion-preventer; (d) the reinforcement comprises a portion of the lower wall having increased thickness relative to the at least one ramp; (e) each crown connector tube portion includes a crown connector port through which the flow of air is delivered to a respective one of the gas delivery tubes; (f) each crown connector tube portion includes a crown piece connector and each gas delivery tube includes a corresponding tube connector configured to engage a respective crown piece connector to removably connect the crown connector and the gas delivery tubes; (g) each crown piece connector is a rigid female connector insert disposed proximate a corresponding crown connector port; (h) the crown connector includes a sealing flange disposed around the fluid connection opening; (i) the positioning and stabilizing structure may further comprise a swivel ring configured to form a seal with the sealing flange, the swivel ring being removably connectable to the rigid conduit and permitting the rigid conduit to rotate relative to the swivel ring while connected; (j) the crown connector comprises a lip seal that extends radially inwardly of the fluid connection opening at a location within a hollow interior of the crown connector and is adapted to form a seal with a lower end of the rigid conduit.

In further examples: (a) each gas delivery tube is constructed and arranged to extend in use along a respective side of the patient's face between the patient's eye and ear; (b) each gas delivery tube has a patient contacting portion configured to contact the patient in use and a non-patient contacting portion positioned away from the patient in use, and the patient contacting portion and/or the non-patient contacting portion comprises a plurality of layers; (c) each gas delivery tubes comprises a textile material and/or a foam material; (d) the patient contacting portion includes a first outer later comprising a textile material or a foam material; (e) the non-patient contacting portion includes a second outer layer comprising a textile material or a foam material.

According to one aspect of the present technology there is provided a patient interface. The patient interface may comprise 1) a seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use; and 2) a positioning and stabilising structure according to any of the above aspects.

According to one aspect of the present technology, there is provided a patient interface. The patient interface may comprise 1) a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; 2) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; 3) a positioning and stabilising structure according to any one of the above aspects; and 4) a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

Another aspect of certain forms of the present technology is a system for treating a respiratory disorder comprising a patient interface according to any one or more of the other aspects of the present technology, an air circuit and a source of air at positive pressure.

Another aspect of one form of the present technology is a patient interface that is moulded or otherwise constructed with a perimeter shape which is complementary to that of an intended wearer.

An aspect of one form of the present technology is a method of manufacturing the components of the medical device.

Another aspect of certain forms of the present technology is a patient interface comprising a seal-forming structure configured to leave the patient's mouth uncovered in use.

Another aspect of certain forms of the present technology is a patient interface comprising a seal-forming structure configured so that no part of the seal-forming structure enters the mouth in use.

Another aspect of certain forms of the present technology is a patient interface comprising a seal-forming structure configured so that the seal-forming structure does not extend internally of the patient's airways.

Another aspect of certain forms of the present technology is a patient interface comprising a seal-forming structure configured so that the seal-forming structure does not extend below a mental protuberance region in use.

Another aspect of certain forms of the present technology is a patient interface constructed and arranged to leave a patient's eyes uncovered in use.

Another aspect of certain forms of the present technology is a patient interface constructed and arranged to allow a patient to breathe ambient air in the event of a power failure.

Another aspect of certain forms of the present technology is a patient interface comprising a seal forming structure configured to form a seal on an underside of a patient's nose without contacting a nasal bridge region of the patient's nose.

Another aspect of certain forms of the present technology is a patient interface comprising a vent and a plenum chamber, wherein the patient interface is constructed and arranged so that gases from an interior of the plenum chamber may pass to ambient via the vent.

Another aspect of certain forms of the present technology is a patient interface constructed and arranged so that a patient may lie comfortably in a side or lateral sleeping position, in use of the patient interface.

Another aspect of certain forms of the present technology is a patient interface constructed and arranged so that a patient may lie comfortably in a supine sleeping position, in use of the patient interface.

Another aspect of certain forms of the present technology is a patient interface constructed and arranged so that a patient may lie comfortably in a prone sleeping position, in use of the patient interface.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
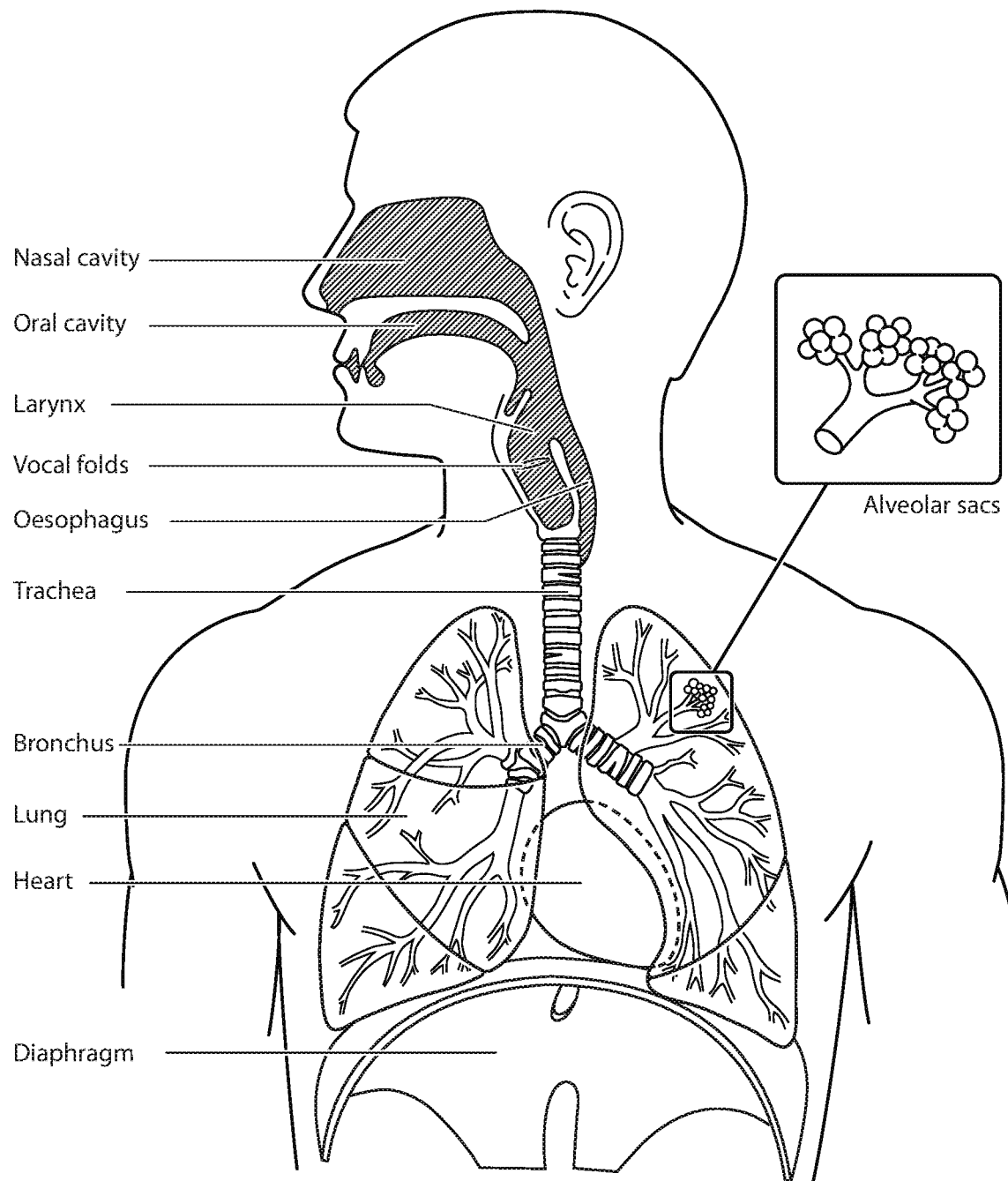
FIG. 2A shows an overview of a human respiratory system including the nasal and oral cavities, the larynx, vocal folds, oesophagus, trachea, bronchus, lung, alveolar sacs, heart and diaphragm.
Figure 2B:
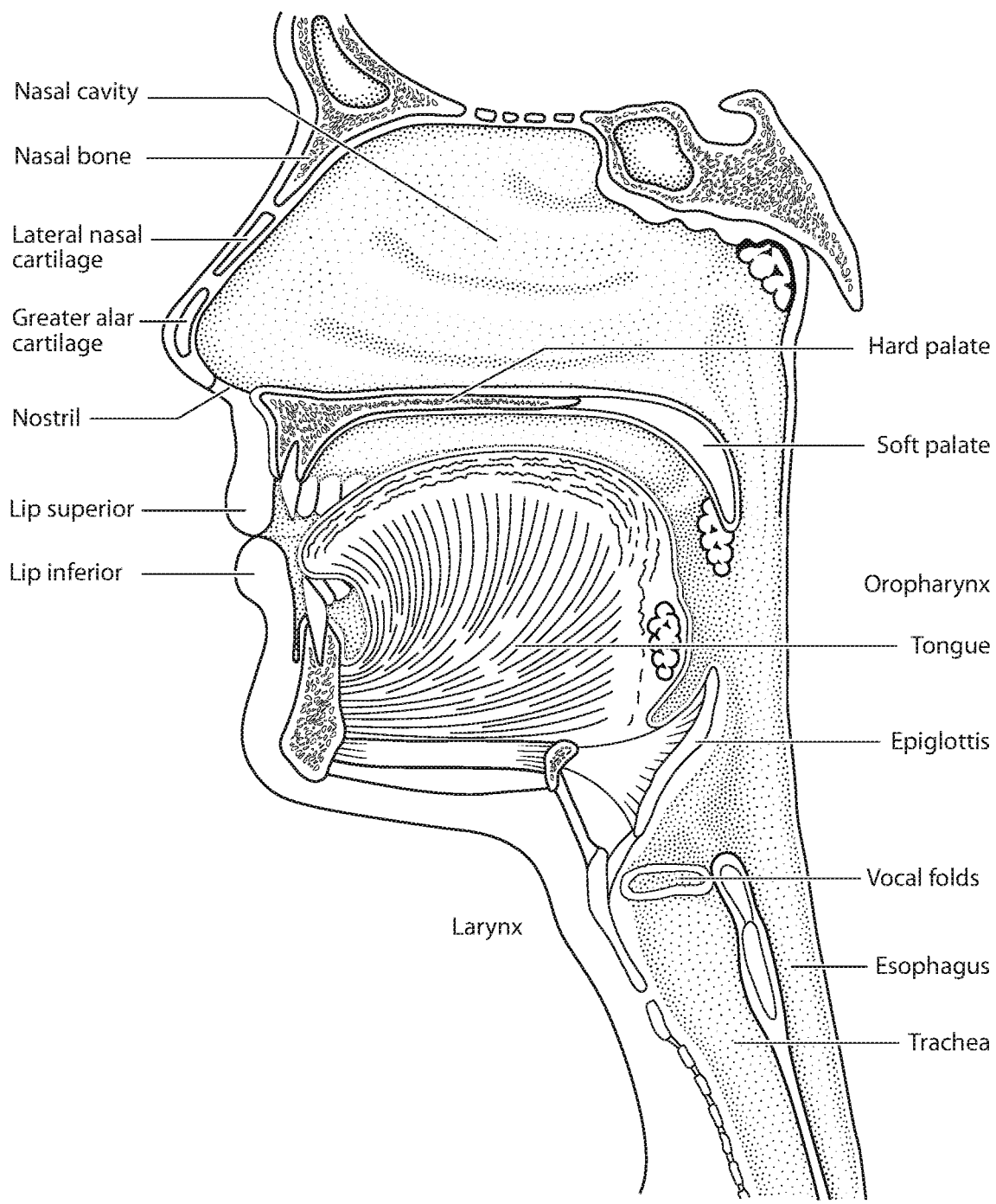
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
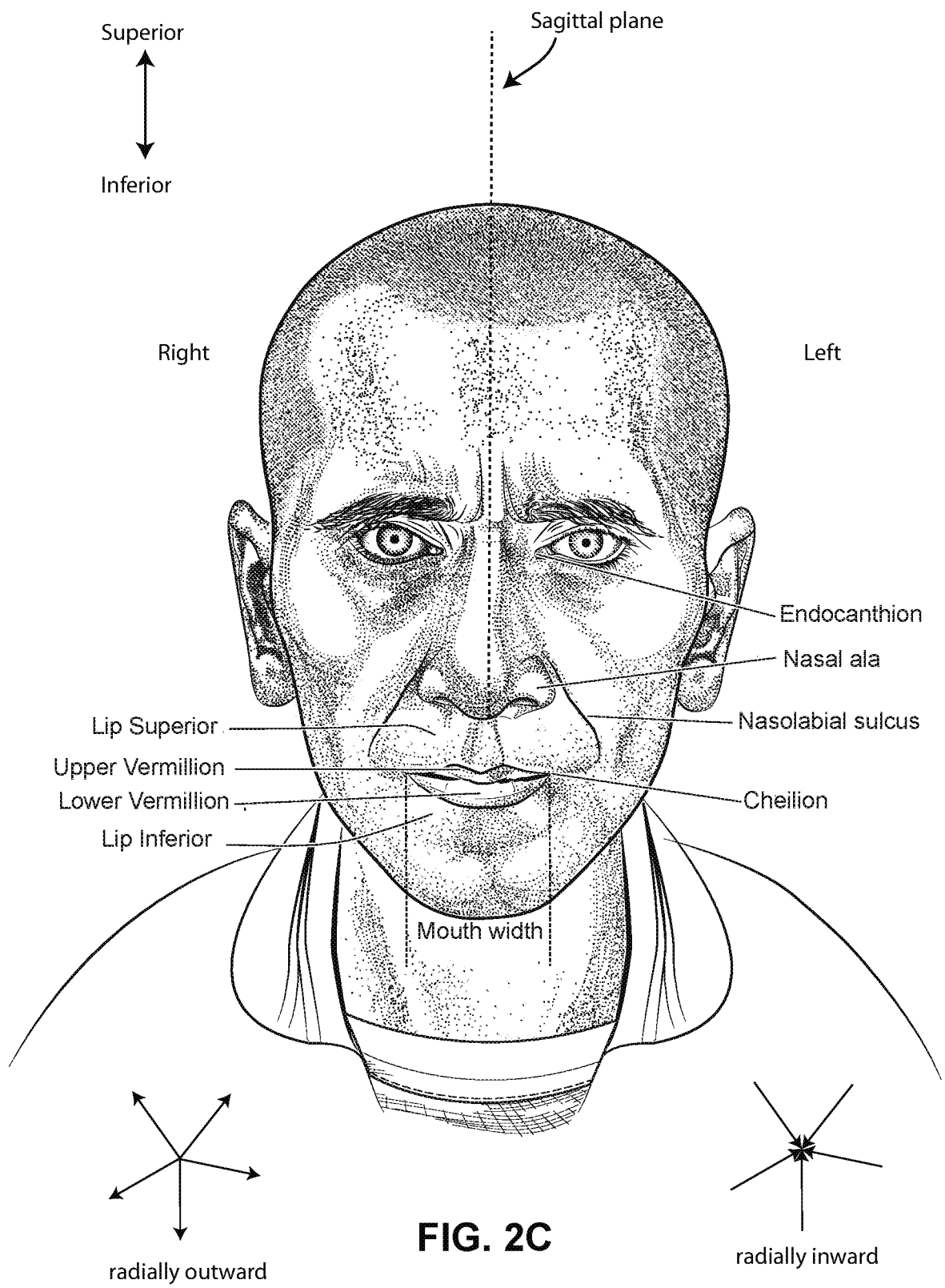
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
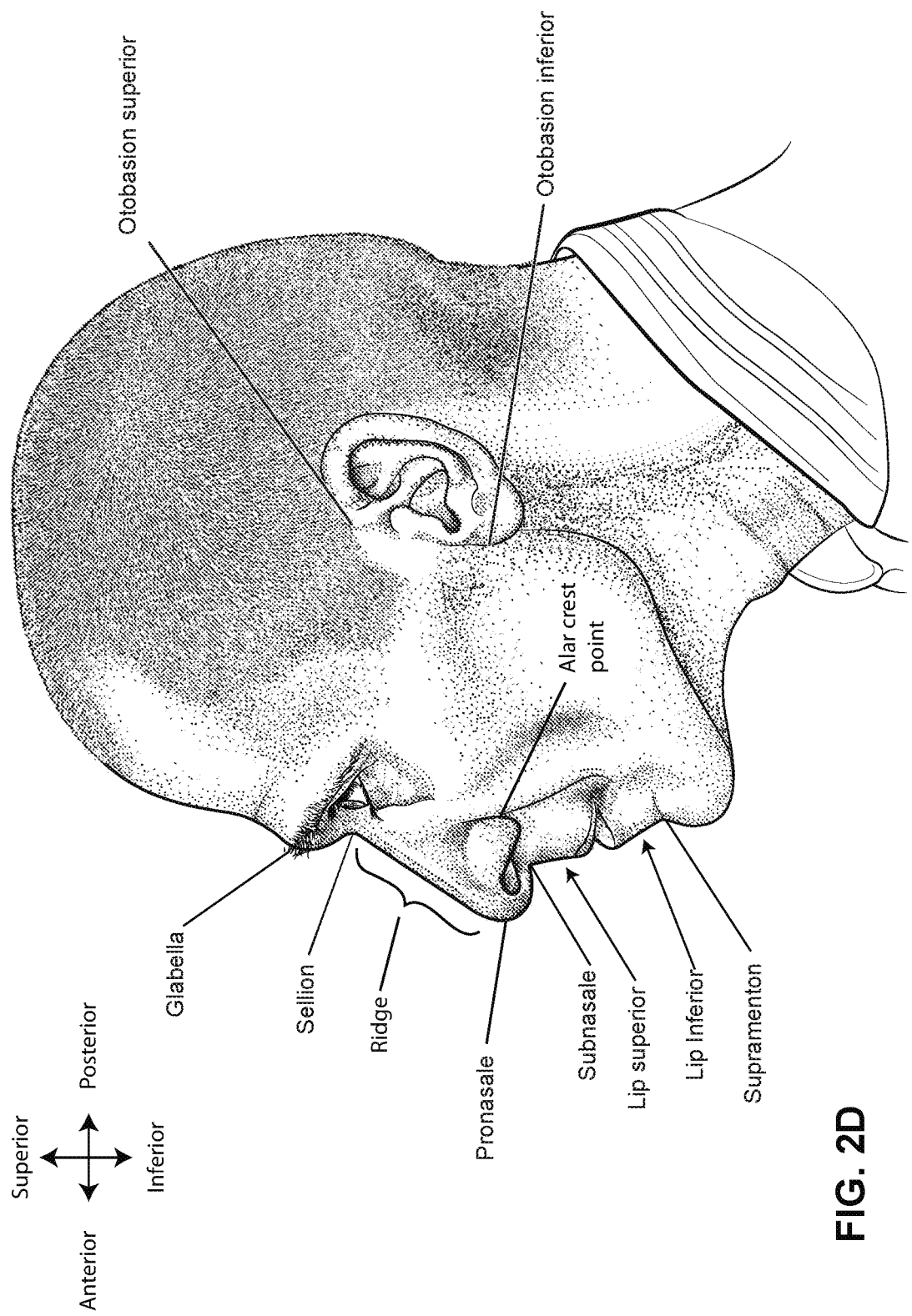
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
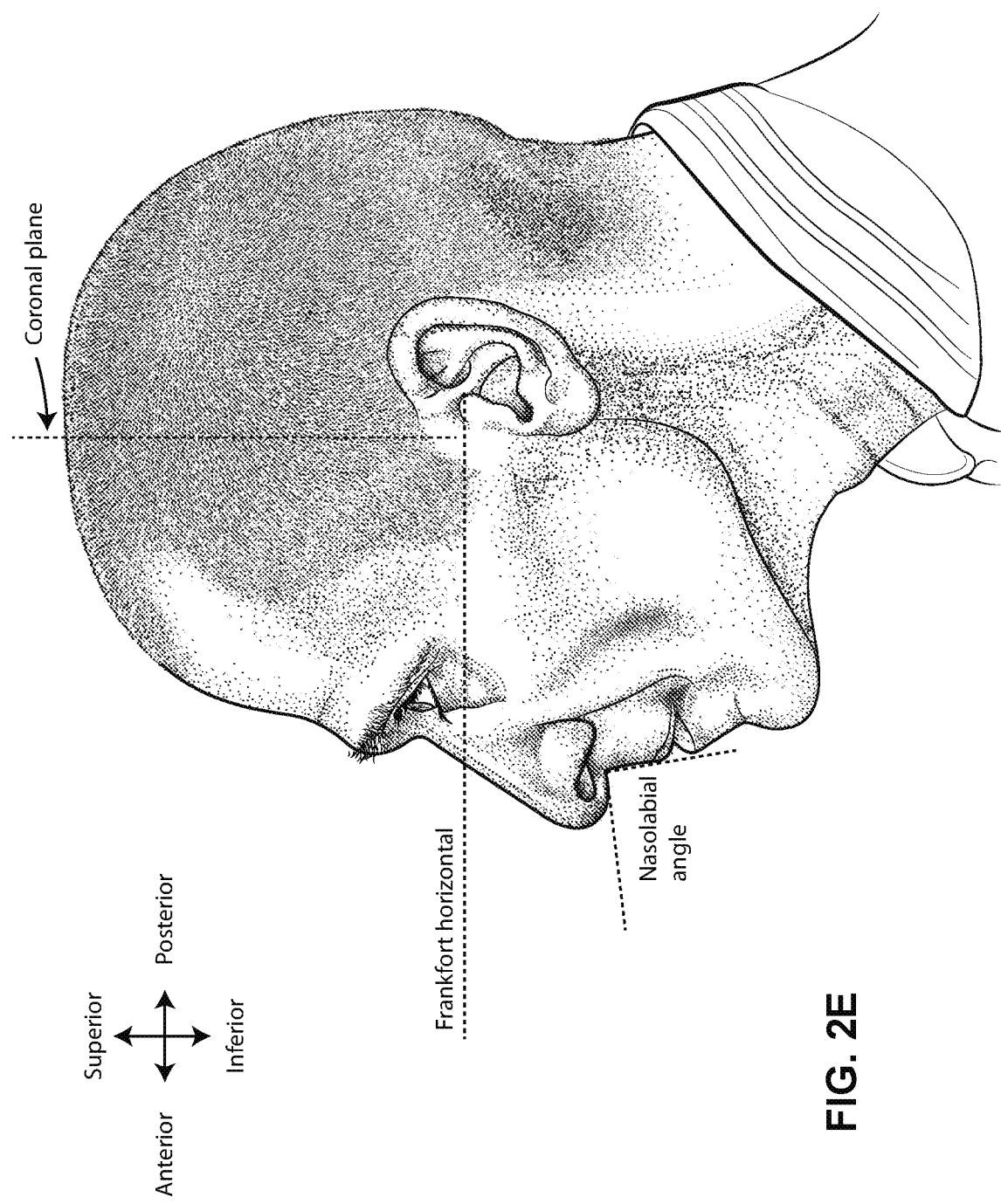

FIG. 2E is a further side view of a head. The approximate locations of the Frankfort horizontal and nasolabial angle are indicated. The coronal plane is also indicated.

Figure 2F:
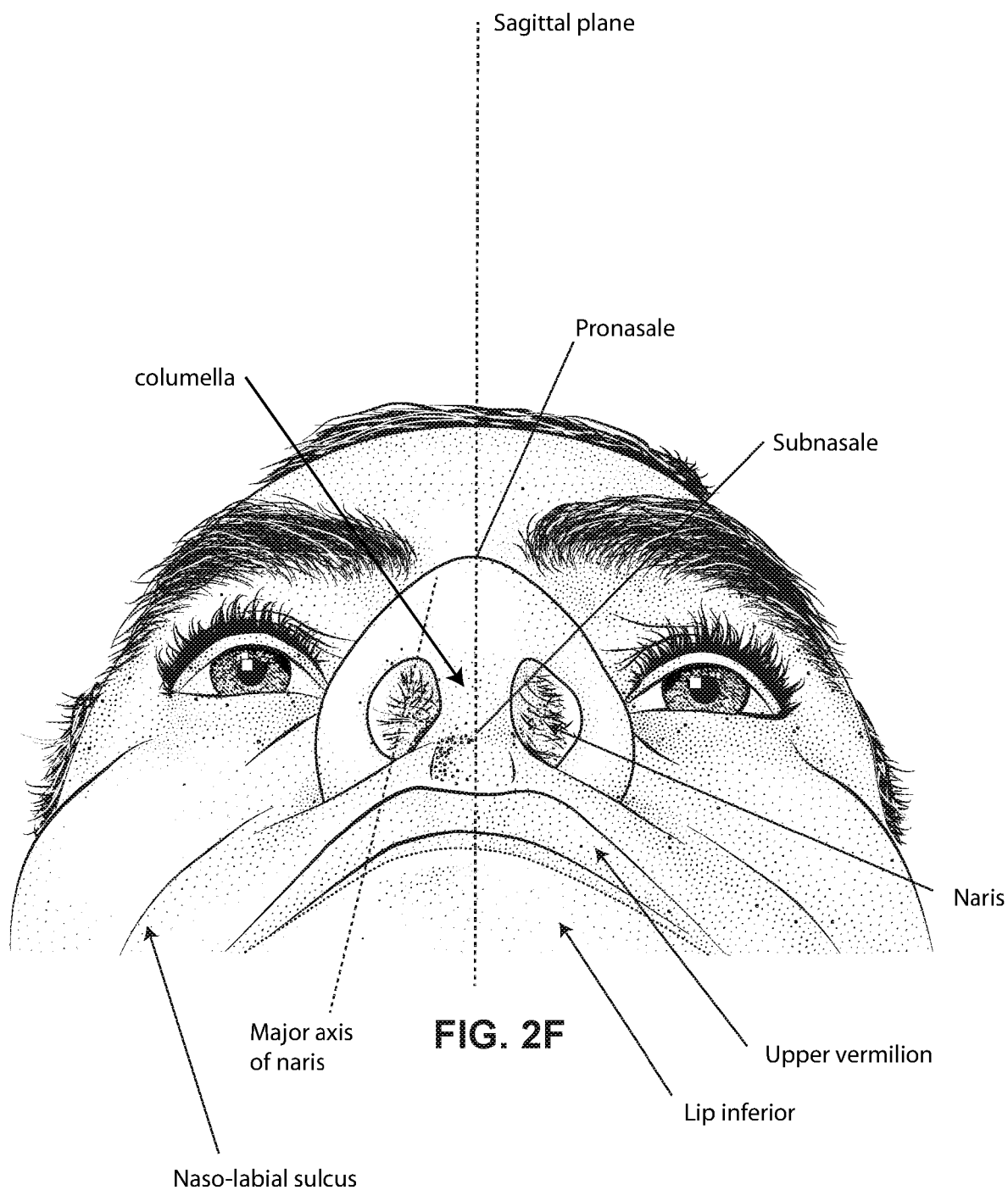

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
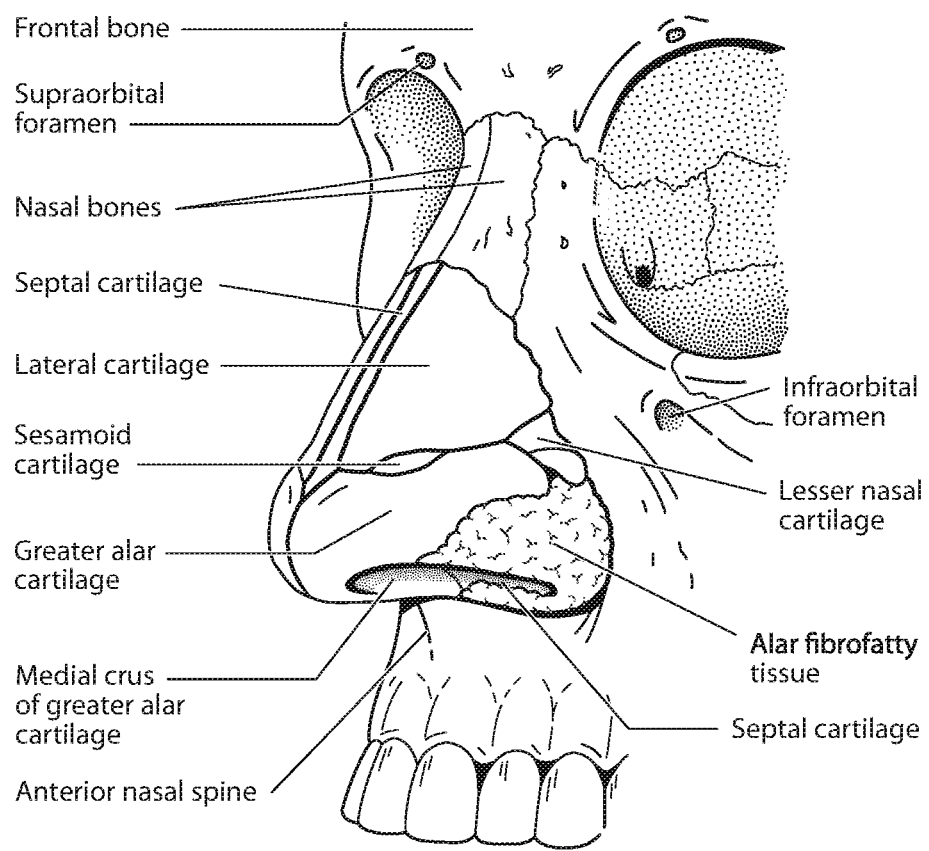

FIG. 2L shows an anterolateral view of a nose.

4.3 Patient Interface

Figure 3A:
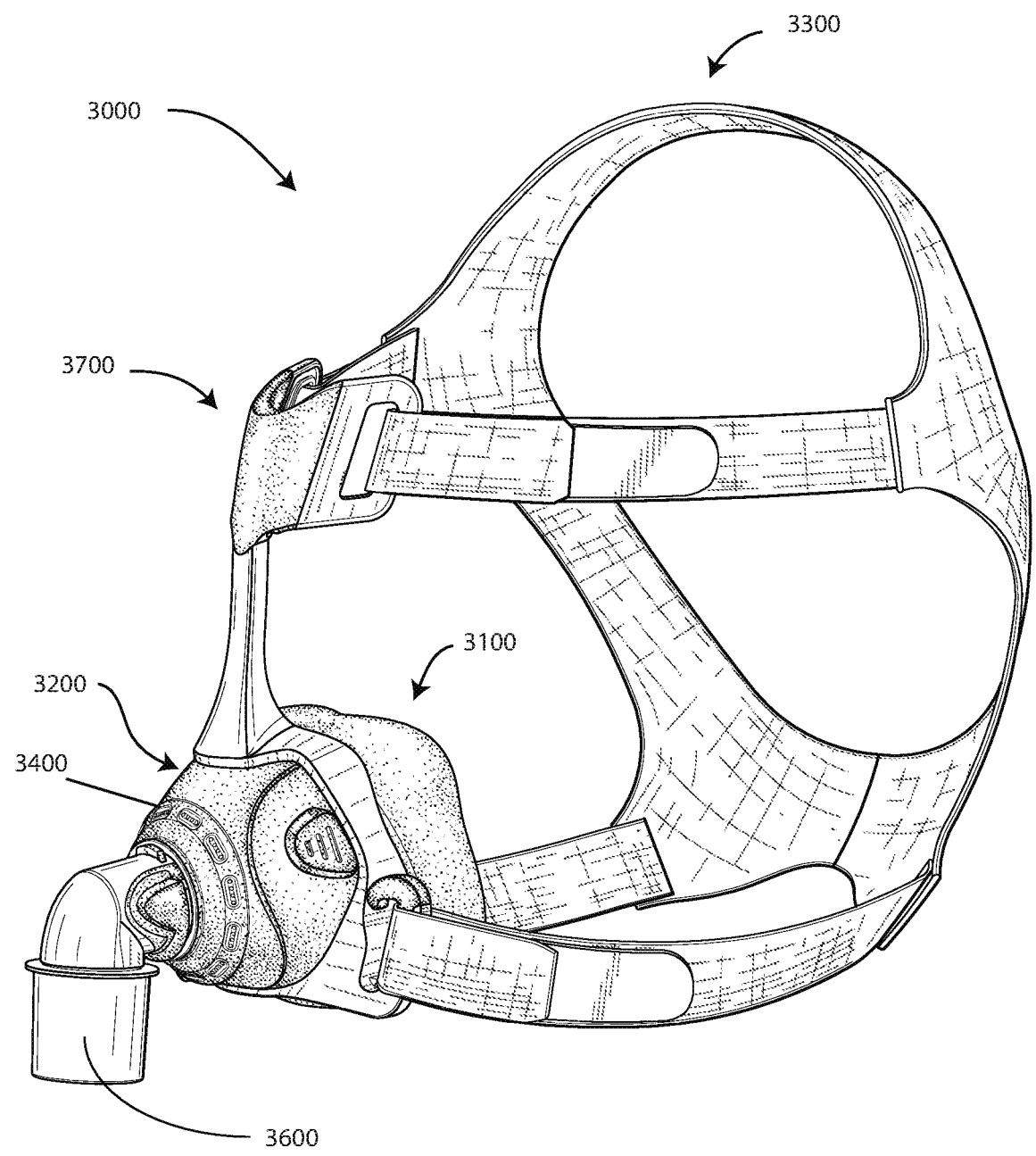

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
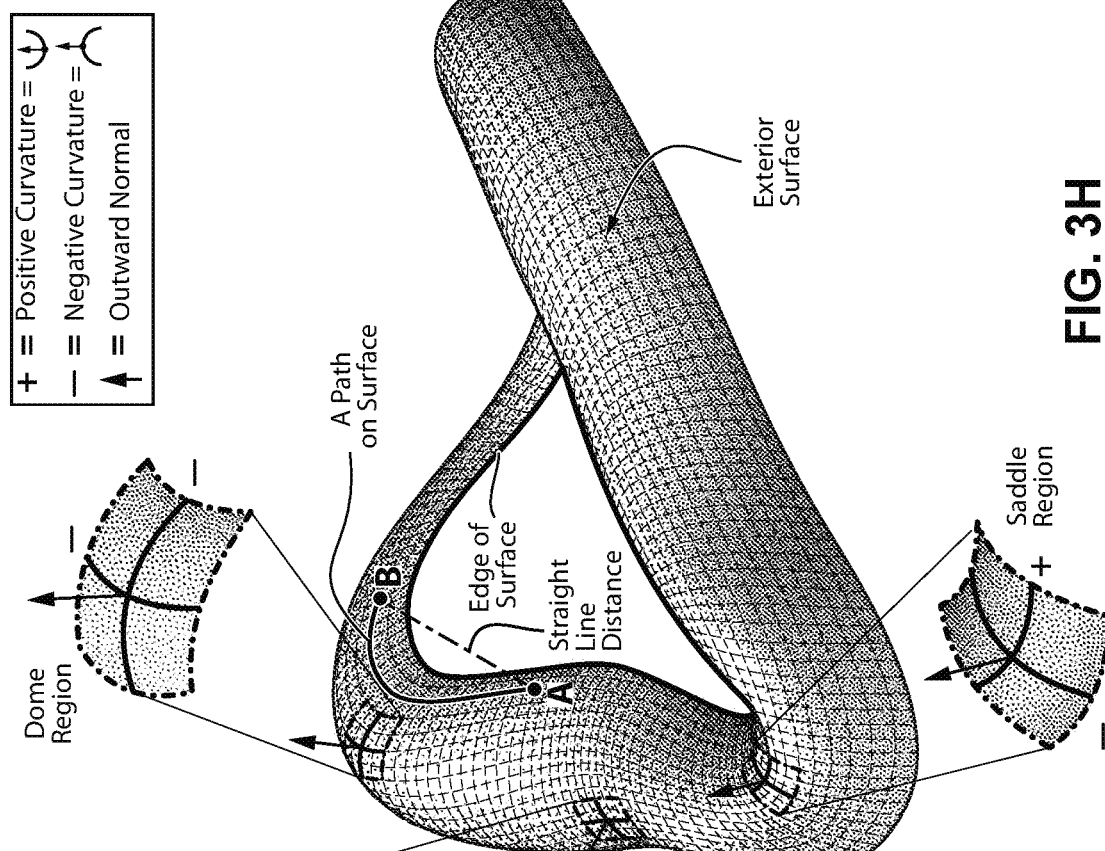
Figure 3G:
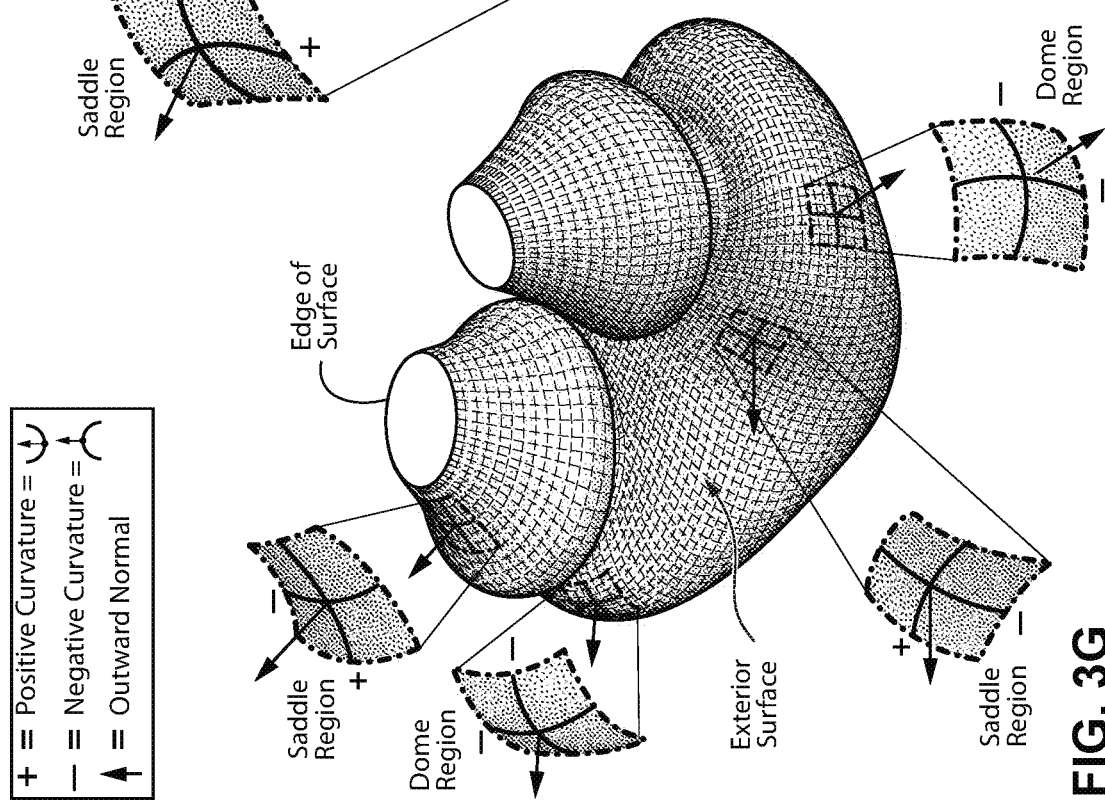

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
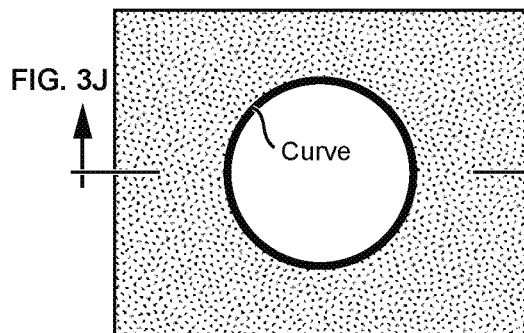

FIG. 3I shows the surface of a structure, with a one dimensional hole in the surface. The illustrated plane curve forms the boundary of a one dimensional hole.

Figure 3K:
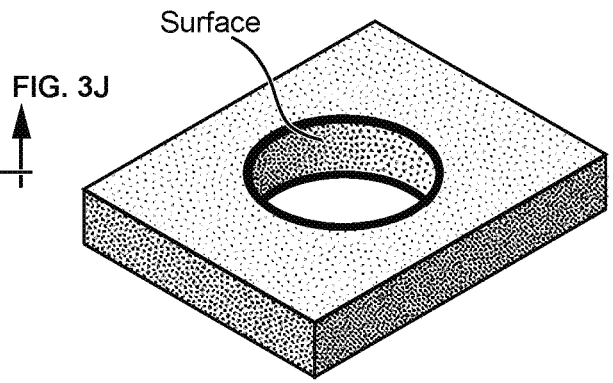
Figure 3J:
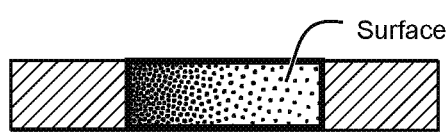

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
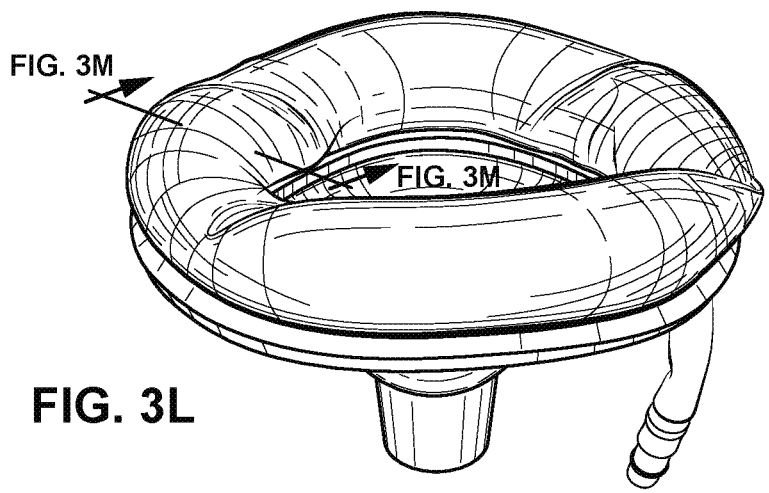

FIG. 3L shows a mask having an inflatable bladder as a cushion.

Figure 3M:
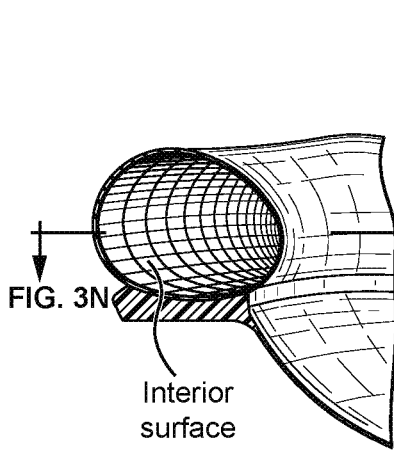

FIG. 3M shows a cross-section through the mask of FIG. 3L, and shows the interior surface of the bladder. The interior surface bounds the two dimensional hole in the mask.

Figure 3N:
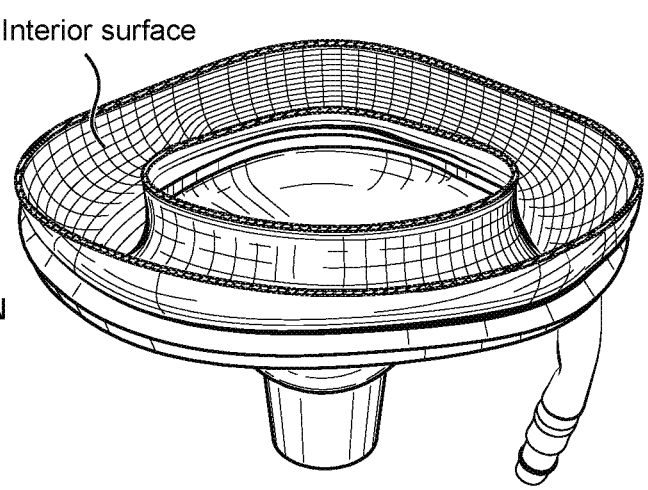

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
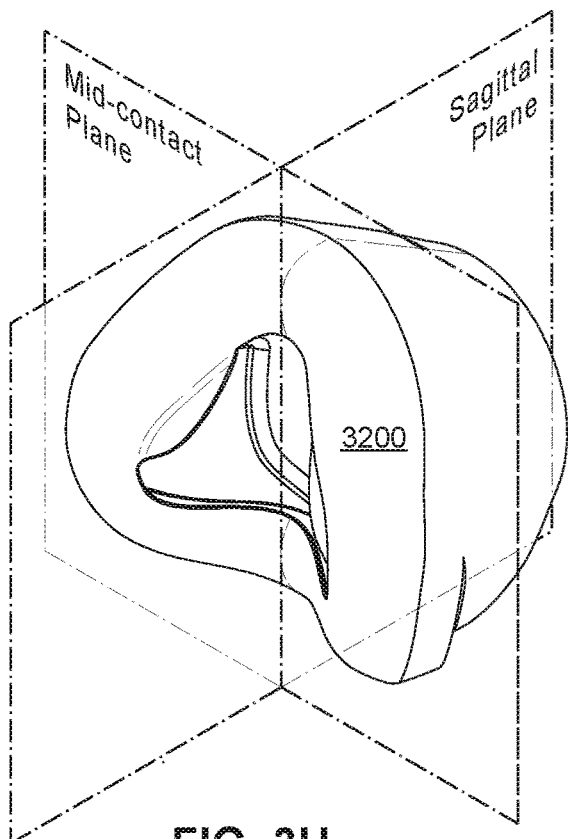

FIG. 3U shows a view of a plenum chamber 3200 showing a sagittal plane and a mid-contact plane.

Figure 3V:
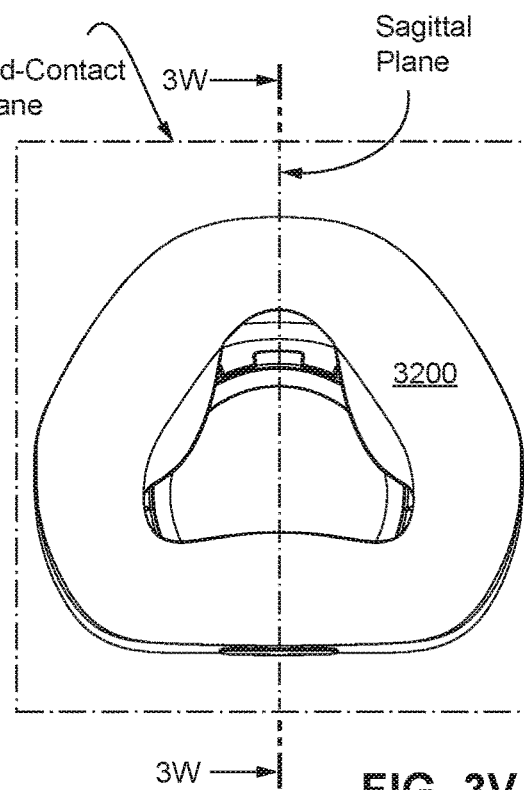

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
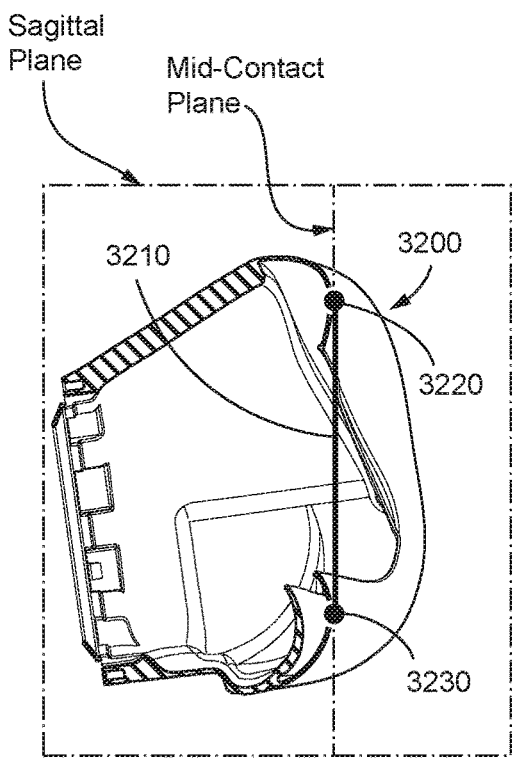

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
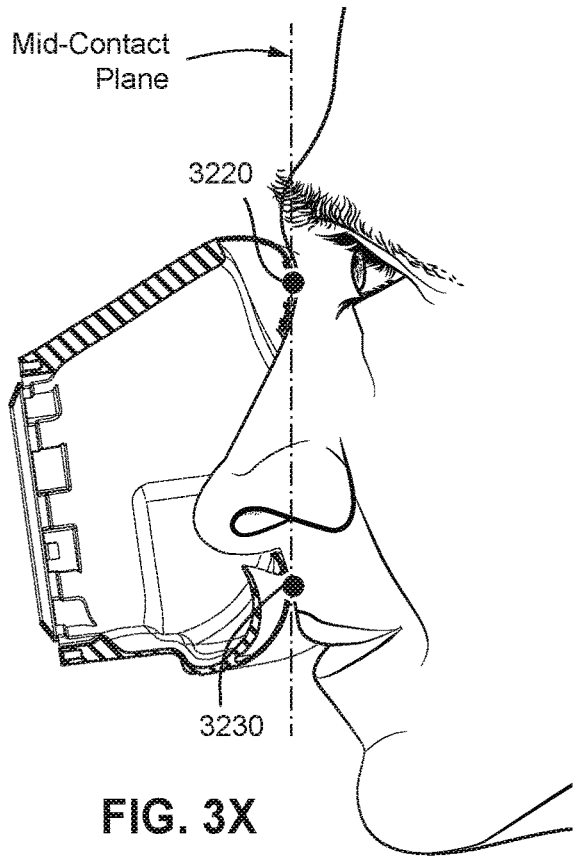

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 4A:
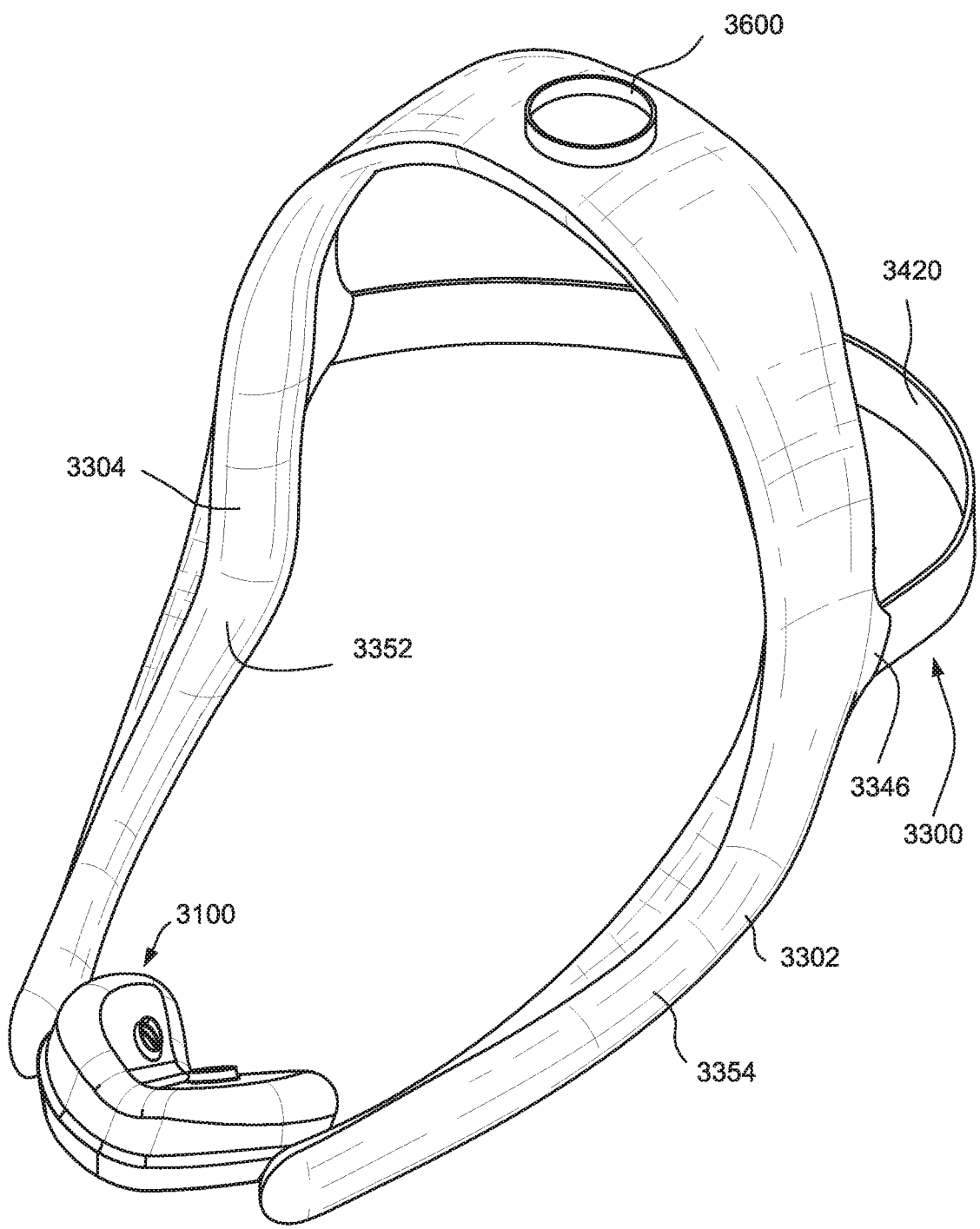

FIG. 4A shows an isometric view of a patient interface in accordance with an example of the present technology.

Figure 4B:
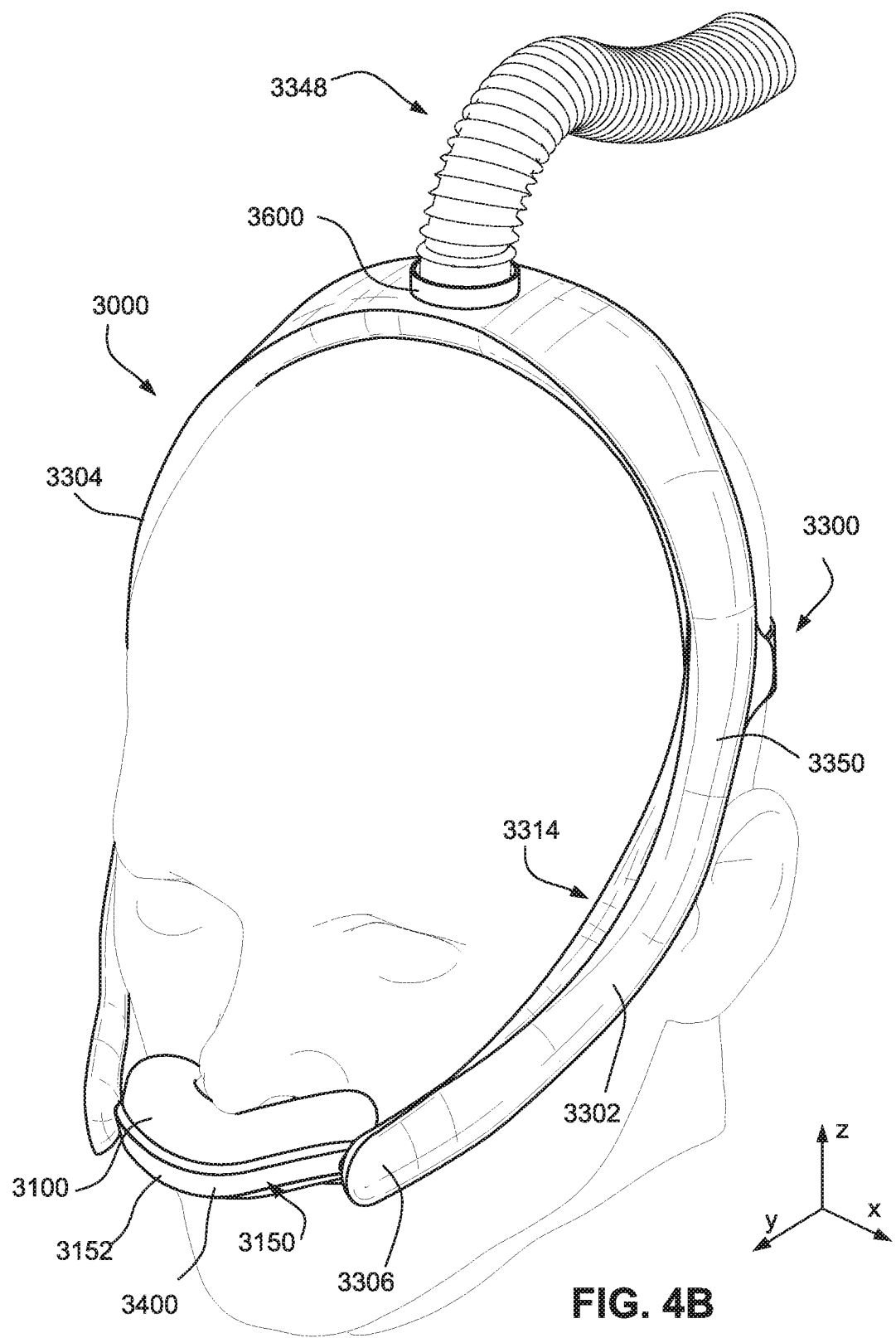

FIG. 4B shows an isometric view of the patient interface worn on a patient.

Figure 4C:
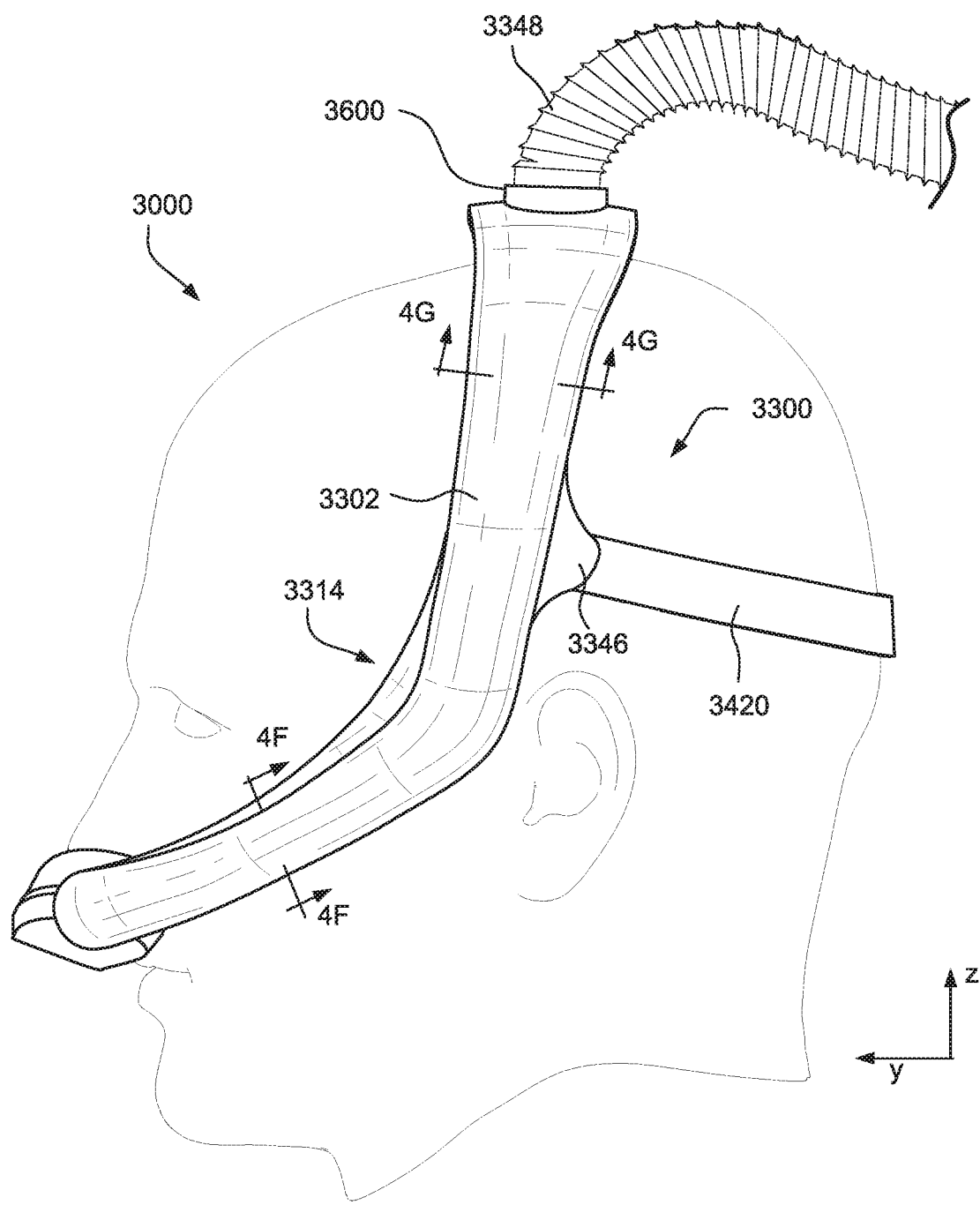

FIG. 4C shows a side view of the patient interface worn on a patient in.

Figure 4D:
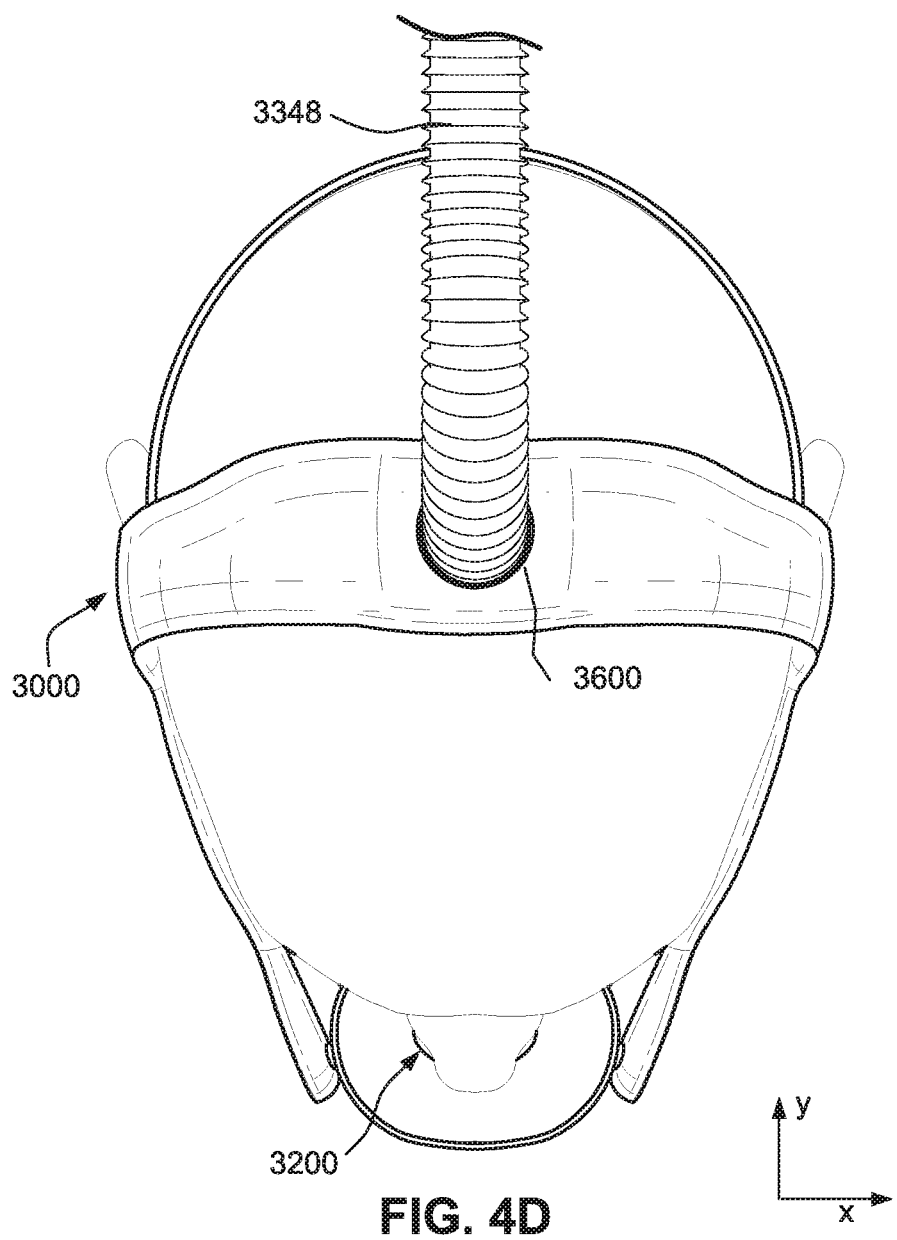

FIG. 4D shows a top view of the patient interface worn on a patient.

Figure 4E:
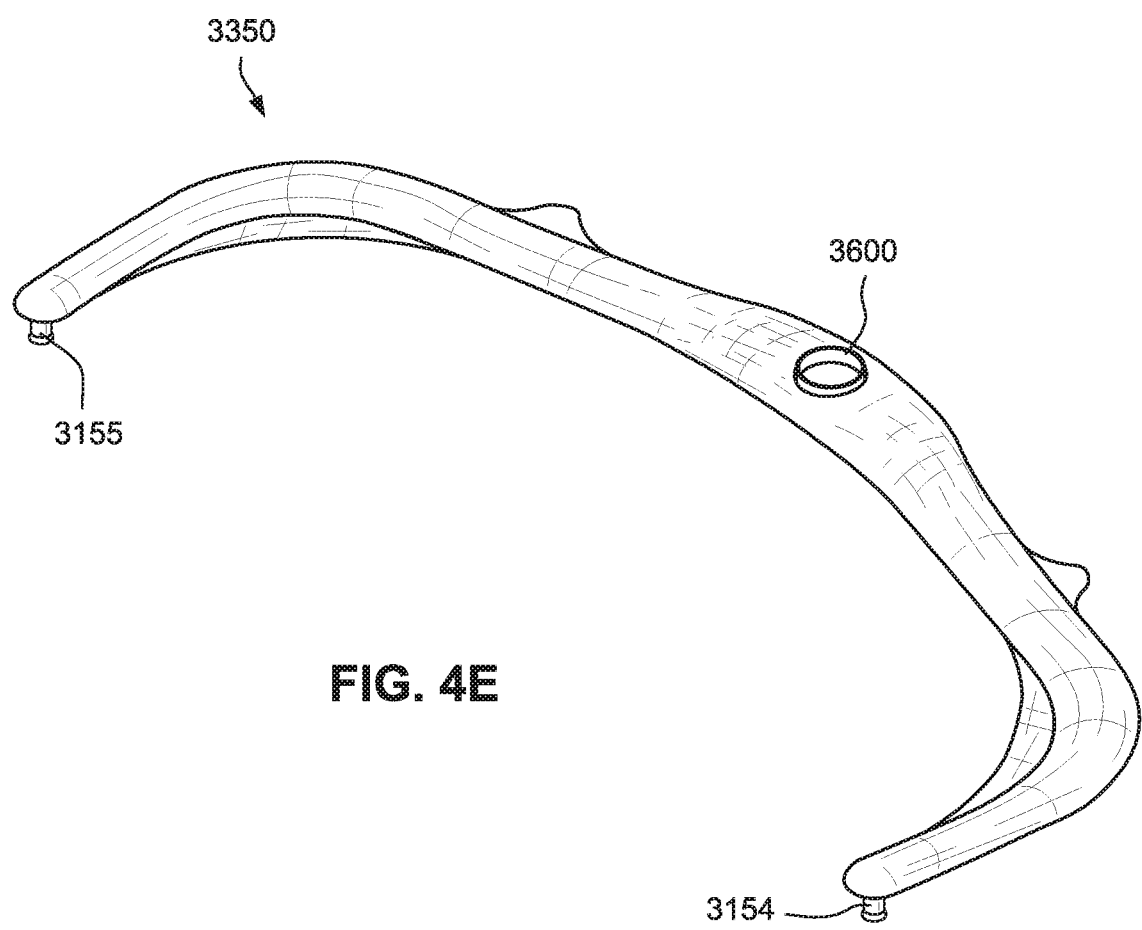

FIG. 4E shows an isometric view of a tube of the patient interface in a planar configuration when laid on a flat surface.

Figure 4F:
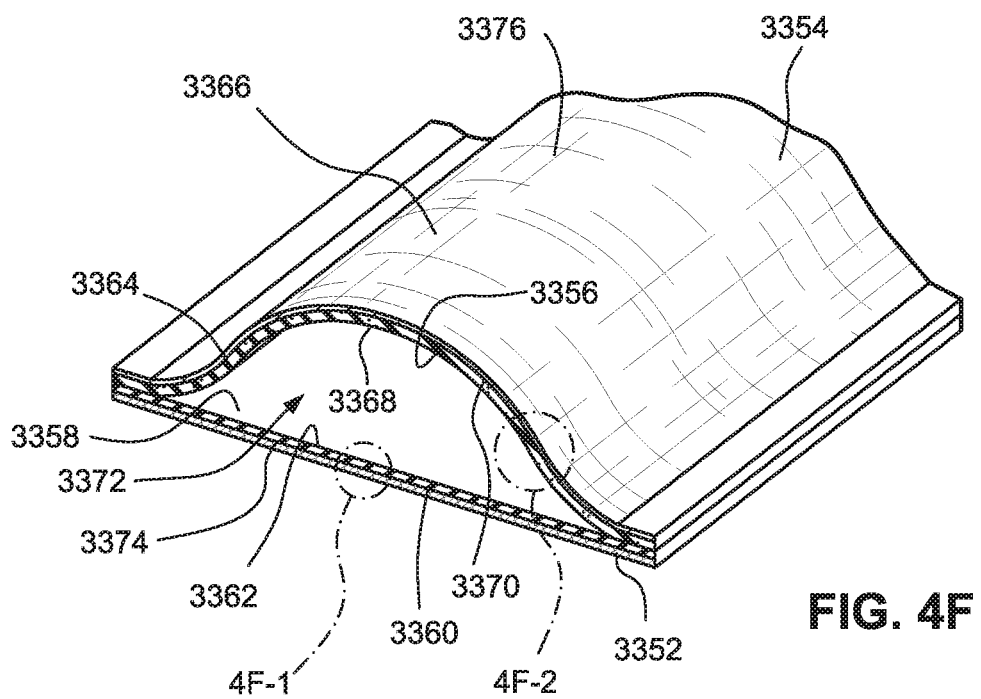

FIG. 4F shows an isometric cross-section of a portion of the tube.

Figures 1, 4F:
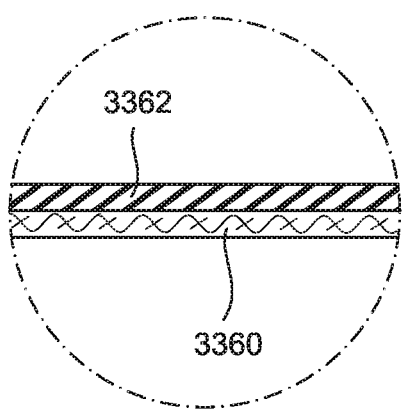

FIG. 4F-1 shows an enlarged portion of a layer of the tube.

Figures 2, 4F:
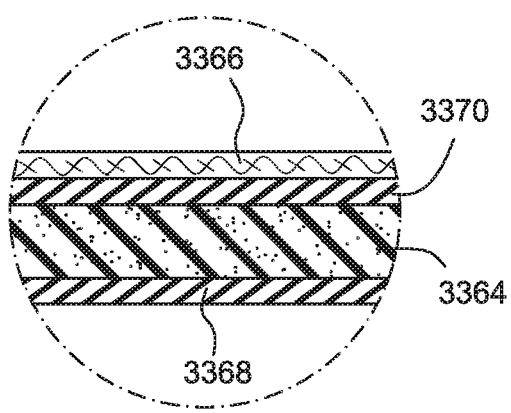

FIG. 4F-2 shows an enlarged portion of a layer of the tube.

Figure 4G:
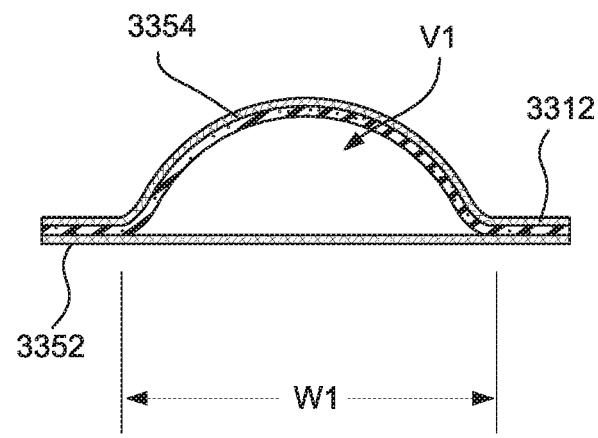

FIG. 4G shows a cross section of a portion of the patient interface as shown in FIG. 4C.

Figure 4H:
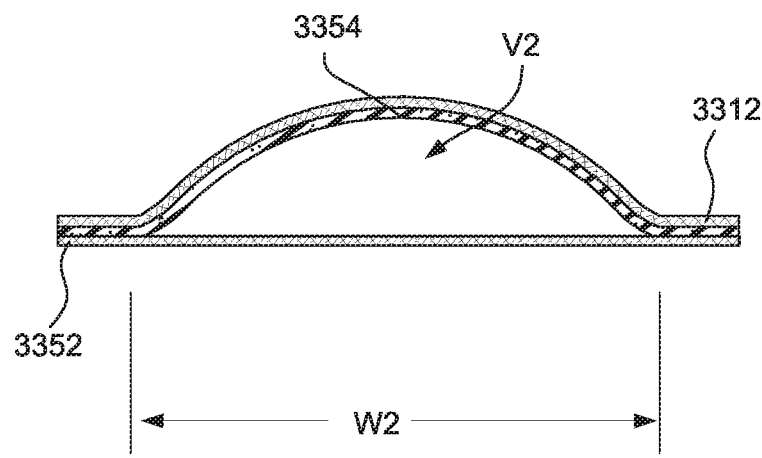

FIG. 4H shows a cross section of a portion of the patient interface as shown in FIG. 4C.

Figure 4I:
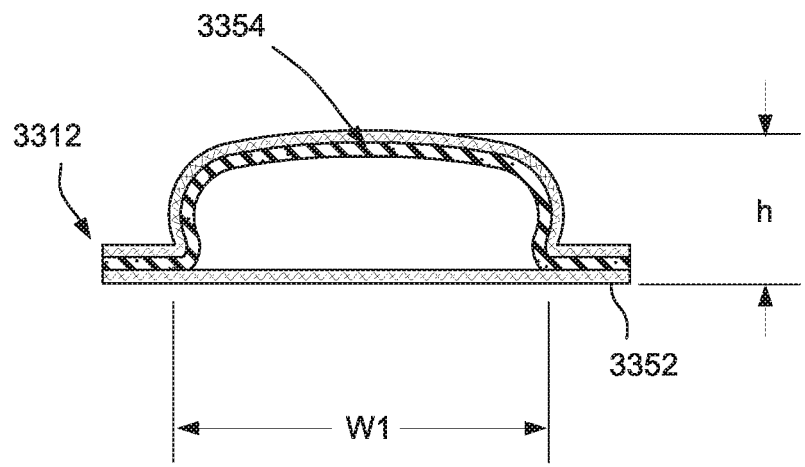

FIG. 4I shows a possible cross-section shape of the tube of the patient interface.

Figure 4J:
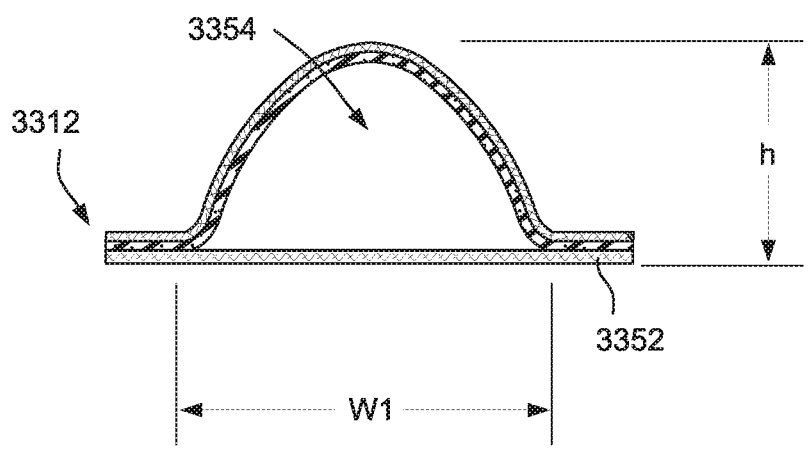

FIG. 4J shows another possible cross-section shape of the tube of the patient interface.

Figure 4K:
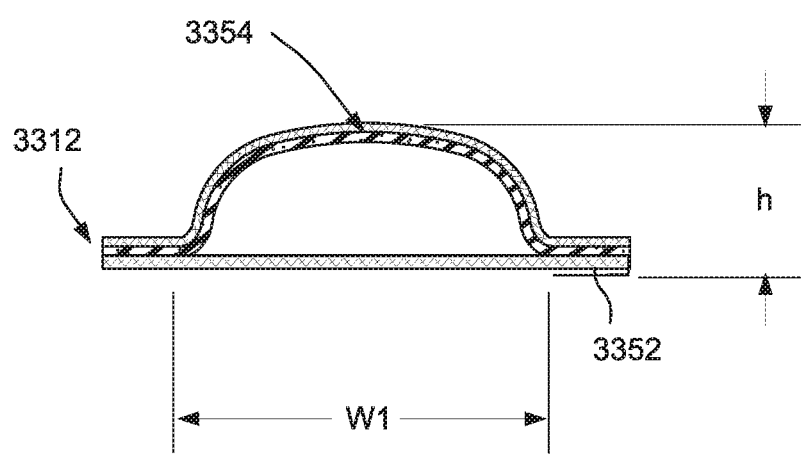

FIG. 4K shows another possible cross-section shape of the tube of the patient interface.

FIG. 4L-1 shows an isometric view of the tube in a pre-determined three dimensional configuration.

FIG. 4L-2 is a side view of a portion of the tube.

FIG. 4L-3 is a front view of a portion of the tube.

FIG. 4L-4 is a top view of a portion of the tube.

FIG. 4M depicts isometric cutaway view of a connection port within the tube.

FIG. 4N depicts an isometric view of the connection port in isolation.

FIG. 4O depicts an isometric view of the connection portion of an alternate form.

Figure 4P:
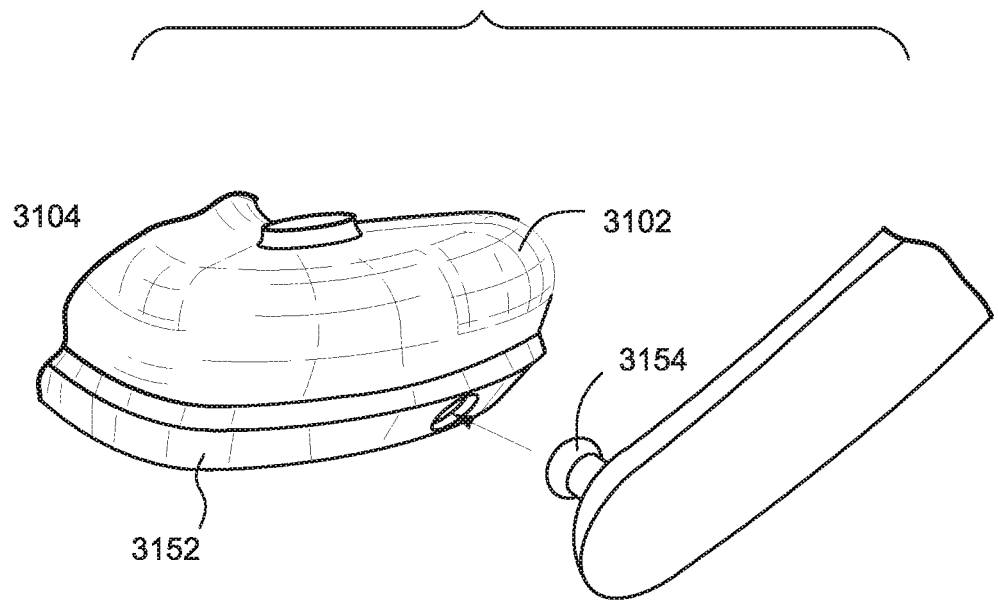

FIG. 4P depicts a connection between the mask and the tube.

Figure 4Q:
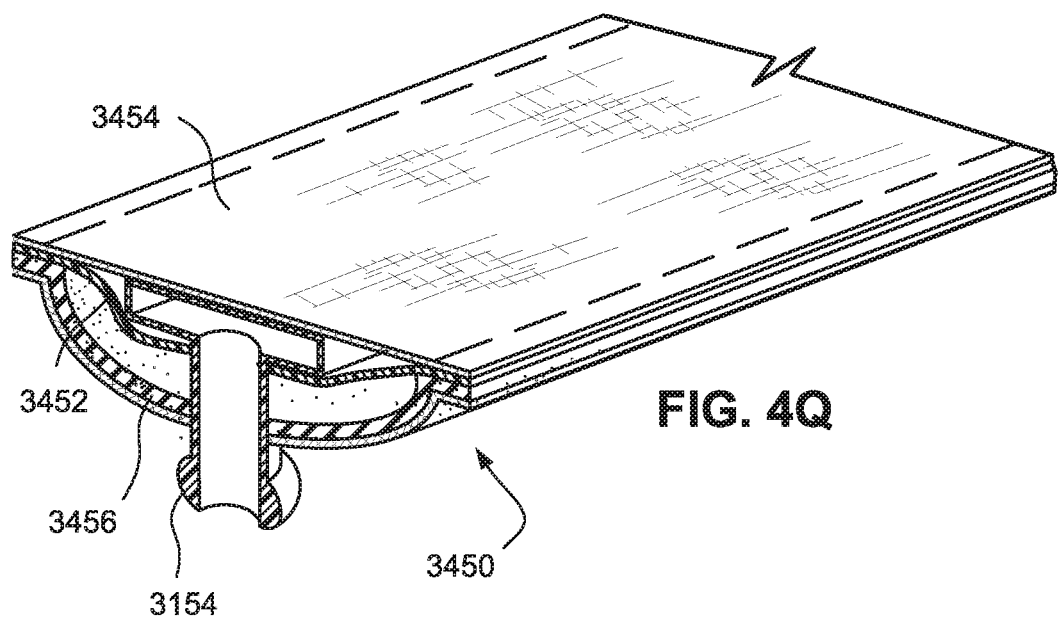

FIG. 4Q depicts an alternate form of a connector for attaching the mask to the tube.

Figure 4R:
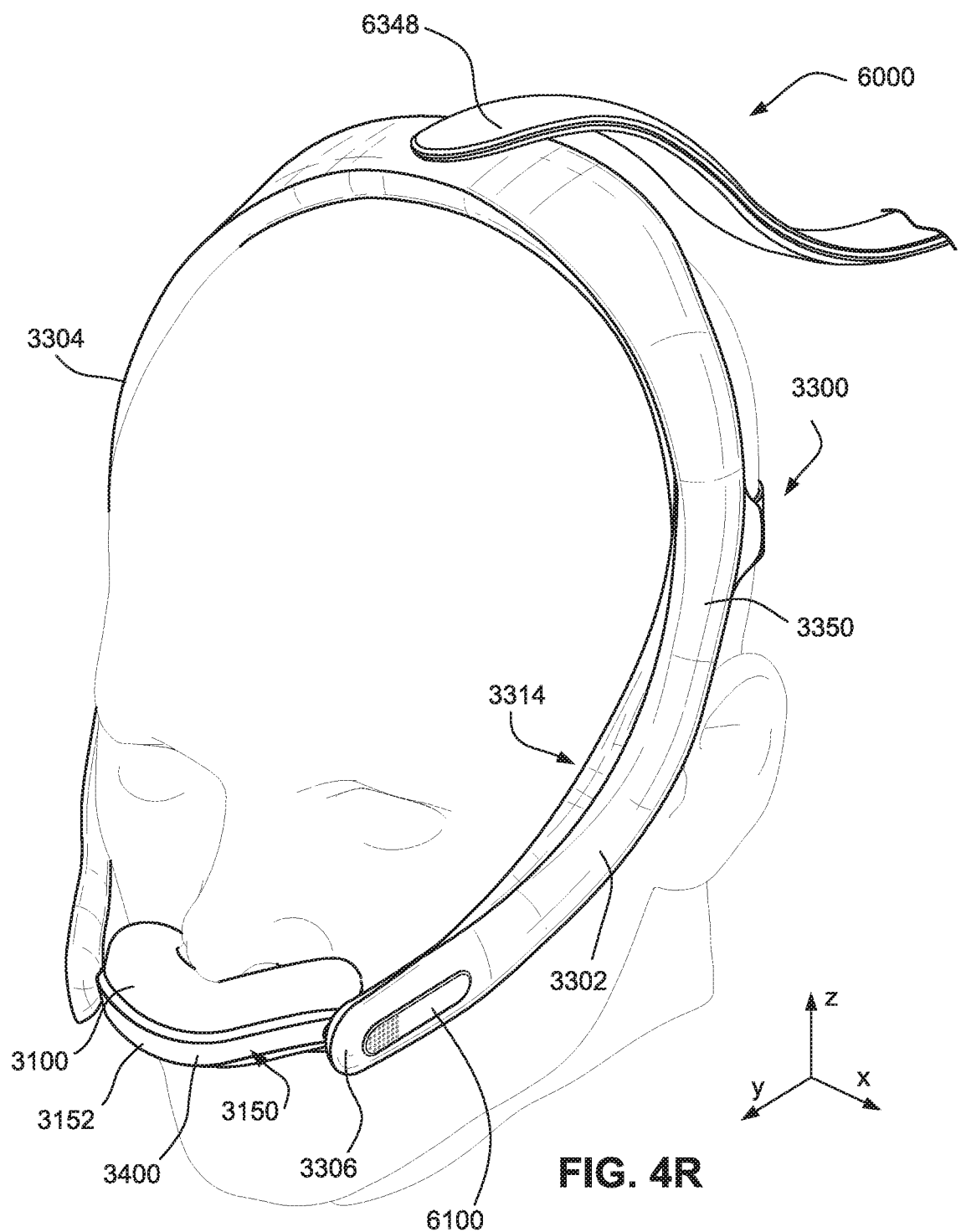

FIG. 4R shows an isometric view of a patient interface according to another example of the present technology worn by a patient.

Figure 4S:
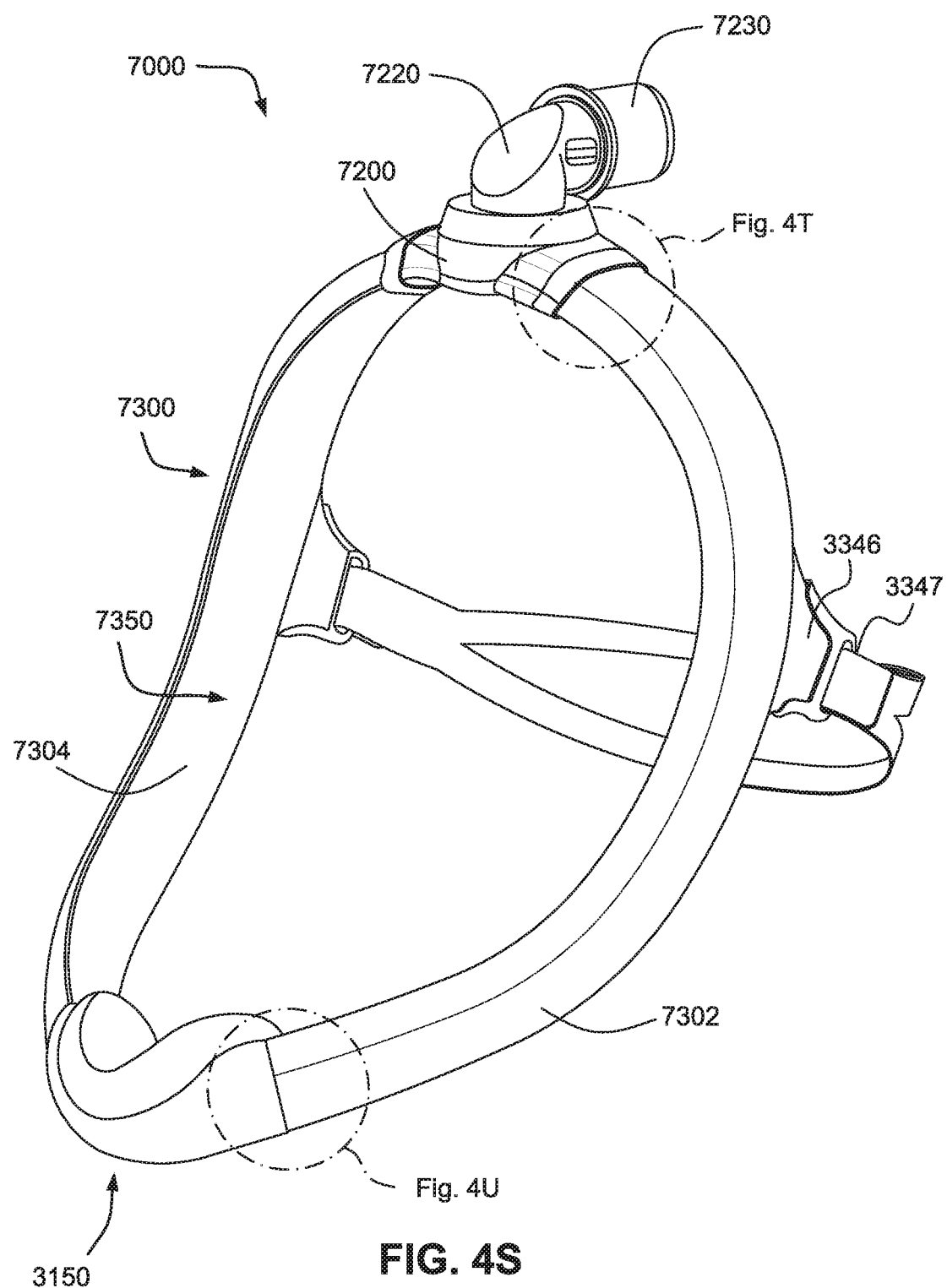

FIG. 4S is a perspective view of a patient interface according to another example of the disclosed technology.

Figure 4T:
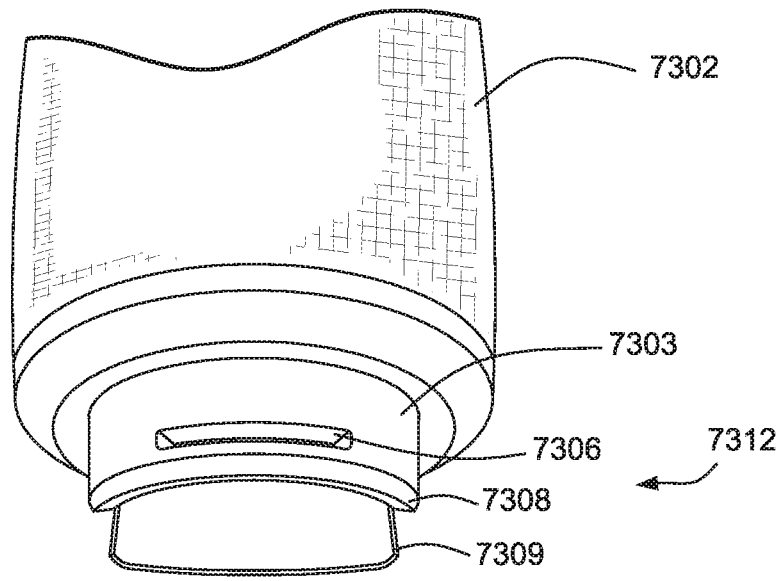

FIG. 4T is a front perspective view of an upper connector of the positioning and stabilizing structure according to an example of the disclosed technology.

Figure 4U:
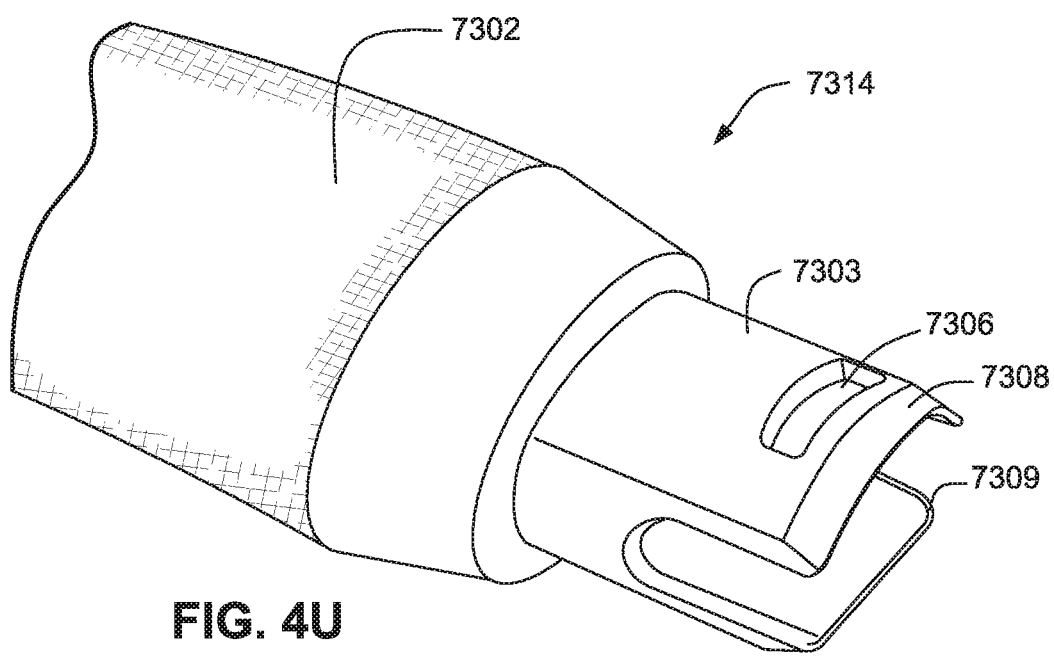

FIG. 4U is a side perspective view of a lower connector of the positioning and stabilizing structure according to an example of the disclosed technology.

Figure 4V:
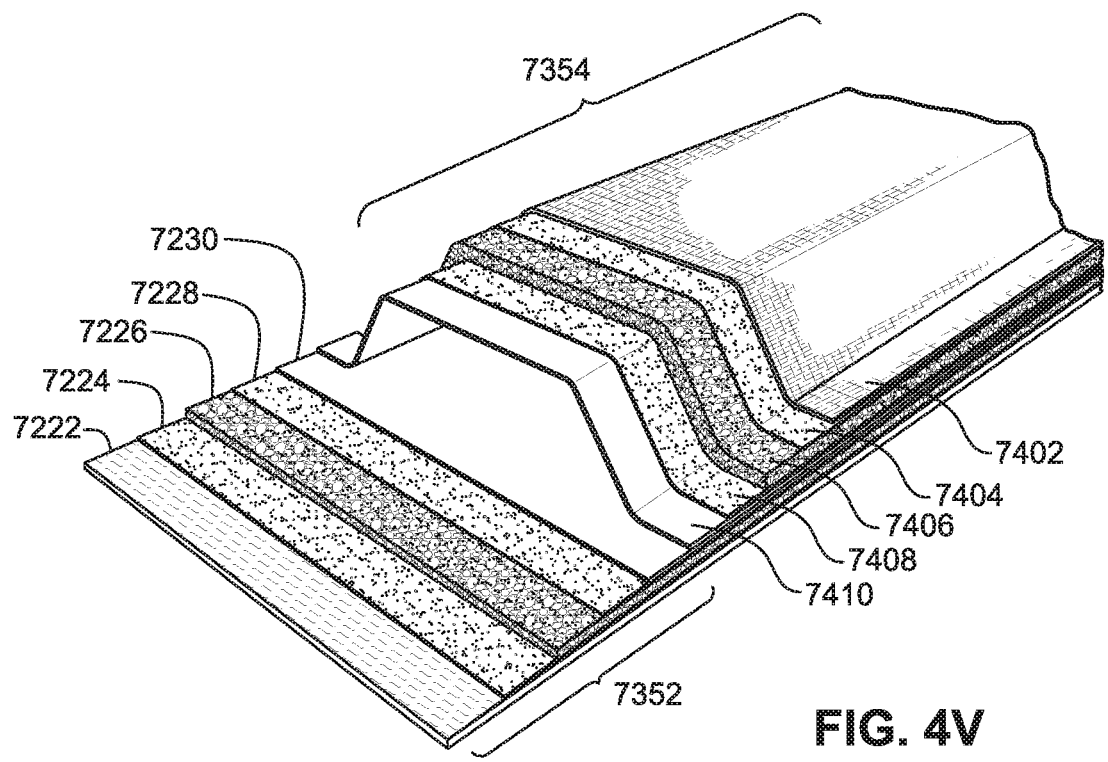

FIG. 4V is an illustration of a cross-section of the positioning and stabilizing structure of FIG. 4S.

Figure 4W:
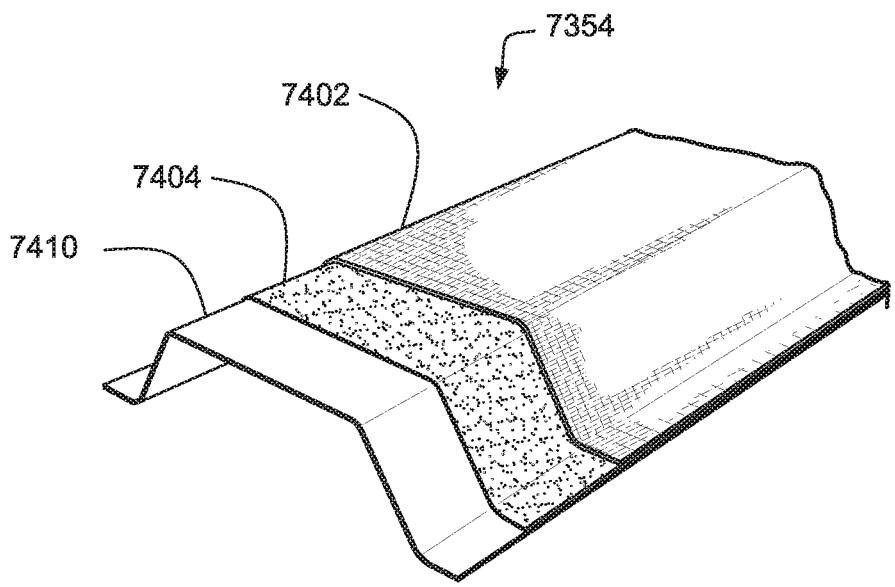

FIG. 4W is an illustration of a cross-section of an outer layer of the positioning and stabilizing structure according to another example of the disclosed technology.

Figure 4X:
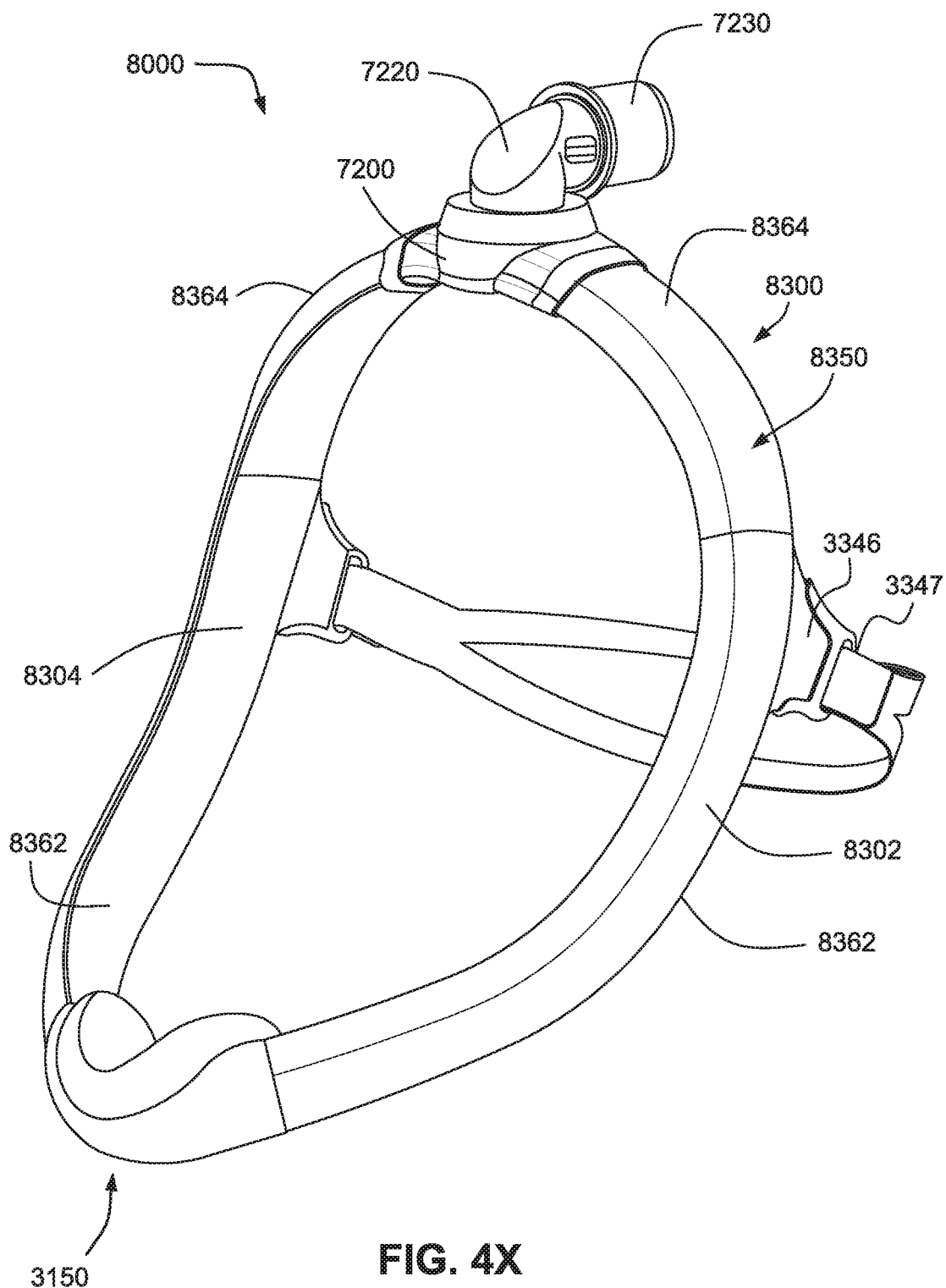

FIG. 4X is a perspective view of a patient interface according to another example of the disclosed technology.

Figure 5A:
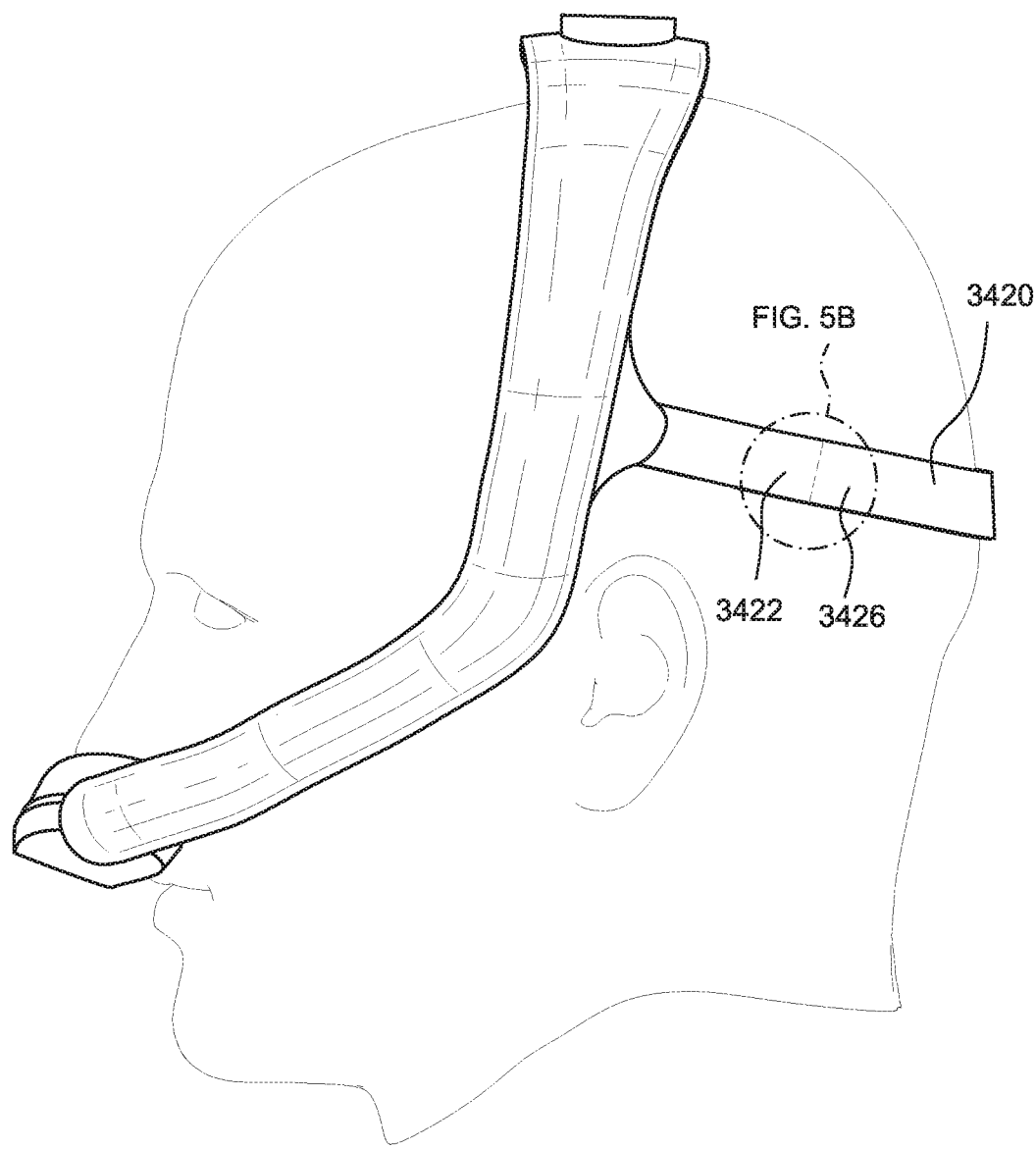

FIG. 5A depicts a view of a strap of the patient interface.

Figure 5B:
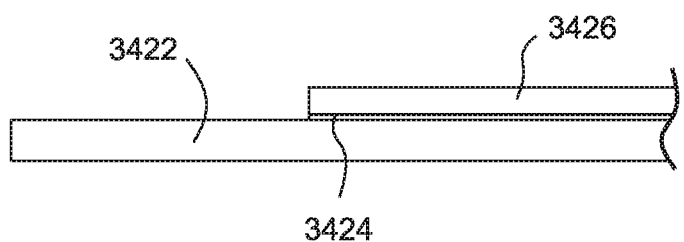

FIG. 5B depicts a side view of a portion of the strap.

Figure 5C:
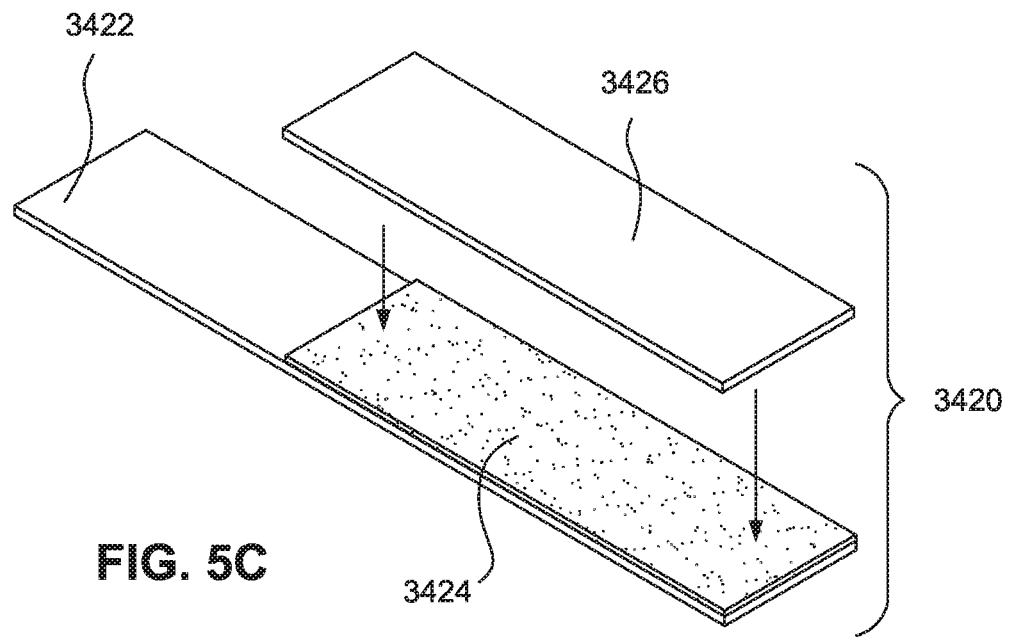

FIG. 5C depicts a partially exploded view of a portion of strap 3420.

Figure 5D:
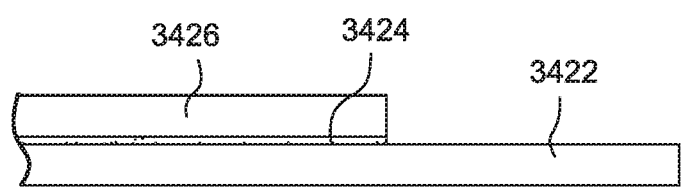
Figure 5E:
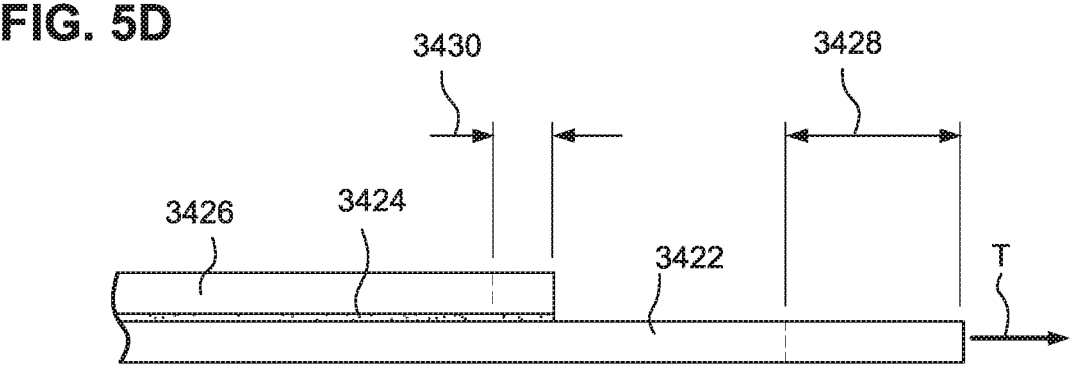

FIGS. 5D and 5E depict a portion of the strap in an untensioned and tensioned state.

Figure 5F:
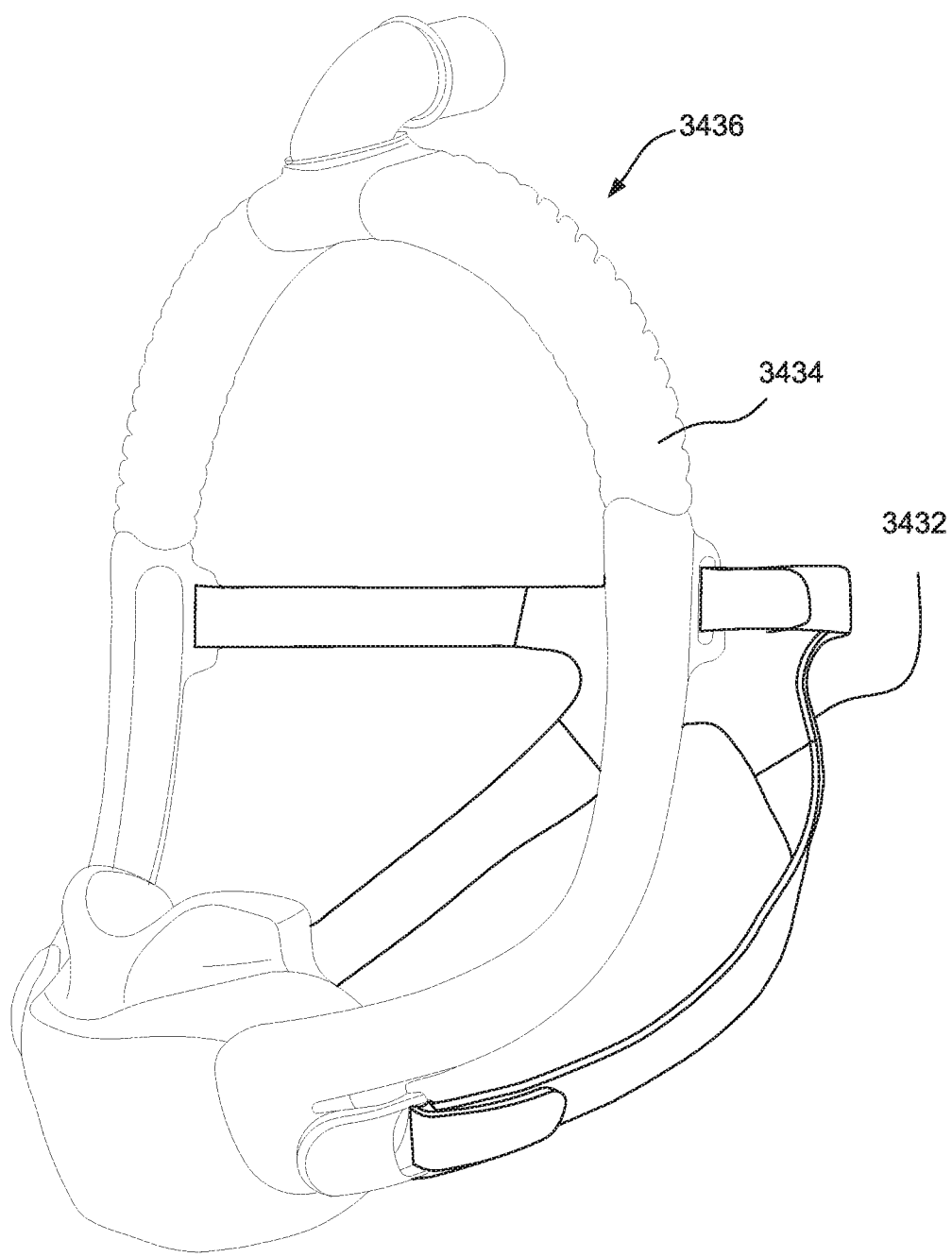

FIG. 5F depicts an alternate patient interface that includes an alternate head strap.

Figure 5G:
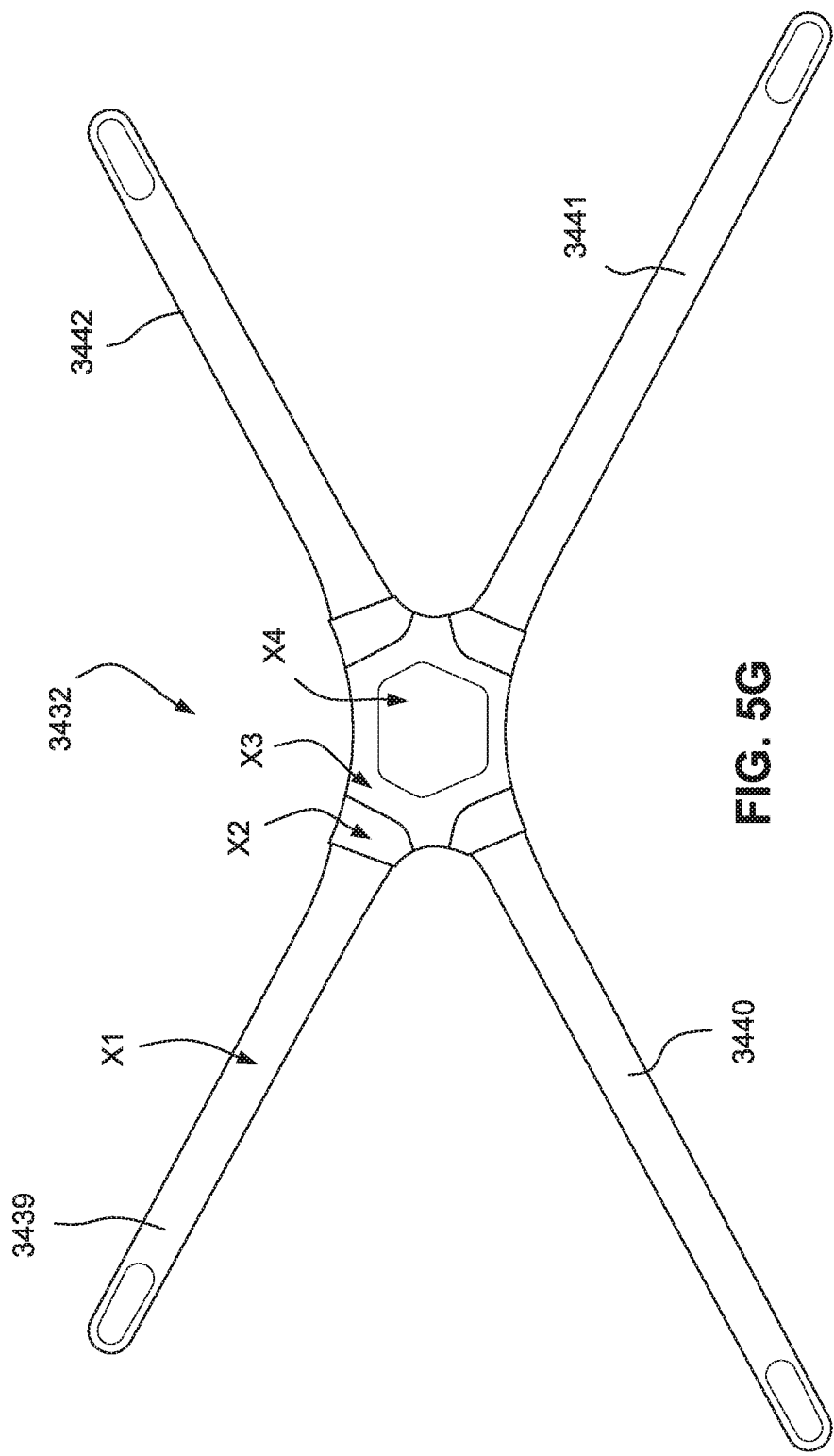

FIG. 5G depicts a top view of the head strap of FIG. 5F in isolation.

Figure 5H:
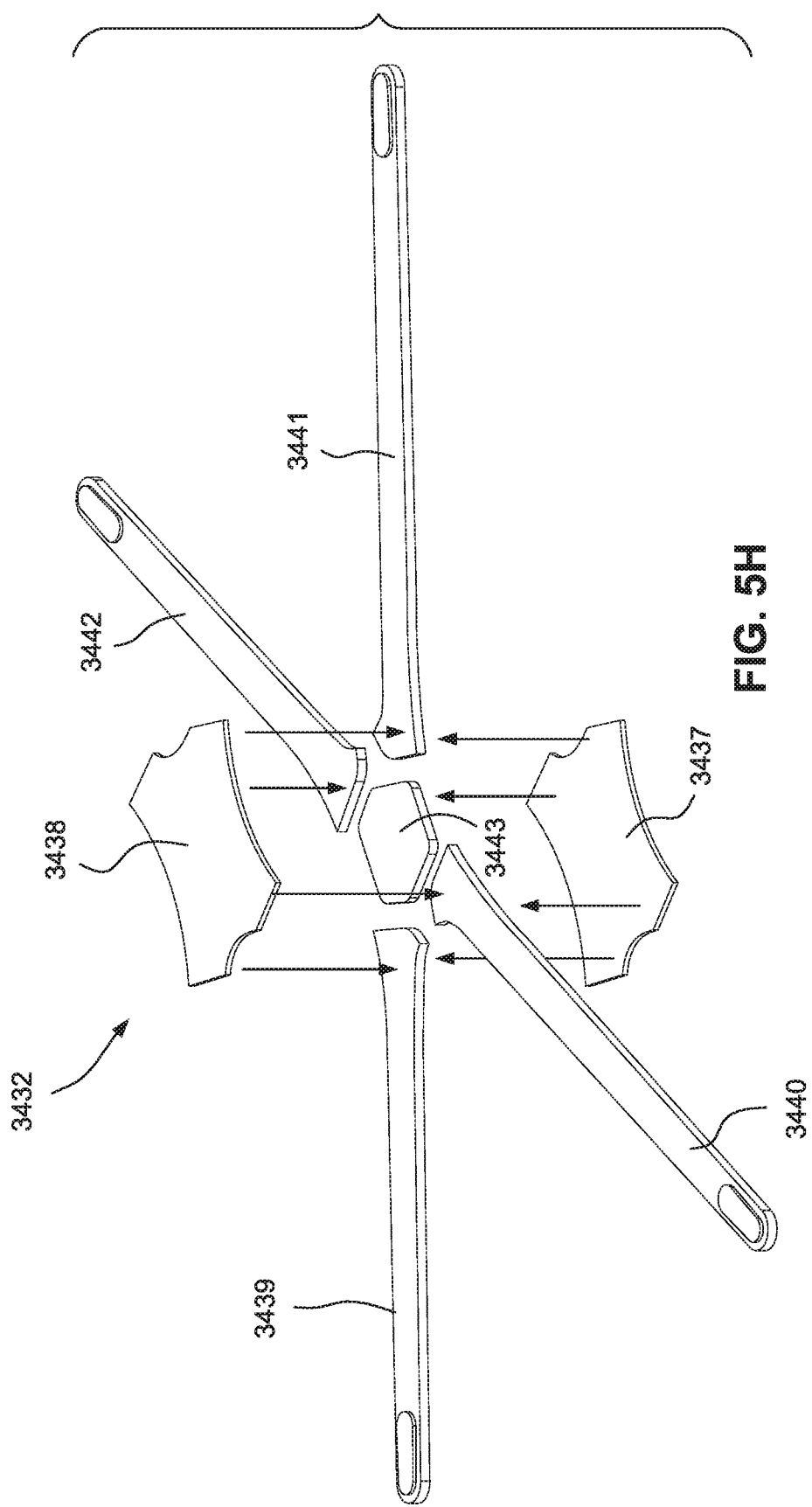

FIG. 5H depicts an exploded isometric view of the head strap.

Figure 6A:
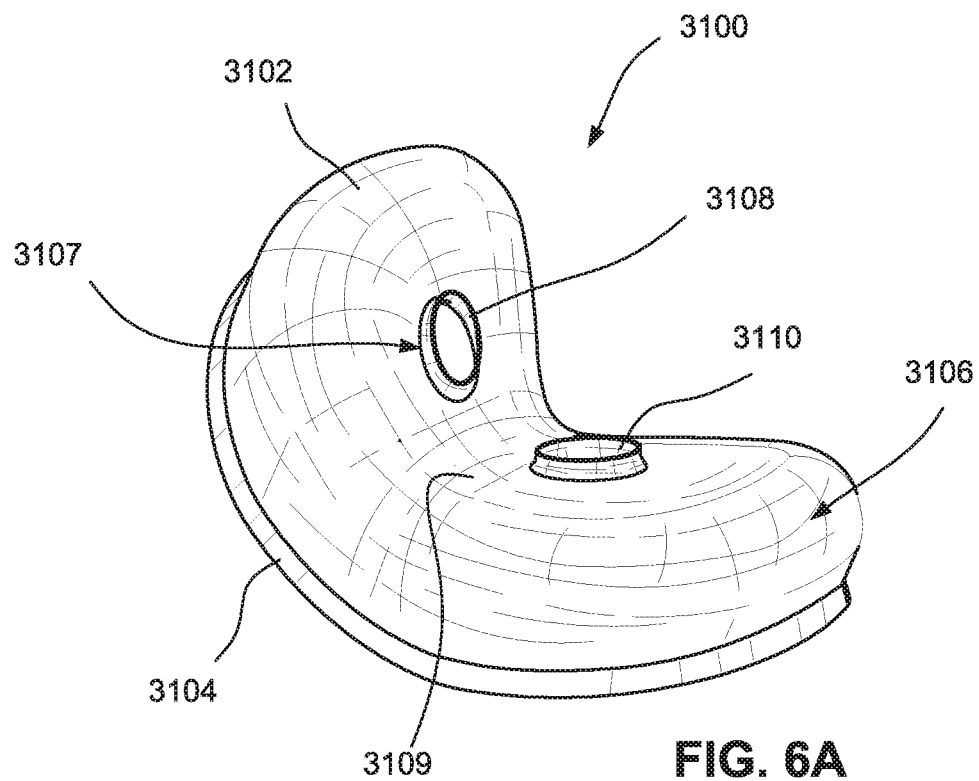

FIG. 6A depicts an isometric top view of the seal-forming structure utilized in the patient interface.

Figure 6B:
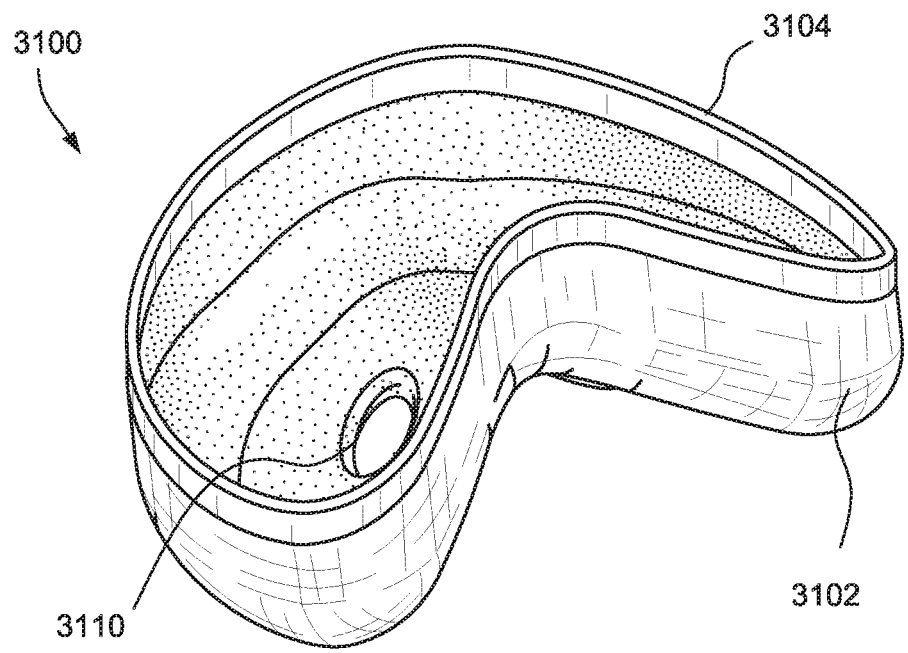

FIG. 6B depicts an isometric bottom view of the seal-forming structure of the patient interface.

Figure 6C:
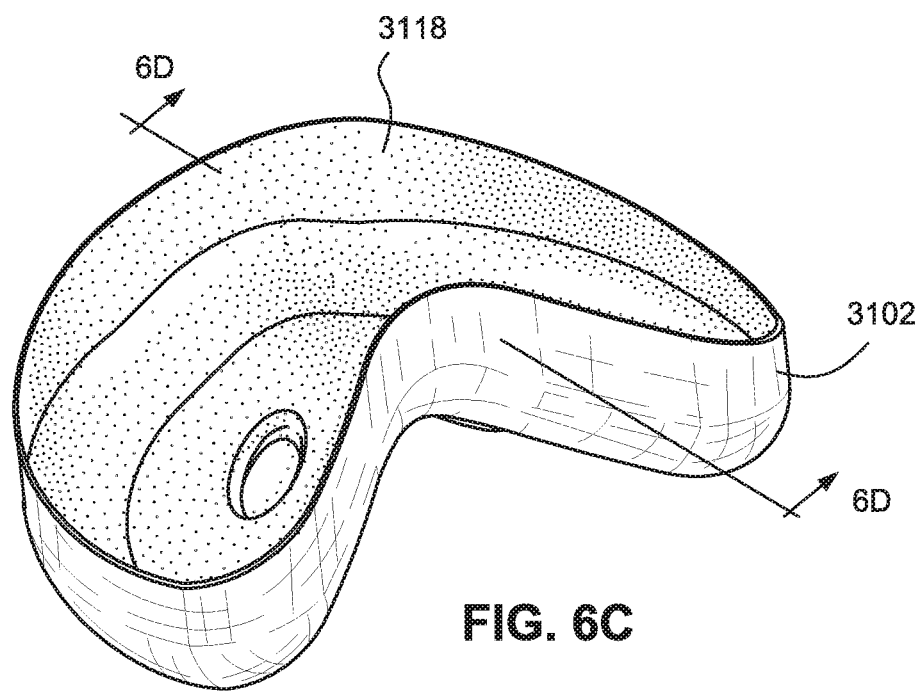

FIG. 6C depicts an isometric view of a sealing layer of the seal-forming structure.

Figure 6D:
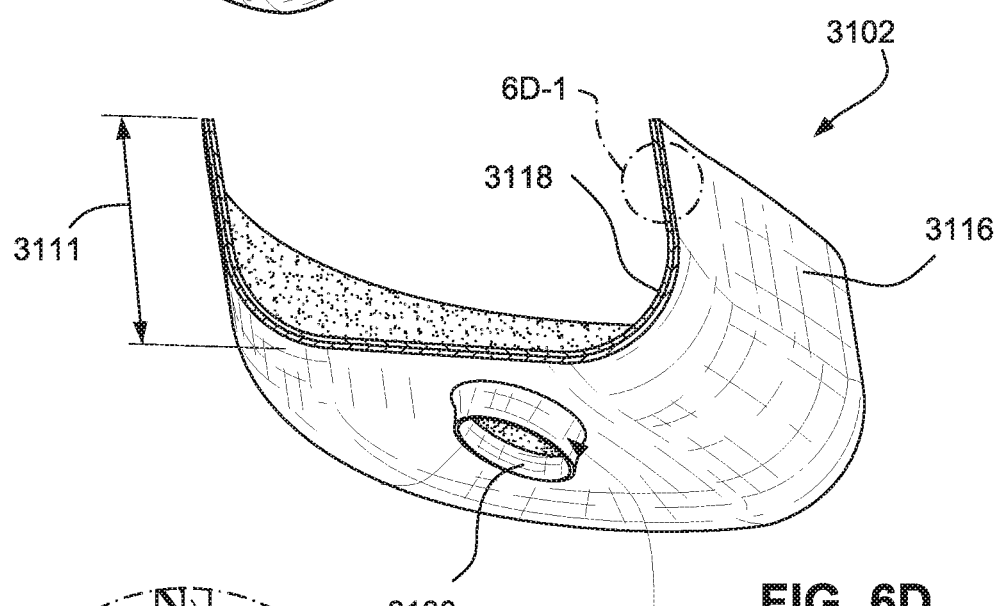
Figures 1, 6D:
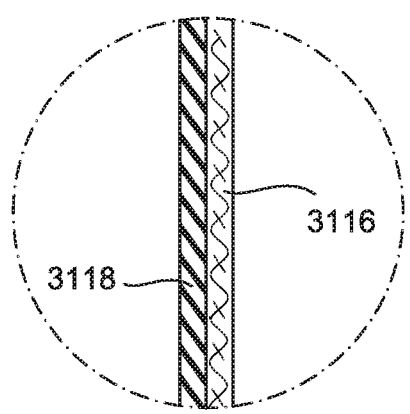

FIG. 6D depicts a cross-sectional isometric view of the sealing layer.

FIG. 6D-1 depicts an enlarged view of a portion of the sealing layer.

Figure 6E:
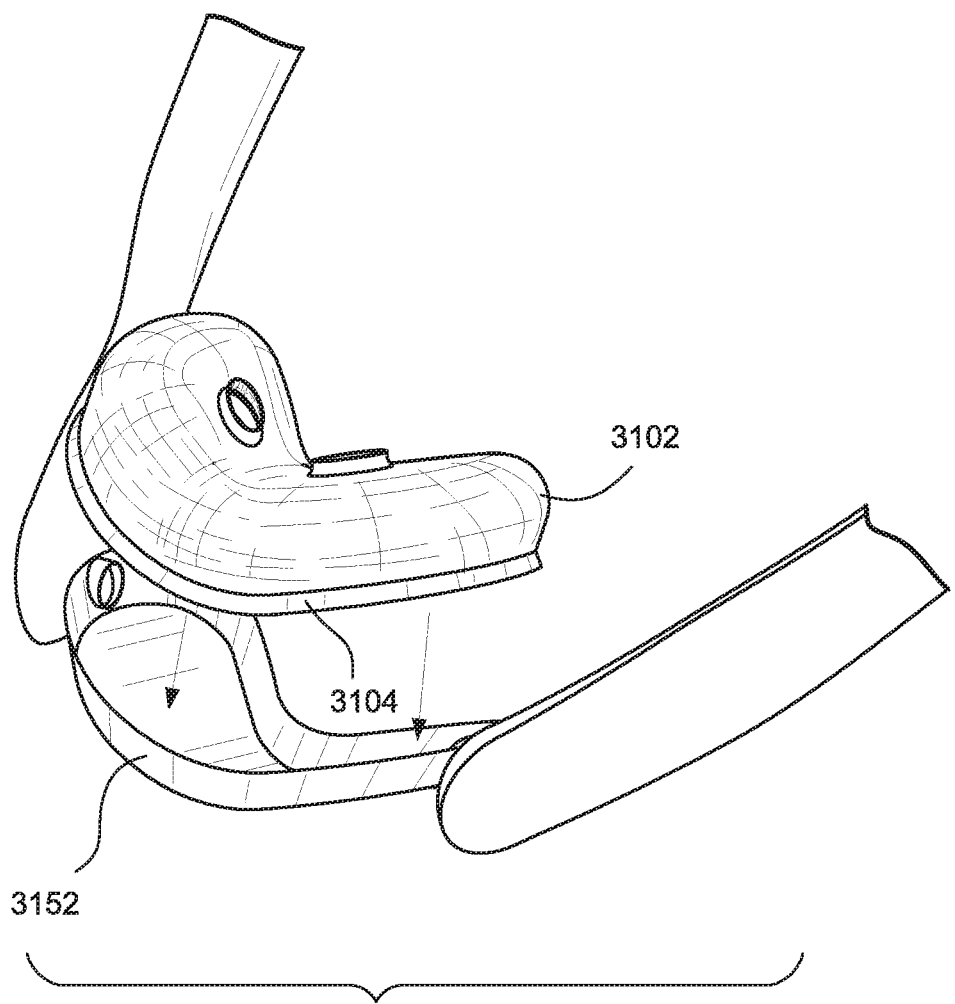

FIG. 6E depicts the seal-forming structure attaching to the frame.

Figure 7A:
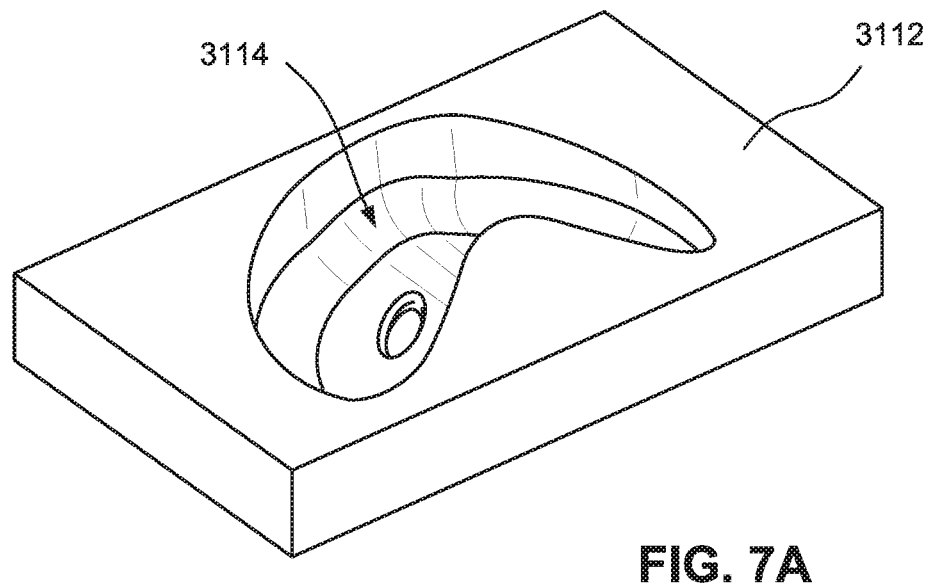

FIG. 7A depicts a mold for use in forming the sealing layer.

Figure 7B:
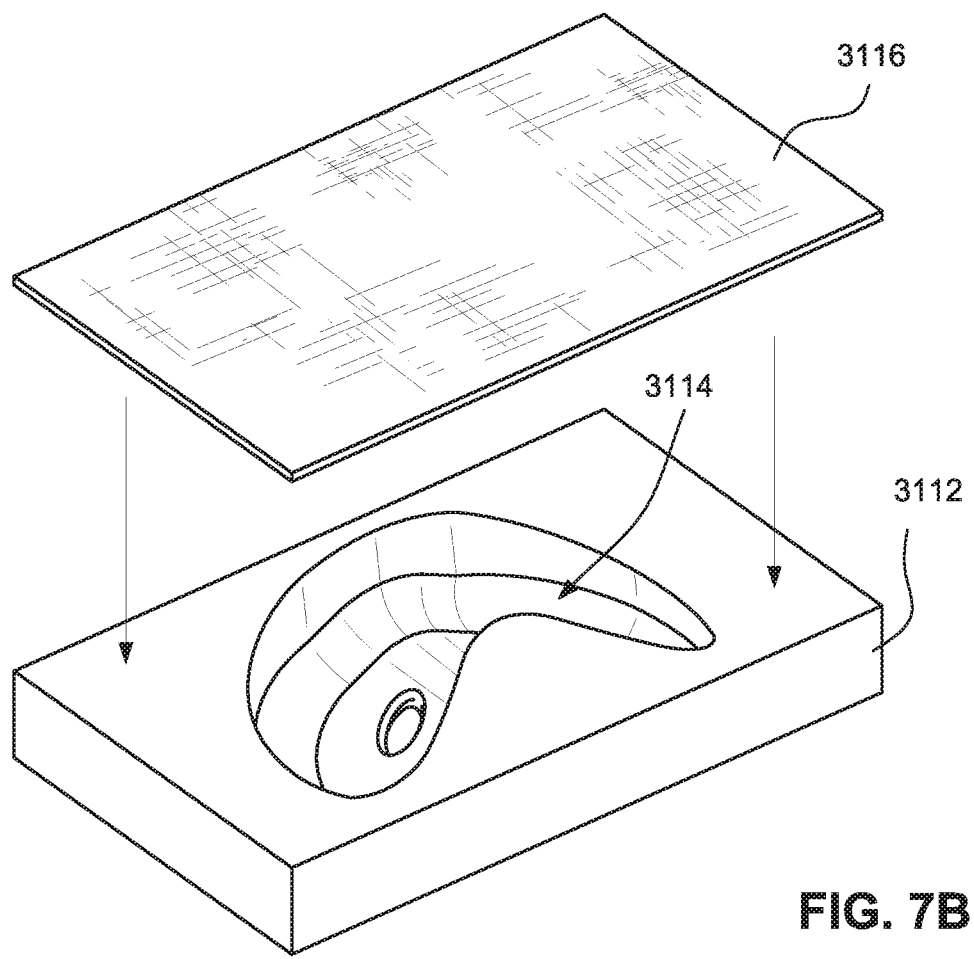

FIG. 7B depicts a textile sheet positioned to engage with the mold.

Figure 7C:
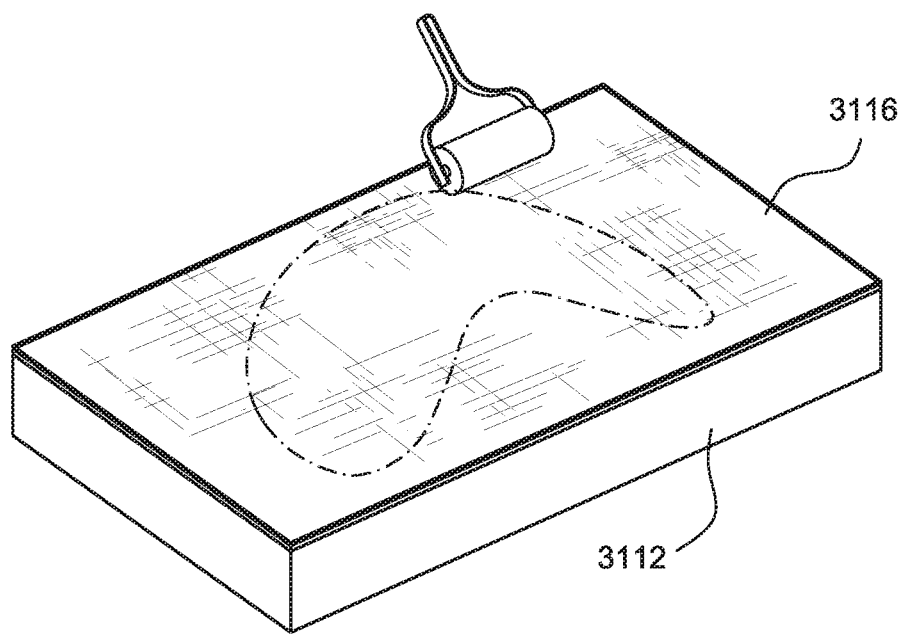

FIG. 7C depicts the textile sheet adjacent to the mold and spread on the mold using a roller.

Figure 7D:
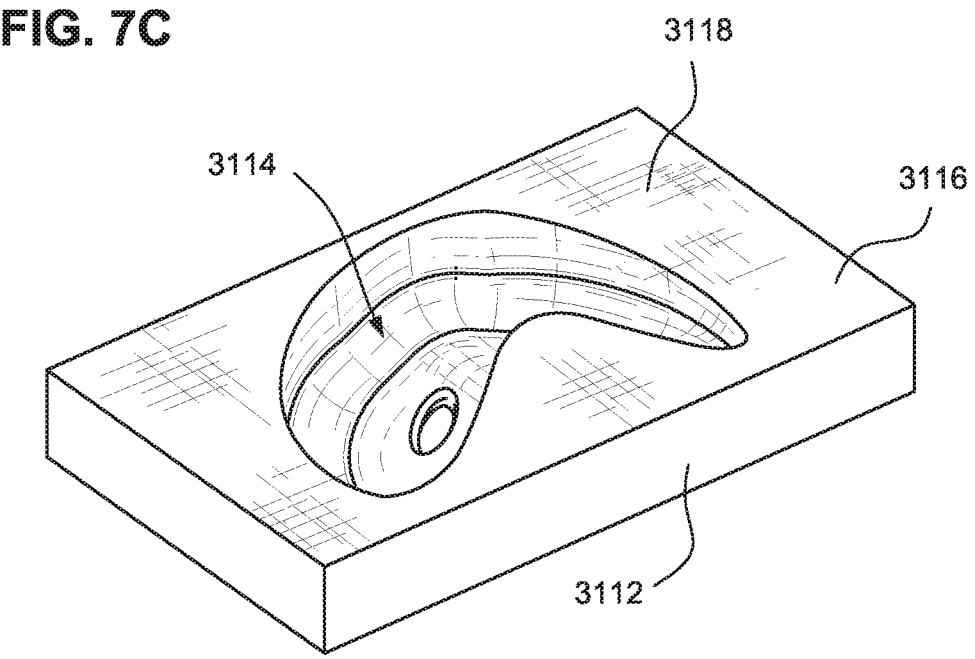

FIG. 7D depicts the textile sheet pressed into the form of the mold.

Figure 7E:
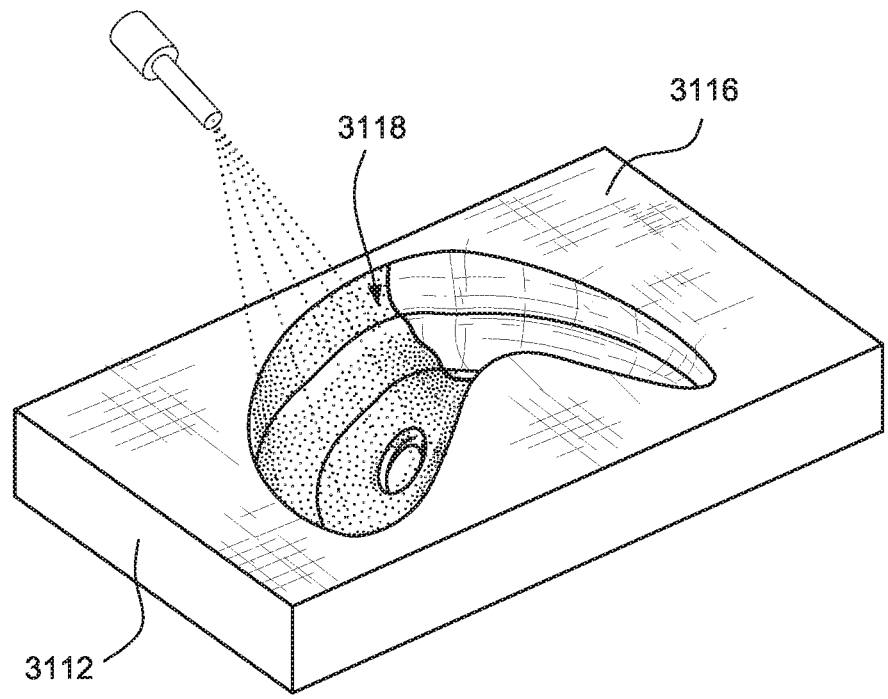

FIG. 7E depicts a membrane layer being administered to the textile sheet within the mold.

Figure 7F:
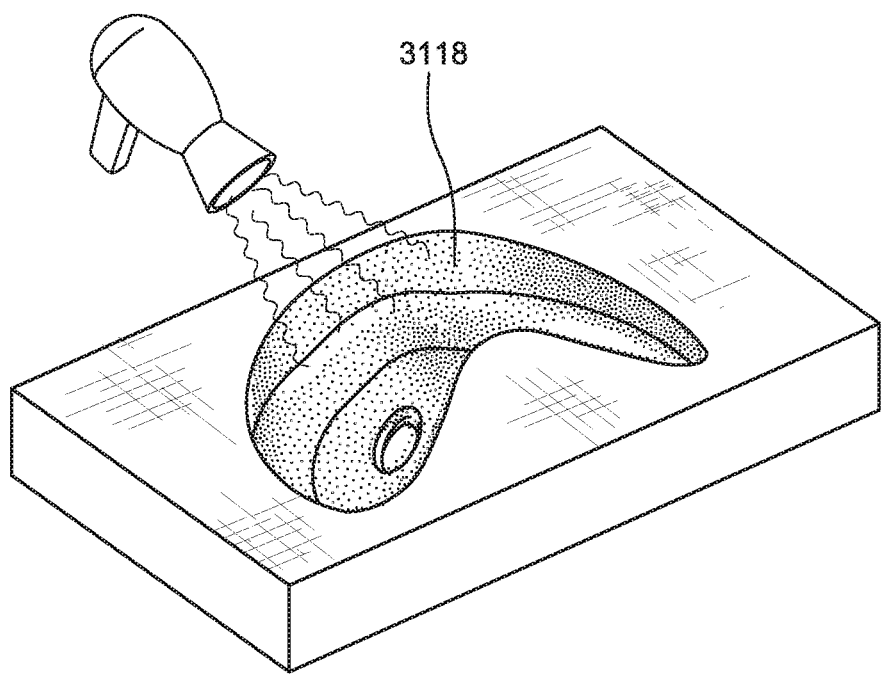

FIG. 7F depicts subjecting the membrane layer to heat.

Figure 7G:
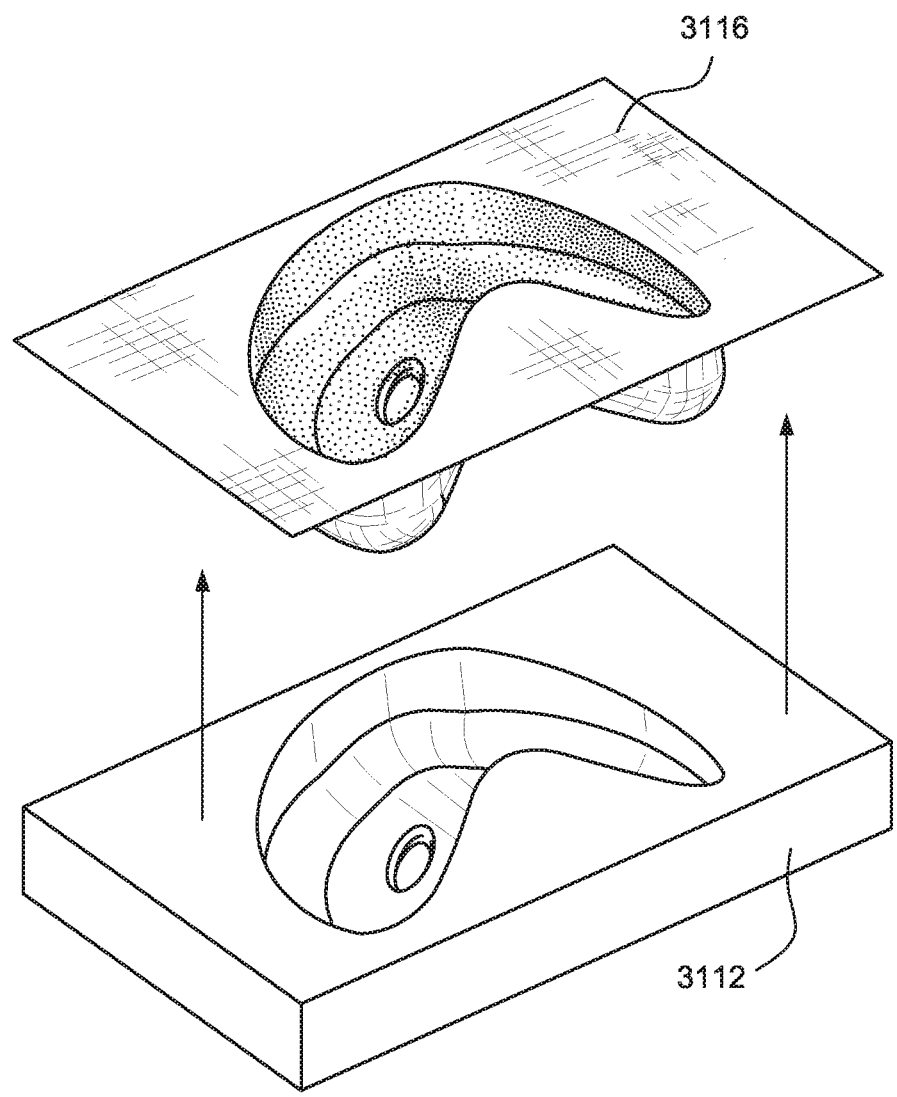

FIG. 7G depicts removing the cured layer from the mold.

Figure 7H:
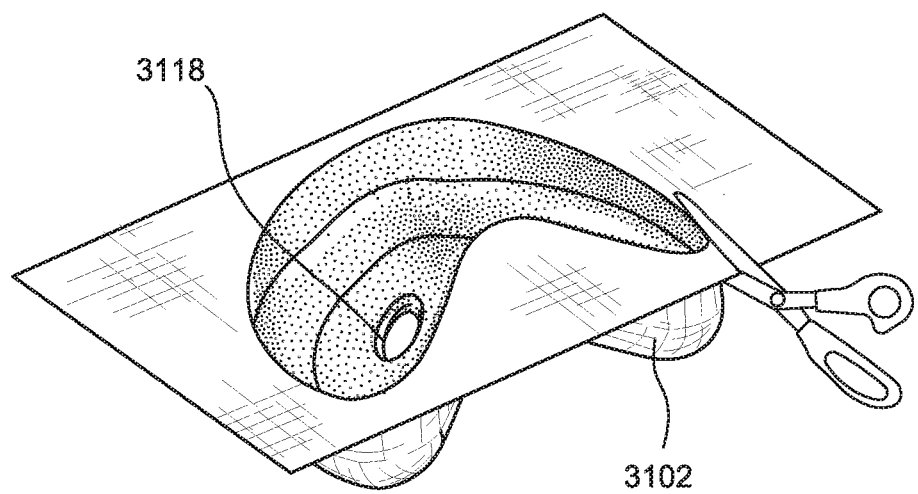

FIG. 7H depicts cutting the sealing forming layer to shape.

Figure 7I:
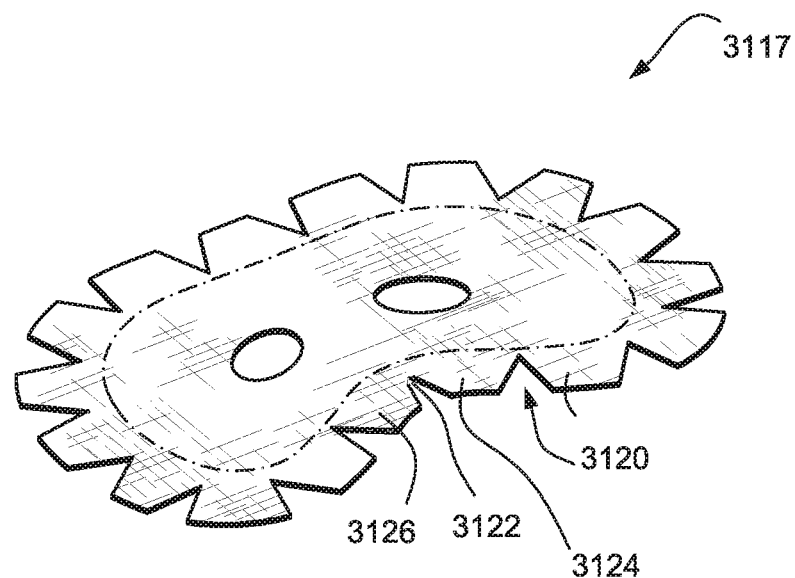

FIG. 7I depicts a planar sheet that is pre-cut prior to insertion within the mold.

Figure 7J:
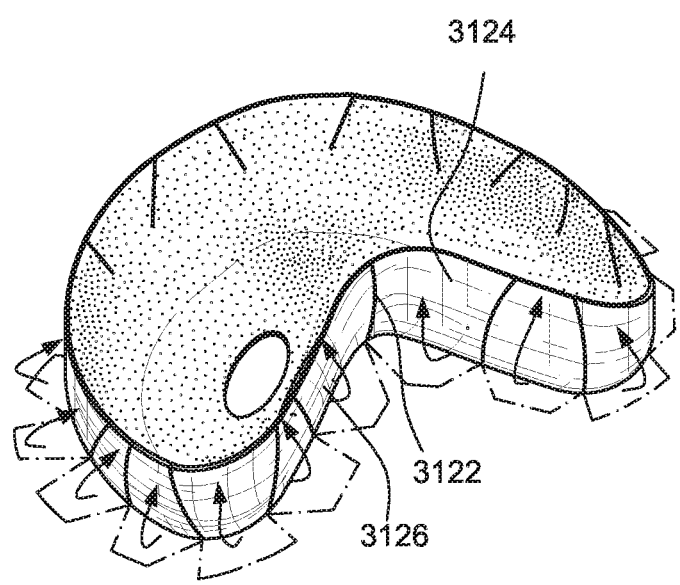

FIG. 7J depicts the sheet after application within the mold.

Figure 8A:
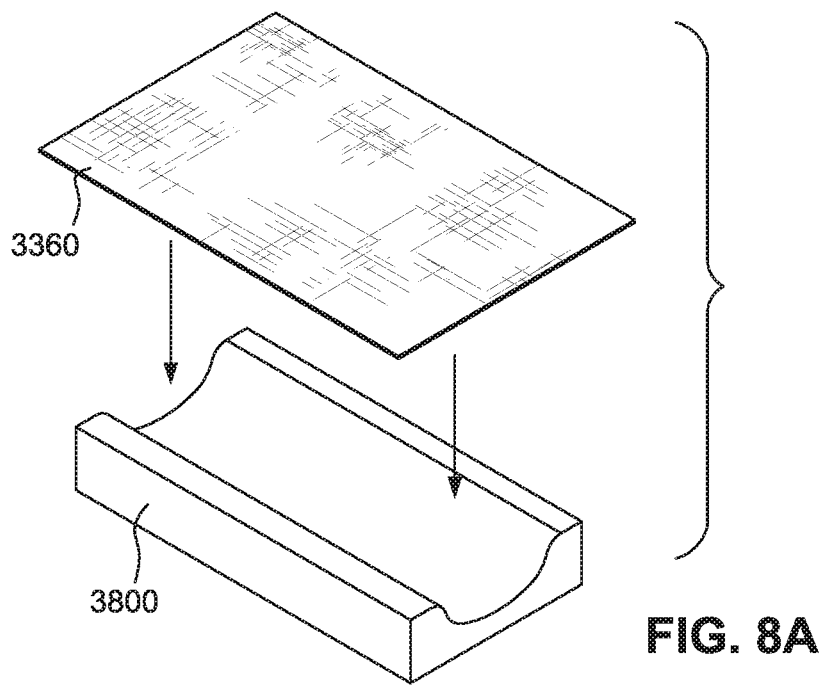

FIG. 8A depicts a sheet being positioned over a mold to form a tube.

Figure 8B:
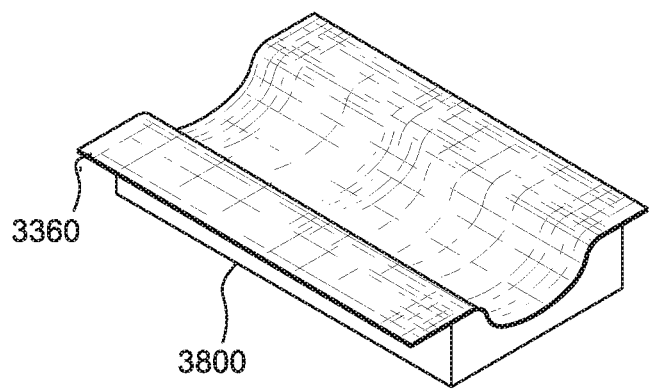

FIG. 8B depicts the sheet within the mold.

Figure 8C:
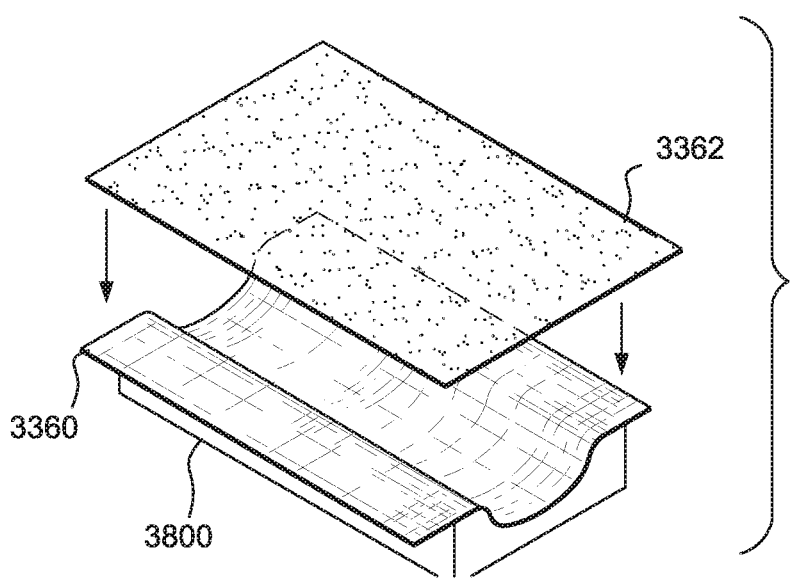

FIG. 8C depicts positioning a membrane layer to interact with the sheet within the mold.

Figure 8D:
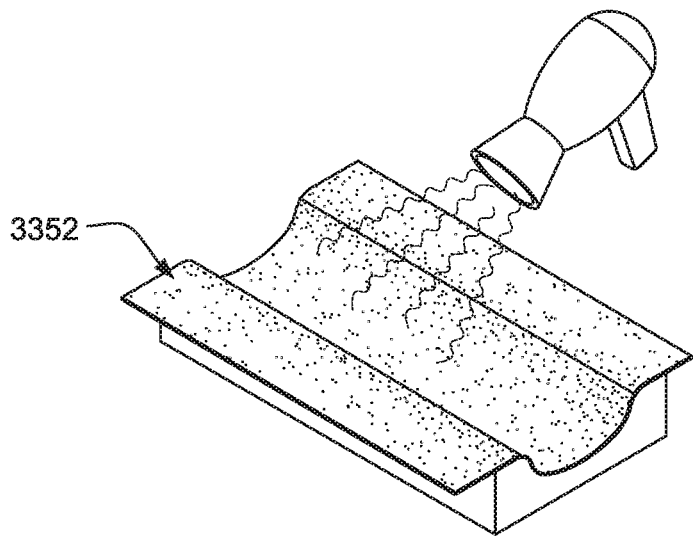

FIG. 8D depicts heating the membrane layer such that the membrane layer cures to the shape of the mold.

Figure 8E:
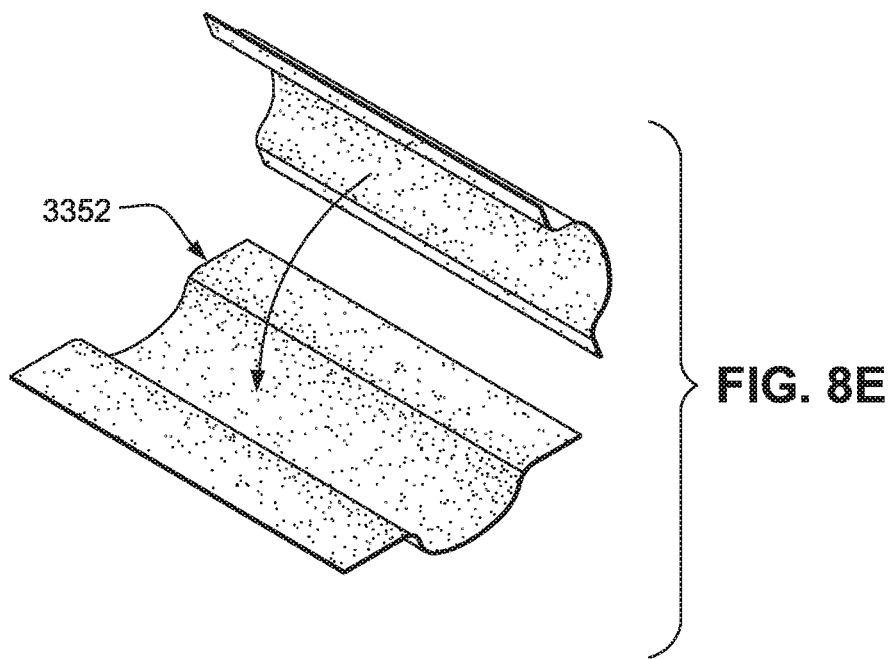

FIG. 8E depicts attaching a cured two cures sheets together.

Figure 8F:
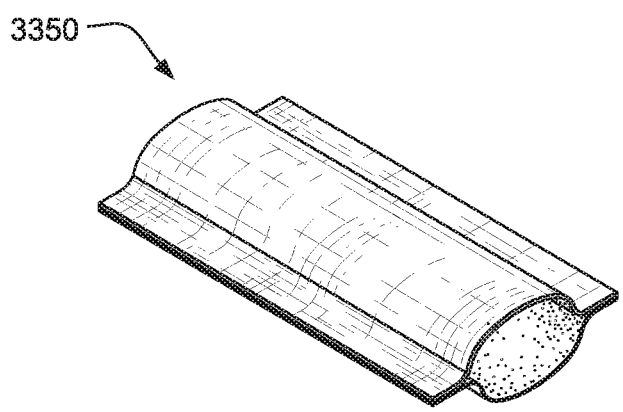

FIG. 8F depicts a portion of a tube formed from two sheet.

Figure 8G:
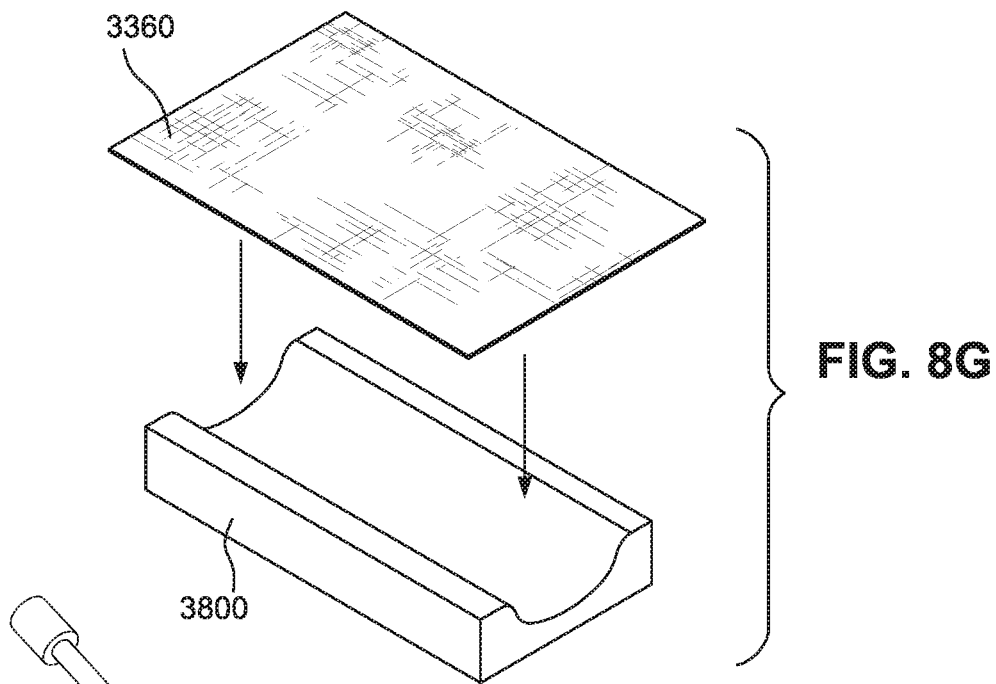

FIG. 8G depicts a sheet positioned above a mold.

Figure 8H:
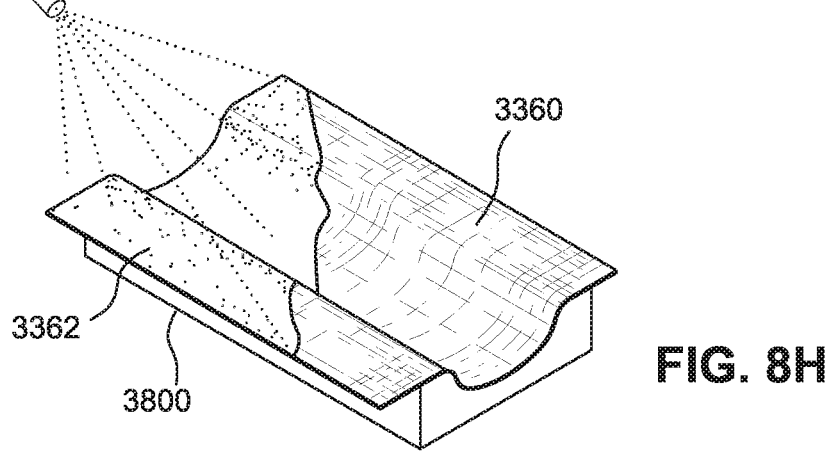

FIG. 8H depicts spraying a membrane layer onto the sheet while the sheet is in the mold.

Figure 8I:
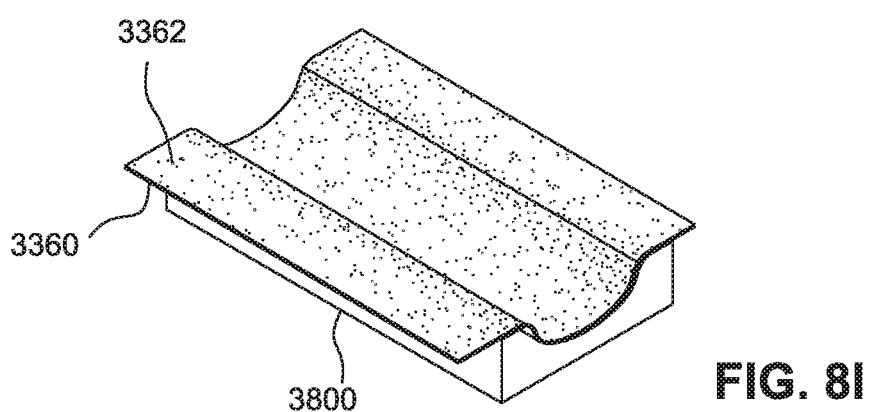

FIG. 8I depicts the sheet and membrane layer within the mold.

Figure 8J:
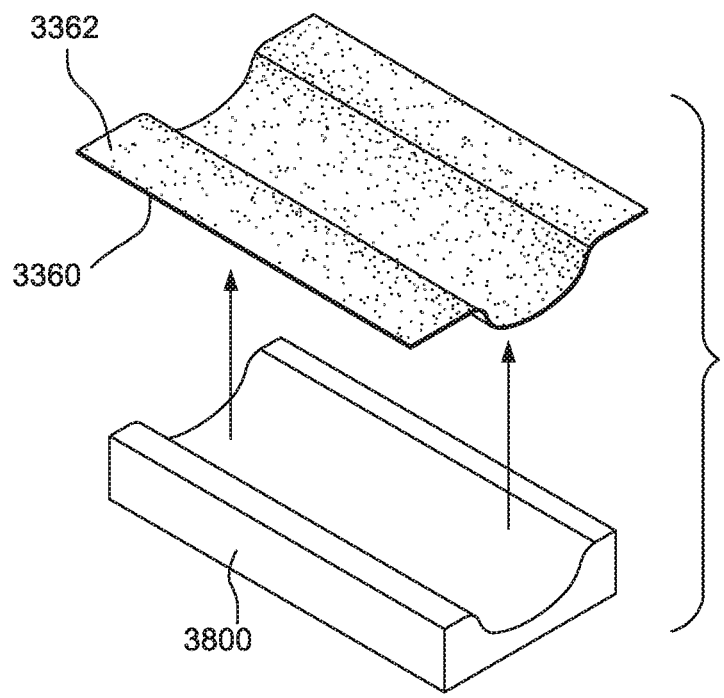

FIG. 8J depicts removing the cured layer from the mold.

Figure 8K:
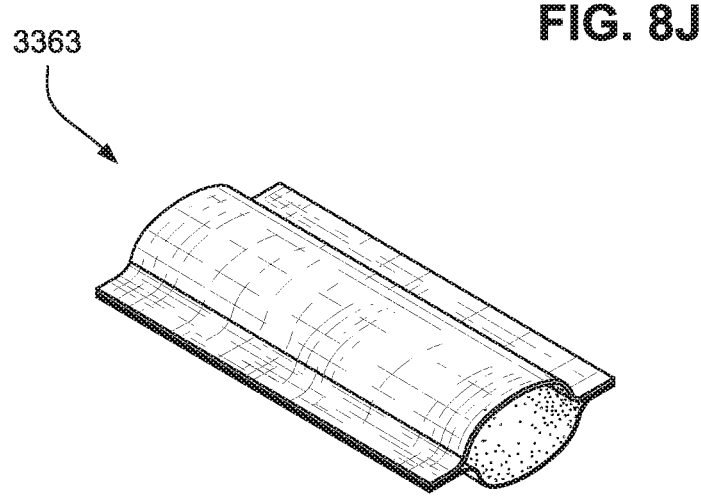

FIG. 8K depicts a tube formed from two cured layers.

Figure 8L:
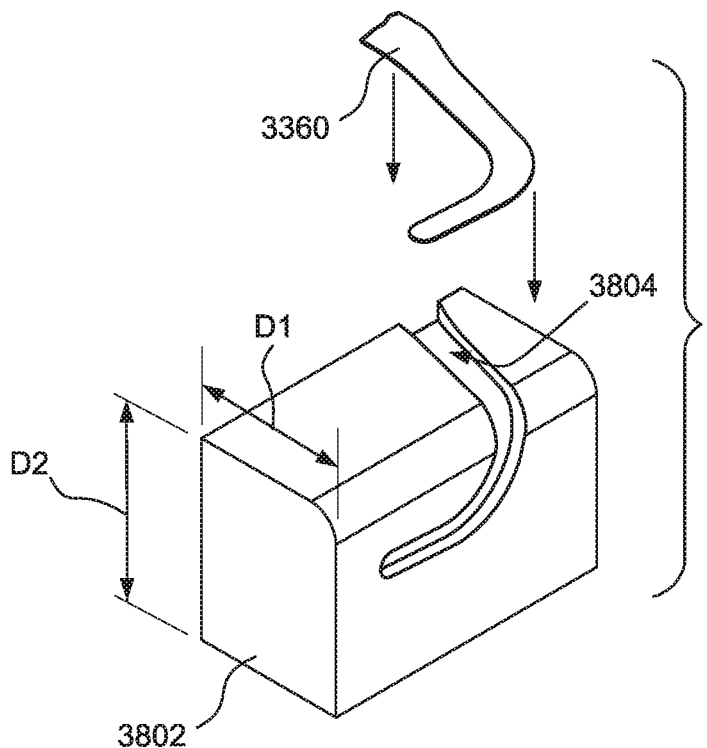
Figure 8M:
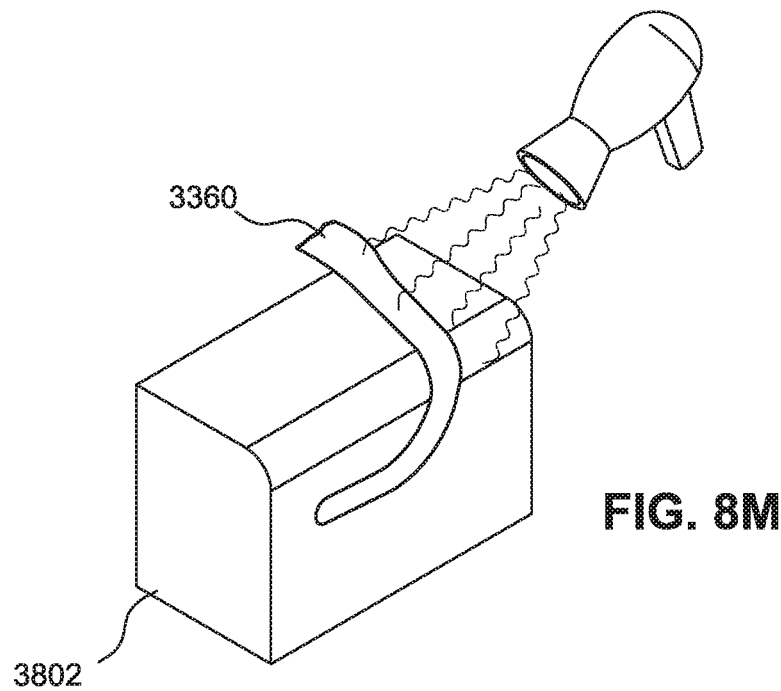

FIGS. 8L and 8M depict another method for forming a tube for use in a patient interface.

Figure 9A:
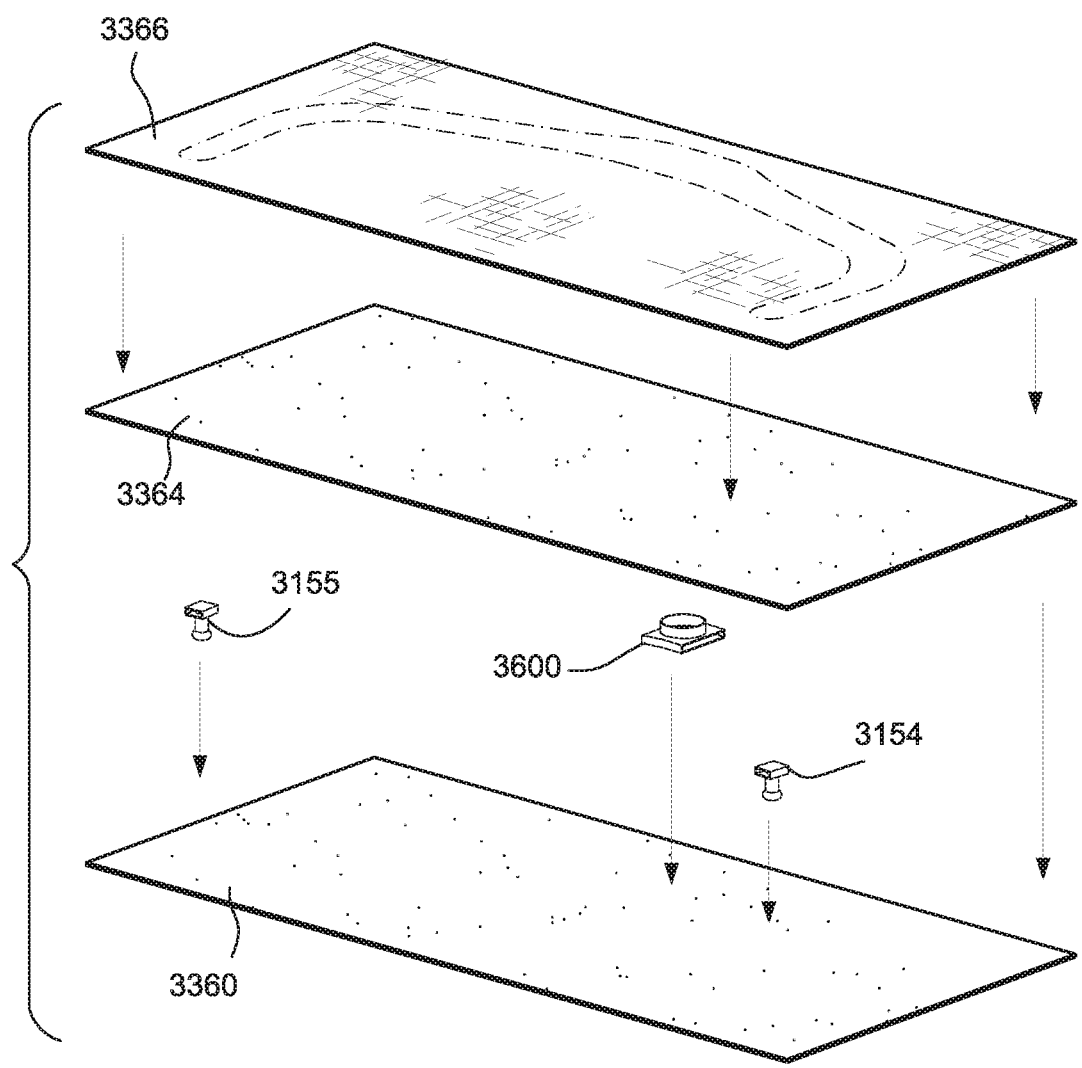
Figure 9B:
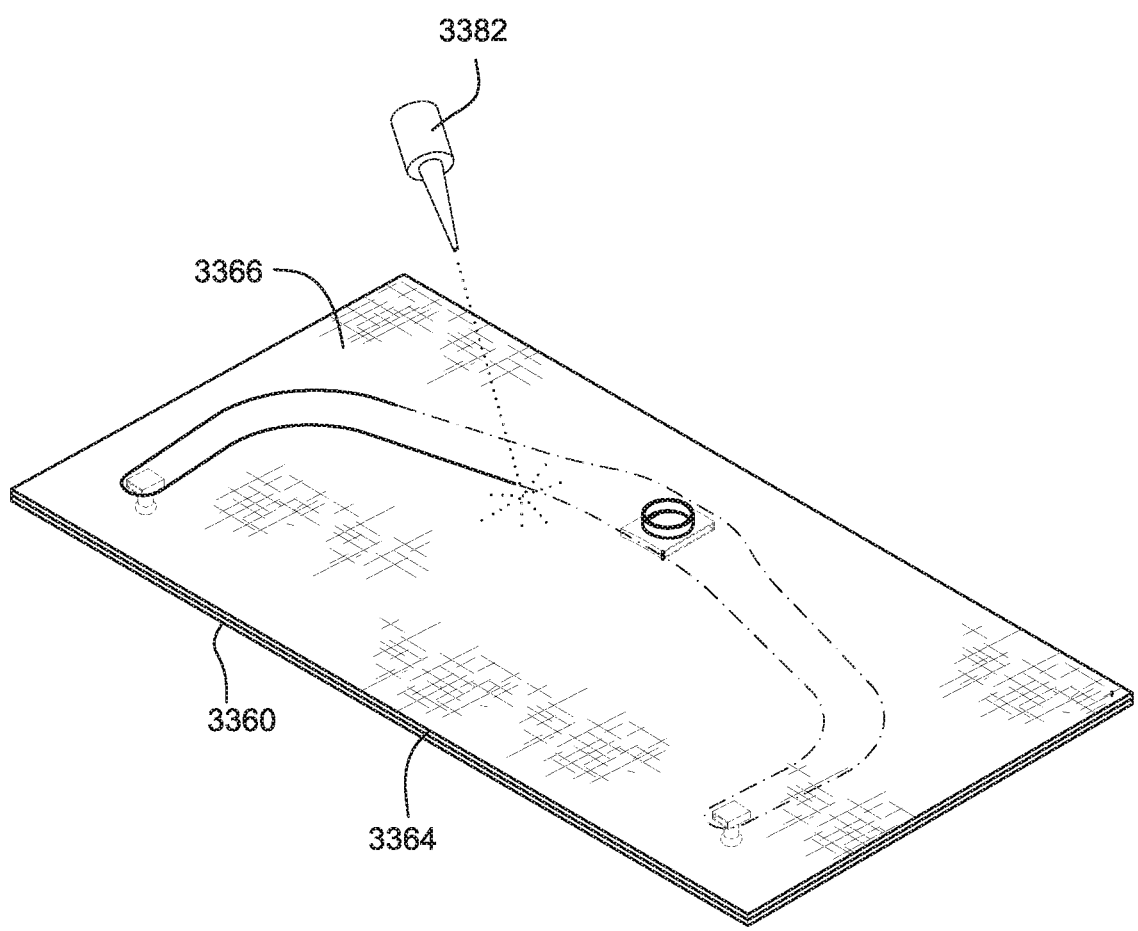

FIGS. 9A and 9B depicts method for forming a tube with an alternate form.

FIG. 9C depicts a tube 3450 of an alternate form.

FIGS. 9D and 9E depict cross-sections of tube 3450 of FIG. 9C in an inflated and uninflated state.

Figure 10:
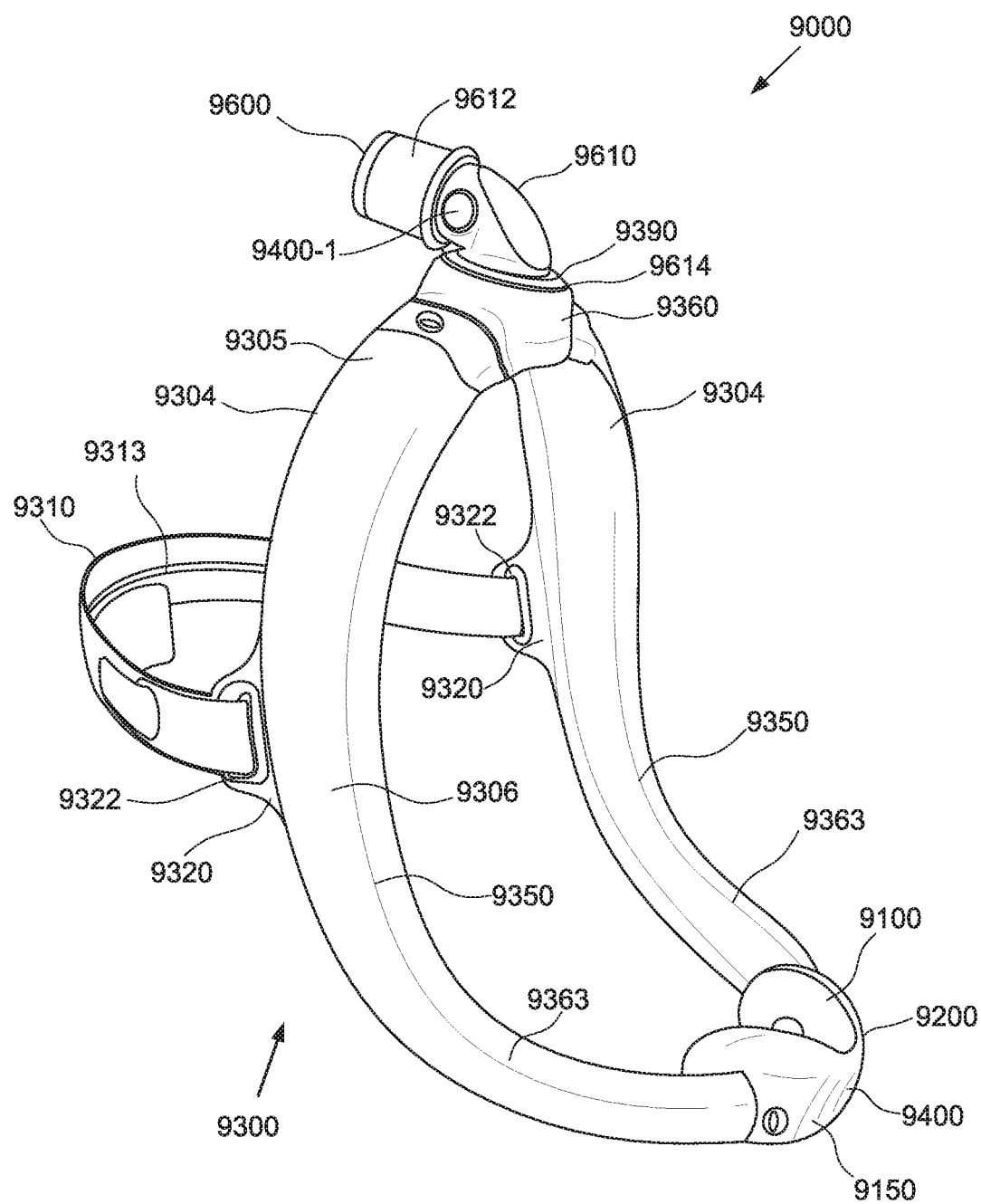

FIG. 10 shows a perspective view of a patient interface 9000 according to an example of the present technology.

Figure 11:
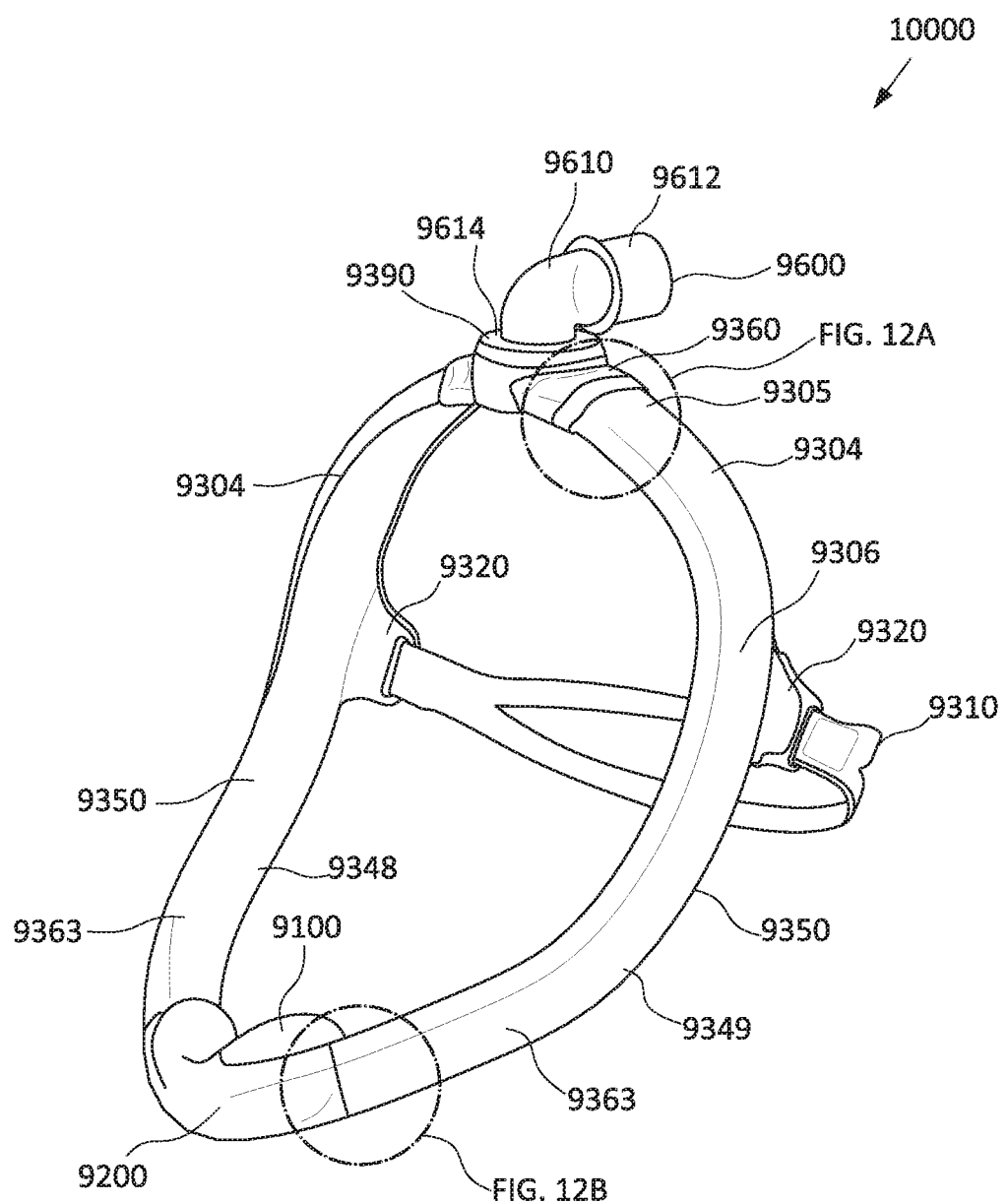

FIG. 11 shows a perspective view of a patient interface 10000 according to another example of the present technology.

Figure 12A:
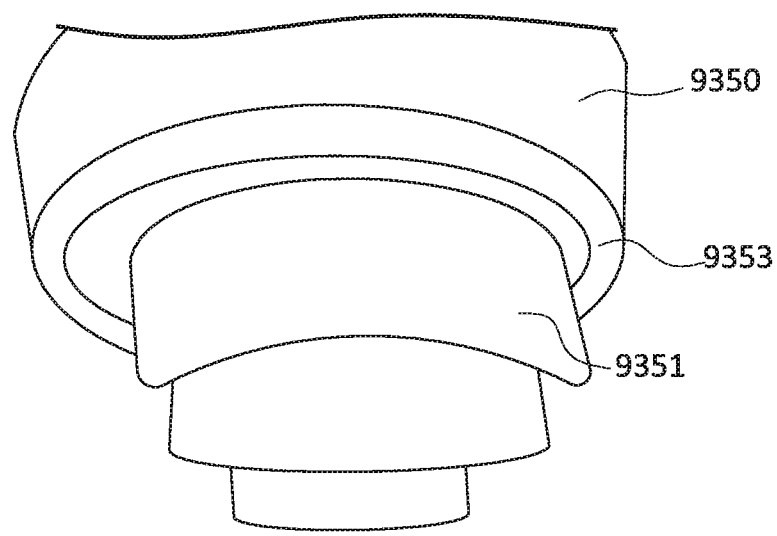
Figure 12B:
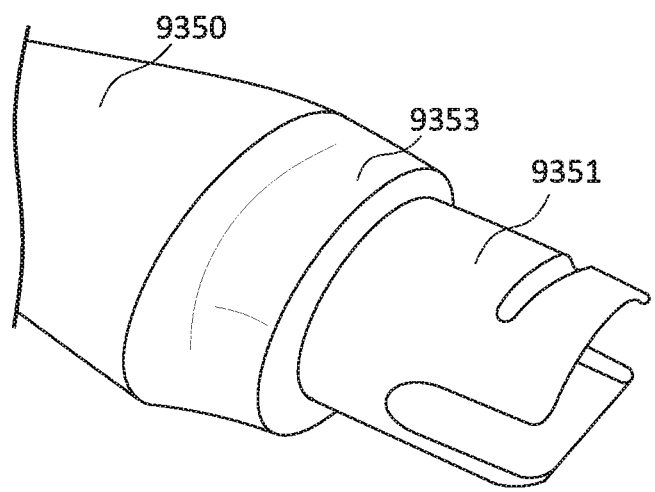

FIGS. 12A and 12B are detail views of the headgear tube connectors according to an example of the present technology.

Figure 13:
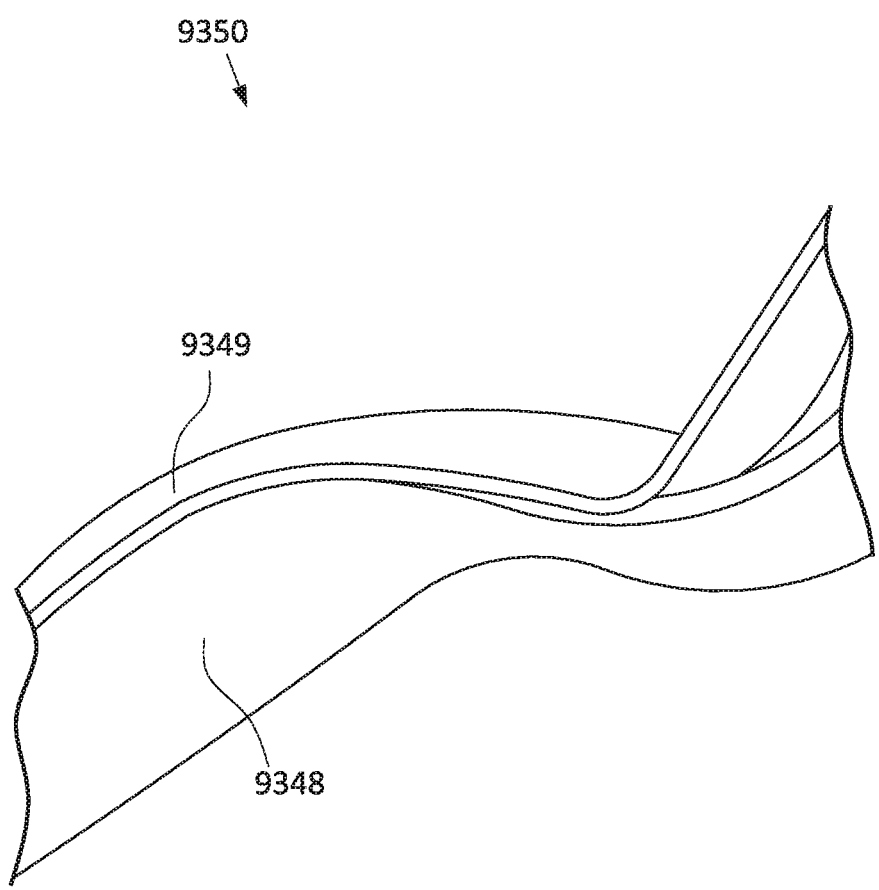

FIG. 13 shows a perspective view of a gas delivery tube 9350 of a patient interface 9000 according to another example of the present technology.

Figure 14:
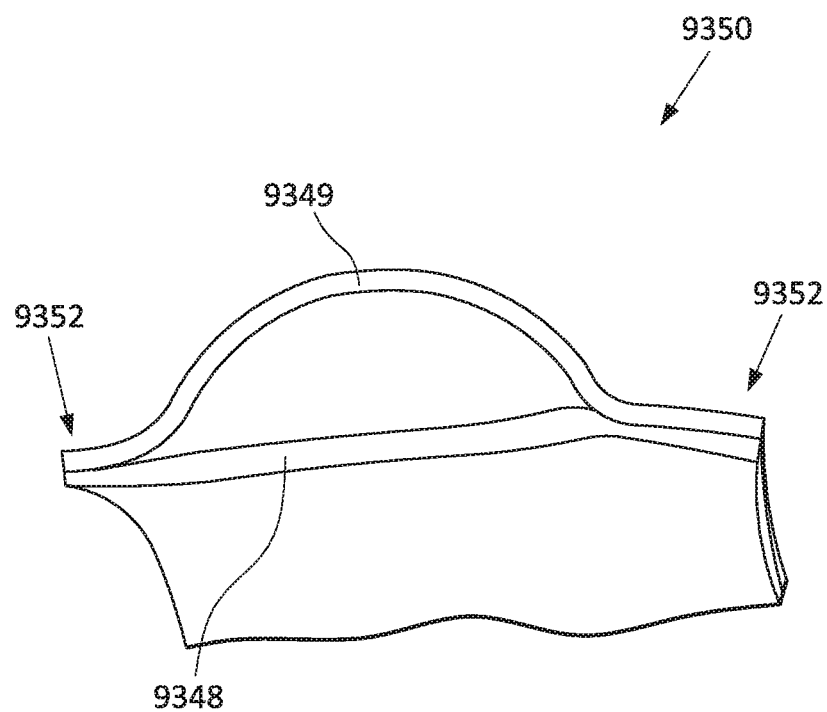

FIG. 14 shows a cross section view of the gas delivery tube 9350 of FIG. 11.

Figure 15:
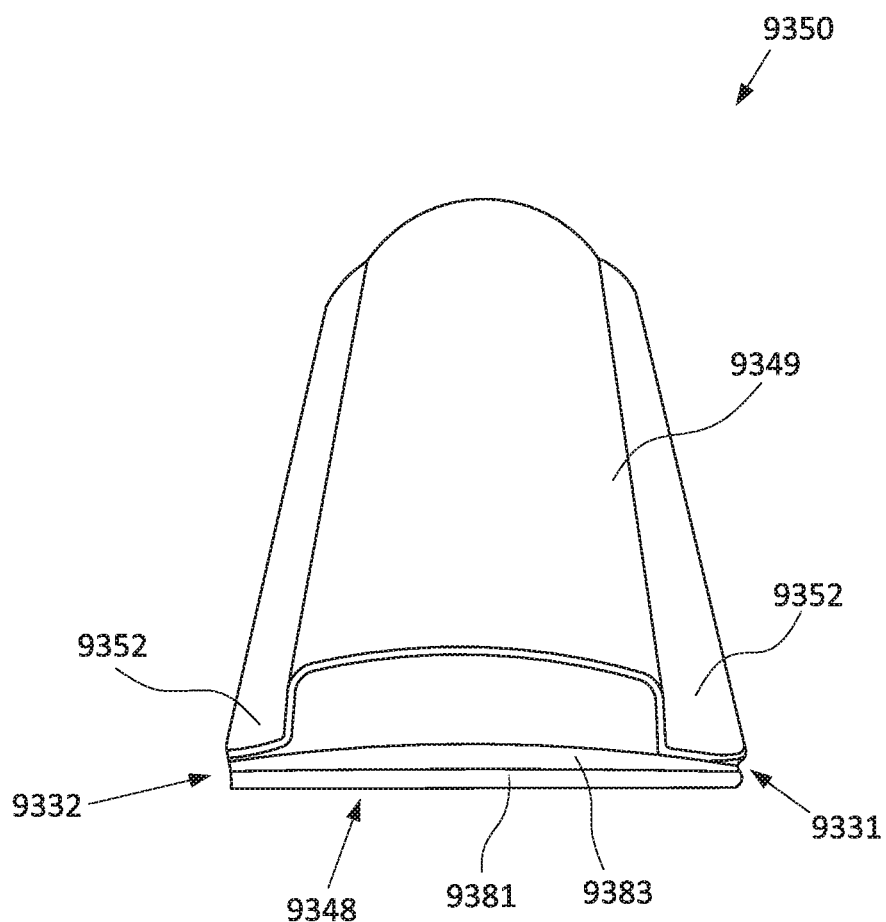

FIG. 15 is a perspective view showing a cross section of a gas delivery tube 9350 according to another example of the present technology.

Figure 16:
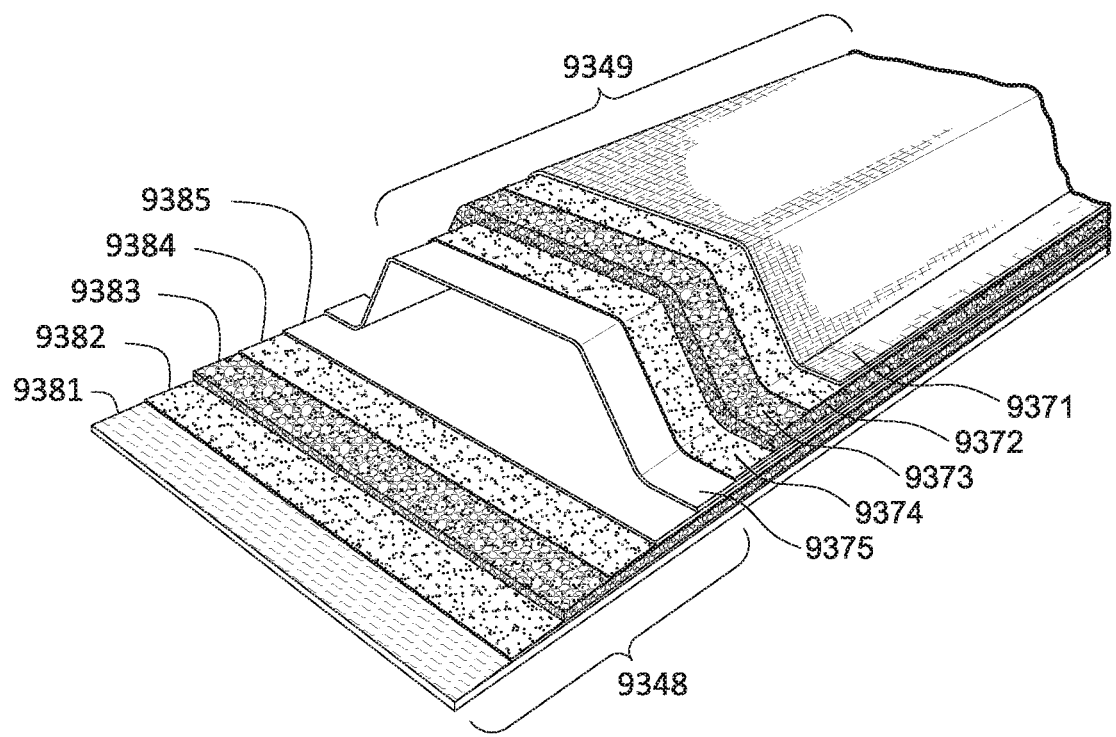

FIG. 16 shows an illustration of a cross-section of a gas delivery tube 9350 according to another example of the present technology.

Figure 17:
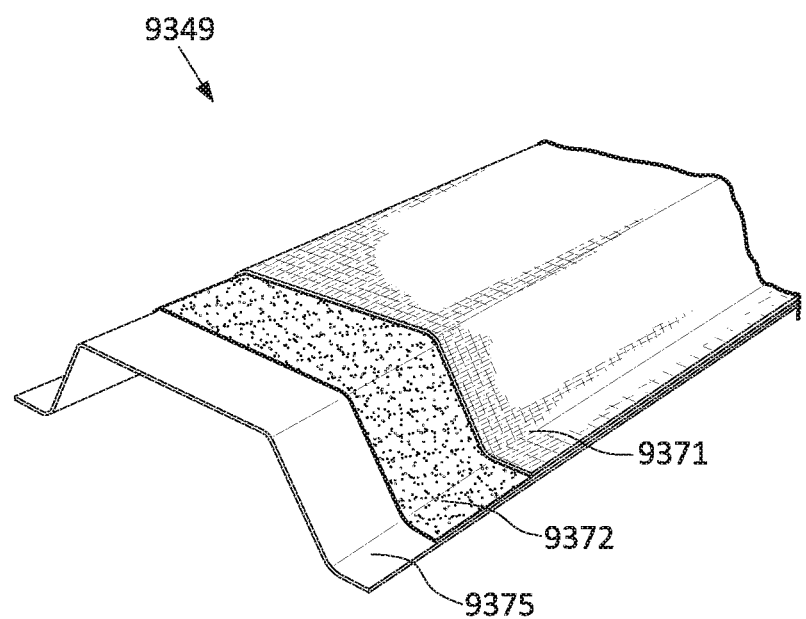

FIG. 17 shows an illustration a cross-section of a non-patient contacting portion 9349 of a gas delivery tube according to another example of the present technology.

Figure 18:
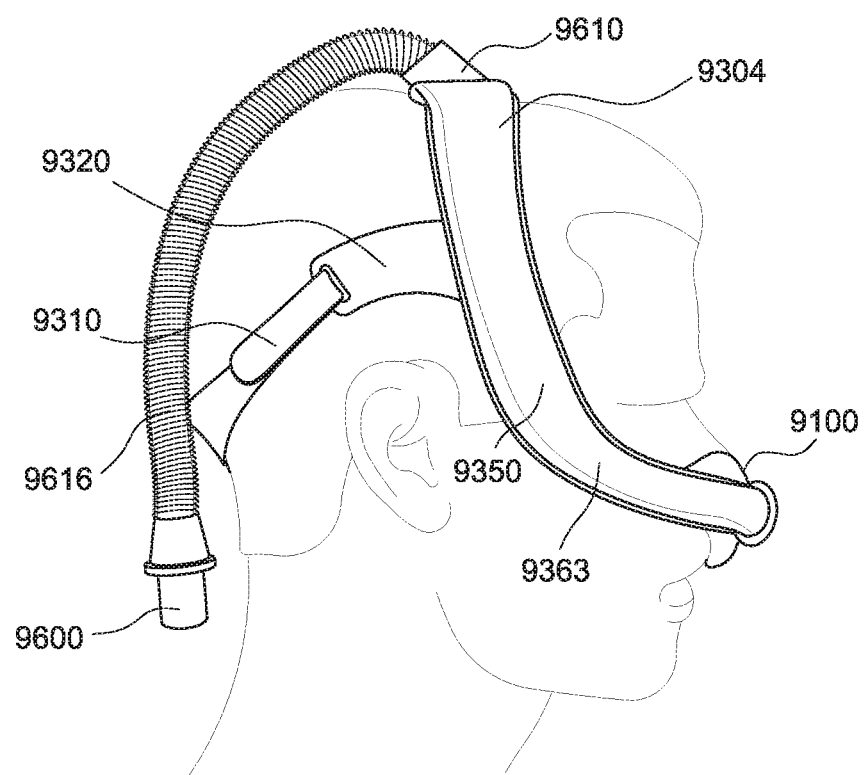

FIG. 18 shows a side view of a patient interface 9000 according to another example of the present technology.

Figure 19:
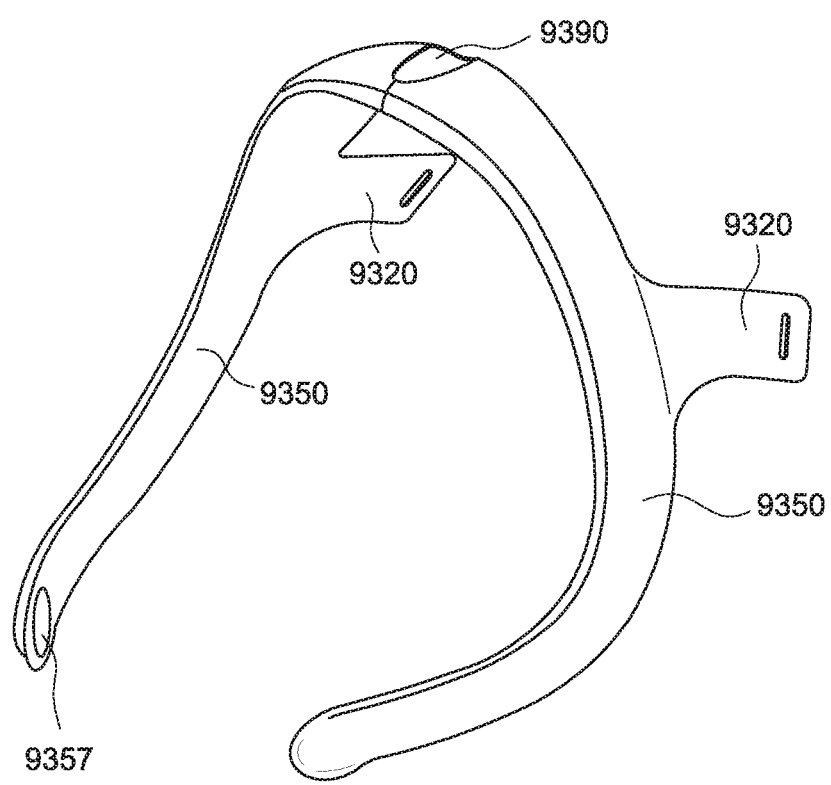

FIG. 19 shows a perspective view of a patient interface 9000 according to another example of the present technology.

Figure 20:
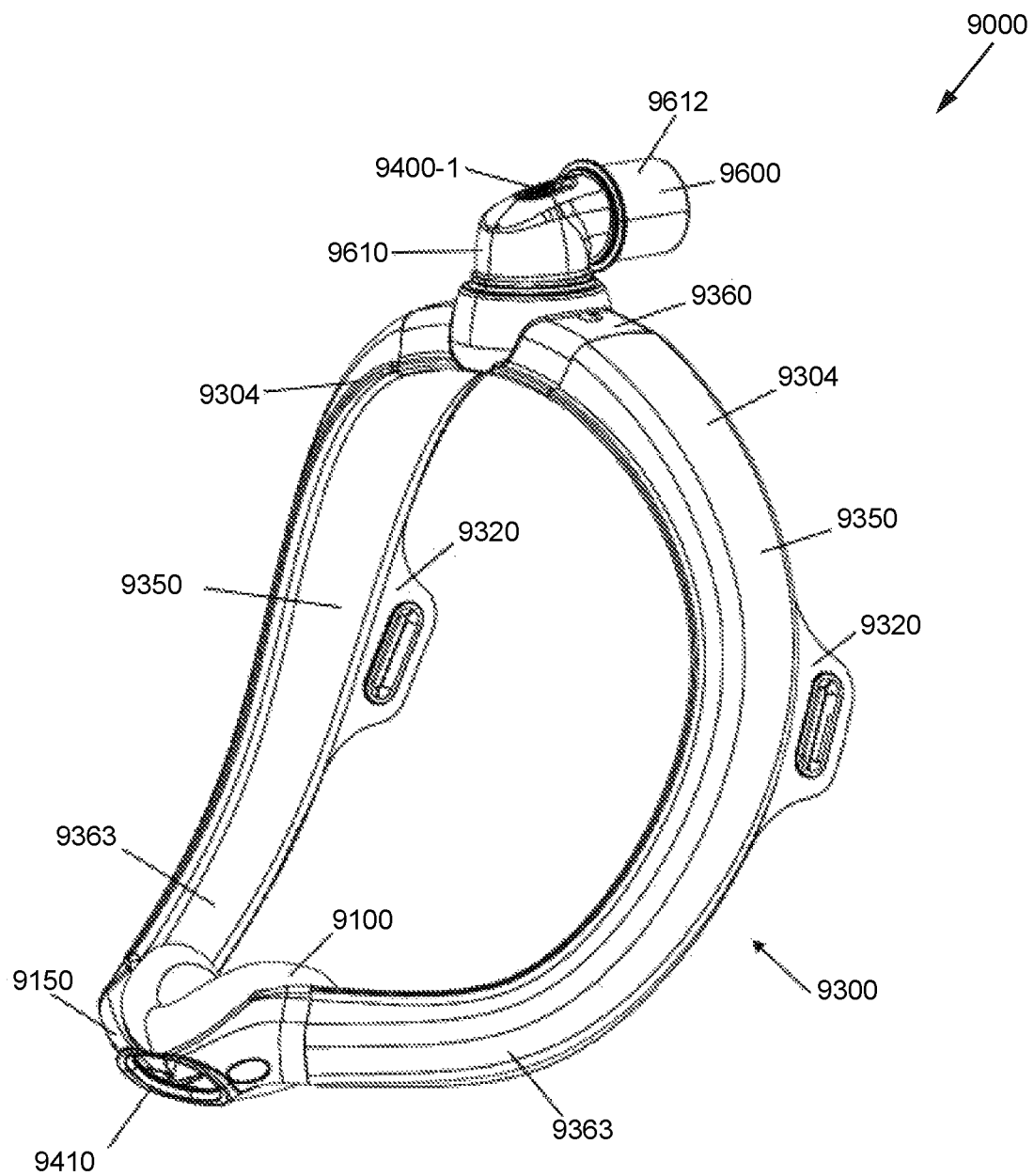

FIG. 20 shows a perspective view of a patient interface 9000 according to another example of the present technology.

Figure 21:
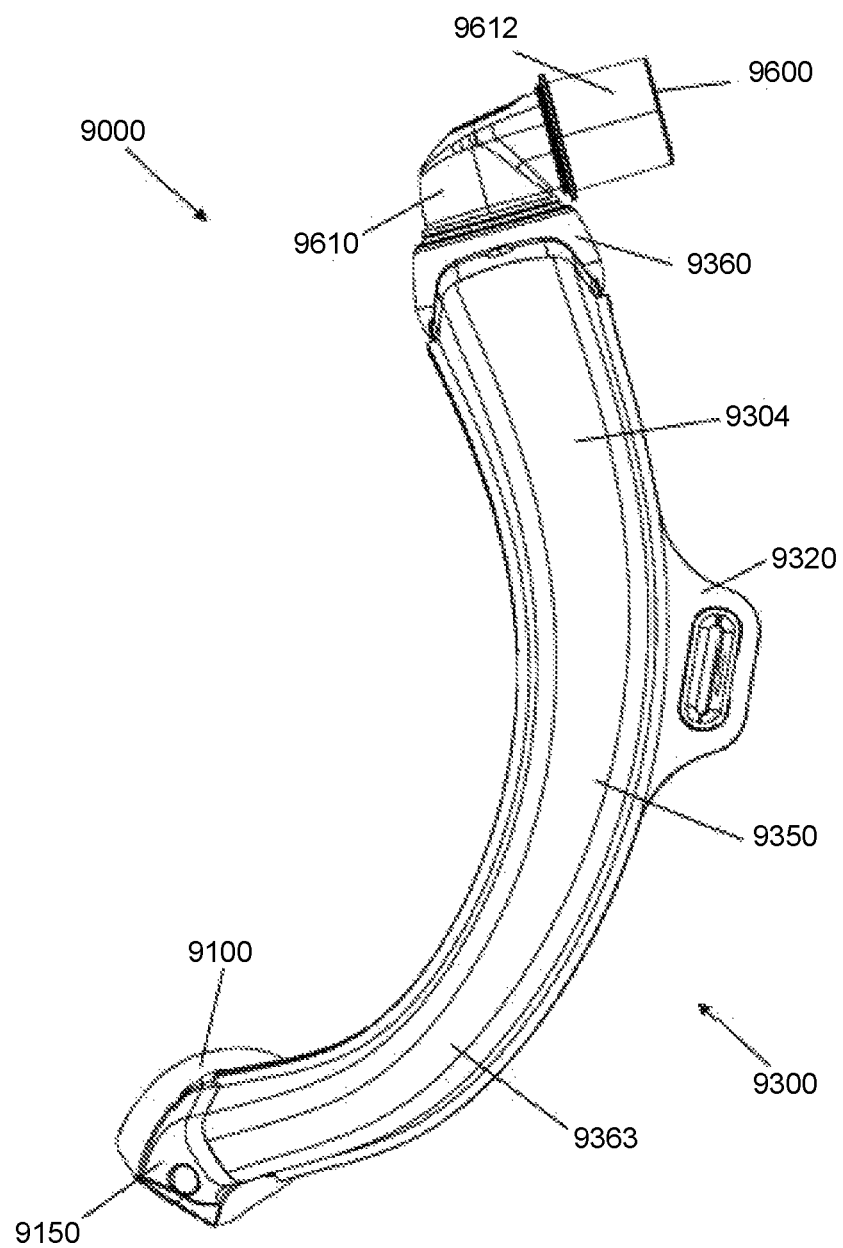

FIG. 21 shows a left side view of the patient interface 9000 of FIG. 20.

Figure 22:
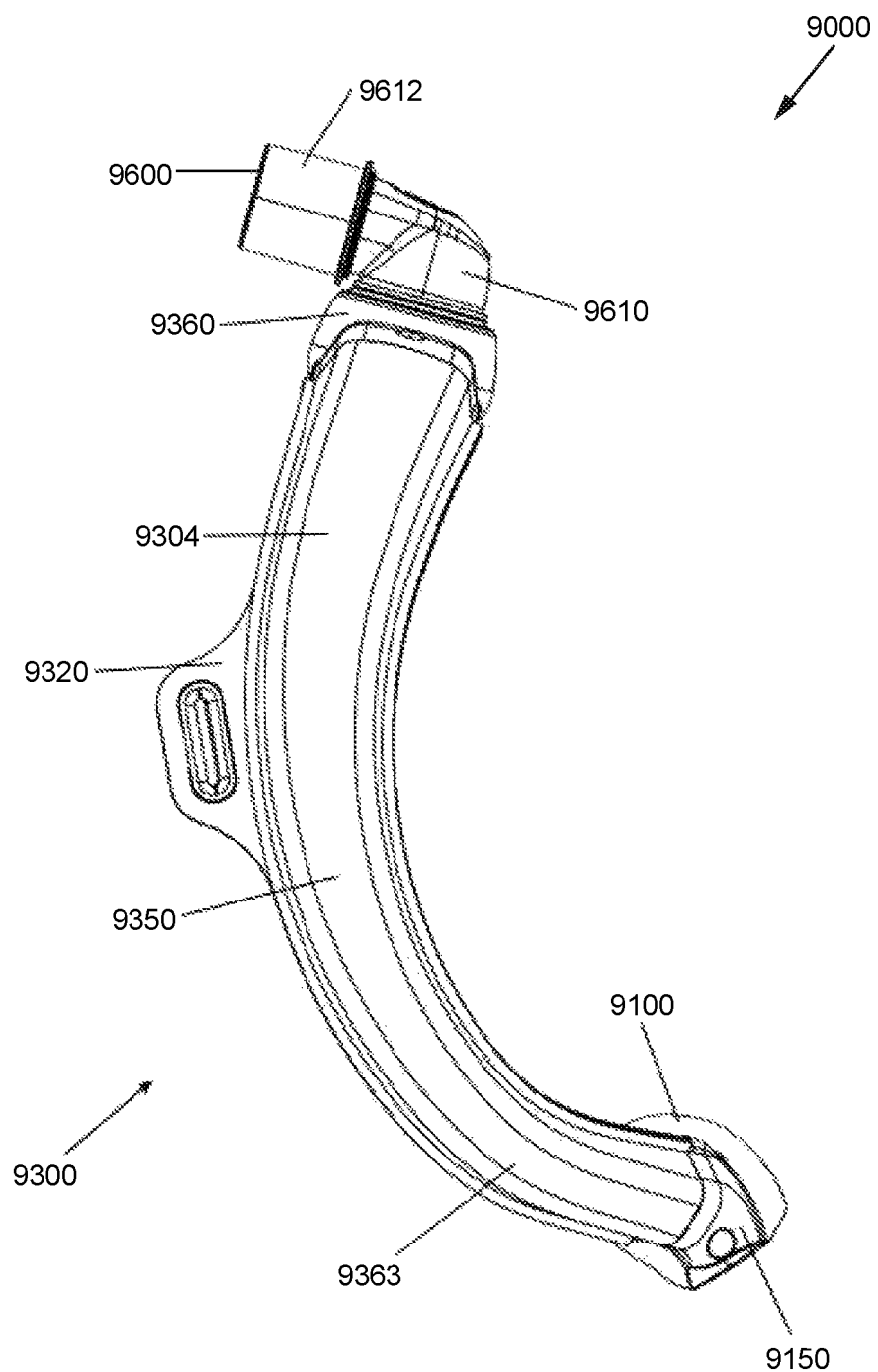

FIG. 22 shows a right side view of the patient interface 9000 of FIG. 20.

Figure 23:
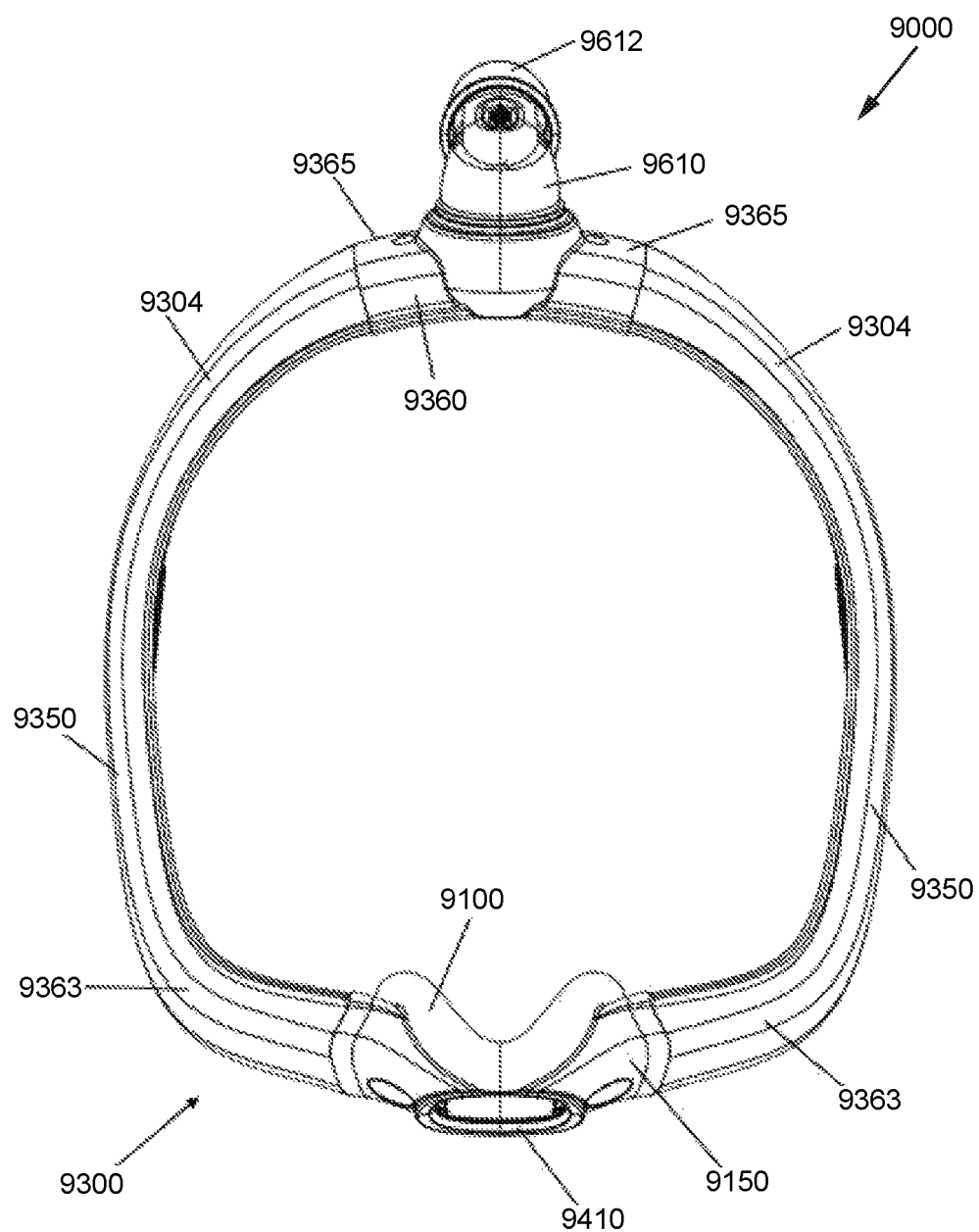

FIG. 23 shows a front view of the patient interface 9000 of FIG. 20.

Figure 24:
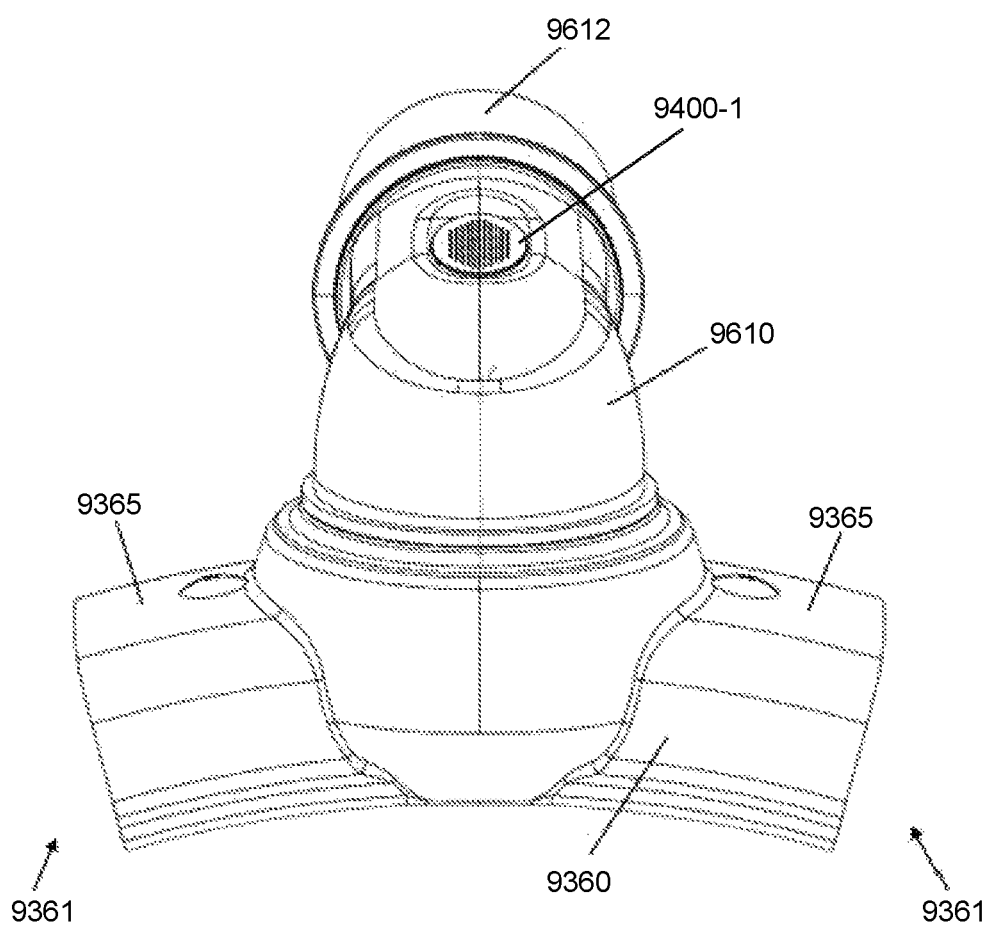

FIG. 24 shows a front view of a crown connector 9360 and elbow 9610 of the patient interface 9000 shown in FIG. 20.

Figure 25:
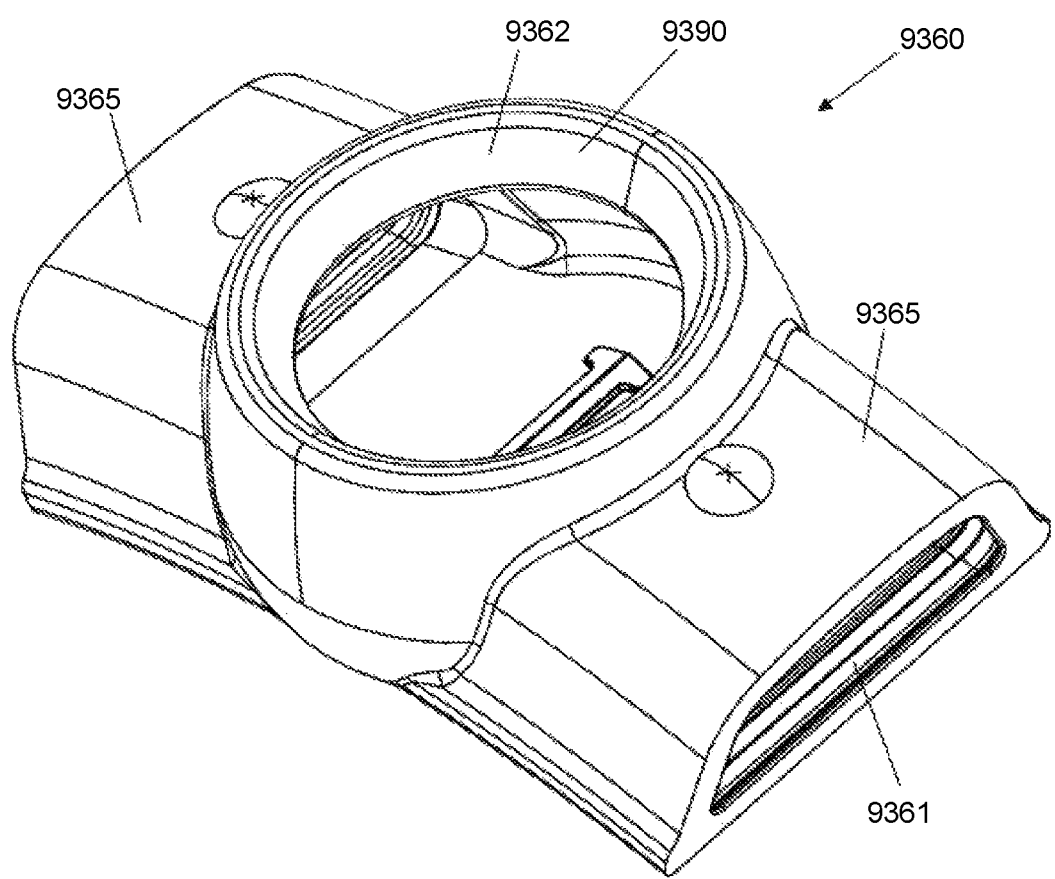

FIG. 25 shows a perspective view of a crown connector 9360 of the patient interface 9000 of FIG. 20.

Figure 26:
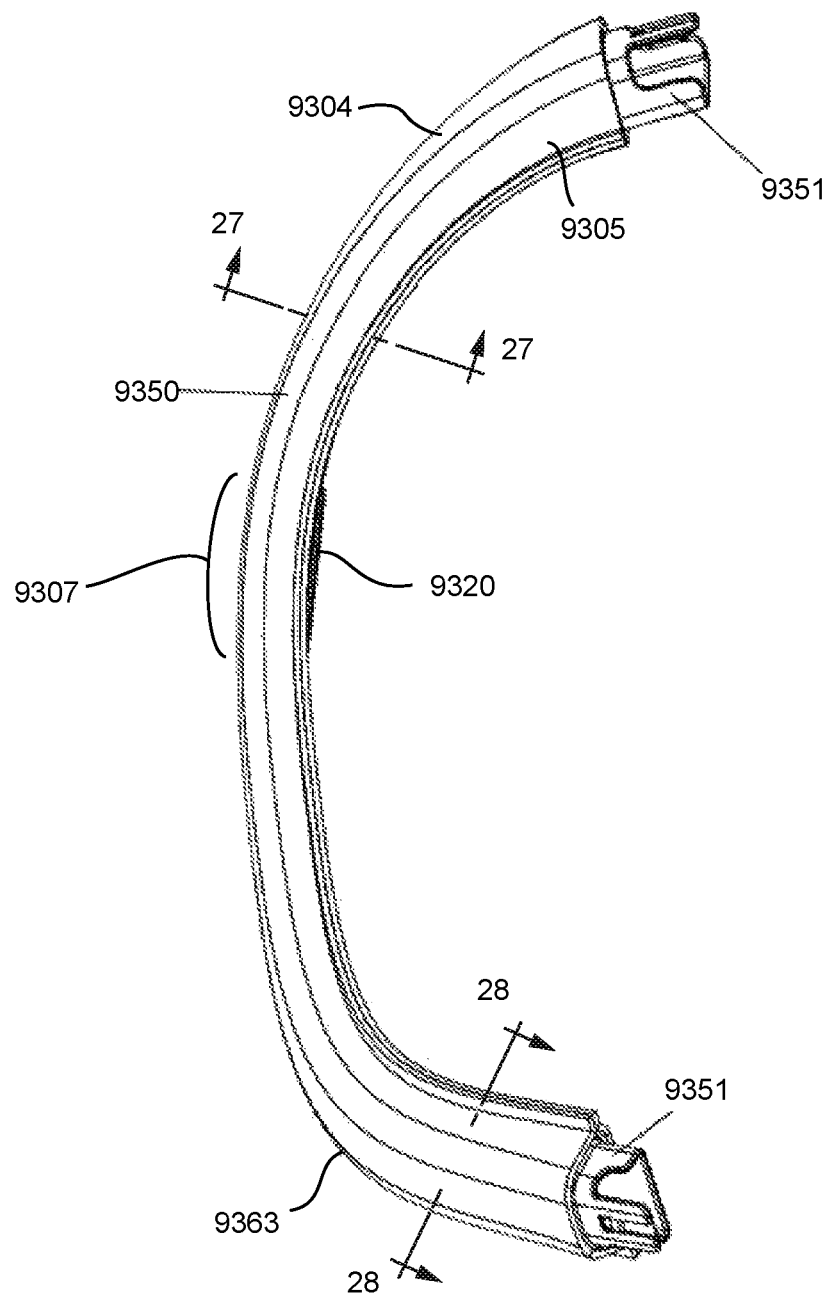

FIG. 26 shows a perspective view of a headgear tube 9350 of the patient interface 9000 of FIG. 20.

Figure 27:
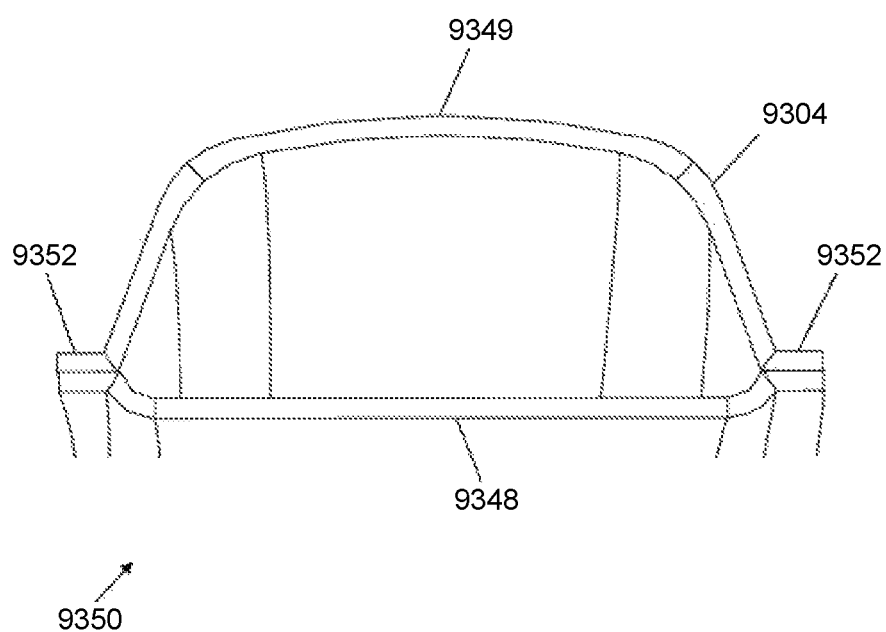

FIG. 27 shows a cross section along the line 27-27 in FIG. 26 of a superior tube portion 9304 of the headgear tube 9350.

Figure 28:
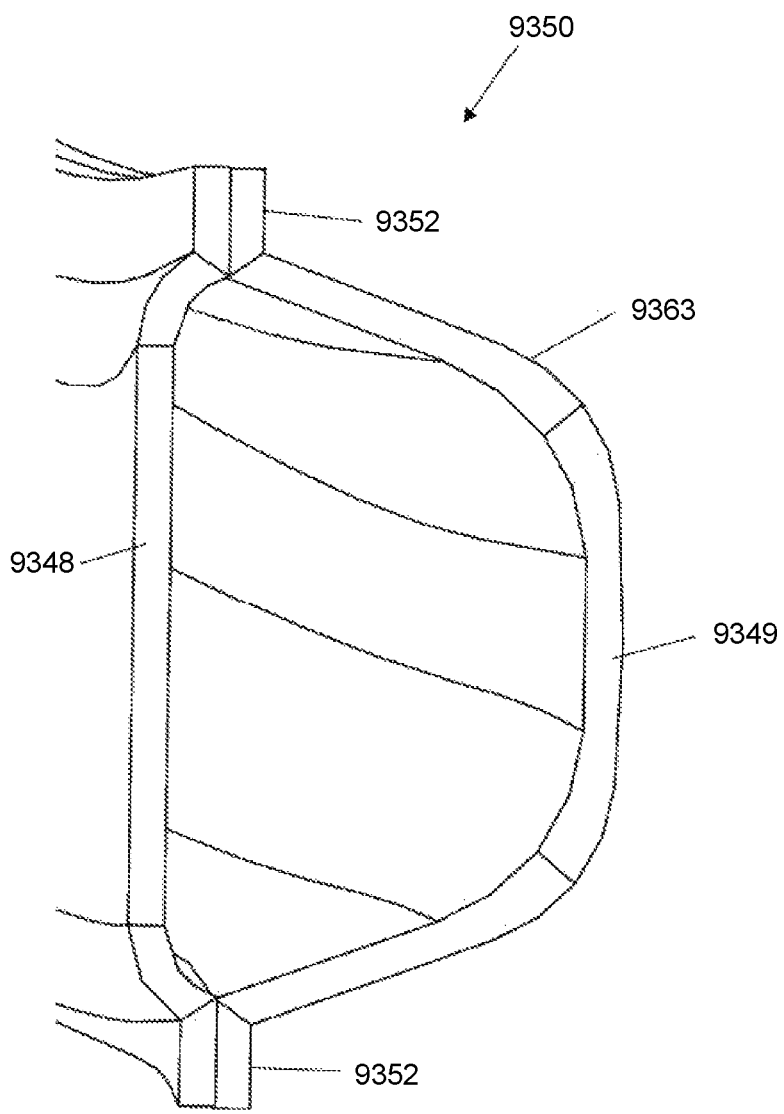

FIG. 28 shows a cross section along the line 28-28 in FIG. 26 of an inferior tube portion 9363 of the headgear tube 9350.

Figure 29:
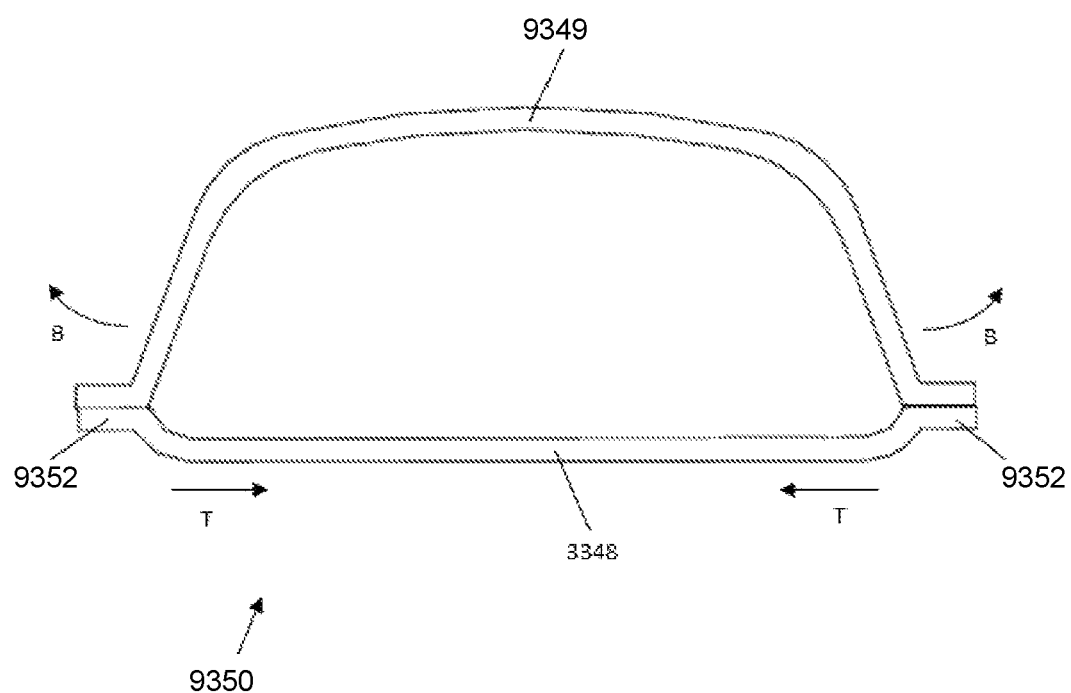

FIG. 29 shows a cross section of a superior tube portion 9304 of a headgear tube 9350 of the patient interface 9000 of FIG. 20 having some forces labelled.

Figure 30:
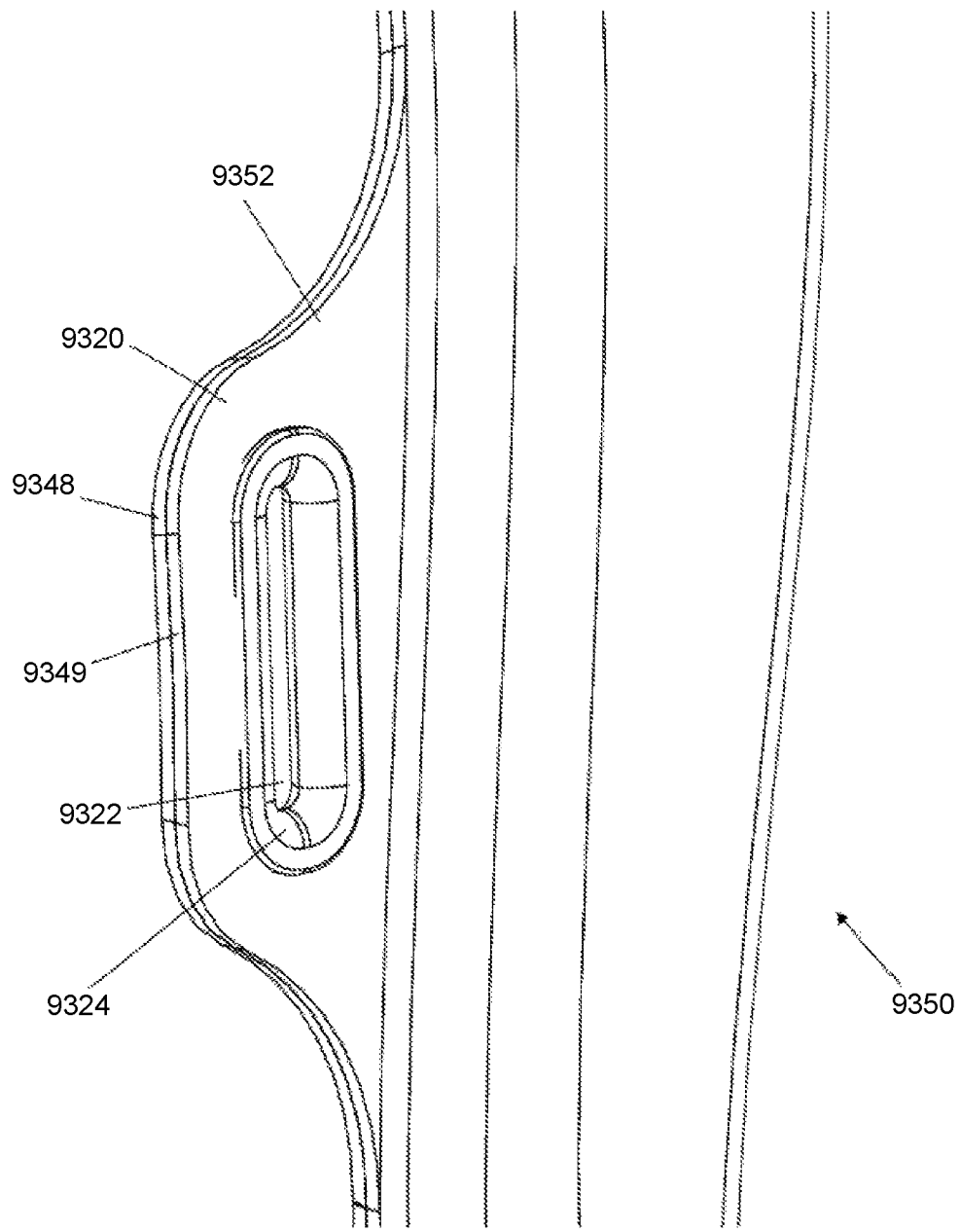

FIG. 30 shows a tab 3320 of a headgear tube 3350 of the patient interface 3000 of FIG. 20.

Figure 31:
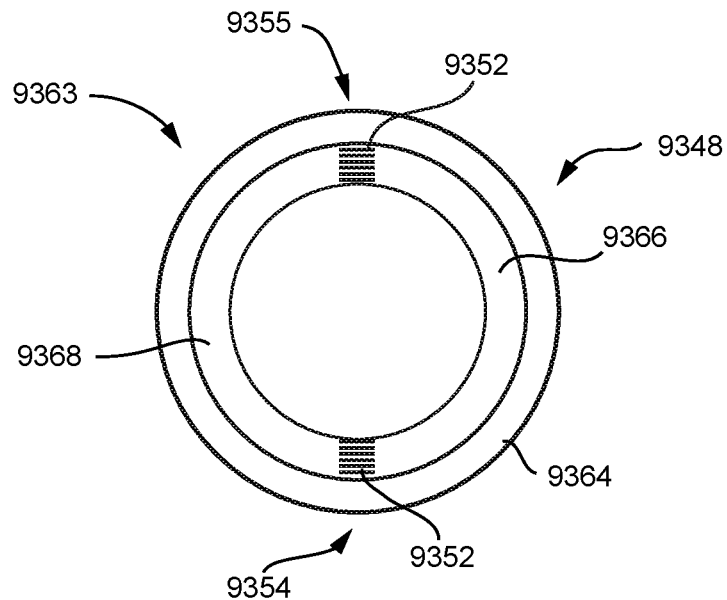

FIG. 31 is a schematic representation of a headgear tube according to an example of the present technology.

Figure 32:
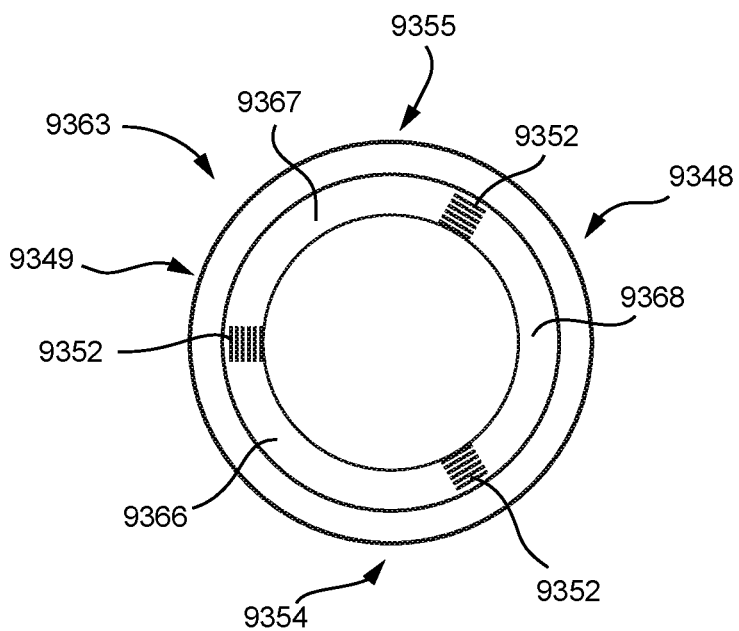

FIG. 32 is a schematic representation of a headgear tube according to another example of the present technology.

FIG. 33 is a perspective view showing a cross section of a gas delivery tube according to example of the present technology.

FIG. 33-1 is an enlarged detail showing a cross section of the seam of the gas delivery tube of FIG. 33.

FIG. 34 is a perspective view showing a cross section of a headgear tube including a tab portion according to an example of the present technology.

Figure 35:
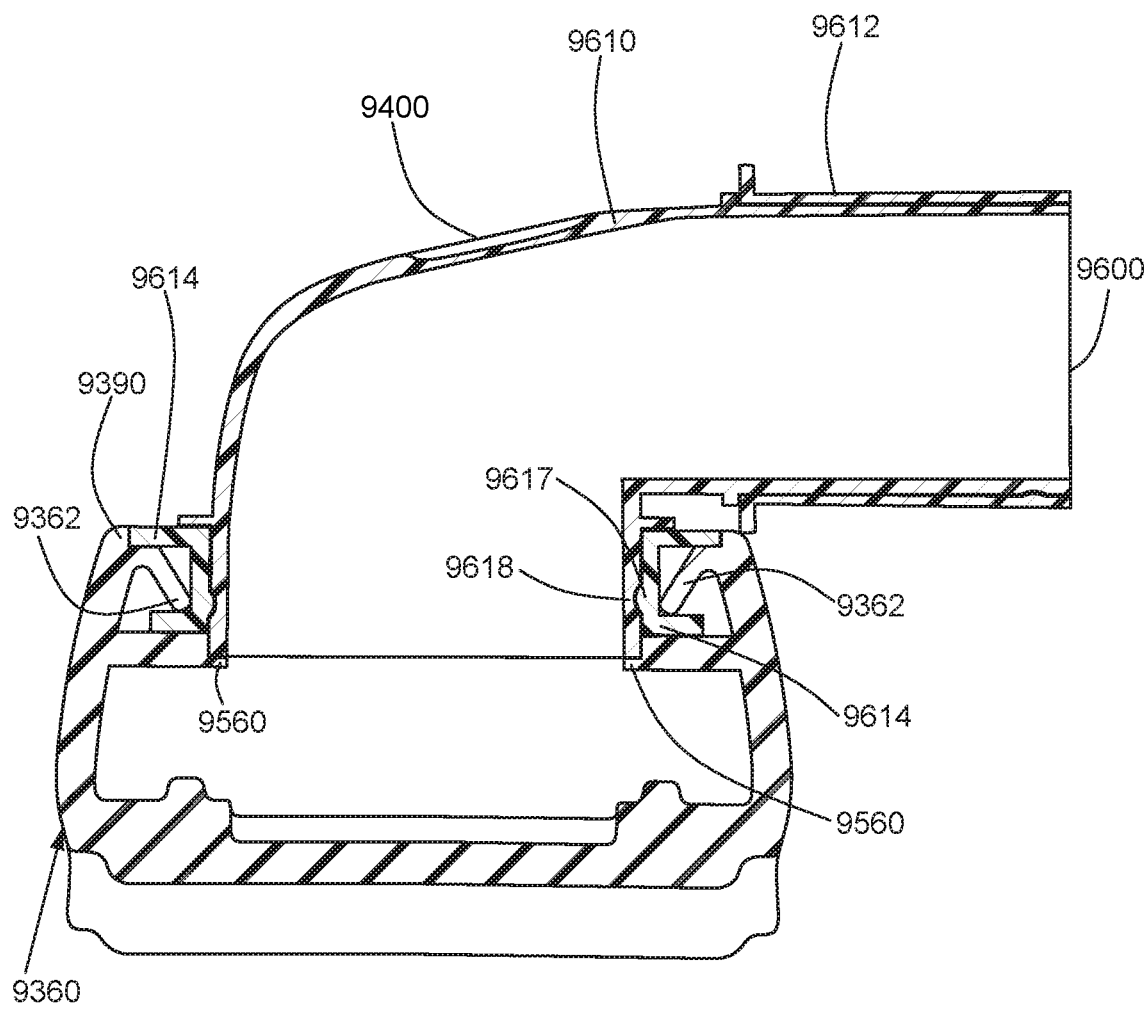

FIG. 35 is a cross-sectional view of a crown connector connected to an elbow according to an example of the present technology.

Figure 36:
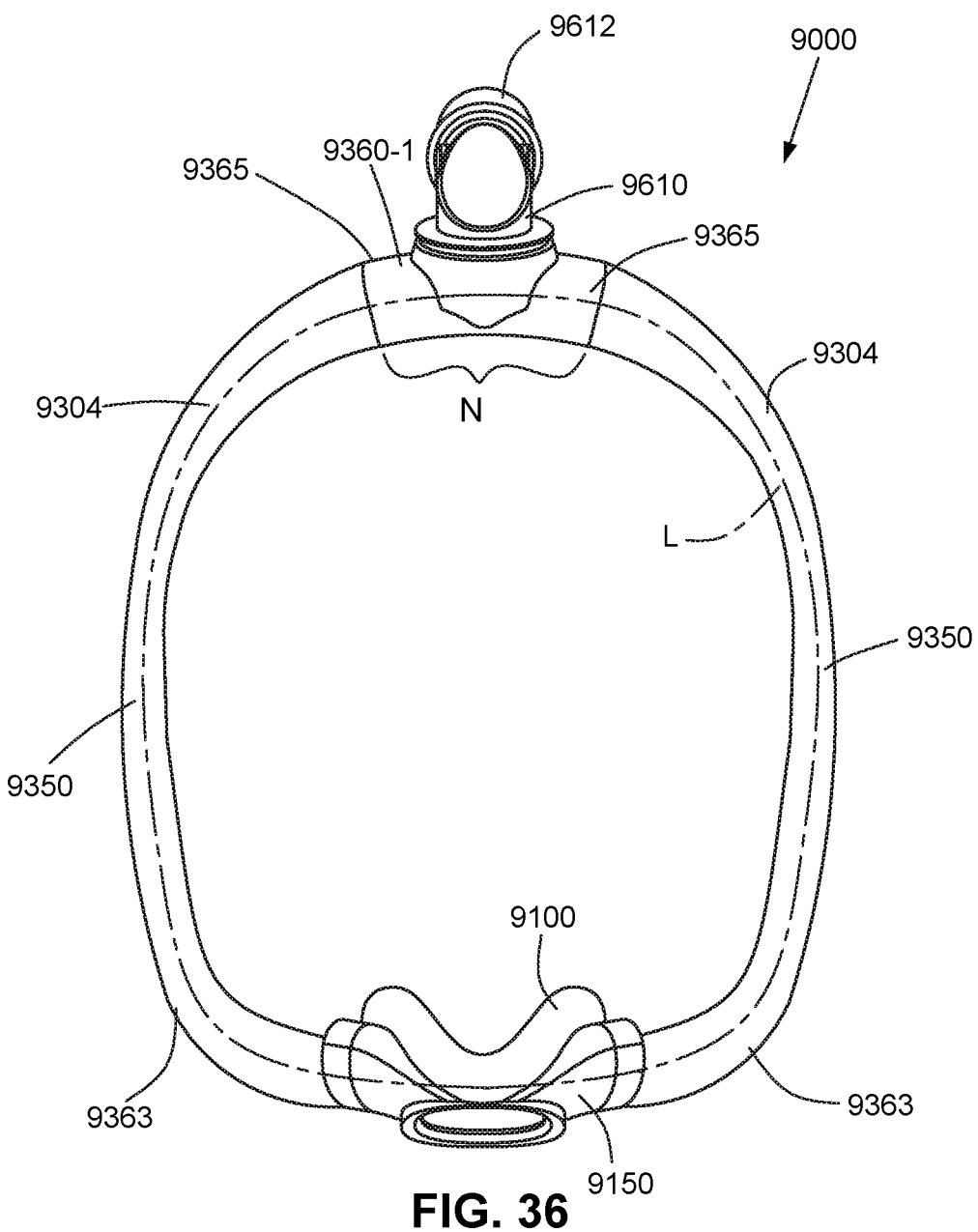

FIG. 36 shows a front view of a patient interface according to an example of the present technology.

Figures 1, 37:
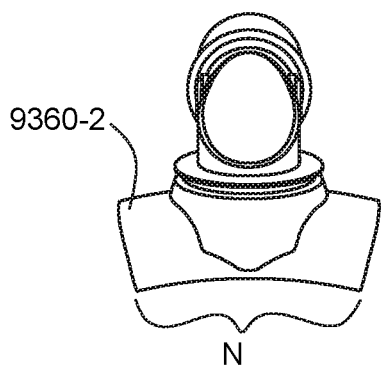
Figures 2, 37:
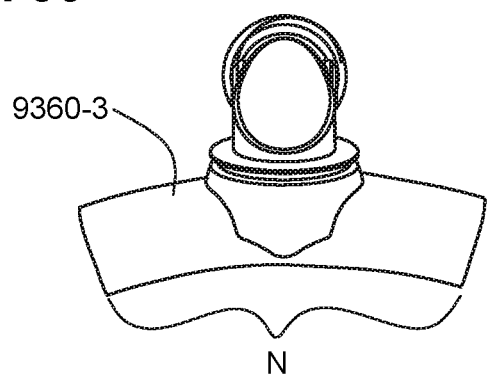

FIGS. 37-1 and 37-2 show interchangeable crown connectors each having a different length according to an example of the present technology.

Figure 38:
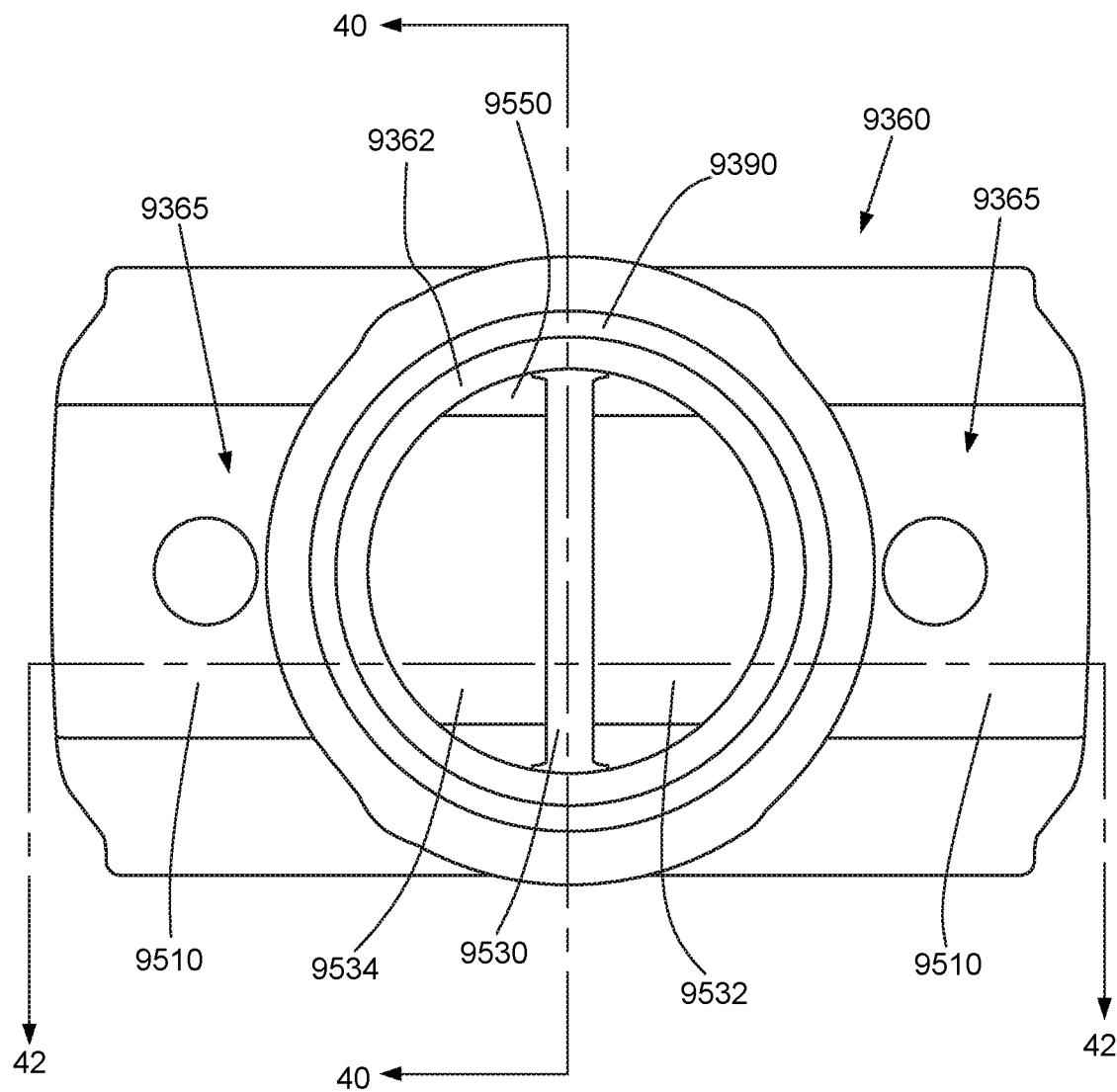

FIG. 38 is a top view of a crown connector according to an example of the present technology.

Figure 39:
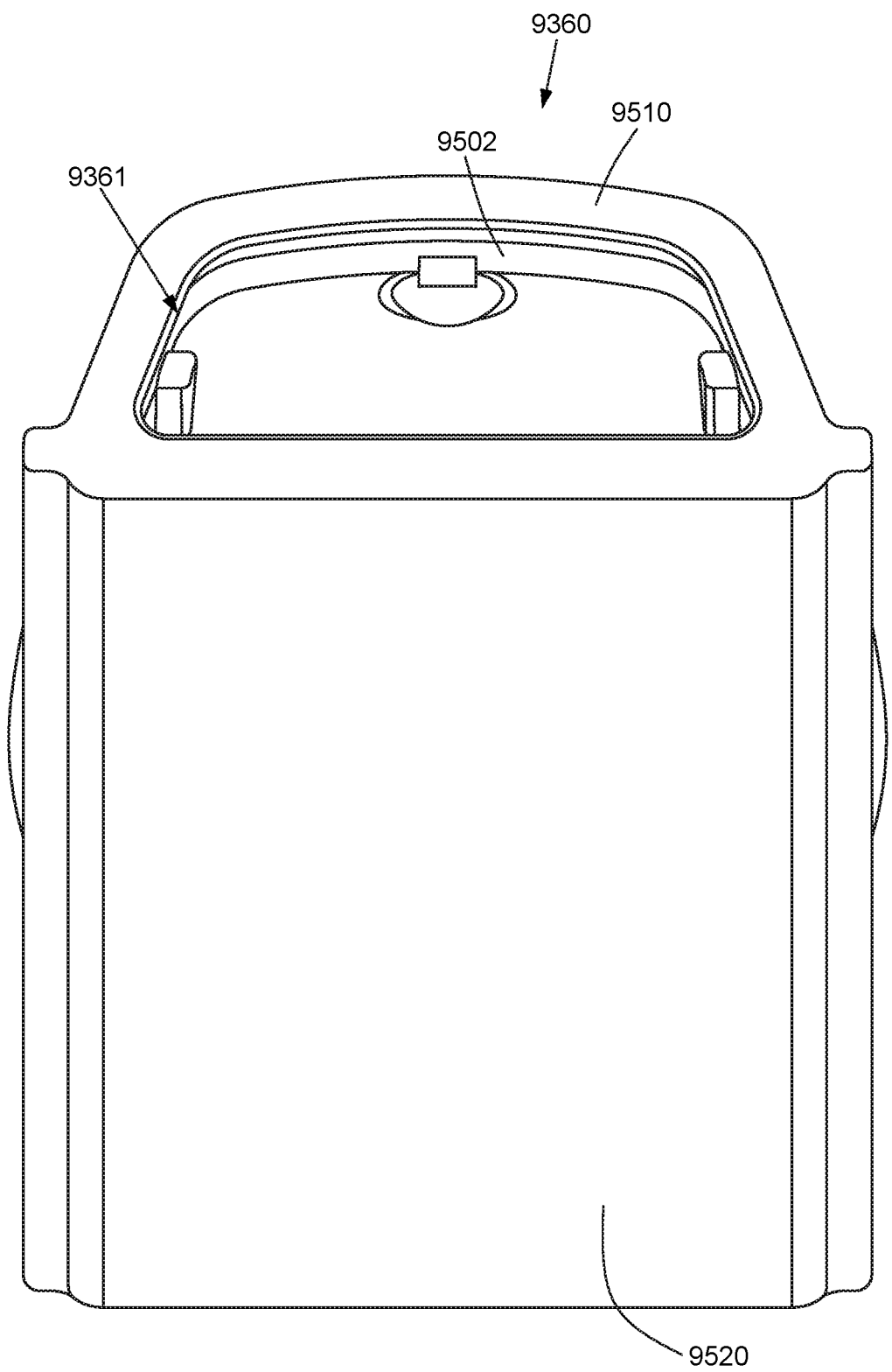

FIG. 39 is a bottom perspective view of the crown connector of FIG. 38.

Figure 40:
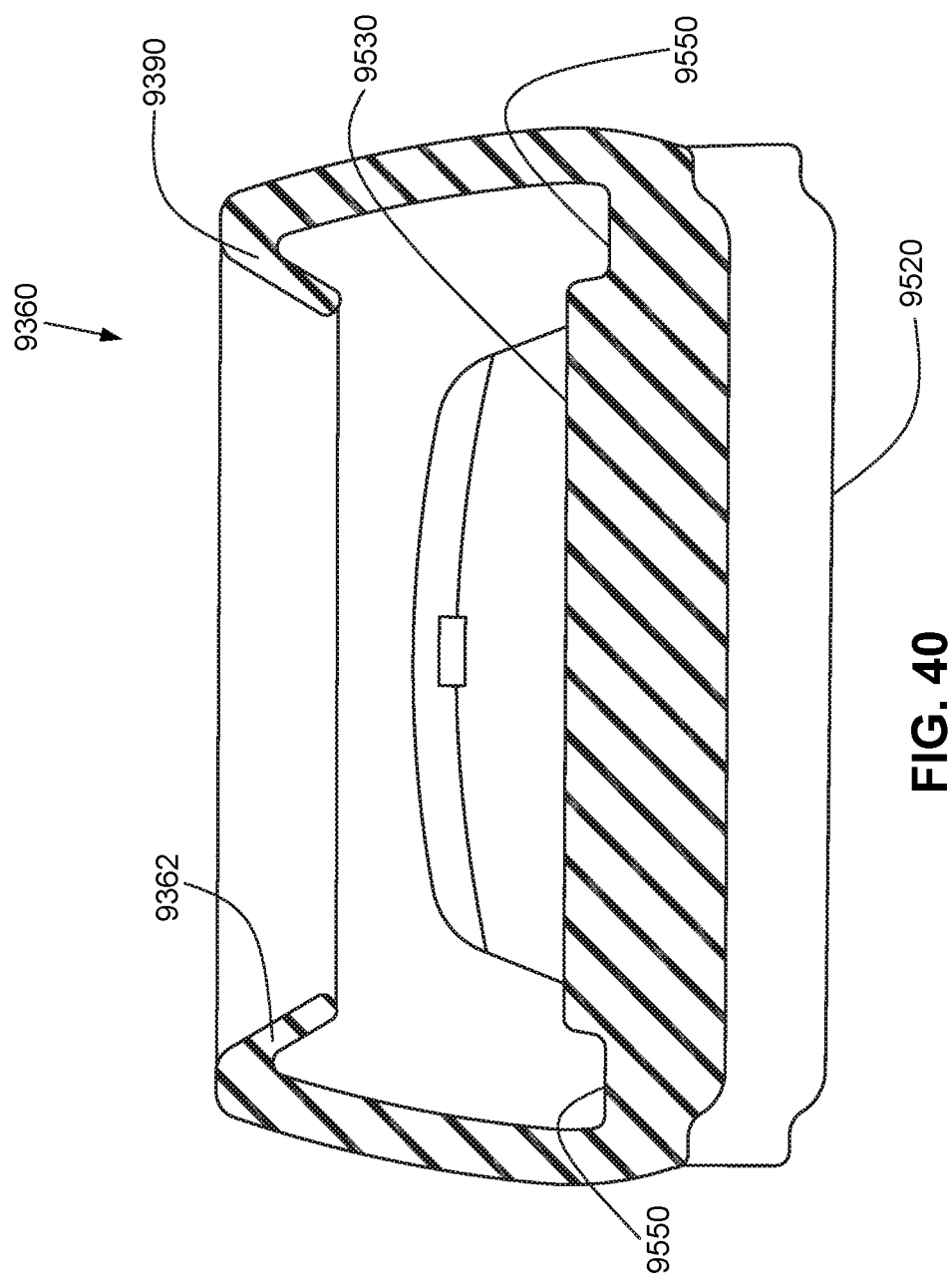

FIG. 40 is a cross-sectional view along the line 40-40 in FIG. 38.

Figures 1, 41:
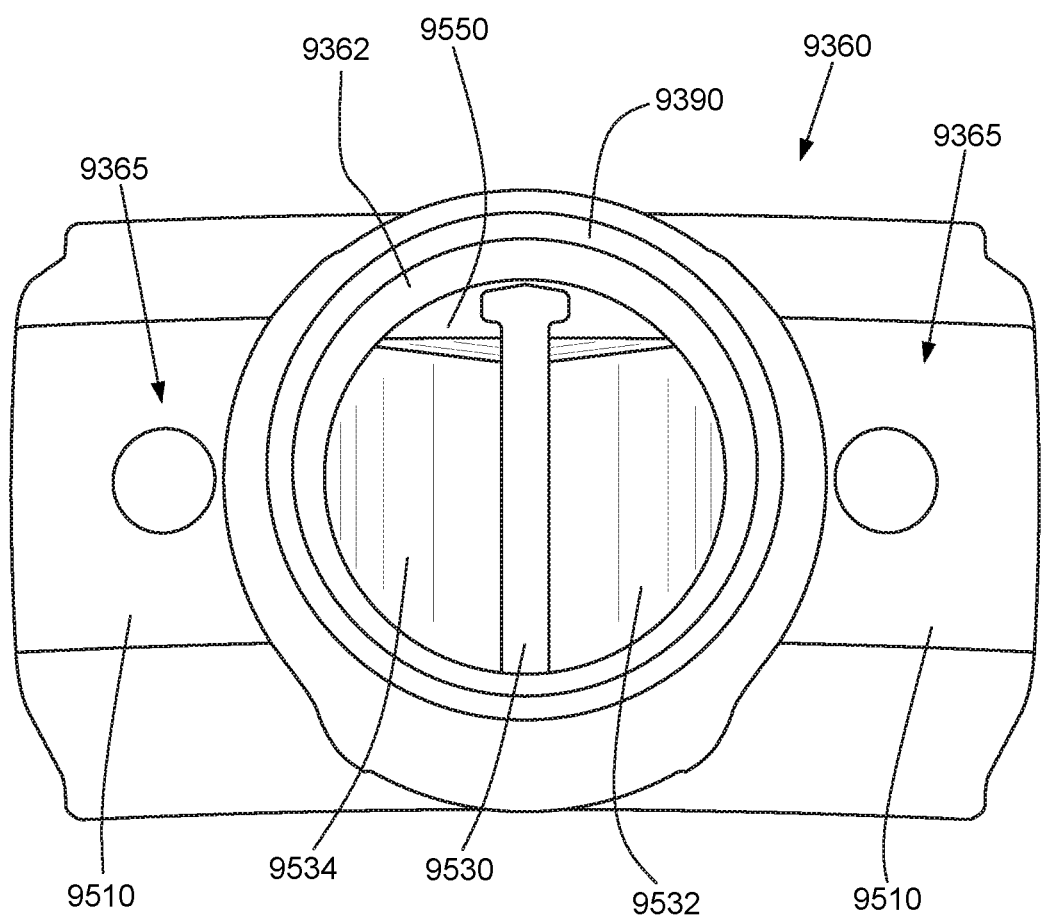
Figures 2, 41:
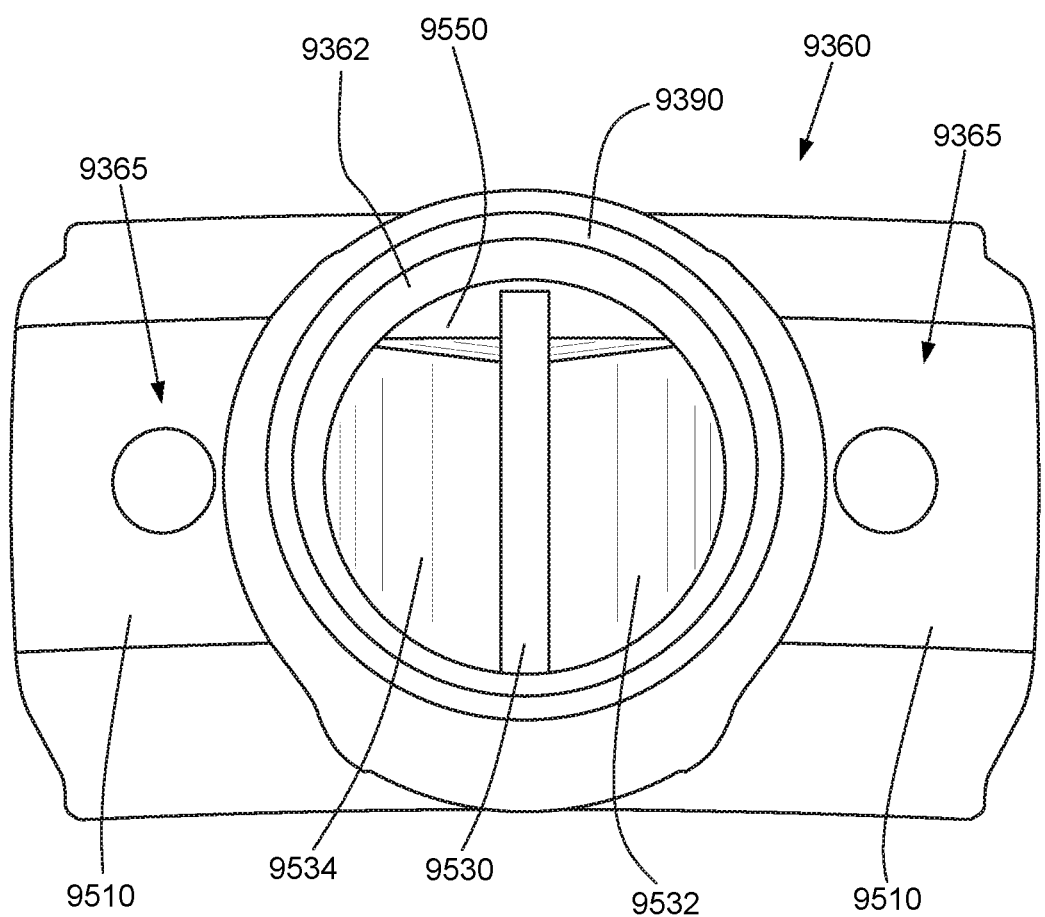

FIG. 41-1 is a top perspective view of the crown connector of FIG. 38.

FIG. 41-2 is a top perspective view of a crown connector according to another example of the present technology.

Figure 42:
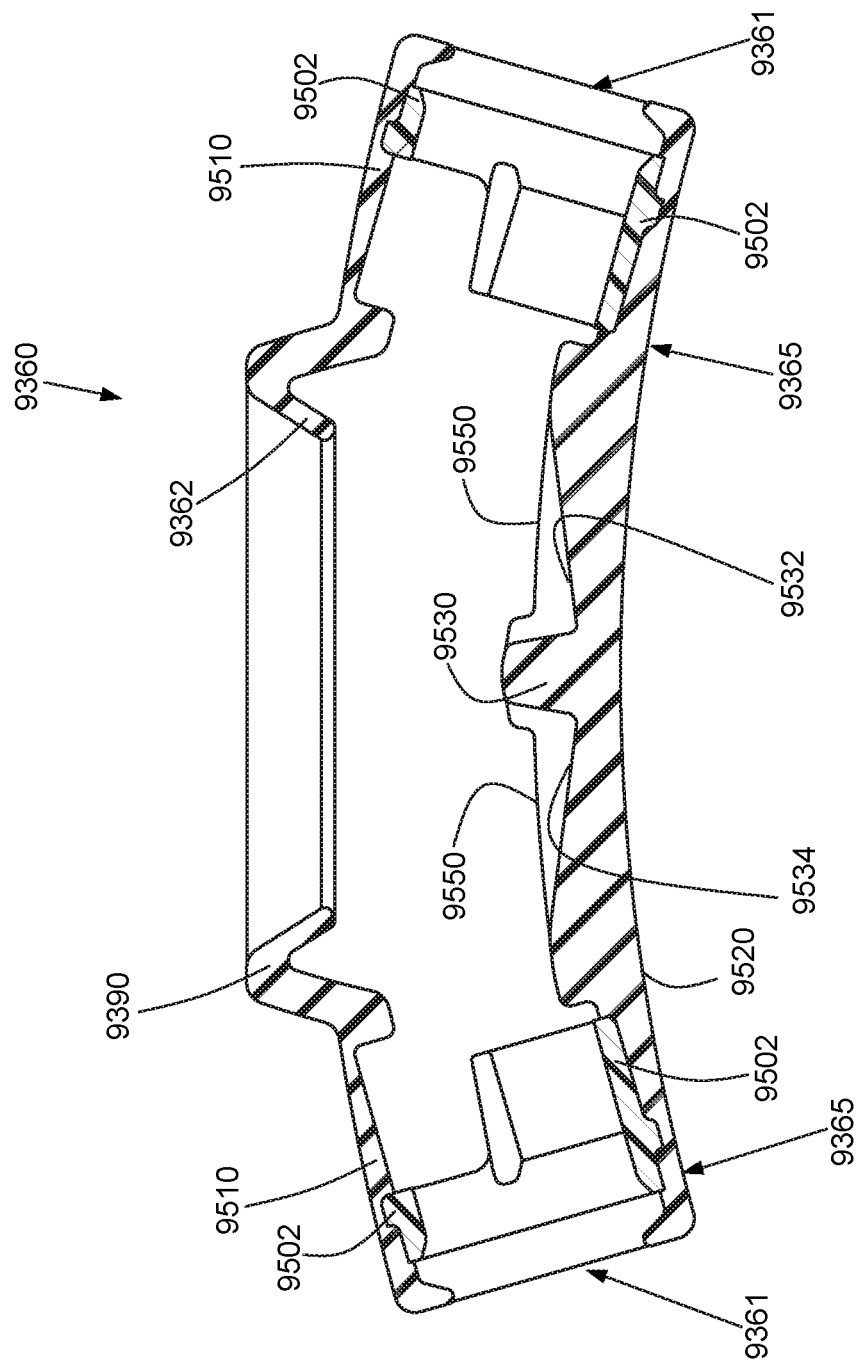

FIG. 42 is a cross-sectional view along the line 42-42 in FIG. 38.

4.4 RPT Device

Figure 43A:
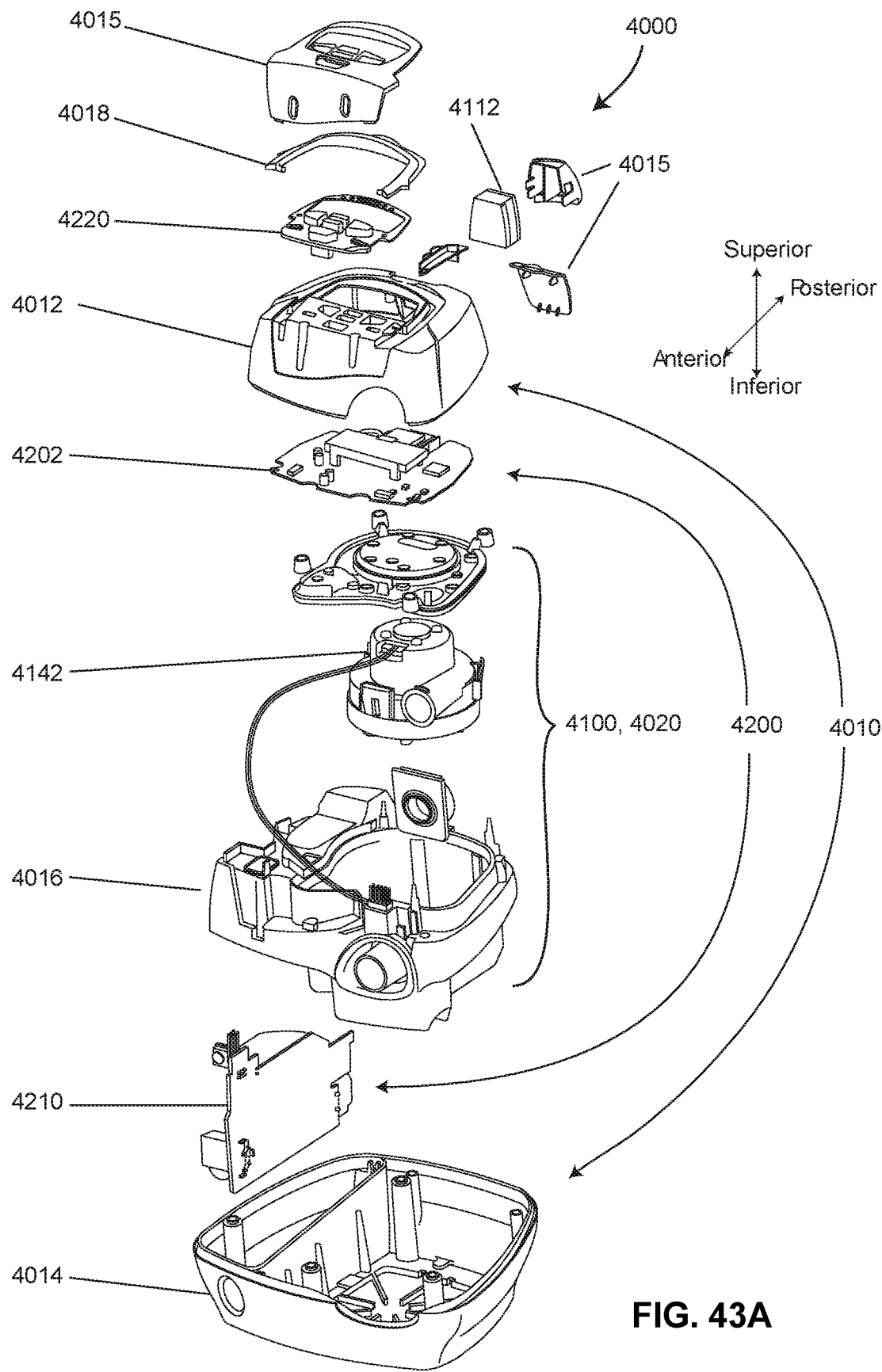

FIG. 43A shows an RPT device in accordance with one form of the present technology.

Figure 43B:
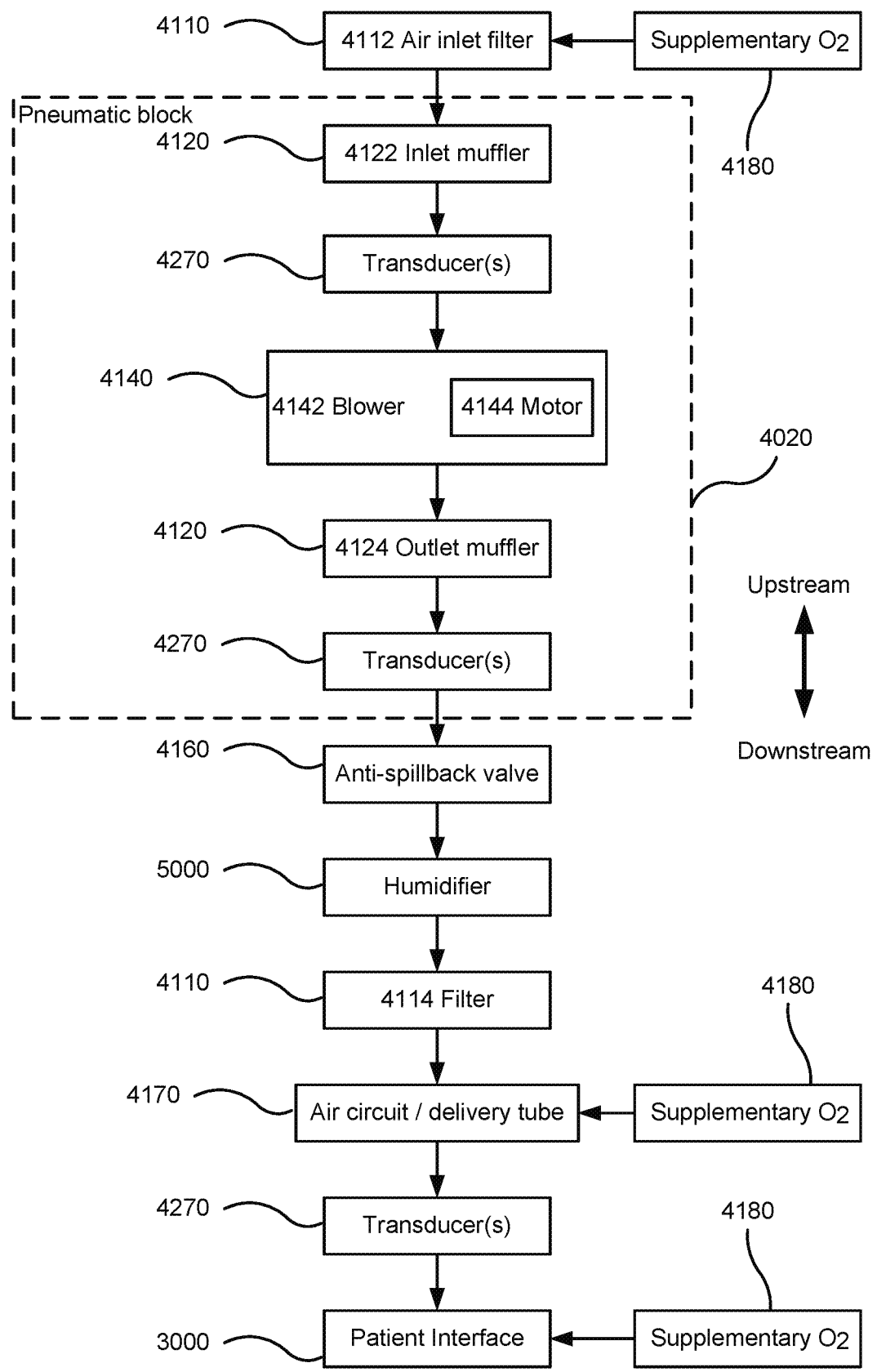

FIG. 43B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 43C:
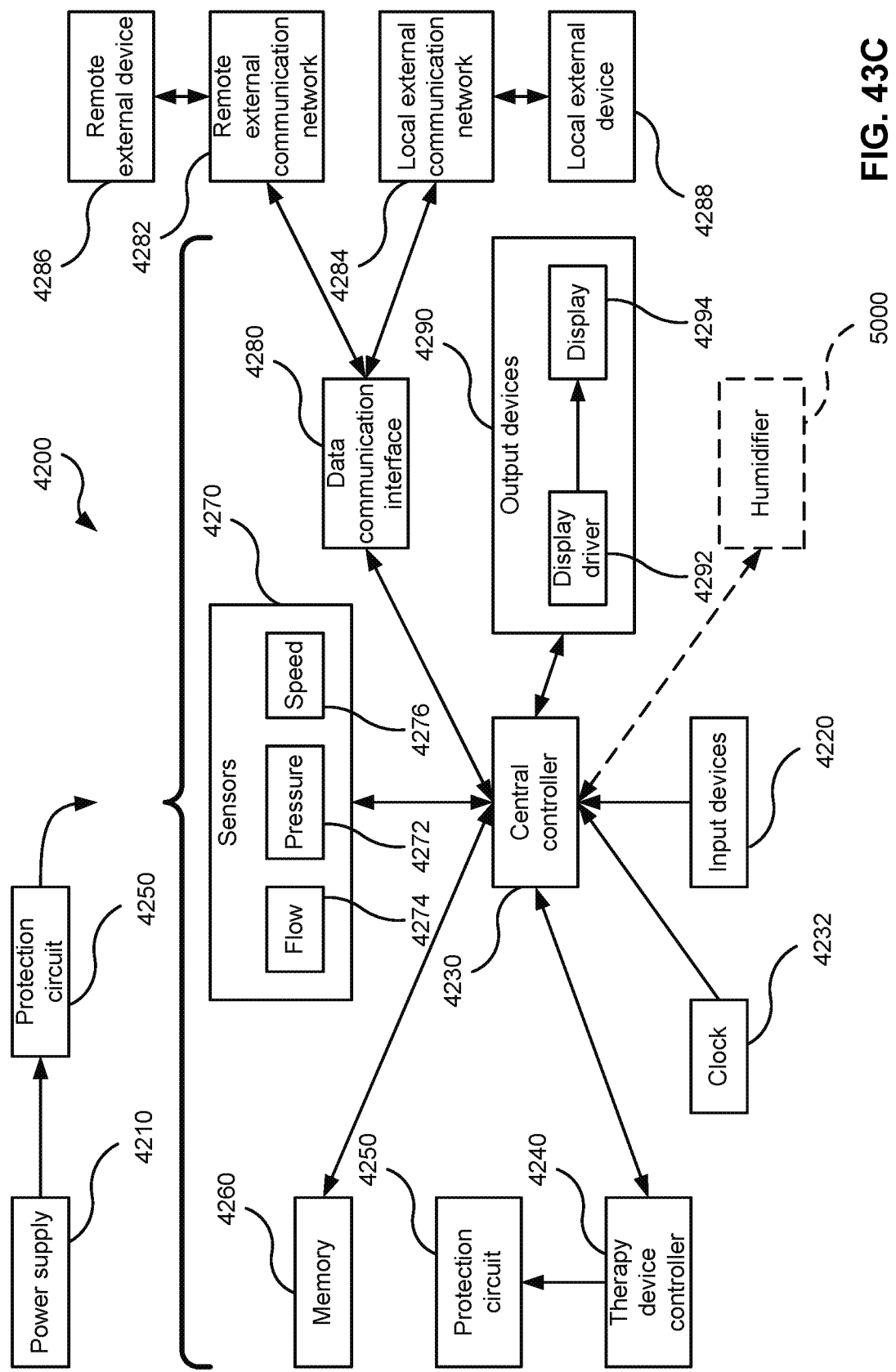

FIG. 43C is a schematic diagram of the electrical components of an RPT device in accordance with one form of the present technology.

4.5 Humidifier

Figure 44A:
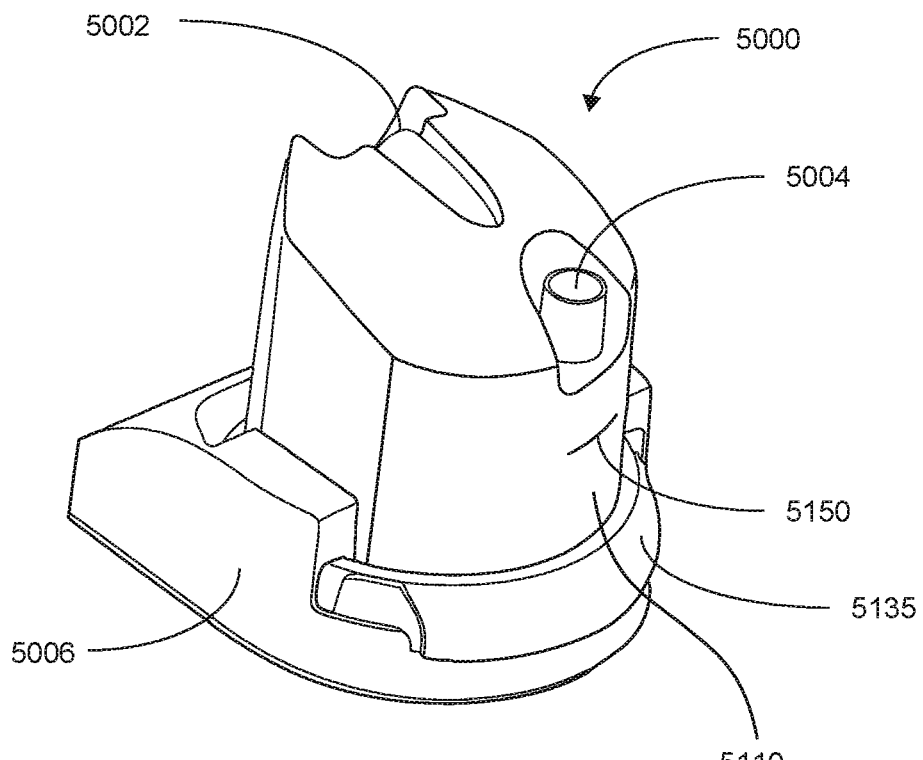

FIG. 44A shows an isometric view of a humidifier in accordance with one form of the present technology.

Figure 44B:
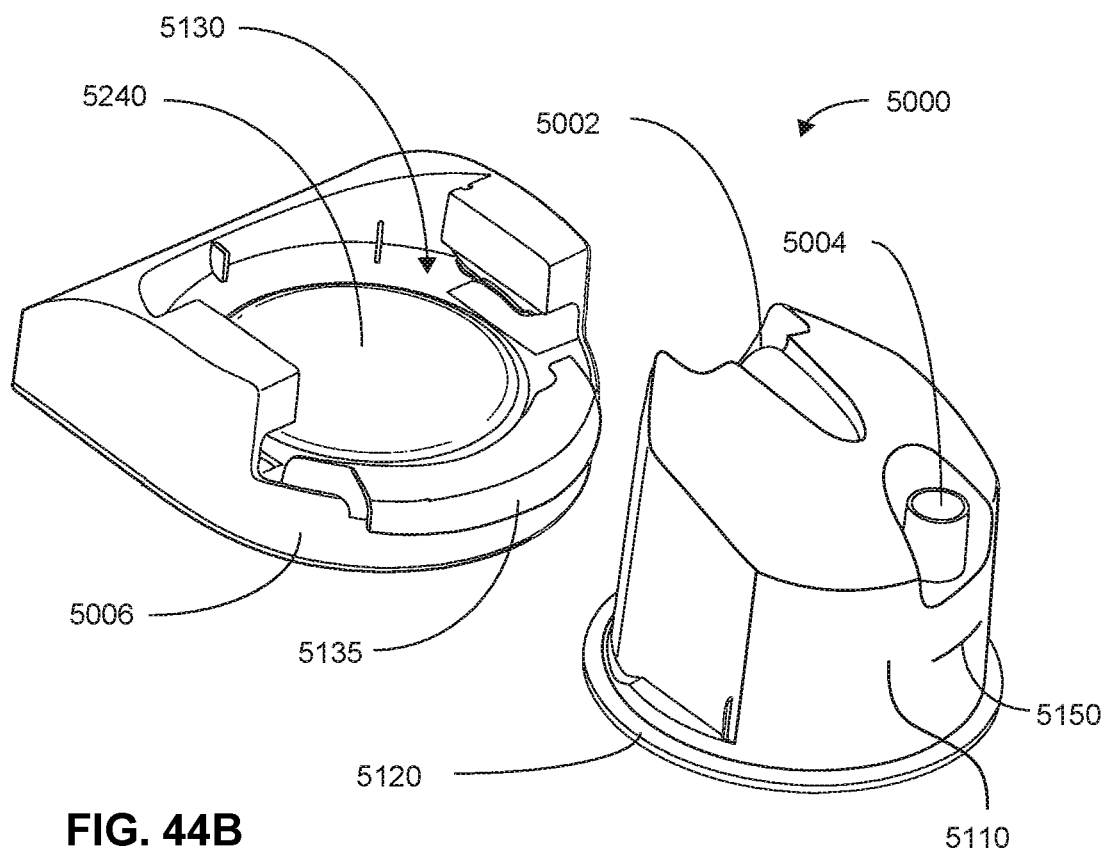

FIG. 44B shows an isometric view of a humidifier in accordance with one form of the present technology, showing a humidifier reservoir 5110 removed from the humidifier reservoir dock 5130.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

With reference to FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function.

The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100. A seal-forming structure 3100 in accordance with the present technology may be constructed from a soft, flexible, resilient material such as silicone or other biocompatible material.

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

The seal-forming structure 3100 may be non-invasive, i.e. does not extend internally of the patient's airways. In some forms of the technology, no part of the seal-forming structure 3100 enters the patient's mouth in use. In some forms of the technology, the seal-forming structure 3100 is configured to leave the patient's mouth uncovered in use. In some forms of the technology, the seal-forming structure 3100 does not cover the patient's eyes in use.

In one form, the seal-forming structure 3100 comprises a sealing flange and a support flange. The sealing flange comprises a relatively thin member with a thickness of less than about 1 mm, for example about 0.25 mm to about 0.45 mm that extends around the perimeter of the plenum chamber 3200. The support flange may be relatively thicker than the sealing flange and the marginal edge of the plenum chamber 3200. And extends at least part of the way around the perimeter. The support flange is or includes a spring-like element and functions to support the sealing flange from buckling in use. In use the sealing flange can readily respond to system pressure in the plenum chamber 3200 acting on its underside to urge it into tight sealing engagement with the face.

In another form, the seal-forming portion of the non-invasive patient interface comprises a pair of nasal puffs or nasal pillows, each nasal puff or nasal pillow being constructed and arranged to form a seal with a respective naris of the nose of a patient. Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the seal-forming structure is configured to form a seal in use with the underside of the nose around the nares and optionally with the lip superior. This type of seal-forming structure may be referred to as a "nasal cradle cushion" or "sub-nasal mask", such as seal-forming structure 3100 of the non-invasive patient interface 3000. The shape of the seal-forming structure may be configured to match or closely follow the underside of the patient's nose, i.e. the profile and angle of the seal-forming structure may be substantially parallel to the patient's naso-labial angle. In one form of nasal cradle cushion, the seal-forming structure comprises a septum member defining two orifices, each of which, in use, supply air or breathable gas to a different one of the patient's nares. The septum member may be configured to contact or seal against the patient's columella in use. In some forms of the technology, the seal-forming structure 3100 is configured to form a seal on an underside of the patient's nose without contacting a nasal bridge region of the patient's nose. A nasal cradle interface 3000 is also shown in FIGS. 4A-4D, 10 and 11, for example. In some examples, patient interface may comprise a seal-forming structure 9100 in the form of a cradle cushion as described in PCT publication WO 2018/176094, filed Mar. 29, 2018, the entire contents of which are incorporated herein by reference.

In one form, the non-invasive patient interface 3000 comprises a seal-forming portion that forms a seal in use on an upper lip region (that is, the lip superior), a nasal bridge region and a cheek region of the patient's face. This is the case, for example, with the patient interface 3000 shown in FIG. 1B. This seal-forming portion delivers a supply of air or breathable gas to both nares of patient 1000 through a single orifice. This type of seal-forming structure may be referred to as a "nasal cushion" or "nasal mask". In some examples of the present technology, the positioning and stabilising structure may be utilised to hold a nasal cushion in sealing position on a patient's face.

In one form the non-invasive patient interface 3000 comprises a seal-forming portion that forms a seal in use on a chin-region, a nasal bridge region and a cheek region of the patient's face. This is the case, for example, with the patient interface 3000 shown in FIG. 1C. This seal-forming portion delivers a supply of air or breathable gas to both nares and mouth of patient 1000 through a single orifice. This type of seal-forming structure may be referred to as a "full-face mask". In some examples of the present technology, the positioning and stabilising structure may be utilised to hold a full-face cushion in sealing position on a patient's face.

In another form the patient interface 3000 comprises a nasal seal-forming structure in the manner of a nasal cushion or nasal cradle cushion and an oral seal-forming structure that is configured to form a seal in use around the mouth of a patient (which may be referred to as a "mouth cushion" or "oral mask"). In such a mask air or breathable gas is supplied in use through separate orifices to the patient's nares and the patient's mouth. This type of seal-forming structure 3100 may be referred to as an "oronasal cushion" or "ultra-compact full face cushion". In one form, the nasal seal-forming structure and oral seal-forming structure are integrally formed as a single component. In some examples, patient interface may comprise a seal-forming structure in the form of a cradle cushion as described in PCT Publication WO2019/183680, filed Mar. 28, 2019, the entire contents of which are incorporated herein by reference. In some examples of the present technology, the positioning and stabilising structure of a patient interface may be utilised to hold an oronasal cushion in sealing position on a patient's face.

In some examples of the present technology, the plenum chamber 3200 has a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure. The seal-forming structure may extend in use about the entire perimeter of the plenum chamber. In some forms, the plenum chamber and the seal-forming structure are formed from a single homogeneous piece of material.

In certain forms of the present technology, the plenum chamber does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber is constructed from a translucent material. The use of a translucent material can reduce the obtrusiveness of the patient interface, and help improve compliance with therapy.

In some forms of the technology, the seal-forming structure 3100 is configured so that the seal-forming structure does not extend below a mental protuberance region of the patient's head in use.

Unless clearly specified otherwise, embodiments of patient interface according to the present technology may comprise any of the above types of seal-forming structures.

5.3.2 Seal-Forming Structure Configuration

In some forms of the present technology, the seal-forming structure 3100 (also referred to as a cushioning structure, conforming structure, or interfacing structure) is constructed of a fabric or textile material. For example, seal-forming structure 3100 may be woven, non-woven, knit, or any other network of fibers. A seal-forming structure 3100 formed from a textile material may increase the comfort and feel of the seal forming structure against the face of a patient. Increased comfort may increase the likelihood that a patient may continue to utilize the apparatus to receive therapy.

These sealing structures may be utilized to form a surface to press against the face of a patient to deliver air to the nose and/or mouth of a patient. Some patients may appreciate the feeling of a textile material against his or her face as opposed to silicone or other material. A sealing structure may be formed using similar techniques and methods as described later in this detailed description with reference to tubes and air delivery system. For example, a cut and seal method may be utilized as well as a laying-up method.

In use, various components may be formed using such a technique. In some forms a mask component of a therapy device may be formed using a lay-up method of manufacturing. In one form, a releasing agent is placed on the mold. Next a layer for use in the mask is placed within the mold. The layer may be formed of various materials. In some forms the layer may be a cloth type material. In other forms, the layer may be plastic, thermoplastic, rubber, silicone or other bendable or pliable material.

Referring to FIGS. 6A and 6B, a seal forming structure that incorporates a textile is depicted. As shown, seal-forming structure 3100 includes sealing layer 3102 and base 3104. Sealing layer 3102 may be secured to base 3104 so that the entire seal-forming structure 3100 may be attached to a receiving receptacle that is attached to a supply conduit such as tube 3350. As shown, sealing layer 3102 includes a pre-defined three-dimensional shape. This pre-defined three-dimensional shape is achieved without the aid of air pressure or additional support structures beyond the material of sealing layer 3102 itself. The pre-defined three-dimensional shape is defined not by the thickness of the material from which sealing layer 3102 is formed, but the geometric positions of the various portions of sealing layer 3102. For example, the material from which sealing layer 3102 bends into various planes, and is configured to maintain its shape within these various planes.

As shown in FIGS. 6A-6E, sealing layer 3102 may be formed to particularly interact and engage with the nasal area of a patient. When worn by a patient the upper surface of sealing layer 3102 may be configured to engage with particular portions of the face of the patient. For example, portions adjacent first naris opening 3108 and second naris opening 3110 may be configured to engage the alar of the patient, whereas saddle region 3109 may be spaced from the columella of the patient. Further, naso-labial sulcus engagement area 3106 may be shaped to engage with the naso-labial sulcus of the patient. Further, seal-forming structure 3100 is configured such that the mouth of the patient is free from obstruction by seal-forming structure 3100 such that the patient is able to breathe through his or her mouth without pressurized air passing through the mouth of the patient. Additionally, as shown in FIGS. 6A-6E, sealing layer 3102 is formed such that sealing layer 3102 does not extend over the bridge of the nose. For example, when used, at least the lateral cartilage portion, nasal bones, and septal cartilage are not covered by sealing layer 3102 (see FIG. 2L).

Although air pressure is not necessary to support the shape of sealing layer 3102 in some forms, portions of sealing layer 3102 may be enhances with air pressure to contribute to a good seal between sealing layer 3102 and the patient's face. For example, in some forms, a concertina-shaped portion of sealing layer 3102 may be formed adjacent base 3104. When pressurized the concertina portion may expand thereby providing additional sealing pressure between sealing layer 3102 and the face of the patient. Further, other portions of sealing layer 3102 may be configured to expand to engage with a particular area of the patients face, for example the nasolabial sulcus.

Sealing layer 3102 may be deformable such that when pressed with a normal amount of force when used with patient interface 3000, sealing layer 3102 deforms. Sealing layer 3102 may conform to the shape of various portions of the face of the patient such that air leakage is minimized Once removed from a patient's face, sealing layer 3102 may resiliently return to its pre-deformed shape. That is, sealing layer 3102 has a 3-dimensional shape when not pressurized that sealing layer 3102 returns to once force is released from sealing layer 3102.

Sealing layer 3102 may be formed of various layers such that sealing layer 3102 is a laminate structure. Each of the layers may impart a particular property to sealing layer 3102. In one form of the present technology, sealing layer 3102 includes thermoplastic or thermoset material. This material is able to maintain a particular shape once cured in such a shape. For example, in one form, sealing layer 3102 may include a thermoset material such as a foam material. This thermoset material may conform to a mold and retain the shape of the mold as shown in FIGS. 7A-7H.

Sealing layer 3102 may be configured to press against particular areas of a nose or nasal area. For example, naso-labial sulcus area 3106 may be configured to press against the naso-labial sulcus region of a patient. Additionally, other areas of sealing layer 3102 may be particularly shaped to correspond to the face of a patient. Sealing layer 3102 includes a first naris opening 3108 and second naris opening 3110 that are configured to align with each naris of a patient. Further, sealing layer 3102 includes a saddle region 3109 that is located between each of the first naris opening 3108 and second naris opening 3110. The saddle region 3109 extends away from the columella of the user when is use such that the material of sealing layer 3102 is spaced from the nose of a patient to increase comfort.

Sealing layer 3102 may also be particularly shaped such that the surface that seals to the patient's face is spaced from base 3104. By spacing sealing layer 3102 from base 3104 a cushioning zone, or a buffer zone between the softer surface of sealing layer 3102 and the hard composition of the base 3104 may be formed. For example, as shown in FIG. 6D, sealing layer 3102 has a height 3111 that spaces the engaging surface of sealing layer 3102 from other components of patient interface 3000. In addition to having a height 3111, as shown throughout the figures, sealing layer 3102 may have various areas that have positive and negative curvatures, saddle regions, and domes, in addition to other configurations. The particular shapes of sealing layer may be formed to engage with the airways of a patient. These particular shapes may be formed using a mold with a complex shape or other technique as described in this detailed description.

In some forms, first naris opening 3108 and second naris opening 3110 may be raised from the surrounding surfaces. That is, in some forms the material around first naris opening 3108 and second naris opening 3110 include flanges 3107 that extend away from the surface of seal layer 3102 toward the nares of a user. By elevating particular areas of seal layer 3102 a better or more secure fit may be achieved over other forms of the technology. For example, first naris opening 3108 and second naris opening 3110 may engage with the nasal walls corresponding to the columella, the alar, or other portions of the nasal opening. The flanges 3107 may provide stability such that the first naris opening 3108 and the second naris opening 3110 may be restricted from moving away from the nasal openings. This alignment provided by first naris opening 3108 and second naris opening 3110 may provide consistent application of oxygen to the patient. In some forms, the shape of the first naris opening 3108 and the second naris opening 3110 may have a substantially frustoconical shape. In other forms, the shape of the openings may not taper as in a frustoconical shape, but rather flanges 3107 may extend vertically. In still other forms, the shape of the openings may be formed to engage with the interior surfaces of the nasal openings. In still other forms, the material around first naris opening 3108 and second naris opening 3110 may be evenly aligned with the surrounding material of sealing layer 3102.

Further, the height or depth of the flanges 3107 of the first naris opening 3108 and second naris opening 3110 may be particularly formed. Some patients may prefer a configuration such that the openings extend a larger distance into the nares of the patient when compared to other patients. The depth of the flanges 3107 of the first naris opening 3108 and the second naris opening 3110 may therefore be adjusted depending on the preference of the patient or the medical professional. The flanges 3107 may be formed in a similar manner as the rest of seal forming structure 3102 in that a foam or thermoset material may be utilized to maintain the shape of the flange even without air pressure or other rigid type of material. The shape of the naris may also depend on the shape of the mold used to form the seal layer 102, as shown in FIGS. 7A-7H.

In some forms, sealing layer 3102 may be particularly arranged to include more rigid and less rigid areas that correspond to particular areas of a patient. Sealing layer 3102 may include more rigid or stiff portions along naso-labial sulcus area 3106 where sealing layer 3102 is configured to engage with the naso-labial sulcus of a patient. This area of the face is less sensitive that other areas of the face and therefore thicker or more rigid portions may be utilized to provide a sturdy structure for sealing. Other areas of sealing layer 3102 may include more floppy or less rigid structures. For example, flanges 3107 of sealing layer 3102 that may contact the columella of a patient may be less rigid so as to not disturb a patient.

In some forms, the rigidity or stiffness of the sealing layer 3102 may be altered or determined by the amount or quantity of membrane material, such as a thermoplastic material that is applied on an interior surface of the sealing layer 3102. In other forms, the rigidity or stiffness of sealing layer 3102 may be determined based on the quantity of material utilized. For example, in some forms, sealing layer 3102 includes bends or folds which increase the thickness or density of sealing layer 3102 at particular locations. By folding the material of sealing layer 3102 in a particular manner, therefore, additional membrane material or support may not be necessary to form rigid areas of sealing layer 3102.

Sealing layer 3102 may be secured to base 3104. Base 3104 may include a clip such that seal-forming structure 3100 is easily removable from a receiving receptacle such as frame 3152 of patient interface 3000 (See, e.g. FIG. 6E). Additionally, base 3104 may be stiffer or more rigid that sealing layer 3102. Base 3104 may therefore resist bending along an edge of sealing layer 3102 such that when sealing layer 3102 of seal-forming structure 3100 is depressed the sides of sealing layer 3102 remain in a secured location.

Additionally, other forms of sealing layer 3102 may be utilized. For example, in some forms a full mask may be utilized rather than sealing structure that only provides air to the nose. In other forms, a mask that provides air solely to the mouth may be utilized. Various configurations may also be utilized. For example, in some forms a single hole or aperture may be utilized rather than separate holes for each naris. Further, in some forms the sealing structure may be designed to accept a nose whereas in other designs the sealing structure may be designed to abut against surfaces of the nose without enveloping or surrounding the nose. Additionally, the masks or sealing structures may be designed for particular comfort. For example, in some forms a nasal mask may be designed such that the tip or pronasale of the patient is spaced from the mask. The pronasale is generally a sensitive area of the nose and therefore designing a mask such that the pronasale is spaced from the mask may increase comfort of a patient.

A cross-section of sealing layer 3102 is depicted in FIG. 6D and an enlarged view of a portion of sealing layer 3102 is depicted in FIG. 6D-1. As shown, membrane layer 3118 is located along an inner surface of sealing layer 3102. Textile sheet 3116 is located along a lower opposite surface of sealing layer 3102. The thickness of membrane layer 3118 may be determined or altered during the manufacturing process depending on the manufacturing requirements. For example, a thicker membrane layer 3118 may provide more rigidity than a thinner membrane layer 3118. A thinner membrane layer 3118 may allow for sealing layer 3102 to be more able to adapt to the face of a patient. In some forms, the thickness of sealing layer 3102 is only determined by the thickness of membrane layer 3118 and textile sheet 3116. That is, in some forms, no other extra components such as rigidizers are used to maintain the shape of sealing layer 3102. For example, sealing layer 3102 may be easily deformable along all portions of sealing layer 3102.

As described previously, naso-labial sulcus engagement area 3107 may have a different thickness of material than adjacent portions of sealing layer 3102. For example, a greater amount of a membrane layer may be applied along the interior surface of sealing layer 3102 at naso-labial sulcus engagement area 3107. This additional material may increase the thickness and rigidity of the naso-labial sulcus engagement area 3107.

In addition to providing structure and support to sealing layer 3102, membrane layer 3118 may also contain air within sealing layer 3102. That is, in some forms, membrane layer 3118 may prevent air from passing through the material of sealing layer 3102. Membrane layer 3118 may therefore direct or air from a therapy device to the naris openings of sealing layer 3102 and to the patient. Further, as described later in other forms, sealing layer 3102 may be designed to allow for particular leak rates such that a separate bleed or leak valve may not be necessary. This feature may therefore reduce the costs of manufacturing by removing a component from therapy device.

In some forms, membrane layer 3118 may be a meltable material such as a thermoplastic material or thermoset material. This material may be able to assume a shape when melted into a mold or other form. As detailed later in this specification and shown in FIGS. 7A-7H membrane layer 3118 may be melted or partially melted (for example, tacky) such that the material is able to conform to a particular shape. Once the membrane layer 3118 is melted, it is allowed to cure to shape (such as the shape of a mold). Once cured, membrane layer 3118 assumes the shape of the mold such that membrane layer 3118 has a predetermined shape. Membrane layer 3118 imparts that shape onto whatever material membrane layer 3118 is laminated or adhered to. For example, membrane layer 3118 may cause textile sheet 3116 to assume the same shape as membrane layer 3118 because membrane layer 3118 is secured with textile sheet 3116 as is able to conform to various shapes. Textile sheet 3116 may also include such characteristics such that textile sheet 3116 includes portions that may be meltable and then conformable to a shape. The amount of pressure required to temporarily alter the shape of the laminate of sealing layer 3102 may depend on the thickness of membrane layer 3118 and from what material membrane layer 3118 is formed.

In some forms of the present technology, membrane layer 3118 may be formed of a thermoset material. Additionally, sealing layer 3102 may include an additional laminated layer that is formed of a thermoset material. An example of a thermoset material is a foam. The laminate with the thermoset material can be placed in a mold and then subjected to heat. The thermoset material may be cured in a similar manner to the thermoplastic material. That is, the thermoset material may be subjected to heat, and, unlike thermoplastic materials, the thermoset material may irreversibly cure to a particular shape. The thermoset material may be used if a more rigid or permanent structure as desired. The flexibility and stiffness of the component, such as sealing layer 3102 may be adjusted based on the material selected and thickness of the thermoset material. Because the thermoset material can be cured to a particular shape, when used as a laminate with sealing layer 3102, the shape of sealing layer 3102 may also be formed to a particular shape.

Referring to FIG. 4P, sealing layer 3102 along with base 3104 and frame 3152 may be incorporated into a mask and air delivery system for use with a therapy. As shown, base 3104 may be attached to assembly connection port 3154. Assembly connection port 3154 may provide air distribution to sealing layer 3102 through tube 3350.

Sealing layer 3102 may be lighter than other forms of the technology and also may be more comfortable to a patient than other forms of the technology. Further, because textile sheets such as textile sheet 3116 may be stored in a flat or planar manner, the storage costs for the materials may be less than other forms. Additionally, use of mold 3112 (see FIGS. 7A-7G) may permit complex shapes to be formed such as sealing layer 3102 while reducing costs. Rather than utilizing injection molding or extrusion molding that requires multiple complex pieces and machinery, the laying up process that includes a mold such as mold 3112 provides a simple process that may reduce manufacturing time as well as costs. Additionally, complex shapes may be formed with relative ease.

Further, in some forms, membrane layer 3118 utilized in forming sealing layer 3102 may be the same material as utilized in forming textile tubing as described later in this detailed description. By using the same material, production costs for various components may be reduced because a large quantity of material may be able to be purchased in bulk.

Referring to FIG. 4Q, a possible assembly of a portion of a tube that is configured to interact with sealing-forming structure 3100 is depicted. As shown, assembly connection port 3154 is secured between layers of the tube. Assembly connection port 3154 is sandwiched between an inner textile layer 3452 and outer textile layer 3454. Further, assembly connection port 3154 extends through exterior foam layer 3456. In this configuration, a air passageway or air conduit is formed between inner textile layer 3452 and outer textile layer 3454 such that assembly connection port 3154 is used to transfer air from the air passageway and through exterior foam layer 3456. In this manner assembly connection port 3154 is secured by inner textile layer 3452 and outer textile layer 3454. Connection port 3154 may then be snap fitted, friction fit, or otherwise secured to frame 3152 to provide air to the patient.

5.3.2.1 Method of Forming Seal Forming Structure

Referring to FIGS. 7A-7J one method of forming a sealing structure is shown. In FIG. 7A, mold 3112 includes accommodating portion 3114. Accommodating portion 3114 may be in the shape of a sealing surface used in conjunction with a full face, nose, or other mask as utilized with a therapy device.

Referring to FIGS. 7B and 7C, a textile sheet 3116 is placed over mold 3112. Textile sheet 3116 may be formed of materials as such as cotton, polyester, rayon, or other materials or a combination of materials. Further, the configuration of textile sheet 3116 may also be formed in the same type of configuration as with respect to sheets described in detail below such as inner layer 3352 and outer layer 3426. That is, textile sheet 3116 may be woven, non-woven, knit, braided, or any other network of fibers. Although not depicted in FIGS. 7A-7H as including a textile membrane before being placed in accommodating portion 3114 of mold 3112, in other forms textile sheet 3116 may include a textile membrane. In still further forms, textile sheet 3116 may be pre-laminated with textile sheet 3116 such as with polyurethane or silicone.

After arranging textile sheet 3116 along mold 3112, textile sheet 3116 may be pressed into place within accommodating portion 3114. In some forms, a roller may be used to ensure that textile sheet 3116 is in the correct position as depicted in FIGS. 7C and 7D. In other forms, a vacuum seal may be utilized that pulls textile sheet 3116 toward accommodating portion 3114. In still other forms, another form may be utilized that presses textile sheet 3116 into accommodating portion 3114.

Once textile sheet 3116 is in place, as shown in FIG. 7E, a membrane material may be placed along an upper surface of textile sheet 3116. Membrane layer 3118 may be thermoplastic or thermoset material, silicone, polyurethane, or other material. The material of membrane layer 3118 may be sprayed on as depicted, may be painted or spread on, or may be pre-laminated on textile sheet 3116. Membrane layer 3118 may be a resin or other material that cures or solidifies through a chemical process or by exposure to air. As shown, membrane layer 3118 is a liquid thermoset material. Membrane layer 3118 is spread along the upper surface covering surfaces as required by the manufacturer. In some forms, the entire upper surface of textile sheet 3116 may not be covered. That is, in some instances, portions of textile sheet 3116 may remain uncovered to provide easier attachment or securement with other components. Further, in other forms, textile sheet 3116 may be a laminate and already include a surface that is formed of a membrane material.

Further, membrane layer 3118 may be thicker in some areas when compared to other areas. Membrane layer 3118 may be administered at different rates in a liquid form to provide different thicknesses. Further, membrane layer 3118 when formed as an independent solid layer, may be pre-manufactured to have thicker regions in some areas (for example, naso-labial sulcus engagement area 3107) than other areas (for example, flanges 3107).

Referring to FIG. 7F, membrane layer 3118 and textile sheet 3116 may be exposed to heat. The heat may melt membrane layer 3118 if membrane material has solidified and may also allow membrane layer 3118 to be consistently spread or layered along textile sheet 3116. In other forms, membrane layer 3118 may be allowed to solidify after the step shown in FIG. 7E, without adding any additional heat to the system.

After membrane layer 3118 has solidified, textile sheet 3116 along with the cured membrane layer 3118 is removed from mold 3112 as shown in FIG. 7G. Textile sheet 3116 that was located within accommodating portion 3114 now assumes the shape of accommodating portion 3114 even when removed from accommodating portion 3114. Because membrane layer 3118 is a thermoset material that is curable to a particular shape, sealing layer 3102 also assumes the same shape as membrane layer 3118.

As shown in FIG. 7H, sealing layer 3102 is cut away from the rest of textile sheet 3116. As depicted, sealing layer 3102 is cut away using scissors or shears, however in other forms sealing layer 3102 may be cut using other techniques or devices such as die-cut. In a non-limiting example, in some forms a hot knife may be used to cut away sealing layer 3102. In other forms, a stamp may be utilized to cut through textile sheet 3116.

As shown (See FIGS. 6A-6C), first naris opening 3108 and second naris opening 3110 may be formed within sealing layer 3102. First naris opening 3108 and second naris opening 3110 may be formed within accommodating portion 3114. That is, accommodating portion 3114 may be shaped such that peaks or valleys are utilized to affect the topography of the accommodating portion 3114. By altering the shape of accommodating portion 3114 various shapes of sealing layer 3102 may be possible.

In some forms, textile sheet 3116 may be pre-cut along the areas of accommodating portion 3114 that correspond with first naris opening 3108 and second naris opening 3110. In other forms, once cured, the material of sealing layer 3102 may be cut away in the area in which first naris opening 3108 and second naris opening 3110 are to be located. Additionally, other post-processing may be performed on sealing layer 3102 after sealing layer 3102 is removed from mold 3112.

In some forms, textile sheet 3116 may be pre-cut prior to placing textile sheet 3116 over mold 3112. In such forms the number of folds within sealing layer 3102 of seal-forming structure 3100 may be reduced when compared to other forms. For example as shown in FIG. 7I, textile sheet 3116 is cut to form pre-cut sheet 3117. Pre-cut sheet 3117 includes various notches 3120. These notches 3120 are particularly formed such that when pre-cut sheet 3117 is placed within mold 3112 the material of pre-cut sheet 3117 is able to fold and not overlap with itself. That is, pre-cut sheet 3117 may be able to form abutting joints as opposed to overlapping joints. This may improve comfort and feel to the user. As shown in FIG. 7I for example, notch 3122 is formed between first flap 3124 and second flap 3126 of pre-cut sheet 3117.

The length of first flap 3124 and second flap 3126 may be used to determine the height 3111 of the sealing layer 3102.

Referring now to FIG. 7J, after sheet 3117 has been placed in a mold and cured with a membrane, the first flap 3124 and second flap 3126 may be folded upwards in accordance with the mold shape. When folded, first flap 3124 and second flap 3126 may abut each other in the area of notch 3122. Based on the geometry of sealing layer 3102, the shape and size of notch 3122 may be altered to allow for various designs and configurations. As shown in FIG. 7J, first flap 3124 and second flap 3126 do not overlap one another. In other forms, however, the flaps may be designed to overlap each other to provide increased stiffness in particular areas (for example, naso-labial sulcus engagement area 3107).

The configuration as shown in FIGS. 7I and 7J may provide for a smooth inner and outer surface of sealing layer 3102. Further, by cutting textile sheet prior to molding, the quantity of time used to arrange the textile sheet within the mold may be reduced when compared to other forms in which the textile sheet may be folded to fit within the mold.

5.3.3 Positioning and Stabilising Structure

The seal-forming structure 3100, 9100 of the patient interface 3000, 6000, 7000, 8000, 9000, 10000 of the present technology may be held in sealing position in use by the positioning and stabilising structure 3300, 7300, 8300, 9300. The positioning and stabilising structure may include or be referred to as "headgear" since it engages the patient's head in order to hold the patient interface in a sealing position.

In one form the positioning and stabilising structure provides a retention force at least sufficient to overcome the effect of the positive pressure in the plenum chamber 3200, 9200 to lift off the face.

In one form the positioning and stabilising structure provides a retention force to overcome the effect of the gravitational force on the patient interface.

In one form the positioning and stabilising structure provides a retention force as a safety margin to overcome the potential effect of disrupting forces on the patient interface, such as from tube drag, or accidental interference with the patient interface.

In one form of the present technology, a positioning and stabilizing structure is provided that is configured in a manner consistent with being worn by a patient while sleeping. In one example the positioning and stabilising structure has a low profile, or cross-sectional thickness, to reduce the perceived or actual bulk of the apparatus. In one example, the positioning and stabilising structure comprises at least one strap having a rectangular cross-section. In one example the positioning and stabilising structure comprises at least one flat strap.

In one form of the present technology, a positioning and stabilising structure is provided that is configured so as not to be too large and bulky to prevent the patient from lying in a supine sleeping position with a back region of the patient's head on a pillow.

The positioning and stabilising structure may comprise at least one tie. A tie will be understood to be a structure designed to resist tension. In use, a tie is part of the positioning and stabilising structure that is under tension. Some ties will impart an elastic force as a result of this tension, as will be described. A tie may act to maintain the seal-forming structure in a therapeutically effective position on the patient's head. In certain forms of the present technology, the positioning and stabilising structure may comprise ties in the form of headgear tube and/or headgear straps, as will now be described.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone. The first tie may be provided, for example, as part of a patient interface that comprises a cradle cushion, nasal pillows, nasal cushion, full-face cushion or an oronasal cushion. For example, the positioning and stabilising structures may comprise a first tie in the form of gas delivery tubes which lie over the top of the patient's head. The gas delivery tubes may also be known as headgear tubes as they provide functions of headgear.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head. The second tie may be provided, for example, as part of a patient interface that comprises a cradle cushion, nasal pillows, full-face cushion, nasal cushion or an oronasal cushion. For example, the positioning and stabilising structures may comprise a second tie in the form of a strap that lies against posterior surfaces of the patient's head.

In one form of the present technology suitable for a nasal-only mask or for a full-face mask or oronasal mask, the positioning and stabilising structure includes a third tie that is configured to anchor against posterior surfaces of the patient's neck. Additionally, in some forms the positioning and stabilising structure comprises a fourth tie that is constructed and arranged to interconnect the second tie and the third tie to reduce a tendency of the second tie and the third tie to move apart from one another.

In certain forms of the present technology, a positioning and stabilising structure comprises a strap that is bendable and e.g. non-rigid. An advantage of this aspect is that the strap is more comfortable for a patient to lie upon while the patient is sleeping. The positioning and stabilising structures may comprise a strap that is bendable. The strap may be considered a backstrap. The strap is sufficiently flexible to pass around the back of the patient's head and lie comfortably against the patient's head, even when under tension in use.

In certain forms of the present technology, a positioning and stabilising structure comprises a strap constructed to be breathable to allow moisture vapour to be transmitted through the strap.

In certain forms of the present technology, a system is provided comprising more than one positioning and stabilizing structure, each being configured to provide a retaining force to correspond to a different size and/or shape range. For example the system may comprise one form of positioning and stabilizing structure suitable for a large sized head, but not a small sized head, and another suitable for a small sized head, but not a large sized head.

In certain forms, the positioning and stabilizing structure may include a gas delivery tube to convey pressurized breathable gas to a patient's airways via a mask interface (e.g., cushion module) and therefore may be referred to as "conduit headgear."

Referring to FIG. 4B, for example, a patient interface is shown. As shown, patient interface 3000 includes gas delivery tube depicted as tube 3350 that extends around the head of the patient along the parietal bone, above the ear and to the seal-forming structure 3100. Tube 3350 may deliver air to seal-forming structure 3100 and support seal-forming structure 3100 in place. Therefore, tube 3350 may be utilized as both a support structure as well as an air conduit. For example, in other forms, a separate tube, such as air delivery tube 3348 may be directly attached to seal-forming structure 3100 and not extend around the head of the patient. In such forms the tube is not supported by the head of the patient, and the tube also does not provide support to the sealing structure. Such forms also include a separate strap for support the sealing structure.

Patient interface 3000 includes head strap 3420 that is attached to tube 3350 of patient interface 3000. Head strap 3420 may be utilized to support tube 3350 as well as assist in providing correct positioning of patient interface 3000. Head strap 3420 may provide tension upon tube 3350 so that tube 3350 does not fall forward or anterior the face of the patient during normal use. Additionally, head strap 3420 may work in conjunction with tube 3350 to provide sufficient upward force to sealing structure 3100 to assist in maintaining sealing structure 3100 in correct position with respect to the face of the patient such that the sealing layer 3102 adequately seals to the air opening of the patient. Therefore, stabilizing structure 3300 may comprise at least tube 3350 as well as head strap 3420.

In some forms, head strap 3420 may be directly and permanently attached to tube 3350. That is, removing head strap 3420 from tube 3350 would damage either or both of head strap 3420 and tube 3350. As shown in FIG. 5A, head strap 3420 is directly attached to tube 3350 between an inner and outer layer of tube 3350. In some forms, head strap 3420 does not require stitching. For example, in some forms, head strap 3420 is sandwiched between the inner and outer layer of tube 3350 and the area is subjected to heat. The inner and outer layer of tube 3350 may include a thermoplastic or thermoset material that is altered when subjected to heat. Therefore, when heated, the material may melt or soften such that the material interacts with head strap 3420 and when the material solidifies the head strap 3420 is secured between the tabs of tube 3350. In other forms, the head strap 3420 may include removably attachable portions, such as hook and loop fasteners. In such forms the tube 3350 may include a slot through which head strap 3420 may pass. Then a patient may adjust the fit of patient interface 3000 by displacing the tabs of head strap 3420 and securing the strap in place. In other forms, a adjustable string, or rope, or line may be utilized to fit patient interface 3000 comfortably on the head of the patient.

As shown, the seal-forming structure 3100 extends to the nose of the patient while leaving the mouth free from obstruction. Some patients may prefer a patent interface that includes a particular type of mask, such as depicted in FIGS. 4A-4D, so that the patient may be able to converse while receiving therapy. Other patients may prefer a full mask or a mask that encompasses the mouth depending on need or comfort. Various forms of the present technology may be utilized depending on the particular usage of the patient. Although depicted as a nasal mask, full face masks may also be utilized.

In some forms the sealing structure includes a base 3104 so that seal-forming structure 3100 may be removably attached to a frame 3152. Base 3104 may include a clip mechanism so that seal-forming structure 3100 is able to be attached to frame 3152 (See FIG. 4P). Frame 3152 may include attachment points or locations to which tube 3350 is attachable. Therefore, air may enter into frame 3152 and then pass to seal-forming structure 3100 and finally to the patient.

In other forms, different frames may be utilized. For example, in some forms, the frame may include various slots or attachment points such that the frame is able to interact with straps such as straps from head strap 3432. For example, although not shown in FIG. 4A, a frame may include a forehead support that includes slots for interacting with a strap. Additionally, as depicted in FIG. 5F lower slots adjacent to a structure such as seal-forming structure 3100 may be utilized to interact with a head strap and allow for adjustable fit of the head gear or stabilizing structure 3300.

In one form of the present technology, a positioning and stabilising structure 3300, 7300, 8300, 9300 is provided with a decoupling portion located between an anterior portion of the positioning and stabilising structure, and a posterior portion of the positioning and stabilising structure. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure and disrupting the seal.

In one form of the present technology, a positioning and stabilising structure comprises a strap constructed from a laminate of a fabric patient-inner layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

5.3.3.1 Positioning and Stabilising Structure According to Examples of the Present Technology 5.3.3.1.1 Headgear Tubing In the form of the present technology illustrated in FIG. 4B, the patient interface 3000 includes at least one tube 3350 that delivers pressurized air received from a conduit such as air delivery tube 3348 forming part of the air circuit 4170 from the RPT device to the patient's airways. For example, through the plenum chamber 3200 and seal-forming structure 3100. The tube 3350 is an integral part of the headgear 3300 of patient interface 3000 to position and stabilize the seal-forming structure 3100 of the patient interface to the appropriate part of the patient's face (for example, the nose and/or mouth). This allows air delivery tube 3348 that provides the flow of pressurized air to connect to a connection port 3600 of the of the patient interface in a position other than in front of the patient's face, which may be unsightly to some people.

Since air can be contained and passed through tube 3350 in order to deliver pressurized air from the air circuit 4170 to the patient's airways, the positioning and stabilizing structure 3300 may be described as being air tight or air retaining. It will be understood that an air tight or air retaining positioning and stabilizing structure 3300 does not require all components of the positioning and stabilizing structure 3300 to be air tight.

In certain forms of the present technology, the patient interface 3000 may comprise a connection port 3600 located proximal a top, side or rear portion of a patient's head. For example, in the form of the present technology illustrated in FIG. 4B, the connection port 3600 is located on top of the patient's head when in use. Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may also cause a problem known as tube drag, wherein the conduit may provide an undesired drag force upon the patient interface thereby causing dislodgement away from the face.

In the example of FIGS. 4A, 4B-4D, the at least one tube 3350 extends between the cushion assembly 3150 from the connection port 3600 across the patient's cheek region and above the patient's ear, i.e. a portion of tube 3350 that connects to cushion assembly 3150 overlays a maxilla region of the patient's head in use and a portion of tube 3350 overlays a region of the patient's head superior to the otobasion superior of the patient's head. Additionally, in some forms such as shown in FIGS. 4A, and 4B-4D, tube 3350 is located along both sides of the face of a user. That is, for example, tube 3350 extends across a right and left cheek region of the patient.

In the form of the present technology illustrated in FIG. 4B, the positioning and stabilising structure 3300 comprises a single tube 3350, that includes a right and left portion, each portion being positioned in use on different sides of the patient's head and extending across the respective cheek region, above the respective ear (superior to the otobasion superior on the patient's head) to the connection port 3600 on top of the patient's head. The form of technology may be advantageous because, if a patient sleeps on the side of their head and one of the tubes in compressed to block or partially block the flow of gas along the tube, the other tube remains open to supply pressurised gas to the patient. In other embodiments of the technology, the patient interface may comprise a different number of tubes, for example one tube, or three or more tubes.

As depicted in FIG. 4B the patient interface has one tube 3350. The single tube 3350 is positioned on one side of the patient's head in use (e.g. across one cheek region) and head strap 3420 forms part of the positioning and stabilising structure 3300 and is positioned on the other side of the patient's head in use (e.g. across the other region) to assist in securing the patient interface 3000 on the patient's head. As shown, tube 3350 extends continuously from one side of cushion assembly 3150 to connection port 3600 and back to the other side of cushion assembly 3150.

As depicted in FIG. 4B, left arm 3302 and right arm 3304 are connected to each other in a continuous manner That is, there are no specific connection points between left arm 3302 and right arm 3304. Rather, the fluid connection extends seamlessly between the two arms. By forming tube 3350 continuously, the number of components of patient interface 3000 may be reduced when compared to other forms of the present technology.

In the exemplary form of the technology illustrated in FIGS. 4A-4D tube 3350 curves around the upper part of the patient's head from the upper end of tube 3350 that includes connection port 3600 on top of the head to tab 3346, the point at which the rear headgear strap 3420 connects to the tube 3350 substantially without any curvature in the coronal plane. In between tab 3346 at which the rear headgear strap 3420 connects to the tubes 3350 and the lower ends of the tube 3350 where tube 3350 connects with the cushion assembly 3150 in front of the patient's airways under the nose, the tube 3350 curves forward or anterior between the patient's ears and eyes and across the cheek region. The radius of curvature of this section of the tubes 3350 may be in the range 60-100 mm, for example 70-90 mm, for example 80 mm. The lower end of the tubes 3350 and the section of the tubes 3350 at which the rear headgear strap 3420 connects to the tubes 3350 may subtend an angle in the range 65-90°, for example 75-80°.

In the exemplary form of the technology illustrated in FIGS. 4A-4D, tube 3350 extends substantially vertically in the superior direction (i.e. upwards) from proximate the otobasion superior to connection port 3600. That is, tube 3350 angles between 0 degrees and 15 degrees to the coronal plane in an area between the otobasion superior and connection port 3600. In other forms the angle may be greater depending on the positioning by the patient. Additionally, tube 3350 is formed such tube 3350 has a greater angle with respect to the sagittal plane from the otobasion superior to airway of the patient.

Further, as shown in FIG. 4B-4D, tube 3350 includes connection port 3600. Connection port 3600 may be located partially within tube 3350. That is, a portion of connection port 3600 extends through outer layer 3354 and between outer layer 3354 and inner layer 3352 of tube 3350. In this manner, connection port 3600 is sandwiched between the layers of tube 3350. Connection port 3600 may be configured to connect to other tubes such as air delivery tube 3348 of a therapy device that provide air flow from air circuit 4170. In some forms, air delivery tube 3348 may form all of air circuit 4170 whereas in other forms air delivery tube 3348 forms a portion of air circuit 4170. Air delivery tube 3348 may be formed of various materials, including textile materials, silicones, and other materials. By integrating connection port 3600 within tube 3350, the quantity of seams or connection points along tube 3350 may be diminished when compared to other forms of the present technology. Further, by integrating connection port 3600 within tube 3350 the use of additional connecting mechanisms such as adhesives, fasteners, or other additional mechanism features may be minimized or removed. In other forms, connection port 3600 includes an inner portion and an outer portion. The inner portion may be located between inner layer 3352 and outer layer 3354. The outer portion interacts with the inner portion such that outer layer 3354 is sandwiched between the inner portion and outer portion of connection port 3600.

In some forms textile is used to form various components of stabilizing structure 3300. As depicted, tube 3350 is formed of a textile material. Some patients may find silicone tubes uncomfortable during use when the tubes rest against the face of the patient. Additionally, patients may also find silicone tubes uncomfortable even when a sleeve or sock of textile material is placed over the silicone tube. The thickness and weight of the silicone tubes may cause a patient to stop use of the device. Further, when a patient lays on his or her head, the silicone tube may crease or bend such that the thickness of the tube is easily felt on the face of the patient, even when covered with a textile sleeve. A textile conduit or tube such as tube 3350 may increase comfort to some patients.

The textile material may be a flat planar sheet of material, or the textile material may be formed with a three dimensional configuration such that the textile material has a positive or negative curvature. As used in this specification "textile material," or a "textile" may be used to describe any network of fibers. For example, a textile material or textile may be woven, non-woven, knit, braided, or any other form of a network of fibers. Different configurations of textile materials may be utilized for different properties. For example, a woven configuration may be utilized for particular strength laterally and longitudinally, whereas a knit structure may be utilized for flexibility and stretchability. Further, in some forms, the textile material may combine different configurations to achieve particular properties. Additionally, the density of the material may be varied depending on the various properties desired. For example, if greater stretch is desired, a less dense network of fibers may be utilized.

Further, a textile may be formed of various materials. A textile may be formed of natural or synthetic materials. Some examples include cotton, rayon, polyester, linen, silk, leather, polyurethane, monofilament or multifilament materials may be used, or any combination of the materials, in addition to other materials. A material may be selected based on the feel, texture, rigidity, flexibility, extensibility as well as other factors. In addition, a textile may include both natural and synthetic materials. Natural fibers or strands, such as cotton, may be utilized to provide a soft feel and comfortable fit to a patient. A synthetic fiber may be used to provide rigidity or strength to particular areas of the textile as well as for other properties.

In some forms of the present technology, different material may be utilized within the same textile material. Different materials may be utilized to provide particular properties to the textile component. For example, a stretchable fiber, strand, or yarn, may be included within a textile at a particular orientation to provide strength along a longitudinal or first direction. A second fiber that is substantially un-stretchable, inextensible, or stretch resistant may be included within the textile along a lateral or second direction. In this manner the textile may be an anisotropic material that has different properties in various directions to provide support to the particular component. For example, a tube may be formed with a textile material. The textile material may be formed such that in a first direction the textile material is configured to expand or stretch when subjected to pressure. In a second direction that is different from the first direction the textile material may be configured to resist stretching or deforming when subjected to pressure or force. For example, a tube may be configured such that the textile material expands radially when subjected to air pressure. This stretching may allow for the tube to accept or receive air and also allows the tub to be comfortable against a patient. The tube, however, may have a particular longitudinal orientation along the face of a patient such that it is undesirable for the tube to stretch in a longitudinal direction. By securing or restricting stretch in the longitudinal direction, the positioning of the tube may be able to be maintained to allow a patient to receive consistent therapy.

In some forms, a textile tube may be formed of one or more sheets or layers of textile material. In some forms a single sheet may be folded or rolled and secured to itself along the lateral edges of the sheet such that a tube is formed with a single seam. In other forms more than one sheet is utilized. For example, the textile tube may be formed with a first side that is configured to contact the patient. This may be referred to as the inner layer. The textile conduit may also include a second side that is attached to the inner layer, but faces away from the patient that may be referred to as the outer layer. The inner layer and the outer layer may each be secured to each other along the edges of the inner layer and the outer layer such that a channel or passageway is formed between the seams of the inner layer and the outer layer. That is, the space between the seams remains unattached.

As discussed in this detailed description, each of the inner layer and the outer layer includes an interior surface and an exterior surface. The interior surface of the inner layer is the surface that faces the exterior layer. The interior surface of the exterior layer is the surface that faces the interior layer. Likewise, the exterior surface of the outer layer faces away from the interior layer and the exterior surface of the inner layer faces away from the outer layer. Further, in forms that include a single sheet, the interior surface is the surface of the sheet that faces inwards and towards itself.

In some forms, the sheet or sheets of the tube may include an air impermeable layer or textile membrane. In some forms, the interior surface of both of the layers includes a membrane that is configured to restrict or restrain air from passing through the layer from the interior surface to the exterior surface. The impermeable layer may be a thin layer that is less than the thickness of the textile sheets of the inner layer or outer layer. In other forms, the impermeable layer may be greater than the thickness of the sheets of textiles of either of the layers. The impermeable layer or textile membrane or film may be completely impermeable to air transfer or may be formed to allow a predetermined rate or air transfer and particular pressures. In still further forms, the membrane may be particularly designed to allow a certain amount or quantity of air or water vapor or moisture to pass through the textile such that the tube 3350 is breathable allowing moisture vapor to escape and/or be transmitted therethrough. By removing air through the membrane the need for a separate bleed-off valve for waste air may be removed as the air may escape through the component, such as a tubing conduit or sealing structure itself. Further, in some forms, the permeability may be adjusted in particular areas. For example, the permeability may be altered in tube 3350 along a cheek region. This area may become warm during use and causing discomfort to the user. The permeability may be altered to allow some air to pass through the tube 3350 to the patient's skin thereby causing a cooling effect. The type of membrane and the permeability of the membrane may be altered or tuned depending on the nature or use of the textile on which the membrane is located.

In some forms, the thickness of the textile membrane may be varied. In some forms of the present technology, the textile membrane may be less than 5% of the thickness of the textile. In other forms, the thickness of the textile membrane may be between 5% and 25% of the thickness of the textile. In still further forms, the thickness of the textile membrane may be between 25% and 50% of the thickness of the textile. Additionally, the thickness of the textile membrane may be between 50% and 100% or greater of the thickness of the textile. Varying the thickness of the textile membrane affects the rigidity and stretchability of the textile. For example, a textile that includes a textile membrane that is 1% of the thickness of the textile may be less rigid and more stretchable than a textile that includes a textile membrane that is greater than 50% of the thickness of the textile. In some forms, a thicker textile membrane may be utilized to provide additional strength in particular areas of a conduit or sealing interface. That is, the thickness of the textile membrane may be increased in high stress areas or areas more likely to experience kinking or folding during use.

The membrane may be formed of thermoplastic or thermoset materials such that when exposed to a particular temperature the membrane material may be able to be molded or shaped into a particular form and then cures or solidifies or sets upon cooling. In some forms the membrane may be formed of silicone or polyurethane.

Further, in some forms, the membrane material may assist in joining the seams of the layers together. For example, a thermoset or thermoplastic material when exposed to a particular heat may cross-link such as in thermoset materials or may melt such as in thermoplastic materials. When solidified, the materials may be joined together. For example, the membrane along interior surface 3356 of outer layer 3354 and the membrane along interior surface 3358 of inner layer 3352 may be subjected to heat along the edges of outer layer 3354 and inner layer 3352 to form a seam between the two layers.

The inner layer may be attached to the opposite outer layer along a first and second seam. Once the layers are attached to one another, a tube or conduit may be formed between the two layers. By securing the layers along the edges, a central chamber is formed that allows for the flow of air or other gas or liquid medium when secured with air circuit 4170.

Tube 3350 as shown in FIG. 4B is formed using a textile that includes a membrane. Tube 3350 includes inner layer 3352 and opposite outer layer 3354. Both inner layer 3352 and outer layer 3354 include an impermeable membrane along the interior surface of the layers. Although described and depicted as including only an interior surface coated with an impermeable layer, in some forms, both the interior surface and exterior surface of the layers of tube 3350 may include an impermeable membrane. In some forms, the impermeable membrane, however, may be oriented away from a patients face. By orienting tube 3350 in such a manner, the soft feeling of fabric may be pressed against a patient while the impermeable membrane layer is spaced from the patient. This allows for a single piece of material to be formed that has different properties depending on the side of the material that is utilized. This may reduce production costs as well as the time necessary or required to form the component.

5.3.3.1.1.1 Shape and Composition of Tube

Referring to FIG. 4F a cross section of tube 3350 is depicted. In some forms, the inner layer 3352 and outer layer 3354 may be formed of multiple layers of textile material and/or membrane material. By varying the thickness and composition of the layers of tube 3350, different characteristics may be achieved. As shown in FIG. 4F, and in particular FIG. 4F-1 inner layer 3352 comprises a textile sheet 3360 along with textile membrane 3362. Textile sheet 3360 may be formed of felt, spacer fabric, foam, woven, knit, or non-woven material or other network of fibers. As shown, textile sheet 3360 is a felt-type textile. In this manner, exterior surface 3374 of inner layer 3352 may have a soft feel against the face of a patient. Outer layer 3354 is composed of multiple sheets of textile. Outer layer 3354 includes tube sheet 3364 and outer covering 3366. In some forms, both sides of tube sheet 3364 may be covered with a textile membrane. As shown in FIG. 4F-2, tube sheet 3364 includes textile membrane 3368 exposed to the chamber of tube 3350 and textile membrane 3370 along an opposite surface of tube sheet 3364. Textile membrane 3368 may assist in providing a seal between inner layer 3352 and outer layer 3354 as well as forming an air tight tube. Textile membrane 3370 may assist in joining tube sheet 3364 to outer covering 3366. In other forms, tube sheet 3364 may directly bond or join to outer covering 3366. In other forms, outer layer 3354 includes a shape holding material or material that is able to be thermoformed such as a foam layer located between tube sheet 3364 and outer covering 3366. In other forms, tube sheet 3364 may be able to be thermoformed. As discussed in detail later in this detailed description, the shape holding material may be utilized to provide a predetermined shape for tube 3350.

The configuration, orientation, and composition of the sheets of inner layer 3352 and outer layer 3354 may assist in providing a support structure to tube 3350 to prevent occlusion during use. As shown in FIG. 4F, the cross-section of tube 3350 is substantially D-shaped such that an air passage 3372 is formed between inner layer 3352 and outer layer 3354. Inner layer 3352 is substantially planar such that inner layer 3352 has zero curvature. Outer layer 3354 curves away from inner layer 3352 such that interior surface 3356 of outer layer 3354 has a positive curvature between the joints. As shown, the curvature of the interior surface 3356 changes between the joints of tube 3350. That is, the curvature may be negative adjacent to where inner layer 3352 and outer layer 3354 are joined together. It should be recognized however, that the overall curvature when taken from the central point between the joined edges of tube 3350 is positive. In other words, the outer layer 3354 has a non-planar configuration forming an arc-shaped portion, in cross-section, between the joined edges. That is, interior surface 3356 of outer layer 3354 may have a concave shape and an exterior surface 3376 of outer layer may have a convex shape. The curvature of outer layer 3354 may be fixed such that when outer layer 3354 is not subjected to force such as by weight of an external force or air pressure, interior surface 3356 of outer layer 3354 has a substantially positive curvature. Thus, inner layer 3352 and outer layer 3354 are asymmetrical which is in contrast to some conventional conduit portions which have identical or symmetrical shapes.

Further, the interior surfaces of inner layer 3352 and outer layer 3354 may be D-shaped in cross-section. That is, the interior surface may bound a D-shape air passage 3372. In some forms, therefore, the interior surfaces of inner layer 3352 and outer layer 3354 may form a D-shape in cross-section, and the exterior surfaces of inner layer 3352 and outer layer 3354 may also form a D-shape in cross-section.

In another manner, outer layer 3354 may curve away from inner layer 3352. As shown in FIG. 4F, outer layer 3354 and inner layer 3352 are attached to each other along longitudinal edges such that the edges of inner layer 3352 and outer layer 3354 are flush with one another. Between these attachment points, adhering zones or joints, outer layer 3354 is curved away from inner layer 3352. That is, between joints 3312 (see FIG. 4H), interior surface 3356 of outer layer 3354 is position away from interior surface 3358 of inner layer 3352. In some forms, outer layer 3354 may be pre-formed such that in an unpressurized or supported state, outer layer 3354 is pre-positioned and pre-formed to extend away from inner layer 3352 between the opposing joints 3312. That is, outer layer 3354 may support its own weight such that when not supported by pressurized air or other support mechanism, outer layer 3354 remains spaced from inner layer 3352 between joints 3312.

The generally D-shaped cross-section may vary along its length, e.g., tall, thin D-shaped cross-section near the patient's nose and wide, shallow D-shaped cross-section along cheek and near the top of the patient's head. For example, FIGS. 4I-4K illustrate various cross-sections of tube 3350 along its length according to one form of tube 3350. As illustrated, the D-shape of the cross-section varies along its length. Specifically, each cross-section has a width w and a height h, and the width and height of the various cross-sections varies along the length of the tube, e.g., a relatively long width and short height at the manifold end compared to a relatively short width and tall height at the interfacing structure end. In some forms, the D-shaped cross-section of the tube 3350 may be asymmetrical along an entire length of the tube or at least along a portion or portions of the tube. Also, all of the cross-sections have a very similar or common hydraulic diameter, e.g., about 10-15 mm or about 13 mm. Further, the width and height may refer to the chamber size rather than the entire size of the cross-section including external seam areas.

Additionally, tube 3350 may provide flatter regions in certain areas, e.g., where the patient rests on the tube during sleep. In this way, the tubes can be said to be an organic extension of the patient's facial contours. The shape may be configured based on aesthetic and/or impedance requirements. In addition, the shape may be configured to provide low profile, comfort, and/or stabilization. However, tube 3350 may have other suitable cross-sectional shapes, e.g., trapezoidal, semi-circular, cylindrical, oval, elliptical, flatter section, etc. Also, the tubes may have a flat configuration with anti-crush ribs. This arrangement is disclosed in U.S. patent Ser. No. 10/385,701, the entirety of which is incorporated herein by reference.

Further, tube 3350 as depicted in FIGS. 4L-1 to 4L-4 may be soft so that tube 3350 is readily deformable under finger pressure. That is, tube 3350 may not be formed of a rigid structure that is unable to deform. Rather, tube 3350 is formed such that tube 3350 is able to deform when subjected to finger pressure. Tube 3350, however, is also able to maintain its shape when under no force from air pressure or otherwise.

Additionally, outer layer 3354 may be a resilient structure. Outer layer 3354 is able to deform when subjected to pressure or force during normal use to accommodate a patient's movement during sleep and use. For example, tube 3350 may collapse such that outer layer 3354 is pressed against inner layer 3352 not only at the sealed edges, but also between the sealed edges. When force is removed from outer layer 3354, however, outer layer 3354 may return to its pre-determined shape that includes an interior surface of positive curvature. That is, outer layer 3354 is not a floppy structure because outer layer 3354 is able to support its own weight without changing in shape such as by bending or twisting. Outer layer 3354 may have a hardness of between Shore 0010 to Shore 0030. In other forms, outer layer 3354 may be harder such that outer layer 3354 is configured to resist larger forces.

Outer layer 3354 may comprise materials that resist plastic deformation. For example, outer layer 3354 may be bent or folded such that portions of exterior surface 3376 may abut itself when subjected to force. Once the force is released, however, the outer layer 3354 returns to its pre-force shape. Rather than plastically deforming, or failing, outer layer 3354 elastically deforms and returns to its pre-determined shape. Further, a majority of tube 3350 may be able to be bent, folded, or twisted in a similar manner. That is, tube 3350 may be formed of materials that when folded onto themselves do not plastically deform.

In contrast, inner layer 3352 may be a floppy component. Inner layer 3352 may be attached and secured to the edges of outer layer 3354 such that inner layer 3352 is a substantially planar layer. The shape of inner layer 3352 may be influenced by the shape of outer layer 3354. As shown, inner layer 3352 may be planar because of the force exerted to inner layer 3352 through the seams of tube 3350. Because outer layer 3354 resists deformation, outer layer 3354 is able to maintain the tautness of inner layer 3352 so that inner layer 3352 is planar. In other forms, inner layer 3352 may be cut such that inner layer 3352 is wider than outer layer 3354, however inner layer 3352 is still connected to outer layer 3354 along the edges of tube 3350. In such forms, the unsecured portions of inner layer 3352 may be able to move inwards toward outer layer 3354.

In some forms, inner layer 3352 may be floppy in some areas and rigid in others. For example, in some forms a rigidizer may be utilized at within arm support 3314 thereby imparting a rigidity to inner layer 3352 such that inner layer 3352 is not floppy in the particular area. In some forms, between the seals of tube 3350 however, inner layer 3352 may remain floppy. That is, no additional rigidizer is utilized between the seals or joints of tube 3350. A rigidizer may have a shore hardness of between Shore A30 and Shore A90 or higher.

In other forms, inner layer 3352 may be at least semi-resilient. That is, although inner layer 3352 may not be able to support its own weight, inner layer 3352, with assistance from outer layer 3354 may be able to support some of its own weight such that inner layer 3352 resides in substantially the same location when not subjected to additional force such as air pressure or other external forces.

Inner layer 3352 as depicted is relatively flat and adapted to sit substantially flush against the patient's face in use. Inner layer 3352 may have a tapered configuration from an inner edge to an outer edge to provide a comfortable fit for a wide range of patients. Inner layer 3352 provides a relatively large surface area which results in a more even load distribution. This arrangement is less likely to create pressure points in use. Also, internal layer 3352 may have grip-like material to help stabilize the patient interface on the patient's face.

In some forms, outer layer 3354 may be more resilient than inner layer 3352. That is, outer layer 3354 may be more resistant to deformation than inner layer 3352. Further, outer layer 3354 may return readily to a pre-determined shape to a greater degree than inner layer 3352. Further, in some forms, outer layer 3354 may be stiffer or more rigid that inner layer 3352. As shown in FIGS. 4F to 4F-2, outer layer 3354 may include more layers than inner layer 3352, and the outer layer 3354 may have a greater thickness than inner layer 3352. Such configuration of the outer layer 3354 and inner layer 3352 may assist in providing a relatively stiffer or more rigid outer layer 3354. The increased stiffness, rigidity, and/or resiliency may assist in maintaining an open passageway through which air can travel. Further, in some forms, outer layer 3354 may include harder materials than inner layer 3352. This composition of materials may assist in providing a stiffer or more rigid outer layer 3354.

Outer layer 3354 has a smooth contour that blends with the patient's face. That is, outer layer 3354 has a profile or organic form with edges that blend into the patient's face, e.g., in a tangential manner, to prevent any edges from catching on bedclothes, pillows, etc., during sleep (e.g., when the patient rolls over). As illustrated, tube 3350 has a non-cylindrical cross sectional shape which provides a blending contour to blend with the patient's face (See FIGS. 4A-4D). The blending contour is smooth, streamlined, sleek, and blends or tapers tube 3350 with or into the contours of the patient's head, e.g., anatomically coherent, less obtrusive and more aesthetically appealing. In addition, the blending contour has no sharp edges that could cause discomfort, e.g., skin irritations or abrasions.

In some forms, outer layer 3354 may be thermoformed such that materials within outer layer 3354 assume the shape of a mold or mandrel. When cured or cooled, the thermoformed material assumes the shape as shown in FIG. 4F. In some forms, an additional layer may be located between outer covering 3366 and tube sheet 3364. In some forms the additional material may be a foam or other thermoset material. In other forms, tube sheet 3364 or outer covering 3366 or both may be formed of a foam or thermosetting material. In still other forms, thermoplastic material may be utilized. In still other forms, any other shape holding material may be utilized. As shown, the cross-sectional shape of tube 3350 may be maintained without additional rigidizers or components beyond the sheets of outer layer 3354 and inner layer 3352. Further, the thickness of the inner layer 3352 may be substantially the same along the width of inner layer 3352. Further, outer layer 3354 may also be substantially the same thickness along the width of outer layer 3354. When thermoformed, outer layer 3354 may be able to maintain its pre-determined shape without assistance from inner layer 3352. That is, outer layer 3354 is able to maintain its predetermined shape without tension, force, or support, from inner layer 3352.

Turning to FIG. 4R, patient interface 6000 may include a vent formed in the tube 3350 (e.g., in the outer layer 3354) to expel exhaust gases to atmosphere. In the illustrated example, the vent 6100 is formed near the cushion assembly 3150. Additionally, air delivery tube 6348 may have a textile construction. For example, air delivery tube 6348 may have a construction similar or identical to any of the tube embodiments disclosed herein.

Referring to FIG. 4S, patient interface 7000 includes positioning and stabilizing structure 7300. Positioning and stabilizing structure 7300 includes tube 7350 having left arm 7302 and right arm 7304. The left and right arms may be separate structures having connectors at upper and lower ends thereof so that the arms are individually removably connectable to both the cushion assembly 3150 and the hub 7200. For example, at the upper and lower ends of each of the left and right arms 7302, 7304, an upper connector 7312 and a lower connector 7314 are respectively provided, as shown in FIGS. 4T and 4U. The upper connectors 7312 are configured to removably connect to the hub, whereas the lower connectors 7314 are configured to removably connect to the cushion assembly 3150.

Referring to FIGS. 4T and 4U, each of the upper and lower connectors 7312, 7314 in these examples may include a connector body 7303, a slot 7309, a chamfered edge 7308, and a notch 7306 that may be removably connected to clips in the cushion assembly 3150 and hub 7200 with a snap-fit. In an alternative example, the connectors 7312, 7314 may be provided in the cushion assembly 3150 and/or hub 7200 and the receiving portions may be provided on the left and right arms 7302, 7304.

As shown in FIG. 4S, an elbow 7220 may be swiveably connected to the hub 7200 and include a swivel connector at an opposing end thereof for connection to an air delivery supply tube.

Turning to FIG. 4V, an illustration of a cross-section of tube 7350 is shown. Similar to outer layer 3354, outer layer 7354 may be structured so that it can support its own weight. As can be seen, outer layer 7354 includes an outer covering 7402 forming an exterior surface of the outer layer that is positioned away from the patient's face in use. An outer cushioning layer 7406 (e.g., foam) is positioned between the outer covering 7402 and a textile member 7410 that forms an air impermeable surface of the air passageway. The outer cushioning layer 7406 may be thermoformed to hold its shape. Adhesive layers 7404, 7408 may be respectively provided between the outer covering 7402 and the outer cushioning layer 7406 and between the outer cushioning layer 7406 and the textile membrane 7410. In an alternative example shown in FIG. 4W, the outer cushioning layer 7406 and adhesive layer 7408 may be removed.

Turning back to FIG. 4V, inner layer 7352 includes a textile sheet 7222 configured to engage the patient's face in use. An inner cushioning layer 7426 (e.g., foam) is positioned between the textile sheet 7222 and a textile member 7230 that forms an air impermeable surface of the air passageway. Adhesive layers 7224, 7228 may be respectively provided between the textile sheet 7222 and the inner cushioning layer 7226 and between the inner cushioning layer 7226 and the textile membrane 7230.

Turning to FIG. 4X, patient interface 8000 includes positioning and stabilizing structure 8300 having tube 8350. Each of left arm 8302 and right arm 8304 may have a lower portion 8362 and an upper portion 8364 which may have different rigidities. For example, lower portion 8362 may be more rigid than upper portion 8364, or vice versa. This may be accomplished, for example, by constructing the inner layer 3352 of lower portion 8362 to have a different rigidity than the inner layer 3352 of upper portion 8364 and/or constructing the outer layer 3354 of lower portion 8362 to have a different rigidity than the outer layer 3354 of upper portion 8364. It is noted that instead of only a lower portion and an upper portion, each of the left arm and right arm may have three sections with different properties (e.g., rigidity).

In the illustrated example, the inner layer 3352 and the outer layer 3354 of lower portion 8362 are respectively more rigid than the inner layer 3352 and the outer layer 3354 of upper portion 8364. As such, the upper portion 8364 is more flexible and better able to conform to the curvature along the side of the patient's face up to the top of the patient's head. Tab 3346 may be provided on lower portion 8362 which may allow for better connection to the strap 3420 since the increased rigidity of the lower portion aids in resisting torsion and maintaining the desired application of vector forces. Alternatively, tab 3346 may be provided on the upper portion 8364 or bridging the upper portion 8364 and lower portion 8362.

In some forms, the cross-sectional shape of the tube may be particularly formed. For example, in some forms, the tube may be pre-formed to have a flat or planar contacting surface, and a convex outer layer. The shape of the conduit may be formed in particular shapes to provide a particular feel as well as to regulate the amount or quantity of oxygen or air that is forced through tube 3350 to the patient. That is, the conduit may be formed to limit how much the conduit stretches or expands when subjected to an air or oxygen source. Further, the cross-sectional shape of tube 3350 may change along the length of tube 3350. For example, the cross-sectional shape tube 3350 may be different adjacent to connection port 3600 as compared to adjacent cushion assembly 3150. The cross-sectional shape as well as volume encompassed by the particular shape may be changed or altered depending on how patient interface 3000 is configured to interact with the patient. For example, an end of left arm 3302 may have a smaller cross section than the point at which left arm 3302 connects with connection port 3600. Because the end of left arm 3302 is more likely to be associated with a sensitive portion of the face of a patient, limiting the cross-sectional size of the end of left arm 3302 may increase comfort to the patient when compared to other forms of the present technology.

Further, changing the width of the inner layer or the outer layer may permit the size of the chamber to be altered or varied. For example, the portion of inner layer 3352 that forms a portion of air passage 3372 may have a width W1 at a first location of left arm 3302 as shown in FIGS. 4C and 4G. When joined together, inner layer 3352 and outer layer 3354 form a cavity or chamber associated with air passage 3372 with a cross-sectional area and also a volume V1. As shown in FIG. 4H inner layer 3352 and outer layer 3354 may also have a width W2 that is spaced along left arm 3302 from width W1. Width W2 may be greater than width W1. Additionally, as shown, the cavity formed in the area of W2 is volume V2 that is larger than volume V1. Therefore, when breathable air is passed through the area of width W2, the cross-section area of tube 3350 at a location with width W2 is greater than the cross sectional area of tube 3350 at a location with width W1. Further, at a location with second width W2 the volume of the chamber may be greater than the volume at the first width.

The width may be varied to provide various properties or functions. In some forms, changing the volume of air or oxygen within a particular point may be used to alter the flow speed through various portions of the textile conduit. For example, if a textile conduit has a large cross-sectional area at a first location, breathable air that passes through the textile conduit may flow at a first speed. If the textile conduit also has a smaller cross-sectional area at a second location, the breathable air that passes through the textile conduit at the second location may flow at a second speed is greater than the first speed. Therefore, the conduit volume size may be changed to speed up or slow down the speed of the air through the conduit.

In some forms, the chamber size of a textile conduit may be changed by varying the shape of the textile layers and/or varying the width of the joining or joint of the textile tube or conduit. The joint refers to the area of one layer of the tube that is joined to the other layer of the tube, or in some forms where one layer attaches to itself when a tube is formed of a single layer. For example, as shown in FIG. 4G the joint 3312 is where a layer such as inner layer 3352 is joined to lower layer 3354. Varying the width of the joint 3312 varies the size of the chamber formed within the textile conduit. For example, a wider joint reduces the chamber volume compared to a narrower joint. The width of the joint may be different on either side of the textile conduit. Further, the width of the joint may also vary along the length of the textile conduit.

Varying the width of the joint 3312 may permit the rigidity of the textile conduit to be varied along the length. For example, in a location that may be subjected to higher stress or greater likelihood of bending, the width of the joint may be greater than in areas that do not have the same likelihood of bending. The width of joint 3312 may be dependent on how wide the welding mechanism or cutting mechanism is that is used to form tube 3350. In other forms, a separate heating mechanism may also be utilized to join the layers together. In such circumstances the heating mechanism may be moved about to create a wider or narrower joint 3312. Although shown along an outside portion of tube 3350, in some forms tube 3350 may be flipped inside out such that the joint is located within the chamber of tube 3350.

In some forms, the location of the joint 3312 around the D-shaped cross-section of the tube 3350 may be altered to adjust flexibility and rigidity of the tube along the length of the tube.

In some forms, the joints may be formed using various techniques that impart particular properties to the joint. For example, in some forms, the joints are formed using ultrasonic welding, radio frequency welding, as well as cut and weld techniques. Heat may be applied in particular areas that activates a thermoset or thermoplastic material used in tube 3350. This heat may not only be used to join the layers together, but may also be used to thermoform the layers, such as outer layer 3354. Further, in some forms stitching or an adhesive such as a glue may be utilized to join the layers together. In some forms, stitching is not used. In still further forms, material beyond what is located within the layers is not utilized to join the inner and outer layers of tube 3350. For example, in some forms the inner and outer layers may be formed such that no additional material such as glue or stitching, is necessary to join the inner and outer layers together.

In some forms, a sleeve (e.g., constructed of textile) may cover the tube 3350 to replicate the impression of bedclothes.

5.3.3.1.1.2 Shape of Patient Interface

Tube 3350 also may have various curvatures along its length to correspond with the shape of the face of the patient. As discussed previously, the cross-section of tube 3350 may have a particular shape. The shape of tube 3350 may vary along its length (rather than just its width as depicted in FIG. 4F). For example, interior surface 3358 of inner layer 3352 may have generally positive curvature along the length of inner layer 3352. This curvature may be included into tube 3350 to correspond to the generally negative curvature of the face of a patient along the areas in which tube 3350 contacts the head of the patient. It is recognized that the curvature of the face of a patient is complex and varied, however, overall, at the points at which tube 3350 contacts the head of the patient the head is generally negatively curved. Further, this curvature may be accomplished even when headgear 3300 is not worn by a user. That is, the curvature of the length of tube 3350 may correspond to a pre-determined, non-planar configuration.

Referring to FIGS. 4L-1 to 4L-4, tube 3350 is shown in isolation. As shown, tube 3350 is bent or formed along three dimensions such that inner layer 3352 and outer layer 3354 are located about various planes. For example, outermost portion 3378 of outer layer 3354 adjacent to connection port 3600 extends along the XY plane. In contrast, outermost portion 3380 of outer layer 3354 of right arm 3304 is located along the YZ plane. In addition, in some forms, tube 3350 may include additional bends such that right arm 3304 is rotated along the Z axis so that a portion of outermost portion 3380 extends along the XZ plane. In this manner, tube 3350 may have a three dimensional pre-determined shape.

Particular views of portions of tube 3350 are depicted in FIGS. 4L-2 to 4L-4. Specifically, FIG. 4L-2 depicts a side view of a portion of tube 3350. FIG. 4L-3 is a front view of a portion of tube 3350. FIG. 4L-4 is a top view of a portion of tube 3350.

Tube 3350 may be stiffer in particular regions based on geometry of tube 3350. As shown in FIG. 4L-1 bending or twisting tube 3350 about various axes may require differing levels of force. That is, tube 3350 may resist deformation or bending along a plane or axis to a greater extent in a first area than to a second area. For example, twisting or bending tube 3350 along the XY plane may require different levels of force at first area 3308 adjacent to connection port 3600 compared to second area 3310 of right arm 3304. By arranging tube 3350 in particular directions, the strength of the cross-sectional shape of tube 3350 may be utilized to resist bending in particular directions to assist in providing a secure patient interface 3000.

Additionally, tube 3350 as depicted in FIG. 4L-1 may be bent or oriented to varying degrees. For example, left arm 3302 and right arm 3304 may be oriented closer than depicted to each other. That is, the spacing between left arm 3302 and right arm 3304 along the X axis may be smaller. The spacing between the arms may be modified during the manufacturing of tube 3350 depending on the particular shape desired. Further, in some forms the shape of tube 3350 may be configured to align or conform to the face of a patient. Tube 3350 may have a complimentary shape to that of the patient. For example, a portion of the patient's face has a negative curvature. The exterior surface 3374 of inner layer 3352 may be configured to have an opposite positive curvature such that inner layer 3352 lies flush against the face of the user. Additionally, in other areas the patient's face has a positive curvature. The exterior surface 3374 of inner layer 3352 may be configured to have an opposite negative curvature such that that inner layer 3352 lies against the face of the user. Tube 3350 may be formed with an inward bend at the arms, such that tube 3350 provides compression to the face of the user. That is, in some forms, left arm 3302 and right arm 3304 may be oriented at an angle with respect to the planes. Left arm 3302 may be located within a plane that if extended intersects the plane on which right arm 3304 is located. This orientation may provide compression against the head of the user to assist in providing comfortable, and form-fitting placement.

In some forms, the left arm 3302 and right arm 3304 may have concertina-shaped portions to increase flexibility of the left and right arms allowing the arms to bend to conform to the patient's face.

In some forms, the shape of the tubes may be particularly formed. The top view shape of the conduit may be varied. In contrast to silicone tubes, the shape of a textile tube may be cut and formed to produce a particular shape rather than being formed entirely by molding such as injecting molding. This ability to determine the particular shape without complicated molds may permit the cost of manufacturing to decrease when compared to other forms.

In some forms, the layers may be knit in a particular manner such that the layer is knit to shape. In other forms, a woven, non-woven or other textile of a network of fibers may be cut to shape. In some forms, an L-shaped conduit may be formed. In other forms, for example as shown in FIG. 4E, a U-shaped tube 3350 may be formed. By forming an air delivery system from a textile material, various other shapes and configurations may be formed. Further, working with flat or planar sheets may assist in manufacturing and assembly. Because the material may be worked within 2-dimensional space the complexity of the joints, connections, or bends is reduced. Although shown in two dimensions in FIG. 4E for ease of viewing, in other forms, such as shown in FIGS. 4A-4D, tube 3350 may also be bent or twisted during manufacturing such that tube 3350 has a pre-determined 3-dimensional shape.

In some forms, multiple layers may be combined to form a tube. In contrast to other forms, by forming a tube with multiple separate sheets, intricate designs and specific shapes may easily be formed. For example, rather than forming a tube in a 3-dimensional shape, the shape may simply be cut out of a two dimensional layer. The layer then may be subjected to additional processing such that a 3-dimensional shape is formed. By initially forming or planning the forming of the shape in 2-dimensions, processing may be simpler, less time consuming, and cost effective than in other forms.

Patient interface 3000, in addition to maintaining a shape without pressure or force, may be configured to spring to shape. Patient interface 3000 may be located within packaging prior to a patient opening and using patient interface 3000. Some patient interfaces that exist today are difficult to orient to don on a patient's head. The straps of some interfaces entangle with each other such that it is not clear how to correctly wear the patient interface. Patient interface 3000, however, is formed such that when removed from packaging, or luggage, or any confined space, patient interface 3000 will spring to its predetermined shape. That is, without additional effort from a user, patient interface 3000 will orient the arms of patient interface 3000 such that how patient interface 3000 is worn is apparent to a patient without additional untangling or arranging of the components of patient interface 3000. This configuration may allow the patient to easily utilize patient interface 3000.

5.3.3.1.1.3 Structural Support

In some forms, a joint may be utilized as both a seal for tube 3350 as well as a rigidizer or support structure for tube 3350. Arm support 3314 is a wider joint that may be utilized to particularly direct force vectors and to provide a seal between seal-forming structure 3100 and the airways of a patient. Arm support 3314 may resist bending such that sufficient force is provided both rearwardly and upwardly to cushion assembly 3150 through tube 3350 to provide a seal between seal-forming structure 3100 and the airways of a patient. Referring to FIGS. 4A-4D, stabilizing structure 3300 includes arm support 3314. Arm support 3314, as shown, extends along a portion of left arm 3302. An arm support may also be included along a portion of right arm 3304. Arm support 3314 resists bending of left arm 3302 such that when patient interface 3000 is worn by a patient seal forming structure 3100 maintains the correct positioning with regard to the face or nose of a user. For example, when worn, headgear 3300 may tend to straighten out between the otobasion superior of the patient and the airway of a patient. That is, headgear 3300 may tend to straighten out where tube 3350 bends toward cushion assembly 3150. Arm support 3314 resists the rotation of left arm 3302 about the X axis. Arm support 3314 as depicted is formed of inner layer 3352 and outer layer 3354. That is, no additional material or components are utilized in arm support 3314 such that arm support 3314 is only formed of the materials and layers used to form tube 3350. In this manner, stabilizing structure 3300 may be formed in an efficient manner that does not require additional components. Further, separate rigidizers beyond inner layer 3352 and outer layer 3354 may be included in various portions of tube 3350, such as within arm support 3314 or along the outer surfaces of arm support 3314. In other forms of the present technology, separate rigidizers are used to provide rigidity to tube 3350. A rigidizing element in accordance with one form of the present technology is preferably thin and conforming when a patient lies upon it, yet has sufficient stiffness to resist out-of-plane bending. That is, the rigidizing element is structured to allow bending in some planes and resist bending in other planes, e.g., allow bending towards and away from the patient's face. The rigidizing element also makes tube 3350 inextensible in areas in which a rigidizing element is utilized or not stretchy so that tube 3350 is strong in tension and maintains its size. The rigidizing element may be located within the airflow path of tube 3350 or may be located outside of tube 3350.

Further, a rigidizer may correspond to a component that has a greater hardness and/or stiffness than surrounding material. Additionally, the rigidizer is utilized to resist finger deformation. Further, a rigidizer may refer to a component in addition to the layers that form inner layer 3352 and outer layer 3354. For example, particular areas of tube 3350 may include additional components beyond the materials used to form inner layer 3352 and outer layer 3354. In some forms, connection port 3600 (see FIGS. 4M and 4N) may be considered a rigidizer. Connection port 3600 may be formed of a material that is harder than the surrounding material, and connection portion 3600 may resist finger deformation. In other forms, a rigidizer may refer to a material other than inner layer 3352 and outer layer 3354 that is permanently attached to either inner layer 3352 or outer layer 3354. Further, a rigidizer may increase the rigidity of the layers with which the rigidizer is in contact when compared to the material layers without the rigidizer.

In one form, the rigidizing element may provide structural integrity or self-holding form to the patient interface so that the patient interface can hold its shape and not fall into a heap, e.g., shape memory, whether the patient interface is on or off the patient's head. The shape holding arrangement maintains the tubes in a desired position and may facilitate donning of the patient interface in use.

In some forms, a rigidizing element may be utilized in particular locations. For example, a rigidizing element may be utilized between the layers of stabilizing structure 3300. For example, a rigidizing element may be located between inner layer 3352 and outer layer 3354. In other forms a rigidizing element may be located between the various sheets that form inner layer 3352 and outer layer 3354. In other forms a rigidizing element may be located along an inner or outer surface of stabilizing structure 3300. In further forms, a rigidizing element may be located at areas of high stress such as when head strap 3420 interacts with tube 3350. A rigidizing element may be utilized to providing rigidity to the overall shape of patient interface 3000, as well as providing support for the cross-section of tube 3350, thereby resisting the collapse of tube 3350.

In some forms, a rigidizing element may be located along an outer surface of headgear 3300. For example, a rigidizing element may be located along exterior surface 3376 of outer layer 3354 at the location of arm support 3314. In some forms, between connection port 3600 and assembly connection ports 3154 and 3155 there is no rigidizer within the chamber of tube 3350. In other forms, between connection port 3600 and assembly connection ports 3154 and 3155 there is no rigidizer between the joints of inner layer 3352 and outer layer 3354. In still further forms, there is no rigidizer that contacts inner layer 3352 between connection port 3600 and assembly connection ports 3154 and 3155.

In other forms, the structure and orientation of the inner layer 3352 may allow bending in some directions and have sufficient stiffness to resist bending in other directions. That is, the inner layer 3352 may be structured to allow bending in some planes and resist bending in other planes, e.g., allow bending towards and away from the patient's face to conform to the patient's head and resist bending along the plane in which the inner layer 3352 extends. Thus, a first plane in which the inner layer 3352 is configured to bend may be perpendicular to a second plane in which the inner layer 3352 resists bending. The outer layer 3354 also may allow bending and resist bending similarly to the inner layer 3352.

As mentioned above, the joint 3312 may form a rigidizer. The joint 3312 may be configured such that the tube 3350 allows bending in some planes and resists bending in other planes, e.g., allows bending in a first plane towards and away from the patient's face to conform to the patient's head and resists bending along a second plane in which the inner layer 3352 extends. Further, the joint 3312 may be configured to be substantially rigid so as to resist bending in the first and/or second plane.

In other forms, the size of the conduit may contribute to the resistance to bending. For example, in some forms the conduit may have a smaller cross-section in a first area. In the first area, for example an area that has a width W1, there is a greater density of material when compared to the volume or space that the first area can contain. By increasing the density of material at a given location, the strength or rigidity or resistance to bending or deformation normal to outer layer 3354 in a particular area may be increased when compared to other areas. Particular areas that may be subjected to increased forces such as bending or kinking may be particularly shaped such that particular material is utilized to resist bending or kinking. For example, as shown, tube 3350 is narrower at an end point 3306. End point 3306 may be connected to cushion assembly 3150. A mask area may be more likely to be exposed to bending and kinks Therefore, by changing the density of the material at the mask connection location, the likelihood of kinks and bends within the tube 3350 may be reduced.

5.3.3.1.1.4 Tube Layer Properties

In some forms, inner layer 3352 and outer layer 3354 are formed of different materials. In some forms, inner layer 3352 may be formed of a softer or gentler textile material than outer layer 3354. Because inner layer 3352 is exposed to the skin of the patient, the material of inner layer 3352 may be particularly formed to feel comfortable along the skin of a patient. Outer layer 3354 may be a different material than the inner layer. Outer layer 3354 may be more likely to be caught by an abrasive material or rub against an object. Therefore, in some forms outer layer 3354 is formed of a durable material that may not be as soft as the inner layer. Further, exterior surface 3376 of outer layer 3354 as well as exterior surface 3374 of inner layer 3352 may have different surface properties than the interior surfaces of the respective layers. Additionally, exterior surface 3374 may have a higher coefficient of friction than the exterior surface 3376 of outer layer 3354 to maintain the location of the positioning and stabilizing structure of the patient's face.

In some forms, particular surfaces may be layered with a membrane. For example, in some forms, only the interior of the conduit or sealing structure includes a membrane. Therefore, the exterior surface and the interior surface may have different properties. The exterior surface may be softer and breathable and may be formed of cotton. This surface may be more pleasing or comfortable to a patient than a silicone or polyurethane surface. The interior surface, however, may be layered or coated with a membrane. Therefore, the membrane surface may be spaced from or isolated from the skin of the patient. By having different material properties on either the interior or exterior surface of a textile conduit, the comfort of particular components may be improved.

Additionally, exterior surface 3376 may include only the textile surface. That is, exterior surface 3376 may not be covered or layered by a textile membrane. In some forms, the exterior surface of particular sheets may or may not be layered with a textile membrane depending on the design of a particular tube. For example, exterior surface 3374 of inner layer 3352 may not be covered or lined with a textile membrane in order to provide a comfortable surface to a patient. Exterior surface 3376 of outer layer 3354, may however include a membrane for added protection or resistance to abrasion or other external forces. Further, because outer layer 3354 is spaced from the skin of a patient, it may be unnecessary to form outer layer 3354 with different surface properties along interior surface 3356 and exterior surface 3376. For example, outer layer 3354 may be dipped into a thermoplastic or thermoset material such that both surfaces are covered by a textile membrane. The manufacturing costs may be diminished for outer layer 3354 in such a configuration as the time necessary to dip outer layer 3354 may be less than the time necessary to layer a single surface of a layer.

The overall weight of the positioning and stabilizing structure is preferably less than 50 g (e.g., less than 40 g or less than 30 g). Each of the inner layer 3352 and outer layer 3354 may have a thickness of less than 2 mm (e.g., less than 1 mm).

By utilizing sheets of textile, easy color customization may be possible. For example, one sheet may be blue and the other sheet may be white. Different colors may allow for consumers to select a particular combination that may increase the likelihood of the patient continuing to receive therapy utilizing the device.

By forming a headergear, tube, or conduit in such a manner the headgear may be particularly formed to adjust or conform to the contours of the face of a patient. Rather than a straight cylindrical tube, the shape of the textile conduit may be determined by the how the inner layer and the outer layer are cut and attached to one another.

5.3.3.1.1.5 Patient Interface During Use

Patient interface 3000 as depicted in FIG. 4B-4D may be donned on the head of the patient. Once in place, pressurized air is supplied through air delivery tube 3348. From air delivery tube 3348, pressurized air passes through either left arm 3302 or right arm 3304 or both arms. The air then passes through the assembly connection port or ports 3154 and 3155 and into cushion assembly 3150. In this manner air is supplied to the patient.

In some forms, when pressurized air is passed through tube 3350, the cross-section of tube 3350 may be altered or changed. As shown in FIGS. 4F, 4G and 4H, inner layer 3352 is substantially planar. In some forms, during use inner layer 3352 may bulge or bend away from outer layer 3354 between the joints 3312. That is, interior surface 3358 of inner layer 3352 may have a positive curvature. In other words, exterior surface 3374 of inner layer 3352 has a negative curvature between the joints 3312. This curvature may assist in spacing other portions of inner layer 3352 away from the face or head of the patient. For example, the curvature may space the joints away from the face of the patient and increase the comfort to the patient.

In some forms, outer layer 3354 may also expand when subjected to pressurized air during use of patient interface 3000. Although outer layer 3354 is formed in a predetermined shape, outer layer 3354 is not a rigid structure and may expand when exposed to pressurized air. This expansion may be in the material itself (for example, outer layer 3354 may stretch) or the expansion may be caused by the edges of tube 3350 moving toward each other. For example, the joints 3312 may move toward each other causing the curvature of interior surface 3356 of outer layer 3354 to become more positive than when in an unpressurized state. The changes in shape may be tuned for particular comfort and feel for the patient during use.

Additionally, as described previously, the permeability of tube 3350 may be tuned in specific areas. In one area, the tube 3350 may be completely impermeable to air, whereas in another area a particular quantity of air may be permitted to transfer through tube 3350. For example, in some forms the permeability of tube 3350 may be tuned to allow a particular quantity of air to transfer from tube 3350 to the cheek of the patient. Additionally, the tube 3350 may be tuned such that air is only permitted to move through one layer of tube 3350 (i.e. toward the patient through inner layer 3352 or away from the patient through outer layer 3354).

The textile construction of the tube 3350 allows the positioning and stabilising structure to be less resonant than conventional air delivery tubes and conduits, which is less disruptive to the patient and thereby facilitates compliance with therapy.

5.3.3.1.1.6 Headgear Positioning

In certain forms of the technology, the stabilizing structure 3300 comprises a mechanism for connecting a headgear strap to the seal forming structure 3100. The headgear strap may be connected directly or indirectly to the seal-forming structure 3100. As depicted in FIG. 4C, for example, a tab 3346 configured to connect to head strap 3420 projects outwardly from tube 3350 in a generally posterior direction. The tabs 3346 may have holes or slots in them to receive the ends of head strap 3420. As depicted, however, strap 3420 may be secured between inner layer 3352 and outer layer 3354. That is, strap 3420 may be secured without any additional material beyond the material of inner layer 3352 and outer layer 3354. For example, strap 3420 may be secured using thermoset or thermoplastic material of inner layer 3352 and outer layer 3354. Further, strap 3420 may extend into the chamber of tube 3350 may be located outside of tube 3350. In other forms, strap 3420 may be in the form of a wire or string or other tubular structure that passes through an opening in tab 3346.

In some forms of the present technology, rear strap 3420 is adjustable. In some forms strap 3420 may include a hook and loop fastener such that a portion of rear strap 3420 that may pass through a hole in tab 3346 and be secured to itself. In some forms of the technology the angle of the strap 3420 relative to tube 3350 or patient's head is able to be adjusted to fit around the patient's head at a different location. This adjustability assists the headgear 3300 to accommodate different head shapes and sizes.

In certain forms of the technology, strap 3420 exerts a force on tube 3350 to pull the tube in an at least partially posterior (e.g. rearwards) direction at the locations of tabs 3346. The strap 3420 may also exert a force on tube 3350 to pull the tube in an at least partially inferior (e.g. downwards) direction. The magnitude of the force may be adjusted by altering the length of the strap 3420 between the tabs 3346.

In some forms of the technology, such as the form shown in FIG. 4C, the direction of the force applied to the tube 3350 by strap 3420 may also be altered. This direction may be altered by adjusting the angle of the strap 3420 relative to tube 3350 or the patient's head. In some forms of the technology, the location at which strap 3420 exerts a force on the tube 3350 may be altered by adjusting the location at which strap 3420 is secured to tube 3350.

In some forms of the technology, when worn by a patient, seal forming structure 3100 tends to fall away or anterior, as well as down or inferior from the patient. Headgear 3300 is arranged to combat or counteract these tendencies. Tube 3350, in conjunction with strap 3420 provide both superior as well as posterior force so that in use seal forming structure 3100 remains in place. Further, tube 3350 along with strap 3420 also provide addition forces posterior and superior so that sealing layer 3102 provides a seal to the patients airways. Headgear 3300 receives a downward force from seal forming structure 3100 that is at least partially counteracted by arm support 3314. Further, the top portion of tube 3350 allows headgear 3300 to remain in place along a superior/inferior direction, while strap 3420 assists in maintaining the position of headgear 3300 in an anterior/posterior direction.

The directions and magnitudes of the forces required for a secure fit and effective seal may vary between patients based on the position of the stabilizing structure 3300 on the head, which may vary due to, for example, differences in head shapes and sizes. In some forms of the technology, the adjustability of the strap 3420 enables the forces to be balanced for a range of head shapes and sizes to hold the headgear 3300 in a comfortable position while maintaining an effective seal.

5.3.3.1.1.7 Connection Port Configurations

Tube 3350 includes a plurality of connection components that are configured to transfer air into and out of tube 3350. These connection components are integrated within the tube 3350 to provide a seamless or smooth transition and connection to other components of the therapy device. The connection components may be formed of a different material than tube 3350. In some forms the connection components are a hard or rigid plastic that resists bending or compressing. Such materials may be utilized to reduce the possibility of restriction of air through the connection components.

Referring to FIGS. 4M and 4N connection port 3600 is depicted. As shown, connection port 3600 includes an upper surface 3602 and an opposite lower surface 3604. A channel 3606 extends between upper surface 3602 and lower surface 3604 to guide air from intake 3608 to either side of tube 3350. Air is guided into and through intake 3608, through upper surface 3602 and into channel 3606. The air then is guided along tube 3350 to the mouth and/or nose of a patient.

Referring specifically to FIG. 4M, connection port 3600 is depicted within a portion of tube 3350. In some forms, connection port 3600 may not be sealed or connected with the layers of tube 3350. That is, connection port 3600 may be able to slide along the interior surfaces of the layers of tube 3350. Rather than being sealed or mechanically connected to the layers of tube 3350, connection port 3600 may be restricted from moving laterally by the shape of tube 3350. For example, the width of tube 3350 may taper or reduce such that connection port 3600 is not able to slide to a large degree.

Referring to FIG. 4O, an alternate form of the present technology of a connection port is depicted. As shown, connection port 3701, includes an outer portion 3702 and an inner portion 3704. Inner portion 3704 may be inserted into tube 3350 such that inner portion 3704 is located between inner layer 3352 and outer layer 3354. Outer portion 3702 includes an extension that interacts with inner portion 3704. Outer portion 3702 is positioned about an opening in tube 3350 and aligned with inner portion 3704. Outer portion 3702 may be snapped into inner portion 3704 or otherwise secured to inner portion 3704. In this manner, outer layer 3354 is secured between inner portion 3704 and outer portion 3702 of connection port 3701. Further, inner portion 3704 may be equipped with a support to prevent inner layer 3352 from abutting outer layer 3354 at the connection port. As shown, inner portion 3704 includes support 3706. Support 3706 is a cage-type structure that allows air to flow through the opening of connection portion 3700 and to the rest of tube 3350 while also providing a gap or space between inner layer 3352 and outer layer 3354 of tube 3350.

Additional connection components may connect tube 3350 to seal-forming structure 3100. As shown there are two connection components attached to tube 3350 that connect on either side of frame 3152 of seal-forming structure 3100. Assembly connection port 3154 may be formed in a similar manner as with connection port 3600. Further, assembly connection port 3154 is configured to engage with an opening of seal forming structure 3100 such that cushion assembly 3150 is in fluid connection with tube 3350. By utilizing more than one connection component, air will be delivered to a patient even if one side of tube is collapsed, such as by the weight of the head of a patient when the patient sleeps on his or her side.

5.3.3.1.1.8 Method of Making Headgear Tube

The air delivery system of stabilizing structure 3300 such as tube 3350 may be formed and manufactured using various techniques. In some forms, each of the layers or sheets of the textile used to form tube 3350 may be pre-formed to have a particular cross-section. The layers or sheets may be coated with a silicone, polyurethane, thermoplastic, thermoset or other conformable material. This material may be the same material utilized to form a textile membrane as discussed previously. In some forms, this layer may also act as the textile membrane. After receiving the conformable material the sheets or layers may then be placed within a mold. Next the layers or sheets may be subjected to heat such that the conformable material melts. The heat is then removed from the layers such that the conformable material is allowed to cure. Then the layer may be removed from the mold such that the layer assumes the shape of the mold.

Referring now to FIGS. 8A-8F, an overview of one process used to form a tube or air delivery system is depicted. As shown, mold 3800 is formed with a substantially concave shape. The shape of mold 3800 may be altered or modified depending on the desired shape of the tube that is to be produced. Textile sheet 3360 may be a textile sheet that is formed of the materials as described above. In some forms, textile sheet 3360 may already include a textile membrane layer along a surface of textile sheet 3360. In the form depicted in FIGS. 8A-8F, however, textile sheet 3360 does not already include a textile membrane. Textile sheet 3360 is then placed within the mold as shown in FIG. 8B. After textile sheet 3360 is adequately oriented another sheet is placed on top of textile sheet 3360. As shown in FIGS. 8C and 8D, textile membrane 3362 is oriented against textile sheet 3360. Textile membrane 3362 may be a membrane that is formed of silicone, thermoplastic or other materials as described previously with respect to a textile membrane. At the step shown in FIG. 8D, the combination of textile sheet 3360 and textile membrane 3362 may be subjected to heat such that membrane melts or partially melts and/or otherwise adheres to a surface of textile sheet 3360. The combined textile sheet 3360 and textile membrane 3362 may then be removed from mold 3800 after textile membrane 3362 has cured. Once textile membrane 3362 cures, textile membrane 3362 may assume the shape of mold 3800 and therefore textile sheet 3360 may assume the shape of mold 3800, forming inner layer 3352 described previously. It is noted that one or both of inner layer 3352 and outer layer 3354 may be thermoformed to a predetermined shape. In other examples, neither of the inner layer 3352 and outer layer 3354 is thermoformed.

In some forms, multiple formed sheet and membrane combinations may be utilized to form a tube or portion of an air delivery system. As shown in FIGS. 8E and 8F, inner layer 3352 and outer layer 3354 are both thermoformed and may be combined to form tube 3350. Tube 3350 may have a steady state shape that includes a specific volume for the acceptance of pressured air. Further, tube 3350 may be able to be folded and easily collapsible for storage. Because tube 3350 includes textile membrane 3362, tube 3350 may revert to the shape as shown in FIG. 8F even after being folded or stored. Further, additional or different layers may be utilized in order to form more or less rigid structures. For example, outer layer 3354 may be formed to include a thermoset material such as a foam layer than when subjected to heat takes the form of mold 3800. Additional layers such as textile sheets, foam layers, textile membranes, or other layers may be utilized to provide sufficient shape retaining features or to provide sufficient rigidity or stiffness to tube 3350 such that tube 3350 maintains its shape.

In other forms, a mandrel may be utilized. Rather than using a negatively shaped mold such as mold 3800, a mandrel may be covered by various layers such as inner layer 3352. Once covered by the desired layers, the mandrel may be heated or the layers may be heated to activate the thermoplastic or thermoset material. Then the mandrel is removed thereby forming inner layer 3352 or other layers in the shape of the particular mandrel shape.

In another form of the present technology, the membrane or conformable layer may be a liquid or paste. In still further forms, the conformable layer may not require heat to cure. For example, the conformable layer may cure when exposed to air, in a similar manner to a glue adhesive. In still further forms, a chemical reaction may be utilized such as an epoxy or fiberglass resin. In some cases, the process of molding may limit the shape and design of a particular component. In some forms, therefore, a laying up method may be utilized to form various components. Laying up includes a mold of a particular shape. A layer such as a fabric or textile layer may be placed into the mold. Then a resin, membrane material, or other material is placed over the layer. The resin or other conformable material is then cured such that the shape of the layer corresponds to the shape of the mold. In some forms, a releasing agent may be placed between the fabric layer and the mold to assist in providing an easier removal of the layer from the mold. Once removed from the mold, the layer may maintain or retain the shape of the mold.

As shown in FIGS. 8G-8K, a tube 3363 may be formed using the technique described above. As shown in FIG. 8G, textile sheet 3360 is placed in mold 3800. In FIG. 8H, textile membrane 3362 is placed along textile sheet 3360. In this form, textile membrane 3362 may be administered in liquid form as opposed to the method depicted in FIG. 8C. As shown in FIG. 8I, textile membrane 3362 is spread along textile sheet 3360 such that all appropriate portions of textile sheet 3360 are covered by textile membrane 3362. After textile membrane 3362 has cured by either heat or other manner, inner layer 3352 that includes textile sheet 3360 and cured textile membrane 3362 is removed from mold 3800. In a similar manner as with respect the tube 3350 as shown in FIGS. 8A-8F, inner layer 3352 may be combined with outer layer 3354 to form tube 3350.

After these two layers (for example, inner layer 3352 and outer layer 3354) are formed they may be joined along longitudinal edges to form a chamber. In some forms, the two layers may be joined using a glue or other adhesive. In other forms, the layers may be joined using mechanical fasteners such as nails, screws, or buttons. In other forms, the two layers may be stitched or sewn together. In still further forms, the two layers may be welded together. In regard to welding, the two layers may be welded using high frequency or radio frequency welding. In still further forms, a hot knife may be used to cut the layers and when cutting may also form a seal between the two layers as portions of the two layers melt and cure, thereby forming a seal between the first layer and the second layer.

In some forms, welded connections may be used in various locations of a textile conduit. In some forms, welded connections may be utilized to connect other components to the textile conduit or to connect the textile conduit to other components. Rather than relying on physical fasteners such as thread, clips, snaps or the like, components may be secured to one another by utilizing various types of welding. By using welding, there may be fewer bulky connections. Further, by utilizing a welding connection technique, there may not be a need for additional connection components. For example, a connection between the textile tube and an adaptor or connector may be formed by placing a portion of a layer of the textile conduit around the adaptor such that the membrane of the layer is against the adaptor. The combination of the layer and the adaptor may then be subjected to heat such that the membrane melts or conforms to the adaptor. When the membrane cures, a secure connection may be formed between the layer and the adaptor.

Referring to FIGS. 8L and 8M, the technique described above may be applied to more complicated shapes. Rather than utilizing a mold and thermoplastic or thermoset material to only shape the internal cross section, the mold and thermoplastic material may also be used to form a three-dimensional shape over the length of a component. That is, in addition to forming a chamber, the mold may be used such that tube 3350 can be bent or turned along three axes and maintain this shape without additional support. As shown in FIG. 8L, mold 3802 includes a groove or accommodating portion 3804 that extends in a first direction D1 and a perpendicular direction D2. Textile sheet 3360 may be cut to a particular shape and then placed along accommodating portion 3804 of mold 3802. For simplicity, textile sheet 3360 may already be layered with a thermoset or other conformable membrane. As shown in FIG. 8M, textile sheet 3360 is subjected to heat such that the membrane melts or conforms to the shape of accommodating portion 3804. Once cured, textile sheet 3360 is removed from mold 3802 and retains the shape of accommodating portion 3804.

Tube 3350 may be formed using sheets that are molded in mold 3802 (See FIGS. 4L-1 to 4L-4). For example, a second sheet similar to textile sheet 3360 may be formed and joined with textile sheet 3360 in a similar manner as depicted in FIGS. 8A-8F. As shown in FIGS. 4L-1 to 4L-4, tube 3350 may be oriented in various directions. That is, tube 3350 may be formed or conformed to return to a three dimensional object. By forming tube 3350 as a three dimensional object, the amount or quantity of creases or bends in tube 3350 may decrease when used. For example, rather than requiring a patient to bend or twist tube 3350 to conform to the face of the patient, tube 3350 may be pre-formed with a bend or a twist Kinks that may decrease airflow through tube 3350 may be reduced by providing a bend or turn naturally within the shape of tube 3350 as opposed to shaping the tube 3350 in a separate step afterwards. As seen in FIGS. 4A-4D, when tube 3350 is used by a patient, tube 3350 may be shaped to correspond to the shape of the face and head of a patient. By particularly shaping tube 3350 during the manufacturing process, pressure points may be reduced.

Additionally, in some forms, only a first sheet such as textile sheet 3360 is molded or formed within a mold such as mold 3802. A sheet that is not pre-molded may be attached to the molded sheet such that the second sheet conforms to the shape of textile sheet 3360.

The textile membrane may be located along various surfaces of the textile. The textile may be dipped into a material such that all sides are covered or layered with the membrane. Other forms of the textile may coat or layer a single surface of the textile. In some forms, the membrane or curing material may only be located along a single surface of the fabric layer. That is, in some forms, a first surface of the fabric material may be coated by another material such as a thermoset and a second surface may be an uncovered fabric. That is, there may be different properties on either side of the material. The membrane also may be formed of various materials. In some forms the textile membrane is formed of silicone, and in other forms the membrane is formed of polyurethane. In other forms, different materials may also be utilized.

In some forms, the textile membrane may be located along a flat or planar sheet of textile. That is, sheets of textile may be manufactured and include a layer of membrane material along a surface of the textile. In some forms, the membrane may be layered onto a textile in a sheet-like manner. In other forms, the membrane may be spread about the textile while in liquid or semi-liquid form such that the membrane covers a surface or a portion of the surface of the membrane. The membrane may then cool or dry such that the membrane cures along a surface of the textile.

In some forms, various methods and techniques may be utilized to form the various components of a therapy device. In some forms, flat or planar materials may be manipulated to form three dimensional structures for utilization in a therapy device. These materials may be custom formed or tuned to allow for greater comfort when compared to other forms. In some forms, the seal forming structure may be formed of a textile material. This material may be less obtrusive, more comfortable, and less heavy than other configurations. Additionally, other components may also be formed of planar materials that are manipulated to form three dimensional structures. For example, tubing may be formed from planar materials. Further, other components that contain or are contacted by pressurized air may also be formed from planar materials. In addition to components that contain or guide pressurized air, other components such as straps may be formed from planar materials that are manipulated to form three dimensional structures.

Known patient interfaces typically also include separate headgear and air delivery components that are used to locate and supply breathable gas to a mask or the like. Known headgear typically includes an assembly of elastic (or inelastic) straps, buckles, locks, and/or clips. Known air delivery components typically include 15-22 mm diameter spiral reinforced tubing and swivel connectors. These known arrangements of headgear and air delivery components can be difficult to use for those who are less dexterous and/or unfamiliar with them. These known arrangements of headgear and air delivery components can also be uncomfortable or impractical to lie on.

5.3.3.1.1.8.1 Cut and Seal Method

Components may be formed and connected using various methods and techniques. In one form multiple components may be formed using a cut and seal method. In this method each of the components may be cut to a particular shape. In some forms, the components may then be layered on top of one another after cutting has taken place. In other forms, multiple layers may be layered on top of one another and then all of the layers may be cut at once. In some forms, during the cutting process the layers also may be connected to one another. For example, in some forms a hot knife may be used that both cuts and fuses the layers together. In such a method the time required to manufacture a particular component may be reduced when compared to other methods of manufacturing.

The sheets utilized to form the textile conduits may be less than 750 mm by 350 mm. In other forms, the sheets may be larger or smaller than or equal to 750 mm by 350 mm. The small size of the sheet may permit multiple textile conduits or tubes to be formed within a small location. By decreasing the footprint of the elements used to form the textile conduits the cost of manufacturing may decreased because less space that requires rent or upkeep is required.

Referring to FIGS. 9A-9E, the present form of the technology is depicted such that a tube is formed through the use of a cut and seal method. Outer covering 3366, tube sheet 3364, and textile sheet 3360 are depicted. As shown, each of the sheets include a textile membrane or other fusible membrane as described in previous forms. As described previously, outer covering 3366 may be utilized as an exterior layer and therefore may have different material properties than tube sheet 3364. Textile sheet 3360 may be an interior layer and formed of material that is soft against the skin of a user on an exterior surface, while also including a textile membrane configured to reduce the quantity of air that passes through textile sheet 3360. In some forms exterior surface 3374 of textile sheet 3360 may be configured to rest against the skin of a patient.

As shown in FIGS. 9A and 9B, the layers are stacked upon each other. In some forms of the present technology, a guide may be placed upon the layers that indicates the desired cut location. In some forms textile sheet 3360 may be pre-stretched prior to assembly. For example, textile sheet 3360 may be stretched horizontally, vertically, or both horizontally and vertically to provide a particular configuration. After the upper and lower layers are joined, the tension may be released from textile sheet 3360 such that it assumes an unstretched position. This may cause the upper layer to bend as textile sheet 3360 is unstretched. Therefore a particular shape may be realized by pre-stretching the lower layer during manufacturing and then releasing the tension.

In FIG. 9B a laser 3382 is utilized to both cut and seal the various sheets of material. In some forms, welding techniques such as High-Frequency (HF) welding or Radio Frequency (RF) welding may also be utilized to form a seal. Additionally, in other forms a hot knife may be utilized. As the material is cut, the thermoset, thermoplastic, or conformable membrane adjacent to the cut line may melt or change properties. The melting of the membrane allows for the membrane to interact with adjacent layers. For example, the membrane of outer covering 3366 may interact with the upper surface of tube sheet 3364. Likewise, the membrane of tube sheet 3364 may interact with the lower surface of outer covering 3366. Further, the membrane of tube sheet 3364 may interact with the interior surface of textile sheet 3360. In other forms, tube sheet 3364 may only include a membrane along the lower surface and outer covering 3366 may include a membrane that melts and interacts with the upper surface of tube sheet 3364. After the membranes have melted, they may cure. Upon curing the sheets are connected to one another along the cut lines. In this manner a tube such as tube 3450 (See FIG. 9C) is formed. In contrast to tube 3350, tube 3450 may not have a thermoformed inner and outer layer. Rather, outer layer 3354 and inner layer 3352 may be connected along the outer edges along a joint and not further subjected to heat to maintain a particular cross-sectional shape when not exposed to internal air pressure or other forces.

In some forms, additional components may be incorporated into the textile conduit during the formation of the textile conduit. For example, in some forms connection components may be incorporated into the textile conduit during the manufacturing process. In some forms, an elbow or tube connection may be placed along the inner layer before the outer layer is secured to the inner layer. After the tube connection is placed along the inner layer the outer layer is lined over the inner layer. Next a connection is formed between the inner layer and the outer layer. As described previously, the connection may be formed by various welding techniques. In some forms, the connection between the inner layer and the outer layer may also secure the tube connection. In other forms, however, the tube connection may be trapped within the chamber of the conduit, however, the tube connection may not be physically secured to either the inner layer or the outer layer. That is, in some forms the tube connection may be restricted from movement by friction or space restrictions within the chamber. In other forms, the tube connection may be clipped into place, such as described previously.

As shown, connection port 3600 is arranged between tube sheet 3364 and textile sheet 3360. Additionally, assembly connection ports 3154 and 3155 may also be similarly situated. Connection port 3600 and assembly connection ports 3154 and 3155 are sandwiched between tube sheet 3364 and textile sheet 3360. Once sealed as shown in FIG. 9B, the connection ports may be located within tube 3450 without requiring another step to insert or located the connection portions within the tube.

Referring to FIGS. 9C through 9E, tube 3450 is depicted in various states. As shown in FIG. 9D, tube 3450 is depicted in a steady state and not subjected to internal air pressure. In this form, as shown in the cross section, outer layer 3354 and inner layer 3352 lie substantially planar along the surface of one another. That is, in contrast to previously discussed forms of the present technology, tube 3450 is not pre-formed to have a particular cross section. Tube 3450 therefore does not occupy as much space when not being used as compared to other forms of the technology. Further, tube 3450 may be easily storable such that tube 3450 may be a convenient tube with which to travel.

As shown in FIG. 9E, once subjected to internal pressure, such as air pressure from a therapy device, tube 3450 may expand or open. Air may be forced through connection port 3600 such that the air fills the internal chamber of tube 3450. Air may then pass to the ends of tube 3450 and to another connection mechanism such as assembly connection ports 3154 and 3155 or to the nose or mouth of a patient. Referring particularly to the cross section of FIG. 9E, as shown, both tube sheet 3364 and outer covering 3366 are located along the upper portion of the cross section whereas textile sheet 3360 is located along the lower portion of the cross section. Because connection port 3600 and assembly connection ports 3154 and 3155 were placed between tube sheet 3364 and textile sheet 3360, the air flow from the therapy device is directed to connection port 3600 and assembly connection ports 3154 and 3155 and therefore does not extend between tube sheet 3364 and outer covering 3366. In other forms, the sheets may be designed such that air is permitted to pass through any of the layers. Additionally, the connection port 3600 and assembly connection ports 3154 and 3155 may be located in various positions depending on the particular circumstances or design requirements.

In some forms, inner layer 3352 and/or outer layer 3354 may be formed of inextensible material. That is, in some forms inner layer 3352 and outer layer 3354 may not stretch when subjected to internal air pressure, but may still inflate such as depicted in FIG. 9E. In other forms, inner layer 3352 and/or outer layer 3354 may be formed of resilient material that stretches when subjected to internal pressure. In still further forms, inner layer 3352 may include a textile that does not stretch while outer layer 3354 includes a textile that stretches. For example, the stretch or extensibility properties of the inner layer 3352 and the outer layer 3354 may be different.

When formed in the manner as described, outer layer 3354 may be cut or slit such that outer layer 3354 extends around intake 3608 of connection port 3600. In a similar manner inner layer 3352 may be cut or slit such that inner layer 3352 extends around assembly connection ports 3154 and 3155. Outer layer 3354 may be cut or sliced before or after outer layer 3354 is secured to inner layer 3352. In some forms, outer layer 3354 may then be subjected to heat in a particular location such that the membrane melts and outer layer 3354 conforms to intake 3608 of connection port 3600. Then the membrane associated with tube sheet 3364 is allowed to cure such that a secure connection is formed between outer layer 3354 and the connection port 3600. A similar arrangement may be utilized with respect to inner layer 3352 and assembly connection ports 3154 and 3155.

In other forms, outer layer 3354 and inner layer 3352 may be flexible, stretchable, and resilient such that outer layer 3354 and/or inner layer 3352 are able to be stretched around intake 3608 of connection port 3600 or similar intakes of assembly connection ports 3154 and 3155. Because outer layer 3354 includes a membrane that contacts connection port 3600, the membrane may assist in providing an adequate seal between outer layer 3354 and connection port 3600. That is, the resiliency of outer layer 3354 may cause outer layer 3354 to contract around the opening of connection port 3600. The resiliency of outer layer 3354 in combination with the membrane allows for a seal to be formed between connection port 3600 and outer layer 3354. Similar to a rubber band, outer layer 3354 may press against intake 3608 through friction rather than by a permanent connection. This friction fit may restrict the movement of connection port 3600 such that connection port 3600 remains in a particular location.

Additionally, the connection between outer layer 3354 and connection port 3600 may be adjusted such that a specific quantity of oxygen or air is able to leak through the connection. This specific leakage may remove the need to include a separate valve that allows for excess air, oxygen, or waste air to be disposed of during use.

In other forms, tube 3450 may be formed such that tube 3450 has a predetermined shape such as tube 3350. For example, inner layer 3352 and outer layer 3354 may be arranged around a mandrel and then subjected to heat to form a particular cross section. Then the layers may be cut and sealed so that in addition to being thermoformed, inner layer 3352 and outer layer 3354 are connected to one another during the cutting process.

5.3.3.1.2 Strap Rigidity

In some forms, components may be formed utilizing various quantities of a conformable membrane. In some forms, a conformable membrane may be particularly placed along various surfaces. The conformable material may be utilized to provide specific reinforcement in various areas of a strap or other component. For example, a strap such as strap 3420 is utilized to assist in securing patient interface 3000 to the face of a patient. In some forms, particular areas of a strap may require increased or additional support when compared to other portions of the strap. Further, in some forms, the stretch or elasticity of the strap may be limited by utilizing the silicone or polyurethane membrane.

Referring to FIGS. 5A-5E a strap is depicted. The strap includes an inner layer, a membrane layer, and an outer layer. Although depicted with an outer layer, it is not necessary that an outer layer be included. That is, in some forms, elastic inner layer 3422 and membrane layer 3424 may be utilized without outer layer 3426. As shown in FIG. 5A, strap 3420 may interact with tube 3350 to secure patient interface 3000 in place with respect to a patient. Membrane layer 3424 is depicted with substantial thickness in the figures for ease of viewing. Membrane layer 3424 may be substantially thinner than either outer layer 3426 or inner layer 3422. For example, membrane layer 3424 may be less than 10% of the thickness of either outer layer 3426 or inner layer 3422

Referring to FIG. 5B, a portion of strap 3420 is depicted in isolation from the rest of patient interface 3000. As shown, strap 3420 includes outer layer 3426 and inner layer 3422. Membrane layer 3424 is located between the layers, and in some forms connects the layers to one another. That is, strap 3420 may be exposed to a heat source such that membrane layer 3424 melts or changes forms and cools such that inner layer 3422 and outer layer 3426 are connected to one another. As shown in FIG. 5B membrane layer 3424 does not extend the full length of inner layer 3422. In other forms, membrane layer 3424 may extend the full length of inner layer 3422. In further forms, one of the layers may not extend the full distance of strap 3420. For example, in some forms, outer layer 3426 may only extend along strap 3420 the same or similar distance as does membrane layer 3424. In that example, the entire length of outer layer 3426 may be secured to inner layer 3422 through the use of membrane layer 3424. Further, in some forms, the membrane may be adhered along the entire length of the shortest layer. Then the two layers may be combined and adhered to one another using a thermoplastic or thermoset material such as membrane layer 3424.

As shown in FIG. 5C, a portion of inner layer 3422 is layered with membrane layer 3424. In some forms, membrane layer 3424 may be formed of the same material as the textile membranes discussed with respect to tube 3350. By utilizing the same material in various parts of a patient interface, the manufacturing costs may be reduced when compared to other forms. Inner layer 3422 may be formed of an elastic or stretchable material that is conformable to the shape of a head of a patient. Additionally, outer layer 3426 may also be made of the same or similar material in the same or similar configuration. The layers may be formed of natural or synthetic materials. In some forms the layers may be textiles whereas in other forms the layers may be rubber or plastic components. Further, although depicted as the same or similar material with the same or similar properties, inner layer 3422 and outer layer 3426 may have different properties such as stretch, rigidity, flexibility, and other properties. The materials for each layer may be chosen depending on the particular properties desired for strap 3420.

Referring to FIGS. 5D and 5E, inner layer 3422 has a different stretchability than outer layer 3426 in areas in which membrane layer 3424 not present. For example, when subjected to a tensile force T, inner layer 3422 stretches a first distance 3428. As shown, membrane layer 3424 along with outer layer 3426 stretch second distance 3430 when subjected to the same tensile force T. Second distance 3430 is smaller than first distance 3428. Membrane layer 3424 therefore may limit stretching in the particular area on which the membrane layer 3424 is applied. That is, although permitted to stretch, membrane layer 3424 may reduce the distance that inner layer 3422 or outer layer 3426 is able to stretch. This type of configuration may be utilized in particular areas that require stepped stretchability to provide adequate support to the apparatus. Although depicted with outer layer 3426, in some forms of the present technology, outer layer 3426 may not be utilized. Inner layer 3422 may be used for the strap without using another layer such as outer layer 3426. In such a configuration, the strap may be oriented such that membrane layer 3424 faces away from the patient. In this manner, the soft texture of inner layer 3422 may be against the face of a patient. Membrane layer 3424 may therefore be utilized to limit stretch without a covering such as outer layer 3426.

In addition to controlling the stretch rate of particular components, the use of membrane layer 3424 may also control the rate of restoration. That is, membrane layer 3424 may increase the ability of an elastic band such as strap 3420 to return to its original, unstretched state.

In some forms, the membrane layer 3424 may be utilized to provide structural support a strap. In some forms, a strap may twist or rotate during use such that the strap is out of position and causes creases and discomfort to the patient. In such instances, a membrane may be utilized to support the strap and to resist that strap from rotating or twisting during patient.

Various straps may be utilized to support a cushion assembly such that the cushion assembly provides adequate sealing to the nasal or mouth areas of a patient. As shown in FIG. 5F, head strap 3432 is shown in conjunction with tube 3434 of an alternate patient interface 3436.

Referring to FIG. 5G a head strap component is depicted. Head strap 3432 may include various features as discussed previously. Referring to FIG. 5H, an exploded view of head strap 3432 is depicted. As shown, head strap 3432 includes interior layer 3437, exterior layer 3438, straps 3439-3442 and pad 3443. Interior layer 3437 and exterior layer 3438 encompass or sandwich a portion or all of the components. As shown, interior layer 3437 and exterior layer 3438 completely sandwich pad 3443 and encompass a portion of straps 3439-3442. In some forms, interior layer 3437 and/or exterior layer 3438 may be layered with a membrane or silicone or polyurethane layer such as described previously with reference to tube 3350. The interior layer 3437 and exterior layer 3438 may be aligned and then subjected to heat such that the membrane between the interior layer 3437 and exterior layer 3438 melts and then joins the layers together. As shown, the interior layer 3437 and exterior layer 3438 also may adhere or join to the pad 3443. In other forms, the membrane layer may be absent in the area of the pad 3443. That is, the pad 3443 may be located in a pocket between interior layer 3437 and exterior layer 3438, however the pad 3443 may not be physically secured to the interior layer 3437 or the exterior layer 3438. Further, in some forms, the straps 3439-3442 may be secured using an adhesive. However, in other forms, the straps 3439-3442 are secured to the interior layer 3437 and the exterior layer 3438 through the membrane.

The components of head strap 3432 may be spaced in various orientations. As shown in FIG. 5G, strap 3442 is spaced from strap 3441 by a portion of interior layer 3437 and a portion of exterior layer 3438. Similarly, strap 3442 is spaced from pad 3443 by a portion of interior layer 3437 and exterior layer 3438. Various other configurations can be utilized. For example, in some forms, strap 3442 may contact strap 3441. In still further forms, strap 3442 and strap 3441 may be a unitary piece. Other variations are possible as well. For example, pad 3443 may be larger or smaller, or may not be present. By varying the size, shape, and orientation of the various components, the feel of the component may be changed and customized. As shown, there may be various different stretch zones of head strap 3432. Zone X1 includes the straps 3439-3442 and they have a first stretchability, and in some forms may be substantially inextensible. The second zone is zone X2 which includes the straps 3439-3442 and a portion of interior layer 3437 and exterior layer 3438. This has a second stretchability which may also be substantially inextensible. The third zone is zone X3 between the end of the straps 3439-3442 and the pad 3443. This has a third stretchability. And finally the last stretch zone is zone X4 which includes the pad 3443 and the interior layer 3437 and the exterior layer 3438. These various areas may be altered depending on the manufacturer's intent or desire for various properties.

The configuration as shown in FIG. 5G allows for various properties to be present in a single head strap 3432 without the need for various connection components that add bulk and may be uncomfortable. By integrating a membrane as a joining material, the weight of the head strap also may be reduced when compared to other forms.

5.3.3.2 Positioning and Stabilising Structure According to Additional Examples of the Present Technology Additional examples of the positioning and stabilising structure are described below. It should be noted that the features described below may be used with or combined with features described in other examples of this disclosure. For example, the tubes described below may be used with the cushion modules/cushion assemblies described in other examples, and vice versa. Moreover, individual features of any of the structures described in any example may be used with or combined with features in other examples.

5.3.3.2.1 Headgear Tubing

Figure 1A:
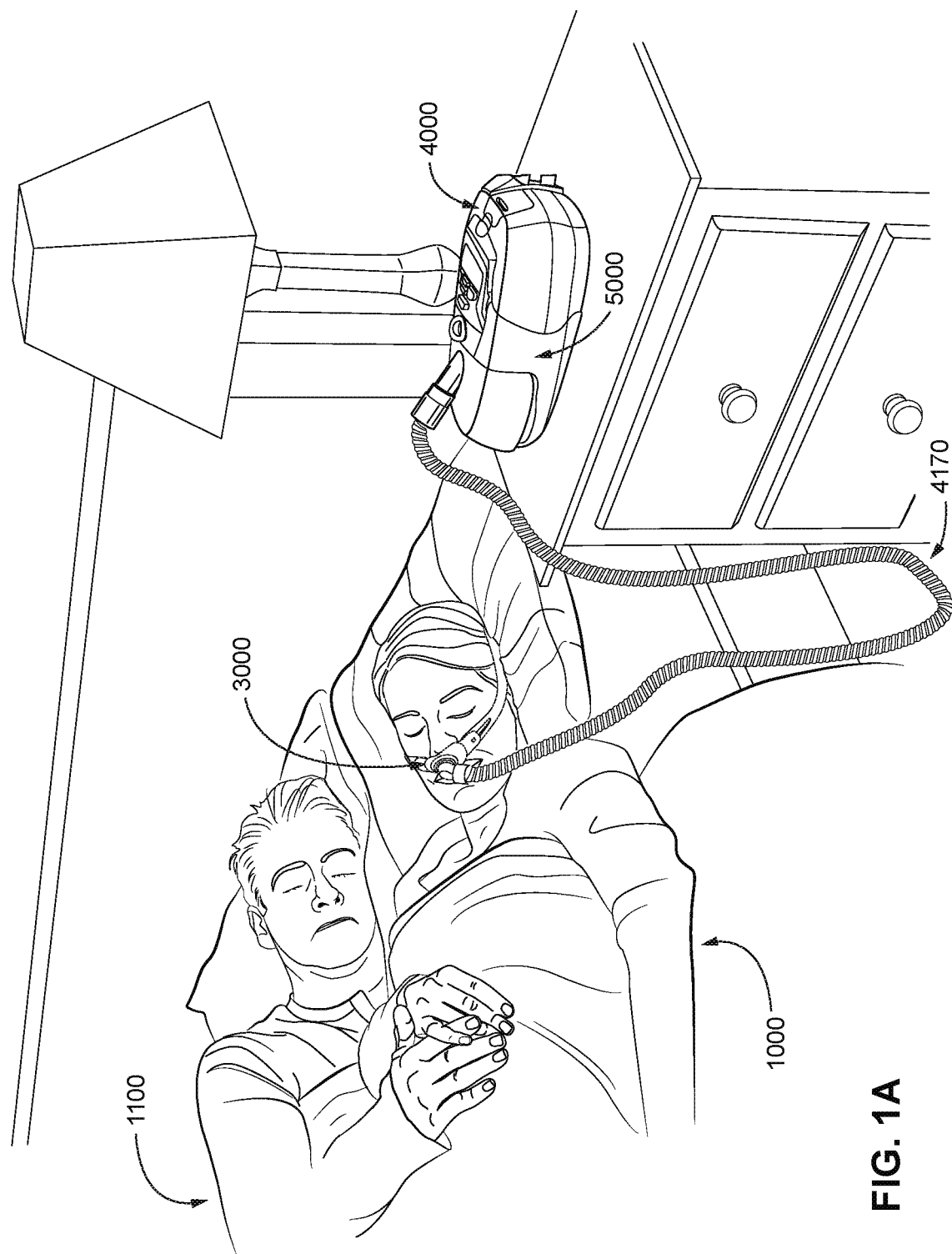
Figure 1B:
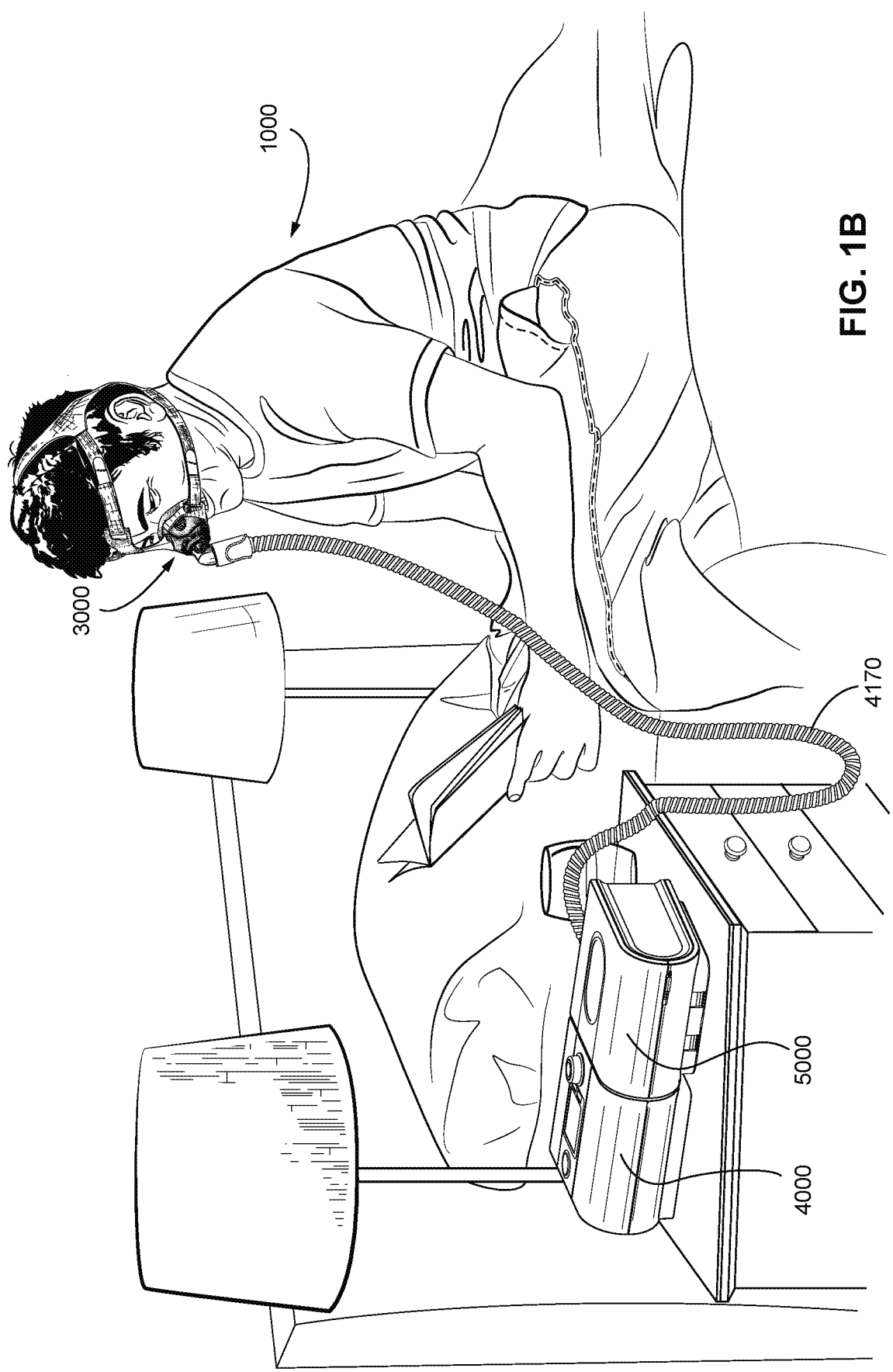
Figure 1C:

As shown in FIGS. 10 and 11, a non-invasive patient interface 9000, 10000 in accordance with examples of the present technology may comprise the following functional aspects: a seal-forming structure 9100, a plenum chamber 9200, a positioning and stabilising structure 9300, at least one vent 9400, 9400-1 and one form of connection port 9600 for connection to an air circuit (e.g. the air circuit 4170 shown in FIGS. 1A-1C). In this example, the seal-forming structure 9100 and the plenum chamber 9200 are provided by a cushion module 9150. The cushion module 9150 in this example is a cradle cushion module. In other examples it may be a nasal pillows cushion module or another type of cushion module.

In some forms of the present technology, the positioning and stabilising structure 9300 comprises one or more tubes 9350 that deliver pressurised air received from a conduit forming part of the air circuit 4170 from the RPT device to the patient's airways, for example through the plenum chamber 9200 and seal-forming structure 9100. In the forms of the present technology illustrated in FIGS. 10 and 11, the positioning and stabilising structure 9300 comprises two tubes 9350 that deliver air to the seal-forming structure 9100 from the air circuit 4170. The tubes 9350 are an integral part of the positioning and stabilising structure 9300 of patient interface 9000 to position and stabilize the seal-forming structure 9100 of the patient interface to the appropriate part of the patient's face (for example, the nose and/or mouth). This allows the conduit of air circuit 4170 providing the flow of pressurised air to connect to a connection port 9600 of the patient interface in a position other than in front of the patient's face which may be unsightly to some people. While a pair of tubes 9350 have some advantages (described below), in some examples, the positioning and stabilising structure 9300 comprises only a single tube 9350 configured to overlie the patient's head on one side. A strap or other stabilising component may be provided to the other side of the patient's head between the top end of the single tube 9350 and the seal-forming structure 9100, to provide balanced forces on the seal-forming structure 9100.

Since air can be contained and passed through headgear tubing 9350 in order to deliver pressurised air from the air circuit 4170 to the patient's airways, the positioning and stabilising structure 9300 may be described as being inflatable. It will be understood that an inflatable positioning and stabilising structure 9300 does not require all components of the positioning and stabilising structure 9300 to be inflatable. For example, in the examples shown in FIGS. 10 and 11, the positioning and stabilising structure 9300 comprises the headgear tubing 9350, which is inflatable, and the strap 9310, which is not inflatable.

In certain forms of the present technology, the patient interfaces 9000, 10000, shown in FIGS. 10 and 11, may comprise a connection port 9600 located proximal a top, side or rear portion of a patient's head. For example, in the forms of the present technology illustrated in FIGS. 10 and 11, the connection port 9600 is located on top of the patient's head. In these examples the patient interfaces 9000, 10000 comprise an elbow 9610 to which the connection port 9600 is provided. The elbow 9610 may swivel (e.g., via a swivel ring 9614) with respect to the positioning and stabilising structure 9300 in order to decouple movement of a conduit connected to the connection port 3600 from the positioning and stabilising structure 3300. The elbow 9610 may connect to a fluid connection opening in the headgear tubing 9350 or in a component to which the headgear tubing 9350 is connected. Additionally, or alternatively, a conduit connected to the connection port 9600 may swivel with respect to the elbow 9610. In the illustrated example, elbow 9610 comprises a swivelling conduit connector comprising the connection port 9600 to which a conduit of the air circuit 4170 is able to connect, such that the conduit can rotate about its longitudinal axis with respect to the elbow 9610. In some examples the air circuit 4170 may connect to the fluid connection opening. The elbow 9610 may rotatably connect to the fluid connection opening or to a ring received in the fluid connection opening.

Patient interfaces in which the connection port is not positioned in front of the patient's face may be advantageous as some patients find a conduit that connects to a patient interface in front of the face to be unsightly and/or obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the forms of the present technology illustrated in FIGS. 10 and 11, the positioning and stabilising structure 9300 comprises two tubes 9350, each tube being positioned in use on a different side of the patient's head and extending across the respective cheek region, above the respective ear (superior to the otobasion superior on the patient's head) to the elbow 9610 on top of the head of the patient. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 9000 may comprise a different number of tubes, for example one tube, or three or more tubes. In one example in which the patient interface has one tube 9350, the single tube is positioned on one side of the patient's head in use (e.g. across one cheek region) and a strap forms part of the positioning and stabilising structure 9300 and is positioned on the other side of the patient's head in use (e.g. across the other region) to assist in securing the patient interface 9000 on the patient's head.

In the forms of the technology shown in FIGS. 10 and 11, the two tubes 9350 are fluidly connected at their upper ends to each other and to connection port 9600. In the illustrated examples, the tubes 9350 are separate tubes that are connected to a crown connector 9360. The crown connector is configured to be positioned on or in front of (anteriorly to) the crown of the patient's head in use. The tubes 9350 are indirectly connected to each other by the crown connector 9360 and may be disconnected, for example for cleaning or storage. In another example, the two tubes are integrally formed and comprise a fluid connection opening to which a swivel elbow connects. In other examples where separate tubes are used they may be indirectly connected together, for example each may be connected to a T-shaped conduit having two conduit arms each fluidly connectable to the tubes 9350. The crown connector 9360 may comprise a third conduit arm. The connection port 9600 may comprise an elbow 9610 received in fluid connection opening 9390 at the centre of the crown connector 9360. The elbow 9610 may be received in a ring in the fluid connection opening 9390 and may form a seal with a sealing flange 9362 provided to the ring. The elbow 9610 may be configured to swivel within the ring. The fluid connection opening 9390 may be also considered a connection port 9600 itself.

The tubes 9350 may be formed from textile, spacer fabric and/or foam materials, in some examples. In some examples, the spacer fabric material itself comprises layers. The spacer fabric may comprise a textile sandwich structure. The spacer fabric may comprise a face layer, back layer and an internal spacer layer. The internal spacer layer may be formed by a network of fibres and be relatively open. Spacer fabric may advantageously be used to provide good cushioning due to the middle layer being highly compressible and also breathable. The middle layer may also be resilient. Spacer fabric may be used in either the patient contacting portion 9348 or the non-patient contacting portion 9349 and may be either an intermediate layer or an outer layer. In other examples, the tubes 9350 may be formed of a semi-rigid material such as an elastomeric material, e.g. silicone. The tubes may have a natural, preformed shape although may have at least some ability to deform if a force is applied to the tubes or conform to a patient's head. For example, the tubes may be generally arcuate or curved in a shape approximating the contours of a patient's head between the top of the head and the nasal or oral region.

The positioning and stabilising structure 9300 in some examples may comprise sleeves around the tubes 9350. In some examples, the patient interface 9000 may not comprise sleeves and in other examples the patient interface 9000 may comprise sleeves 9364 (FIGS. 31 and 32) that cover more, or all, of the tubes 9350. The sleeves 9364 may be formed to fit to the curved shape of the tubes 9350. In some examples, the sleeves are formed from a smooth fabric. The sleeves may be more comfortable against the patient's face than the tube 9350 without any covering.

As described in U.S. Pat. No. 6,044,844, the contents of which are incorporated herein, the tubes 9350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 9350 during use. A crush resistant tube may be advantageous where only a single tube 9350 is present as if the single tube becomes blocked during use the flow of gas would be restricted and therapy will stop or reduce in efficacy.

In certain forms of the technology, one or more portions of the tubes 9350 may be rigidised by one or more rigidising or stiffening elements. Examples of rigidising elements include: sections of the tubes 9350 that are comparatively thicker than other sections; sections of the tubes 9350 that are formed from a material that is comparatively more rigid that the material forming other sections; and a rigid member attached to the inside, outside or embedded in a section of tube. The use of such rigidising elements helps to control how the positioning and stabilising structure 9300 will function in use, for example where the tubes 9350 is more likely to deform if forces are applied to them and where the shape of the tubes 9350 is more likely to be maintained if forces are applied. The selection of where such rigidising elements are positioned in the tubes 9350 can therefore help to promote comfort when the patient interface 9000 is worn and can help to maintain a good seal at the seal-forming structure 9100 during use. Rigidising or stiffening elements may be in positioning and stabilising structures 9300 which are configured to support relatively heavy seal-forming structures such as full face or oro-nasal cushion assemblies.

In certain forms of the technology, one or more portions of the tubes 9350 may be formed lengthways from at least two parts, the rigidising elements being inside, outside or embedded within the intersection of the at least two parts.

The tubes 9350 in the form of the technology shown in FIGS. 10 and 11 have a length of between 15 and 30 cm each, for example between 20 and 27 cm each. The length of the tubes is selected to be appropriate for the dimensions of the heads of typical patients, for example the distance between the region proximate the top of the head where the upper end of the tubes 9350 are situated, and the region proximate the openings to the patient's airways at which the lower end of the tubes 9350 connect to the cushion module 9150 when following a generally arcuate path down the sides of the heads and across the patient's cheek region (such as the arcuate path taken by the tubes 9350 shown in FIGS. 10 and 11). In some examples, the patient interface 9000 may be configured so that the length of the tubes 9350 can be varied. It will be appreciated that the length of the tubes 9350 will depend on the length of other components in the patient interface 9000, for example the length of the crown connector 9360 to which the superior ends of the tubes 9350 connect and/or the size of the plenum chamber 9200.

5.3.3.2.1.1 Positioning of Headgear Components

Each tube 9350 may be configured to receive a flow of air from the connection port 9600 on top of the patient's head and to deliver the flow of air to the seal-forming structure at the entrance of the patient's airways. In the examples of FIGS. 10 and 11, the at least one tube 9350 extends between the seal-forming structure 9100 and the connection port 9600 across the patient's cheek region and above the patient's ear, i.e. a portion of tube 9350 that connects to the cushion module overlays a maxilla region of the patient's head in use and a portion of tube 9350 overlays a region of the patient's head superior to the otobasion superior on the patient's head. Each of the one or more tubes 9350 may also lie over the patient's sphenoid bone and/or temporal bone and either or both of the patient's frontal bone and parietal bone. The connection port 9600 and elbow 9610 may be located in use over the patient's parietal bone, frontal bone or the junction therebetween.

The exemplary forms of the technology illustrated in FIGS. 10 and 11 has tubes 9350 which curve around the upper part of the patient's head from the upper end of the tubes 9350 that connect to elbow 9610 on top of the head to the point at which the strap 9310 connects to the tubes 9350 with relatively little curvature in the sagittal plane. In between the point at which the rear headgear strap 9310 connects to the tubes 9350 and the lower ends of the tubes 9350 at which they connect with the cushion module 9150 in front of the patient's airways under the nose, the tubes 9350 curve forwards between the patient's ears and eyes and across the cheek region. The radius of curvature of this section of the tubes 9350 may be in the range 60-100 mm, for example 70-90 mm, for example 80 mm. The lower end of the tubes 9350 and the section of the tubes 9350 at which the rear headgear strap 9310 connects to the tubes 9350 may subtend an angle in the range 65-90°, for example 75-80°. The actual curvature present in the portions of the tubes 9350 superior to the strap 9310, and the actual curvature in the portions of the tubes 9350 inferior to the strap 9310, depends on patient setup and in practice will vary depending on the shape and size of the patient's head and the patient's preferences.

The degree to which the patient interface 9000 fits an individual patient can be altered by varying the length of the tubes 9350 and, alternatively or additionally, by altering the position of the patient interface 9000 or portions thereof on the patient's head. For example, a patient interface 9000 having tubes 9350 of a certain length can be adjusted to better fit a patient by moving portions of the positioning and stabilising structure 9300 in the posterior or anterior direction on the patient's head. For example, positioning the junction of the tubes 9350 above the patient's head further forward (i.e. in the anterior direction) enables a patient interface 9000 having tubes 9350 of a certain length to fit a larger head than if the junction of the tubes 9350 is positioned further backward (i.e. in the posterior direction). In most patients, if the junction of the tubes 9350 is positioned forwardly, the superior portions of the tubes 9350 lie over a smaller portion of the patient's head than if the junction of the tubes 9350 is positioned rearwardly. In some examples of the technology, the tubes 9350 are less flexible and the patient may have less freedom to move the superior portions of the tubes 9350 anteriorly or posteriorly on their head.

In certain forms of the present technology the patient interface 9000 is configured such that the connection port 9600 can be positioned in a range of positions across the top of the patient's head so that the patient interface 9000 can be positioned as appropriate for the comfort or fit of an individual patient. One way this can be achieved so that the seal-forming structure 9100 forms an effective seal with the patient's face irrespective of the position of the connection port 9600 on the patient's head is to de-couple movement of the upper portion of the patient interface 9000 from the lower portion of the patient interface 9000. Such de-coupling can be achieved by, for example, forming the tubes 9350 to be sufficiently flexible that the superior portions of the tubes 9350 can be moved.

In a certain form of the present technology, the patient interface 9000 is configured such that the connection port 9600 is positioned approximately at a top point of the patient's head. The connection port 9600 may be positioned in the sagittal plane and aligned with the otobasion superior points in a plane parallel to the coronal plane. The otobasion superior points are identified in FIG. 2D. In some forms of the technology, the positioning and stabilising structure 9300 is configured to be worn in different positions, with the effect that the connection port 9600 may be positioned proximate the top of the patient's head in the sagittal plane up to around 20 mm forward or 20 mm rearward of the otobasion superior points.

In some examples of the present technology, the connection port 9600 may be positioned in the sagittal plane and aligned with a junction between the frontal bone and the parietal bones. The connection port 9600 may be positioned approximately over the junction of the coronal suture and the sagittal suture. In this configuration, the superior portions of the tubes 9350 may lie over and/or along a portion of the coronal suture. However, as mentioned above the patient has the ability to move the connection port 9600 anteriorly or posteriorly in order to adjust the fit of the patient interface 9000, in some forms of the present technology.

An advantage provided by the tubes 9350 overlying the patient's head slightly anterior to the superior-most point (e.g. at or proximate the coronal suture) is that the risk of the tubes 9350 riding in a posterior direction in use may be reduced. In many patients there may be a recess or "divot" where the coronal suture meets the sagittal suture. The positioning and stabilising structure 9300 may be particularly stable when tubes 9350 lie within this divot. Accordingly, in some examples the tubes 9350 are configured with appropriate curvature and/or ability to curve in order to lie over the coronal suture.

As described above, in some examples of the present technology the patient interface 9000 comprises a seal-forming structure 9100 in the form of a cradle cushion which lies generally under the nose and seals to an inferior periphery of the nose. The positioning and stabilising structure 9300 may be structured and arranged to pull the seal-forming structure 9100 into the patient's face under the nose with a sealing force vector that has a posterior and superior direction (e.g. a posterosuperior direction). A sealing force vector with a posterosuperior direction may facilitate the seal-forming structure 9100 forming a good seal to both the inferior periphery of the patient's nose and the anterior-facing surfaces of the patient's face on either side of the patient's nose and the upper lip.

In some examples, the positioning and stabilising structure 9300 may in use apply a sealing force vector having a posterosuperior direction at an angle of approximately 35° with respect to the patient's Frankfort horizontal (identified in FIG. 2E). The superior portions of the tubes 9350 (e.g. the portions of the tubes 9350 superior to the strap 9310) may be oriented vertically, and the rear headgear strap 9310 may extend from the tubes 9350 in a posteroinferior direction at an angle of approximately 35° with respect to the patient's Frankfort horizontal. In this particular setup, there is an angle of 125° formed between the strap 9310 and the superior portions of the tubes 9350 where the strap 9310 connects to the tubes 9350.

In some examples the positioning and stabilising structure 9300 may be configured such that the superior portions of the tubes 9350 lie across the patient's head slightly anterior to a superior-most point. For some patients this may result in the tubes 9350 being angled slightly anteriorly rather than aligned vertically (e.g. in the coronal plane) in order to lie within a slight recess at or proximate the coronal suture of the skull. In such an example, the tension in the strap 9310 could be adjusted by the patient to balance the forces and achieve the optimal sealing force vector.

In some examples, the positioning and stabilising structure 9300 may be configured to apply a force on the seal-forming structure 9100 in a posterosuperior direction at an angle that bisects an angle formed between the upper lip and the columella (e.g. the surfaces forming the nasolabial angle).

In certain examples of the present technology, the tubes 9350 are configured to receive the strap 9310 at the locations superior to and proximate the patient's ears. If the strap 9310 connects to the tubes 9350 too high with respect to the patient's head, the strap 9310 may have a tendency to ride up the back of the patient's head. Additionally, the strap 9310 could form too large of an angle with respect to the superior portions of the headgear tubes 9350, resulting in the necessity for the patient to tighten the strap 9310 excessively, which could result in both excessive tension in the positioning and stabilising structure 9300 and make the strap 9310 more likely to ride up the back of the patient's head. Accordingly, it is advantageous for the connection between the strap 9310 and the tubes 9350 to be provided as low as possible but spaced from the top of the patient's ear sufficiently that upon tightening of the strap 9310, the tubes 9350 are not pulled into contact with the patient's ears.

5.3.3.2.1.2 Headgear Tube Fluid Connections

The two tubes 9350 are fluidly connected at their inferior ends to the plenum chamber 9200. In the examples of FIGS. 10 and 11, the tubes 9350 form a fluid connection with the cushion module 9150 and seal-forming structure 9100. In certain forms of the technology, the connection between the tubes 9350 and the cushion module 9150 is achieved by connection of two rigid components so that the patient can easily connect the two components together in a reliable manner. The tactile feedback of a 're-assuring click' or like sound may be easy for a patient to use or for a patient to know that the tube has been correctly connected to the cushion module 9150. In one form, the tubes 9350 are formed from textile and foam materials and the lower end of each of the tubes 9350 is overmolded or bonded to a rigid connector made, for example, from polypropylene, polycarbonate, nylon or the like. The rigid connector may comprise a male mating feature configured to connect to a female mating feature on the cushion module 9150. Alternatively, the rigid connector may comprise a female mating feature configured to connect to a male mating feature on the cushion module 9150. The same manner of connection by which the tubes 9350 are connected to the cushion module 9150 may also be applied to the connection between the tubes 9350 and another plenum chamber 9200 or seal-forming structure 9100, such as a nasal pillows cushion module.

In a hard-to-hard type engagement between the tube 9350 and port, a pressure activated seal such as a peripheral sealing flange may be used. When pressurised gas is supplied through the tubes 9350 the sealing flange is urged against the join between the tubes and the inner circumferential surface of the port of the plenum chamber 9200 to enhance the seal between them. If the port is soft and a rigid connector is provided to the tube 9350, the pressure activated seal as described earlier may also be used to ensure the connection is air-tight.

Similar connection mechanisms may be used to fluidly connect the tubes 9350 with the crown connector 9360 to which the connection port 9600 is fluidly attached in some forms of the technology. In one embodiment, a swivel elbow connected at the connection port 9600 is rotatable in order to drive a port size adjustment mechanism that decreases or increases the size of the ports into which tubes 9350 are inserted in order to improve the fit of the tubes through an increase or decrease of compressive forces and to reduce unintended leakage.

5.3.3.2.1.3 Extendable Concertina Structure

The patient interface 9000 may comprise one or more extendable tube sections. In some examples, an extendable tube section comprises an extendable concertina structure. The patient interface 9000 may comprise a positioning and stabilising structure 9300 including at least one gas delivery tube comprising a tube wall having an extendable concertina structure.

5.3.3.2.1.4 Bendability

In some examples of the present technology, portions of the positioning and stabilising structure 9300 are configured to be more resistant to bending in or about some directions or axes than in or about others.

For example, a superior portion of each tube 9350 of the positioning and stabilising structures 9300 shown in FIGS. 10 and 11 may be more bendable in a particular direction in comparison to an orthogonal direction. Each gas delivery tube 9350 of the positioning and stabilising structure 9300 may comprise a superior tube portion 9304 configured to overlie a superior region of the patient's head in use. In some examples of the present technology, the superior tube portion 9304 may comprise an extendable tube structure (such as one of the options disclosed in PCT Patent Publication No. WO 2017/124155 or in U.S. Patent Application No. 62/764,995 (corresponding to PCT Application No. PCT/AU2019/050874, filed Aug. 20, 2019), the entire contents of each of which are incorporated herein by reference) or may be non-extendable. In the illustrated forms of the technology shown in FIGS. 10 and 11, the tubes are substantially non-extendable, save for any inherent stretchability in the material(s) forming the tube.

The superior tube portion 9304 comprises a first end 9305 and a second end 9306. In this example the first end 9305 is configured to overlie or lie against a superior portion of the patient's head, at approximately sagittal plane of the patient's head (e.g. approximately top and centre of the patient's head). The second end 9306 is configured to overlie the patient's head laterally from the first end 9305 (e.g. closer to the side of the patient's head). The second end 9306 may lie both laterally and inferiorly to the first end 9305. The positioning and stabilising structures 9300 of FIGS. 10 and 11 are able to bend about multiple axes to at least some extent. For example, the superior tube portion 9304 of the positioning and stabilising structure 9300 may be able to drape down over the patient's head and also curve in the anterior and posterior directions.

In some examples of the present technology, the superior tube portion 9304 may also comprise one or more stiffened portions between the first end 9305 and the second end 9306. The stiffened portion(s) may be configured to provide a higher resistance to relative movement between the first end 9305 and a second end 9306 in an anterior and/or posterior direction than in a superior and/or inferior direction. The stiffened portions may in some examples be provided to the entire length of the tube 9350, and in some examples may provide varying stiffnesses to the tube 9350 along the length of the tube 9350.

When the patient dons the positioning and stabilising structure 9300, the superior tube portion 9304 may have a relatively low resistance to bending in the vertical directions such that the second end 9306 is able to move inferiorly with respect to the first end 9305. This advantageously enables the superior tube portion 9304 to "drape" downwardly over the top of the patient's head to the side of the patient's head. Bendability in the superior/inferior directions may be advantageous in enabling the superior tube portion 9304 to conform to the curvature of the patient's head.

Additionally, the superior tube portion 9304 may have a relatively higher resistance to bending in the horizontal directions such that the first end 9305 does not unintentionally move anteriorly and/or posteriorly with respect to the second end 9306. This advantageously enables the superior tube portion 9304 to remain in a desired position across the top of the patient's head. With a lower resistance to bending towards the anterior and/or posterior directions, the superior tube portion 9304, and in particular the connection port 9600, may be less likely to ride forward or backward along the top of the patient's head in use. This resistance to a forward or backward movement of the superior tube portion 9304 is particularly advantageous for the patient interface 9000 given the connection to the air circuit 4170 is provided atop the patient's head, meaning tube drag forces may act directly on the superior tube portion 9304.

In some examples, the superior tube portion 9304 may comprise a shape which inherently provides the advantageous resistance to bending. For example, the superior tube portion 9304 may comprise a somewhat rectangular or trapezoidal cross-section with the parallel long sides configured to lie against the surfaces of the patient's head. The long sides of the rectangular cross section provide a relatively large resistance to bending of the superior tube portion in directions parallel to the long sides (e.g. the anterior and/or posterior directions in use). However, the short sides of the rectangular/trapezoidal cross section may not provide such a large resistance to bending of the superior tube portion 9304 and directions parallel to the short sides (e.g. the inferior and/or superior directions in use).

It will be appreciated that the cross-section of the superior tube portion 9304 may not be perfectly rectangular. For example, the corners and/or short sides may be rounded such that the cross-section of the superior tube portion 9304 may be substantially oval or elliptical. However, a cross-sectional shape that presents a flattened surface of tube on the side that faces and contacts the patient's face or other part of the head may be more comfortable to wear than, for example a tube with a circular cross-section.

The stiffened portion may be formed by one or more rigidising structures formed by or provided to the tube wall of the tube 9350. A tube 9350 that comprises stiffened portions on both the anterior and posterior sides of the tube 9350 may advantageously have a higher resistance to bending towards both the anterior and posterior sides of the tube 9350. However, in some examples a stiffened portion is provided to only one of the anterior or posterior sides of the tube 9350 since, depending on the stiffness, a stiffened portion on one side only may provide a sufficient resistance to bending towards both directions.

In some examples, portions of the tubes 9350 (e.g. anterior and/or posterior portions) may comprise stiffened portions being stiffened with one or more rigidising elements. The tubes 9350 may be rigidised with one or more rigidising components having a higher stiffness than the tube 9350 embedded within the tube wall. For example, the tube wall may be bonded to an elongate bar or rod formed from a material stiffer than the tube wall. In other examples, a stiffened portion of the tube wall may be provided by further features of the geometry of the tube wall. In one example the tube wall may comprise a greater material thickness at the anterior and/or posterior sides of the tube 9350.

5.3.3.2.1.5 Inferior Tube Portions

The patient interface 9000 may comprise one or more inferior tube portions 9363. For example, the patient interfaces 9000 shown in FIGS. 10 and 11 comprise tubes 9350, the inferior portions of which comprise inferior tube portions 9363. The inferior tube portions 9363 are configured to overlie the patient's cheeks and may be configured to contact the patient's face inferior to the patient's cheekbones. Each inferior tube portion 9363 may lie on a curve extending inferiorly from the connection between the respective headgear tube 9350 and then extending in a partially anterior and partially medial direction towards the seal-forming structure 9100 in order to avoid the patient's cheek bones.

It is advantageous that the positioning and stabilising structure 9300 of the patient interface 9000 does not lie over the patient's cheek bones. The regions of a patient's face inferior to the cheekbones are generally more fleshy and a patient may find it more tolerable for the headgear tubes 9350 to lie over these regions of the face. Additionally, since the cheek bone regions of the patient's face are relatively unable to move or deform, the inferior tube portions 9363 lie firmly against the fleshy cheek regions. Further, the patient's cheek bones can assist in preventing the inferior tube portions 9363 of the headgear tubes 9350 from riding up over the cheekbones towards the patient's eyes. When the inferior tube portions 9363 fit snugly against the patient's cheeks below the cheekbones, the hardness and prominence of the patient's cheekbones may provide a barrier to the headgear tubes 9350 riding up towards the patient's eyes (which could affect stability and/or may obscure the patient's vision).

The cross-sectional shape of the inferior tube portions 9363 of the tubes 9350 may be circular, elliptical, oval, D-shaped, trapezoidal or a rounded rectangle, for example as described in U.S. Pat. No. 6,044,844. A cross-sectional shape that presents a flattened surface of tube on the side that faces and contacts the patient's face or other part of the head may be more comfortable to wear than, for example a tube with a circular cross-section.

The cross-sectional width and/or height of the tubes 9350 may be in the range 8-35 mm. In some forms in which the tubes have an approximately D-shaped cross-section, the tubes may have a width in the range 15-25 mm, and a height in the range 6-15 mm. The height may be considered to be the dimension of the tube extending away from the patient's face in use, i.e. the distance between a patient contacting portion 9348 and the outermost part of a non-patient contacting portion 9349, while the width may be considered to be the dimension across the surface of the patient's head.

The cross-sectional thickness of the material forming the tubes 9350 may be in the range 0.8-1.6 mm, for example 1.0-1.5 mm.

A further advantage of the rectangular-shaped cross section of the inferior tube portions 9363 of the tubes 9350 is that the inferior tube portions 9363 that lie in front of the patient's face in use are more resistant to bending in the vertical directions than in the horizontal directions. The D-shaped cross-section makes the inferior tube portions 9363 more resistant to bending parallel to the long axis of the rectangle/trapezoid than to bending perpendicular to the long axis of the rectangle/trapezoid. This is advantageous as the inferior tube portions 9363 are more readily able to bend to curve inwardly around the front of the patient's face to the seal-forming structure 9100, yet retain stiffness in the vertical direction to enable the vertical forces applied on the inferior tube portion 9363 from the superior tube portions 9304 to be transferred to the seal-forming structure 9100 in order to provide the necessary sealing force to the seal-forming structure 9100.

The ability to bend inwardly around the front of the patient's face enables the inferior tube portions 9363 to fit snugly against the patient's cheeks inferior to the patient's cheekbones. As described above in more detail, inferior tube portions 9363 that lie snugly under the patient's cheekbones may provide for a more stable seal than inferior tube portions 9363 that lie loosely over the patient's cheeks or lie high over the patient's cheekbones.

In some examples of the present technology, the inferior tube portions 9363 connect to a cushion module 9150 from a low angle. As described above, the headgear tubes 9350 may extend laterally and inferiorly down the sides of the patient's head and then curve anteriorly and medially to connect to a cushion module 9150 in front of the patient's face. The tubes 9350, before connecting to the cushion module 9150, may extend to a location at the same vertical position as or, in some examples, inferior to the connection with the cushion module 9150. That is, the tubes 9350 may project in an at least partially superior direction before connecting with the cushion module 9150. A portion of the tubes 9350 may be located inferior to the cushion module 9150 and/or the seal-forming structure 9100. The low position of the tubes 9350 in front of the patient's face facilitates contact with the patient's face below the patient's cheekbones.

5.3.3.2.1.6 Conduit Headgear Materials

In some examples of the present technology, such as the examples shown in FIGS. 10 and 11, the headgear tubes 9350 are formed at least partially from a textile material. In some examples, the textile material comprises nylon. In other examples, the textile material comprises polyester. The textile material may comprise other suitable materials and may comprise a combination of materials, for example woven together. Additionally or alternatively, the tubes 9350 may be formed from a foam material. In some examples the tubes 9350 comprise a combination of textile and foam materials. In some examples the tubes 9350 comprise a spacer fabric material. In some examples the textile and/or foam is in addition to the use of silicone. The seal forming structure 9100 may be formed from silicone. The plenum chamber 9200 may also comprise a rigid material such as polycarbonate.

In examples, headgear tubes 9350 comprising textile and/or foam materials may: hold air under pressure, be biocompatible and suitable/approved for use in forming a medical air path, be lighter than silicone tubes, be soft and flexible, generally retain a predetermined shape, be cleanable and be durable for a predetermined lifecycle such as a one month, three months, six months, a year or longer.

In examples, the headgear tubes 9350 of the patient interfaces 9000 shown in FIGS. 10 and 11 may comprise a film barrier to prevent entry of unwanted matter into the air path, which may also provide some structure to the positioning and stabilising structure 9300. The headgear tubes 9350 may be at least somewhat elastically extendable, comprise a low weight (in some examples less than 30 g), have a low wall thickness (in some examples less than 1 mm), have low acoustic resonance, in some examples be formed completely from textiles, have a sufficiently low impedance to flow/pressure, be sufficiently stable, have a seam that may provide rigidity to the tubes 9350, and/or have a seam that varies along the length of the tubes 9350 to provide different rigidities to different parts of the tube 9350. Further, the headgear tubes may comprise asymmetrical seams across the posterior and anterior sides of the tubes 9350, may comprise a flat portion of the tube 9350 on the patient-contacting side which is under tension in use, may be thermoformed, may have a thermoformed seam, may comprise one or more textile spacers, may be assembled with a crown connector 9360 having different properties than the tubes 9350, may have a soft feel on the patient's face, may be highly breathable, may be washable and/or may have similar look and feel to bedclothes and/or a pillow.

As shown in FIGS. 10 and 11, a crown connector 9360 connects between each of the headgear tubes 9350 of the patient interface 9000. The crown connector 9360 may comprise the swivel elbow 9610 and a connection port 9600. The connection port 9600 may be provided by the conduit connector 9612 which is configured to connect to an air delivery conduit, such as air circuit 4170) that provides a supply of breathable gas. The conduit connector 9612 may be rotatable relative to the elbow so as to allow the air delivery conduit to rotate relative to the elbow. The crown connector 9360 is shown together with the swivel elbow 9610 in FIG. 24, and shown in isolation in FIG. 25. In the examples shown in FIGS. 10, 11 and 20-23, the headgear tubes 9350 removably connect to the crown connector tube portions 9365 of the crown connector 9360. The headgear tubes 9350 may comprise male connectors at their ends. As shown in FIGS. 12A, 12B and 26, each headgear tube 9350 comprises a headgear tube connector 9351 at each end. The headgear tube connectors 9351 may respectively form a snap fit connection with a corresponding female connector portion in the crown connector ports 9361 of the crown connector 9360 and the cushion module 9150. Each of the headgear tubes 9350 may comprise a seal portion 9353 proximate each headgear tube connector 9351 (as shown in FIGS. 12A and 12B). The seal portions 9353 may be formed from a compliant material (e.g. silicone) to form a good seal to the crown connector 9360 and cushion module 9150. The crown connector 9360 and cushion module 9150 may be formed from a resilient material such as silicone as well (either in their entirety or only the portions that interface with the headgear tube connectors 9351), or a harder material such as polycarbonate, polypropylene, nylon or the like.

In one example, the headgear tubes 9350 have a lifespan of nine months. They may be machine washable at home designed to withstand 40 to 100 cleaning cycles at 70° C. for 30 minutes, or 30 cleaning cycles at 93° C. for 10 minutes.

In addition to a possible comfort advantage of using a textile material in headgear conduits such as the headgear tubes 9350, a headgear tube 9350 formed using textile material may be able to be made significantly lighter than would be possible using silicone. In some examples the conduit headgear may have a weight that is less than 30 grams. A lighter system is generally more desirable as the patient's head does not need to support as much weight, improving patient comfort. A textile conduit patient interface 9000 may be lighter due to the density of the textile material being lesser than the density of silicone and/or due to the conduits being able to be formed with thinner walls than would be achievable using silicone. In some examples the walls of the headgear tubes 9350 may have a thickness that is less than 1 mm 5.3.3.2.1.7 Conduit Rigidity The headgear tubes 9350 may advantageously be soft and deformable for comfort but may also be stable when in use. The headgear tubes 9350 may be configured to apply appropriate force vectors to the plenum chamber 9200 to achieve an effective, comfortable and stable seal between the seal-forming structure 9100 and the patient's face. Additionally, each headgear tube 9350 may follow a curved path on the patient's head laterally away from the connection port 9600 atop the patient's head, inferiorly down the side of the patient's head and anteriorly towards the patient's nose. This shape enables each headgear tube 9350 to pass between the patient's eye and ear while conveying gas from the swivel elbow atop the patient's head to the cushion at the patient's nose. This means that some rigidity/stiffness in the headgear tubes 9350 is advantageous so that they retain their shape while converting tension in the headgear tubes 9350 and strap 9310 into the necessary force vectors for a good seal.

The headgear tubes 9350 may be configured to: provide the function of headgear, be more rigid in some places than others, be more flexible in some places than others (e.g. more, or less, stretchy and/or flexible), and/or be bendable. U.S. Patent Application No. 62/764,995 (corresponding to PCT Application No. PCT/AU2019/050874, filed Aug. 20, 2019) (the entire contents of which are incorporated herein by reference) discloses a number of ways in which a headgear tube may be configured to bend and behave.

The superior tube portions 9304 of the headgear tubes 9350 may be sufficiently bendable to "drape" down over the superior surfaces of the patient's head, yet have sufficient rigidity/stiffness to resist movement in the anterior-posterior directions to resist riding backwards or forwards on the patient's head. The inferior tube portions 9363 of the headgear tubes 9350 may be sufficiently bendable to wrap around the patient's head in a medial direction from the lateral sides of the patient's head towards the plenum chamber 9200 located under the patient's nose. However, the inferior portions 9363 must retain sufficient rigidity (especially to bending in the superior-inferior directions) to convert and transmit tension in the superior tube portions 9304 of the headgear tubes 9350 and the headgear backstrap 9310 into sealing force vectors applied to the seal forming structure 9100.

The headgear tubes 9350 may be formed from a combination of textiles and/or foam materials yet may have a flexibility similar to headgear tubes 9350 formed from silicone. An appropriate flexibility is important for both stability and comfort.

The textile headgear tubes 9350 may have a predetermined rest shape that approximates the shape that they will have in use when worn by a patient (e.g. the general shape shown in FIGS. 10, 11 and 20-23). However, the headgear tubes 9350 may be sufficiently flexible to conform comfortably and securely to the actual shape of the patient's head.

The textile headgear tubes 9350 may be configured to resist torsional forces. This is particularly advantageous because the headgear tubes 9350 are formed in a three-dimensional loop and receive forces that are nonparallel to the three-dimensional curve along which the headgear tubes 9350 lie.

In some examples, the headgear tubes 9350 themselves are constructed to provide the necessary level of rigidity. In one example, the rigidity is provided to the tubes 9350 by their cross-sectional shape. For example, the cross sectional shape of each headgear tube 9350 may comprise a sufficiently large second moment of area to provide structural stiffness. In some examples, the properties of the materials used to form the tubes 9350 may provide sufficient stiffness to the tubes 9350. For example, the materials may be substantially inextensible and/or the material(s) used may comprise a sufficiently large stiffness. In some examples, the manner in which the materials are assembled may provide stiffness, and/or the processing of the materials (e.g. thermoforming) during or prior to assembly may provide sufficient stiffness to the headgear tubes 9350. In one example, the textile tubes 9350 are constructed from a foam material thermoformed into a predetermined shape, which imparts the necessary rigidity.

In one example, the laterally outward, non-patient contacting side of the tube 9350 may be configured to stretch to allow the tube 9350 to bend such that it curves inwardly (e.g. in a medial direction from a lateral side of the patient's head around in front of the patient's face to approach the patient's nose and/or mouth). The patient contacting side may not stretch (or may stretch to a lesser extent). The patient-contacting portion 9348 of the headgear tube 9350 may be more rigid, comprise a greater stiffness, and/or at least be less stretchable than the non-patient-contacting portion 9349 of the headgear tube 9350 to enable this difference in stretch in use. In other examples this may be reversed such that the non-patient contacting portion 9349 is more rigid, has greater stiffness, and/or is less stretchable than the patient-contacting portion 9348. That is, the structural arrangements described below (and elsewhere) in relation to the patient-contacting portion 9348 may be applied to the non-patient contacting portion 9349, and vice versa. Additionally, in other examples, the patient-contacting portion 9348 and the non-patient contacting portion 9349 may have the same structural arrangement.

There are a number of ways in which the patient-contacting portion 9348 of each of the headgear tubes 9350 can be made more rigid than the non-patient-contacting portion 9349. In one example, the patient-contacting portion 9348 may be formed from a stiffer material than the non-patient contacting portion 9349. In other examples, the patient-contacting portion 9348 may be thicker than the non-patient-contacting portion 9349, may be thermoformed in a way that results in less stretchiness and/or a greater rigidity/stiffness than the non-patient contacting portion 9349, may be laminated with an extra layer of material that is not applied to the non-patient-contacting portion 9349, may be laminated with a stiffer layer of material than any layers that are provided to the non-patient-contacting portion 9349, may include a rigidising member and/or may include a textile material that is formed using a different weaving process that is less flexible or stretchable than the weaving process used on the non-patient-contacting portion.

In one example, the patient contacting portion 9348 may be formed by a first thermoforming process and the non-patient contacting portion 9349 may be formed by a second thermoforming process. The first thermoforming process may provide a greater rigidity to the patient contacting portion 9348 than the second thermoforming process provides to the non-patient contacting portion 9349.

In some examples, the patient contacting portion 9348 and the non-patient contacting portion 9349 are each formed by layers. The patient contacting portion 9348 may comprise a greater number of layers than the non-patient contacting portion 9349, resulting in a higher stiffness than the non-patient contacting portion 9349. In some examples, the patient contacting portion 9348 comprises a rigidising layer and/or a rigidising member.

The non-patient-contacting portion 9349 may also be formed in a shape that lends itself to greater stretchiness and/or lower rigidity than the patient-contacting portion 9348 (e.g. a shape in which the material is not taut). The non-patient-contacting portion 9349 could also be formed to have a concertina, bellows, or corrugated structure that enables the material to unfold to facilitate a change in length. That is, such structure may form a length of headgear tube that has an adjustable length. In other examples, both the patient-contacting portion 9348 and the non-patient contacting portion 9349 have a bellows, concertina, or corrugated structure. For example, the superior tube portion 9304 may have a bellows, concertina, or corrugated structure to facilitate the curvature ("drape down") from the top of the patient's head to the side of the patient's face. In another example, the inferior tube portion 9363 may have a bellows, concertina, or corrugated structure to facilitate the curvature from the side of the patient's face to the area beneath the nose and/or to provide adjustability to the cushion module.

As described above, the headgear tubes 9350 may be formed in portions: an elongate patient-contacting portion 9348 and an elongate non-patient-contacting portion 9349.

In one example, the wall of each headgear tube 9350 comprises at least one seam 9352 formed by an edge of the non-patient contacting portion 9349 being joined to a respective edge of the patient contacting portion 9348. FIG. 27 shows a cross section of the headgear tube 9350 at a superior tube portion 9304 (e.g. the portion that lies against superior surfaces of the patient's head in use) and FIG. 28 shows a cross section of the headgear tube 9350 at an inferior tube portion 9363 (e.g. the portion that lies against lateral and anterior surfaces of the patient's head in use).

As shown in FIGS. 13-15 and 27-29, the patient contacting portion 9348 and non-patient contacting portion 9349 of the headgear tubes 9350 are in some examples connected together along both sides, creating a seam 9352 along each side. This creates two seams 9352 along the length of the tube 9350 on opposing sides of the tube 9350. In use, there may be an anterior seam 9352 that runs along an anterior side of the tube 9350 and a posterior seam 9352 that runs along a posterior side of the tube 9350. The joint at the seams 9352 preferably does not contact the patient's skin in use, as this may cause marking and/or discomfort. However, in some examples, the portion of the seam 9352 formed by the patient-contacting portion 9348 may lie on the patient's head and/or face.

The patient contacting portion 9348 and the non-patient contacting portion 9349 may each comprise an anterior edge and a posterior edge. The anterior edges may be joined along the length of the tube 9350. Similarly, the posterior edges may be joined along the length of the tube 9350. As shown in FIGS. 27 and 28, the anterior edges are in some examples joined to form an anterior seam 9352 of the tube 9350.

Similarly, the posterior edges are in some examples joined to form a posterior seam 9352 of the tube 9350. The anterior seam 9352 and/or the posterior seam 9352 may be thermoformed.

In some examples of the present technology, the seam 9352 may provide rigidity to the conduit. The rigidity of the seam 9352 may contribute to the overall rigidity and behaviour of the tube 9350 and may be selected to achieve tubes 9350 that form a stable positioning and stabilising structure 9300. The rigidity of the seam 9352 may also contribute to the ability of the positioning and stabilising structure 9300 to apply the necessary force vectors to the seal forming structure 9100 for a comfortable, effective and stable seal. An advantage of using the seam 9352 to provide the necessary rigidity is that a tube 9350 having a two-part construction (e.g. a patient-contacting portion 9348 and a non-patient-contacting portion 9349) may necessarily have a seam regardless of whether extra rigidity is required, meaning the seam 9352 and/or the seam forming process can be used to increase rigidity without adding additional parts or applying additional processes, which could have a detrimental effect on comfort and/or cost.

The rigidity provided to the tubes 9350 by the seams 9352 may be predetermined by selecting a particular thickness for the seams 9352. The thickness of the material forming each of the patient-contacting portion 9348 and non-patient contacting portion 9349 may define, or effect, the resulting thickness of the seams 9352. The material thickness of each of the patient contacting portion 9348 and non-patient contacting portion 9349 in the regions of the seams 9349 may be selected to achieve a particular seam thickness. For example, the patient-contacting portion 9348 and the non-patient-contacting portion 9349 of a headgear tube 9350 may be formed with thicker or thinner side edges to achieve a thicker or thinner seam 9350 once the portions are joined along the edges to form the tube 9350.

The seams 9352 may be thermoformed or formed by ultrasonic welding. In further examples, the seams 9352 may be formed by gluing, stitching, over moulding, welding or any other suitable process.

The thermoforming process may affect the stiffness of the seams 9352. For example, a seam 9352 may be compressed to a greater extent during thermoforming to result in a stiffer seam. For example, a seam 9352 formed by a thermoforming process may comprise rigidity provided by compression of the edges forming the seam 9352 during the thermoforming process.

In some examples, the seam 9352 is more rigid in some locations than in other locations. For example, the portion of a headgear tube 9350 between the plenum chamber 9200 and the portion of the headgear tube 9350 proximate the connection of the strap 9310 may be more rigid than the portion of that same headgear tube 9350 between the portion of the headgear tube 9350 proximate the connection of the strap 9310 and the connection to a supply tube atop the patient's head. In some examples, the seam 9352 is thicker in a particular region and/or the material forming the seam 9352 is compressed to a greater extent in a particular region to make the seam 9352 stiffer in that region. The seam 9352 may comprise a greater stiffness and/or thickness in the inferior tube portion 9363 than in the superior tube portion 9304, or vice versa. In some examples, the seam 9352 comprises a greater width in the inferior tube portion 9363 of the headgear tube 9350 than in the superior tube portion 9304, or vice versa.

The seams 9352 may also be formed to stiffen the headgear tubes 9350 at other locations, such as proximate the supply conduit connector atop the patient's head, the backstrap 9310 connections/eyelets and/or the connections to the plenum chamber 9200.

The seam 9352 may also be used to form the tabs 9320. The tabs 9320 may provide eyelets to which a backstrap 9310 can be connected. A particularly large seam 9352 may be provided at the location where a backstrap 9310 is to connect, and a hole may be provided in the seam 9352 through which the backstrap 9310 can be looped. Alternatively, the eyelet could be formed by only one of either the patient-contacting portion 9348 or non-patient contacting portion 9349 of the headgear tubes 9350. FIG. 30 shows the tab 9320 of a headgear tube 9350 according to one example of the technology. The headgear tube 9350 comprises a patient-contacting portion 9348 and a non-patient-contacting portion 9349 joined at the edges to form seams 9352. The posterior seam 9352 is shown in FIG. 30. As shown, the tab is formed by a widening of the seam 9352. That is, the posterior seam 9352 comprises a widened portion, the widened portion configured to connect with a strap 9310 of the positioning and stabilising structure 9300. In this example, the headgear tube 9350 comprises an extension of the seam 9352 forming the tab 9322. In other examples of the present technology, only one of the patient-contacting portion 9348 and the non-patient-contacting portion 9349 extends posteriorly away from the tube wall of the headgear tube 9350 to form a tab 9320.

The headgear tube 9350 comprises an eyelet configured to receive a strap 9310. More specifically, the posterior seam 9352 comprises the eyelet. The eyelet may comprise a hole configured to receive the strap 9310, the hole allowing the strap to be passed therethrough and looped back and secured onto itself in the manner shown in FIG. 10.

In this example, the eyelet is in the form of a slit 9322. The slit 9322 is formed in the tab 9320 is also shown in FIG. 30. The tab 9320 comprises an aperture forming the slit 9322. As shown in FIG. 30, the slit 9322 is elongate and appropriately sized to receive the strap 9310, which as shown in FIGS. 10 and 11 may be a flat strap (e.g. it may be wider than it is thick).

In the example of FIG. 30, the headgear tube 9350 comprises an eyelet rigidiser portion 9324 configured to reinforce the eyelet. The eyelet rigidiser portion 9324 may be formed from a material more rigid than the material from which the headgear tube 9350 is formed. In one example the eyelet rigidiser portion 9324 is formed from a substantially rigid plastics material. The eyelet rigidiser portion 9324 may be formed from nylon, polycarbonate, Hytrel, polypropylene, or the like. The eyelet rigidiser portion 9324 may be provided to an opening in the tab 9320 and have a hole therein to form the slit 9322. The eyelet rigidising portion 9324 may be provided within the hole in the posterior seam 9352 and may be configured to reinforce the shape of the hole. The eyelet rigidiser portion 9324 may reinforce the slit and or distribute the force on the tab 9320 from the strap 9310 over a sufficiently large area of the tab 9320. The eyelet rigidiser portion 9324 may be permanently connected to the tab 9320, for example by overmoulding or gluing, or may be removably attached in the manner of a grommet.

In the positioning and stabilising structure 9300 shown in FIG. 11, the eyelet rigidiser portion 9324 is provided to peripheral edges of the material of the headgear tube 9350 forming the tab 9320 and comprises a slit 9322 located posteriorly to the material of the headgear tube 9350 forming the tab 9320. In this example, the eyelet rigidiser portion 9324 distributes the force of the strap 9310 over a large area of the tab 9320.

In further examples, the headgear tubes 9350 may comprise adjustable tabs 9320. That is, the position and/or angle of the tabs 9320 may be adjustable by the patient, either through a continuous range or through discrete options. U.S. Patent Application No. 62/764,995 (corresponding to PCT Application No. PCT/AU2019/050874, filed Aug. 20, 2019) (the entire contents of which are incorporated herein by reference) discloses a number of features relating to adjustable eyelets/tabs for headgear tubes which are applied to the tabs 9320 of the headgear tubes 9350 in some examples of the present technology.

Additionally, or alternatively, different seams 9352 of a conduit headgear mask may have different rigidities. For example, the seam 9352 on the superior or anterior side of a headgear tube 9350 may be more rigid than the opposing seam 9352 on the inferior or posterior side of the same headgear tube 9350. Alternatively, the inferior or posterior seam 9352 may be stiffer or more ridgid than the superior or anterior seam 9352. Where a headgear tube 9350 comprises an anterior seam 9352 and a posterior seam 9352, a greater rigidity can be provided to the anterior seam 9352 by a greater compression during a thermoforming process of the edges forming the anterior seam 9352 than of the edges forming the posterior seam 9352, or vice versa.

In some examples, the anterior seam 9352 comprises a greater thickness than the posterior seam 9352, or vice versa. The anterior seam 9352 may, additionally or alternatively, comprise a greater width than the posterior seam 9352, or vice versa.

In further examples of the present technology, the seams 9352 may include or otherwise integrate rigidising elements 9358 (e.g., a rigid or semi-rigid material), such as lengths of metal (e.g., metal wire or extrusions) or alternatively, lengths of plastic (e.g., plastic rods or extrusions), into the headgear tube (e.g., the inferior tube portion 9363), as best shown for example in FIG. 33-1. This may allow the use of less dense materials for the inner layers of the headgear tube 9350 while still conferring the tube 9350 with rigidity. The rigidising elements 9358 may be embedded within or layered on top of the seam 9352.

In some examples, the seam 9352 may be positioned away from the skin and/or may be formed with rounded edges to prevent edge marking or discomfort caused by the seam 9352 on the patient's face.

Alternative examples of the technology may comprise forming the seam 9352 by stitching, moulding to shape, 3D printing, gluing, overmoulding, ultrasonic welding, among other processes.

5.3.3.2.1.8 Construction of Headgear Tube

In one example, a headgear tube 9350 is provided which can both hold its cross-sectional shape and conform to the patient's head.

The headgear tube 9350 comprise a patient contacting portion 9348 and non-patient contacting portion 9349. The patient contacting portion 9348 and the non-patient contacting portion 9349 may comprise sufficient rigidity to maintain a hollow interior (i.e. open passage) therebetween yet be sufficiently flexible and/or stretchable to enable the tube 9350 to conform to a patient's head while providing the necessary functions of the positioning and stabilising structure 9300, e.g. supporting a seal forming structure 9100 in the correct position for an effective, stable and comfortable seal in use.

FIGS. 13-17 and 26-28 show examples of the construction of headgear tubes 9350. The use of a patient contacting portion 9348 (also known as a face contacting portion 9348) and a non-patient contacting portion 9349 (also known as a non-face contacting portion 9349) may enable a wider range of different properties than may be possible if the entire headgear tube 9350 is an integrally formed part.

Each of the patient contacting portion 9348 and the non-patient contacting portion 9349 comprises an elongate length of material (or a length formed by a plurality of layered materials). The two lengths may be joined along their long edges to form a headgear tube 9350 in the form of an elongate conduit. As shown in FIG. 15, each of the patient contacting portion 9348 and non-patient contacting portion 9349 may comprise an anterior edge 9331 and a posterior edge 9332. It will be understood that, since the tubes 9350 comprise curvature in three dimensions, the anterior edge 9331 and posterior edge 9332 may not point directly anteriorly and posteriorly, respectively, in use. For example, the anterior edge 9331 may face substantially anteriorly in use proximate the superior end of the headgear tube 9350 but may face partially anteriorly and partially superiorly in use proximate the inferior end of the headgear tube 9350. Similarly, the posterior edge 9332 may face substantially posteriorly in use proximate the superior end of the headgear tube 9350 but may face partially posteriorly and partially inferiorly in use proximate the inferior end of the headgear tube 9350. Overall, the anterior edge 9331 may be the more anterior edge in use and the posterior edge 9332 may be the more posterior edge in use. The anterior edges 9331 and posterior edges 9332 may be joined along the length of the gas delivery tube 9350.

In one example the patient contacting portion 9348 may pull the non-patient contacting portion 9349 into a curved shape to create a D-shaped cross-section within the headgear conduit. The patient contacting portion 9348 may be in tension pulling the non-patient contacting portion 9349 into the curved shape. The non-patient contacting portion 9349 may be biased towards a flat, or flatter, shape.

FIG. 29 shows a cross sectional view of a headgear tube 9350 formed by a patient-contacting portion 9348 and non-patient contacting portion 9349 being joined along the long edges thereof to form a hollow interior to convey a flow of pressurised gas. The non-patient contacting portion 9349 may be biased towards a flat shape. In this example, the non-patient contacting portion 9349 is biased towards a flat or flatter shape than the shape that the non-patient contacting portion 9349 is shown to have in FIG. 29. A bias towards a flat shape will be understood to refer to a bias into a flatter shape. For example, a non-patient contacting portion 9349 of a headgear tube 9350 may be biased towards a flat shape, even if its rest shape, in the absence of force from the patient-contacting portion 9348 acting against the bias, is a flatter shape but not a perfectly flat shape. The bias is represented by the character B in FIG. 29. Due to the bias B, the non-patient contacting portion 9349 has a tendency to return to a flat or flatter configuration. In this example, the non-patient contacting portion 9349 is pulled by the patient contacting portion into a predetermined shape creating the hollow interior of the tube 9350.

In this example, the predetermined shape is a non-flat shape. The predetermined shape approximates a trapezoid in one example. As shown in FIG. 29, the cross sectional shape of the headgear tube 9350 is substantially trapezoidal and may not be a perfect trapezoid. For example, in the FIG. 29 example, the non-patient contacting portion 9349 comprises a curved profile along the side between the two angled sides. Additionally, the corners of the cross sectional shape are rounded.

The patient contacting portion 9348 may also comprise a non-flat shape. As shown in FIG. 29, the patient contacting portion 9348 comprises a flatter shape than the non-patient contacting portion 9349.

The non-patient contacting portion 9349 may be deformed, at least partially elastically, during joining of the edges of the non-patient contacting portion 9349 to the edges of the patient contacting portion 9348. The patient contacting portion 9348 may lack sufficient extensibility in its width dimension for the non-patient contacting portion 9349 to return, under its bias B, to a flat or flatter shape. As the patient contacting portion 9348 holds the non-patient contacting portion 9349 in a deformed configuration against its bias B, after the gas delivery tube 9350 is formed, forces are applied between the patient contacting portion 9348 and the non-patient contacting portion 9349. The patient-contacting portion 9348 may continuously apply forces to the non-patient contacting portion 9349, against the bias B, preventing the non-patient contacting portion 9349 from returning to its flat or flatter shape.

Accordingly, the non-patient contacting portion 9349 may apply opposing forces to the patient-contacting portion 9348. The forces applied to the patient-contacting portion 9348 by the non-patient contacting portion 9349, due to the bias B, may result in tension being created in the patient-contacting portion 9348. This tension is represented by the character T in FIG. 29. The patient contacting portion 9348 may be under tension T across a width of the patient contacting portion 9348, as represented in FIG. 29. The non-patient contacting portion 9349 may be pulled by the patient contacting portion 9348 at the edges of the non-patient contacting portion 9349 (e.g. at the long edges).

As shown in FIG. 29, the non-patient contacting portion 9349 and the patient-contacting portion 9348 are joined at a pair of seams 9352.

The bias B towards a flatter shape means that when the patient contacting portion 9348 pulls the edges of the non-patient contacting portion 9349 together, the non-patient contacting portion 9349 may form a rigidised dome-shape rather than collapsing or crinkling. The resulting headgear tube 9350 may comprise a self-supporting cross-sectional shape. The headgear tube 9350 is able to hold an open shape even in the absence of pressure within the hollow interior of the tube 9350.

There may also be tension in the non-patient contacting portion 9349 when joined to the patient contacting portion 9348 due to the bias in the non-patient contacting portion 9349 back towards a flatter shape. The patient contacting portion 9348 and/or the non-patient contacting portion 9349 may therefore be pretensioned during forming of the headgear tube 9350. Accordingly, the tube 9350 is biased towards an open configuration. The tension in the patient contacting portion 9348 may effectively provide resiliency to the non-patient contacting portion 9349 given it bends the non-patient contacting portion 9349 into a shape that is self-supporting. The bias B within the non-patient contacting portion 9349 and the tension T in the patient contacting portion 9348 may result in both the patient-contacting portion 9348 and non-patient contacting portion being held taut in cross section, preventing collapse. The headgear conduit 9350 also has a pressurised interior in use, which may also help maintain patency of the hollow interior.

It will be understood that the bias B and tension T shown in FIG. 29 are representative of the forces acting on and within the headgear tube 9350 but that the actual forces may be more complex. For example, in some implementations the bias B may result from bending of the non-patient contacting portion 9349 creating both tension and compression within the non-patient contacting portion 9349. In some implementations, the non-patient contacting portion 9349 may apply moments to the ends of the patient contacting portion 9348. In some examples the bias B in the non-patient contacting portion 9349 may have the effect of imparting curvature to the patient contacting portion 9348. In some examples, the stiffness and/or resistance to extension in the width dimension of the patient contacting portion 9348 may be sufficiently high that, under the bias B of the non-patient contacting portion 9349, there is substantially no or only minimal change in shape of the patient contacting portion 9348.

The bias in the non-patient contacting portion 9349 of the headgear tube 9350 may be provided by elasticity in one or more materials forming the non-patient contacting portion 9349. A particular stiffness may be imparted to the non-patient contacting portion 9349 and/or patient contacting portion 9348 by a thermoforming process used to form the non-patient contacting portion 9349 and/or patient contacting portion 9348. Parameters of the thermoforming process (e.g. clamping force, heat, clamping time etc.) may be selected to achieve a predetermined stiffness of each of the non-patient contacting portion 9349 and the patient contacting portion 9348.

Alternatively, one or more structural members may be provided to the non-patient contacting portion 9349 to help the headgear tube 9350 maintain an open shape (i.e. a hollow cross-section through which the therapy flow of gas can pass). In one example, a semi-rigid skeleton is provided to the non-patient contacting portion 9349. In another example, the non-patient contacting portion 9349 includes an additional layer of material which is semi-rigid.

While the headgear tubes 9350 may be structured to maintain an open shape in use, they may also be sufficiently flexible to conform comfortably to the shape of the patient's head. The non-patient contacting portions 9349, in particular, may be formed from a material that is sufficiently stretchable to enable the headgear conduit to bend around curves of the patient's head. The patient contacting portion 9348 may be less stretchable but may lie along a shorter path. That said, the patient contacting portion 9348 may be sufficiently flexible that it can bend to a lesser radius than the non-patient contacting portion 9349, since the patient contacting portion 9340 lies against the surface of the patient's head.

The face contacting portion 9348 may have a higher coefficient of friction with respect to the patient's skin than the non-face contacting portion 9349. The patient-contacting portion 9348 may comprise a medially-facing surface configured to lie against the patient's head having a higher coefficient of friction with respect to the patient's skin than a laterally-facing surface of the non-patient contacting portion 9349. Most or all surfaces of the positioning and stabilising structure 9300 may comprise a low friction, soft feel mimicking the feel of bedclothes. However, additional friction may be provided to the patient contacting side 9348 in order to provide some level of grip which may improve stability.

In an alternative example, each headgear tube 9350 may be formed with a textile face contacting portion 9348 and a silicone or TPE non-face contacting portion 9349. The textile material provided to the face contacting portion 9348 advantageously may provide a comfortable feel on the patient's skin, while the silicone material forming the non-face contacting portion 9349 may provide the advantageous properties of silicone, such as flexibility and resiliency and/or the ability to support itself in a domed shape to maintain an open hollow interior through which the therapy flow of gas can pass. In one example, the headgear tubes 9350 may each have a silicone layer in the non-face contacting portion 9349 and may also have an outermost textile material layer to improve the feel of the mask. An advantage of a headgear tube 9350 that has a silicone non-face contacting portion 9349, is that the interior of the tube 9350 is visible through the silicone. The ability to see the inside of the tube 9350 is advantageous as it may make the conduit easier to clean.

In some examples the headgear tubes 9350 may be provided with windows to enable the patient to view inside the tubes 9350, for example during cleaning or for reassurance of the cleanliness of the hollow interior of each tube 9350. In one example, a headgear tube 9350 comprises an interior transparent layer (e.g. formed from silicone or TPE) in at least the non-patient contacting portion 9349 covered by an external opaque layer (e.g. formed from a textile and/or foam layer) and one or more windows formed in the headgear tube 9350 by holes formed in the exterior opaque layer to enable the patient to view the hollow interior of the tube 9350 through exposed portions of the interior transparent layer. In some examples, one or both of the patient contacting portion 9348 and the non-patient contacting portion 9349 are formed from silicone that is flocked to provide the feel of a textile (e.g. flocked with a textile material or with a material that has the feel of a textile).

In examples, each headgear tube 9350 may be air impermeable (e.g. it may have a laminate or film on the inside), may have textile and/or foam outer layers, may not release an excess of particles into the air flow, and may be comfortable, stable and able to support a seal forming structure 9100 to maintain an effective seal around the entrance to the patient's airways. The specific construction of the patient contacting portion 9348 and the non-patient contacting portion 9349 may be as described in other examples disclosed herein. Alternatively, the patient contacting portion 9348 and/or the non-patient contacting portion 9349 may be formed by blow moulding.

In some examples, the headgear tubes 9350 are thermoformed with a distinct face contacting portion 9348 and non-patient contacting portion 9349, and each may be formed from a plurality of layers). Alternatively, blow moulding could be used to form the headgear tubes 9350. In some examples, the headgear tubes 9350 comprise one or more foam or silicone flocked to produce a textile-like surface.

5.3.3.2.1.9 Layered Construction

In some examples, the patient interface 9000 may comprise headgear tubes 9350 which each comprise a plurality of layers. Each of the patient contacting portion 9348 and the non-patient contacting portion 9349 may comprise a plurality of layers. Each layer may provide a different property to the headgear tube 9350. In examples, the layers may provide: air impermeability, particle impermeability, shape forming, bias towards a particular configuration/resilience/elasticity, compression resistance, stretchiness and/or a soft textile feel.

FIG. 15 shows a cross section of a headgear tube 9350 according to one example. As shown, the tube 9350 is formed by multiple pieces of material connected together to form an air path. In this example the air path is suitable for medical use (e.g. it does not release or permit particles from a material to contaminate the flow of gas). The materials may also be connected in a way that does not create bug traps at the joints (e g small spaces/cavities where bacteria can accumulate/grow).

The headgear tube 9350 may comprise a size that varies along the length of the tube 9350. In the example shown in FIG. 26, the hollow interior of the tube 9350 may have a width in a range of 34 mm to 18 mm (e.g., a width of 24 mm at the superior end of the tube 9350 and a width of 18 mm at the inferior end of the tube). The hollow interior of the tube 9350 may have a height within a range of 8 mm to 6 mm (e.g., a height of 8 mm towards the inferior end of the tube and a height of 6 mm at the superior end). The cross-sectional shape of the air path in this example comprises a domed shape in which one of the long sides of the cross section (the non-patient-contacting side 9349 in this example) is outwardly convex to form a dome-like shape. In other examples of the present technology the cross-sectional shape of the air path may be a trapezoidal or rectangular shape.

FIG. 16 shows a schematic view of the cross section of a headgear tube 9350 according to one example of the technology. In this example, the headgear tube 9350 comprises a laminate construction. The headgear tube 9350 comprises a patient contacting portion 9348 and a non-patient contacting portion 9349, each comprising a plurality of layers forming the conduit. Some layers are layers of material such as plastic film, textile and foam, while other layers are adhesive layers. The outermost layers are in this example a textile material to provide the appearance and feel of bedclothes. In other examples the outermost layers may comprise a foam material. The innermost layer(s) are formed from an air impermeable material, such as a thermoplastic film to provide a medically suitable air path. A foam layer or a spacer fabric layer may also be provided between the textile layers and the air-impermeable layers on one or both of the patient-contacting side and non-patient-contacting sides of the air path, for extra resilience, comfort and/or compression response.

In the example of the present technology shown in FIG. 16, the non-patient contacting portion 9349 comprises a first outer layer 9371. In this example, the first outer layer 9371 comprises a textile material. The textile material may comprise nylon or polyester, as examples. In other examples the first outer layer 9371 comprises a foam material. The non-patient contacting portion 9349 may comprise a first inner layer 9375 defining a portion of the air path. The first inner layer 9375 may be air-impermeable. In some examples, the first inner layer 9375 may comprise thermoplastic material and may be a film. The first inner layer 9375 may comprise a TPU film in some examples. In the FIG. 16 example, between the first outer layer 9371 and the first inner layer 9375 is an intermediate layer 9373. The intermediate layer 9373 comprises a foam material. In other examples the intermediate layer 9373 comprises a spacer fabric material. The intermediate layer 9373 may alternatively comprise a material with a low density similar to or lower than the density of foam and spacer fabric materials, such as a mesh fabric. Alternatively, in some examples the intermediate layer 9373 may comprise a material such as silicone, TPE or a gel.

Between an outer layer and an inner layer of the headgear tube 9350, the headgear tube may comprise at least one adhesive layer. The headgear tube 9350 may comprise a plurality of non-adhesive layers (for example the inner layer defining the air path, the intermediate layer and the outer layer) separated by a plurality of adhesive layers. In some examples, the adhesive layers may comprise film which bonds to the non-adhesive layers upon heating being applied. In some examples, the adhesive layers comprise a thermoplastic film, such as a TPU film. Where the inner layer 9375 is also a film, it may have a higher melting temperature than the adhesive layers. In other examples, the adhesive layers are materials such as films that have adhesive surfaces to adhere to the non-adhesive layers. In further examples, an adhesive substance may be applied to non-adhesive layers to form an adhesive layer in between.

In the example shown in FIG. 16, between the first outer layer 9371 and the intermediate layer 9373 of the non-patient contacting portion 9349 is a first adhesive layer 9372 which bonds these two layers together. Finally, between the first inner layer 9375 and the intermediate layer 9373 is a second adhesive layer 9374 configured to bond the first inner layer 9375 to the intermediate layer 9373.

The patient contacting portion 9348 comprises a second outer layer 9381 configured to lie against the patient's head/face in use. In one example of the present technology, the second outer layer 9381 comprises a textile material. In other examples the second outer layer 9381 comprises a foam material or space fabric. The patient contacting portion 9348, in this example, also comprises a second inner layer 9385 defining a portion of the air path. The second inner layer 9385 may be air-impermeable. In some examples the second inner layer 9385 may be formed from a thermoplastic material and may be a film. Between the second outer layer 9381 and the second inner layer 9385 the patient contacting side 9348 comprises an intermediate layer 9383. The intermediate layer 9383 may comprise a foam material or a spacer fabric material, for example. The intermediate layer 9383 may alternatively comprise another material with a low density similar to or lower than the density of foam and spacer fabric materials. Alternatively, in some examples the intermediate layer 9383 may comprise a material such as silicone, TPE or a gel.

Between the second outer layer 9381 and the intermediate layer 9383 of the patient-contacting side 9348 is a first adhesive layer 9382 which bonds these two layers together. Finally, between the second inner layer 9385 and the intermediate layer 9383 is a second adhesive layer 9384 configured to bond the second inner layer 9385 to the intermediate layer 9383.

The intermediate layers 9373 and 9383 provide form to the headgear tubes 9350. They may provide some rigidity to the overall structure of the headgear tube 9350 while being comfortable for the patient to lie on. The intermediate layers 9373 and 9383 may enable the headgear tube 9350 to have a particular compressive response that is comfortable for the patient to lie on and have against their head. In some examples, one or both of the intermediate layers may be omitted. In other examples, one or both of the outer layers 9371 and 9381 may be omitted. In further examples, there may be multiple intermediate layers formed from foam or spacer fabric materials in either or both of the patient contacting portion 9348 and the non-patient contacting portion 9349.

FIG. 17 shows a cross section of a non-patient contacting portion 9349 of a headgear tube 9350 according to another example of the present technology. In this example the non-patient-contacting portion 9349 comprises a first inner layer 9375 comprising an air impermeable material, a first outer layer 9371 and a first adhesive layer 9372 in between. The first outer layer 9371 may comprise a textile material. Alternatively, the first outer layer 9371 may comprise a foam material. As such, in some examples, the non-patient-contacting portion 9349 of the conduit may not have an intermediate layer formed from foam, spacer fabric or the like. The lack of an intermediate layer in this portion of the headgear tube 9350 may help keep the weight of the tube low and facilitate a low-profile headgear conduit.

In some examples, the patient contacting portion 9348 of the headgear tube 9350 comprises a second outer layer 9381, an air impermeable second inner layer 9385 and an adhesive layer bonding the second outer layer 9381 and the second inner layer 9385 together. In such examples the headgear tube 9350 may not comprise an intermediate layer. The second outer layer 9381 may comprise a sufficiently thick, stiff and/or resilient material (such as a foam or textile material) to provide for stability, comfort and a suitable compression response.

The intermediate layer of one or both of the non-patient contacting portion 9349 and patient contacting portion 9348, while formed from foam or spacer fabric in the examples above described, may be an alternative compliant material in other examples of the technology. It could be another cushion-like material formed from a thick and resilient network of fibres or could be a gel, silicone or TPE, for example.

In further examples, the tubes 9350 comprise outer layers 9371 and 9381 comprising any of a textile, a foam or a spacer fabric material (or combinations thereof), and either or both of the patient contacting portion 9348 and non-patient contacting portion 9349 may comprise an intermediate layer comprising any of a textile, a foam or a spacer fabric material (or combinations thereof).

An appropriate compression response of the headgear tube 9350 is advantageous for patient comfort. The headgear tubes 9350, comprising a combination of foam and textiles, may comprise a similar compression response to a silicone headgear tube 9350.

In some examples, the intermediate layers 9373 and 9383 of the headgear tube 9350 may be more rigid than exterior layers. The innermost layers (e.g. inner layers 9375 and 9385), which may be formed from a gas impermeable film, may also increase the overall rigidity of the headgear tube 9350, even if they are not more rigid than other layers. Softness/flexibility in the exterior layers (e.g. outer layers 9371 and 9381) is advantageous in providing for a comfortable feel on the patient's skin, while some rigidity is advantageous in enabling the headgear tubes 9350 to function as part of a positioning and stabilising structure 9300 for the plenum chamber 9200.

In some examples, in the non-patient contacting portion 9349 of the headgear tube 9350, the intermediate layer 9373 may be thicker than the first outer layer 9371. Similarly, in the patient contacting portion 9348 of the headgear tube 9350, the intermediate layer 9383 may be thicker than the second outer layer 9381. In one example, the intermediate layers 9373 and 9383 each comprise a foam material (or alternatively a spacer fabric material) and the first outer layer 9371 and second outer layer 9381 each comprises a textile material thinner than the foam material forming the intermediate layers 9373 and 9383. The intermediate layers 9373 and 9383 may provide stiffness, compression resistance and resilience to the headgear tube 9350, while the first outer layer 9371 and second outer layer 9381 may provide the appearance and feel of bedclothes to the headgear tube 9350.

The innermost layer(s) of the headgear tubes 9350 may comprise a suitable film such as a medical film that is made specifically for thermoforming. In some examples, different films may be used to form the inner layers of each of the patient contacting portion 9348 and non-patient contacting portion 9349. In one example the film provided to the non-patient contacting portion 9349 may be suited for thermoforming with the other layers of the non-patient contacting portion 9349. However, the film provided to the patient contacting portion 9348 may be able to melt to weld the patient contacting portion 9348 to the non-patient contacting portion 9349.

In some examples, the cross-section of the headgear tube 9350 may not be uniform along the length of the conduit. For example, some layers may be present in certain portions of the headgear tube 9350 but not in others. For example, the inferior portion 9363 of the headgear tube 9350 (e.g. the portion that extends from the plenum chamber 9200 to a point approximately between the patient's eye and ear) may include an extra rigidising layer to increase rigidity and facilitate efficient transfer for headgear forces to sealing force vectors and/or may include an extra textile sleeve layer configured to further increase the softness of the conduit.

5.3.3.2.1.10 Headgear Tube with Portions of Differing Rigidities

The headgear tube 9350 may be formed from two or more portions to form the headgear tube 9350 as shown in FIGS. 20 to 23. This may allow for the headgear tube 9350 to have differing rigidities along its length. This may allow for each portion of the headgear tube 9350 to be optimised for particular comfort and performance characteristics. The overall weight of the headgear tube 9350 may be reduced in comparison to a headgear tube having a uniform stiffness since the portion of the headgear tube 9350 not required to be relatively rigid may then be able to be formed from a material of lesser density.

Referring to FIG. 26, in some examples of the present technology, a headgear tube 9350 may be formed from a superior tube portion 9304 and an inferior tube portion 9363. A first end 9305 of the superior tube portion 9304 may be provided with a snap fit connector 9351 which in use engages with another component. In some examples the first end 9305 of the superior tube portion 9304 may fluidly connect to a crown connector provided with a complementary connector to that of the superior tube portion. The inferior tube portion 9363 may also comprise a snap fit connector 9351 at its inferior end to fluidly connect with a cushion module 9150 in use. The headgear tube 9350 may comprise transition zone 9307 between the superior tube portion 9304 and the inferior tube portion 9363 in a region of the gas delivery tube 9350 configured to lie against a laterally-facing surface of the patient's head in use. The transition zone 9307 may be in the area of the tab 9320 to which the strap is fitted. This may correspond to a point approximately between the patient's eye and ear. However, in some examples, the transition zone 9307 between the superior tube portion 9304 and the inferior tube portion 9363 may be below the patient's ear or alternatively above the eye. The transition zone 9307 may be dependent of the general curvature of the headgear tube 9350 and the placement of the tab 9320, as this may have a bearing on the force vectors applied to the headgear tube. In some examples the transition zone 9307 may be at a location, in use, at which the tangent to the curve along which the headgear tube 9350 lies is substantially parallel to the patient's sagittal plane.

One of the superior tube portion 9304 and inferior tube portion 9363 may be more rigid than the other portion. In use, this may allow for the stiffness of the headgear tube 9350 to be optimised along the length of the headgear tube 9350 for comfort and performance characteristics.

In some examples of the present technology, the inferior tube portion 9363 is constructed to be more rigid than the superior tube portion 9304. In use, this may better transfer forces arising from the superior and posterior portions of the positioning and stabilising structure 9300 to the seal forming structure 9100 for an effective, stable and comfortable seal for the patient. However, in other examples of the present technology, the superior tube portion 9304 may be more rigid than the inferior tube portion 9363. The following discussion regarding the provisions for conferring the inferior tube portion 9363 with a rigidity greater than that of the superior tube portion 9304 may apply also to those other examples in which the superior tube portion is more rigid, as appropriate. That is, the relative structural arrangements between the inferior tube portion 9363 and the superior tube portion 9304 providing more rigidity to the inferior tube portion, as described below, may be reversed so as to provide the superior tube portion 9304 with more rigidity as compared to the inferior tube portion. In other examples, both the inferior tube portion and the superior tube portion may be provided with increased rigidity.

In some examples of the present technology, the inferior tube portion 9363 and the superior tube portion 9304 are constructed in layers substantially as described in respect of the headgear tube 9350 of FIGS. 13 to 17. Each portion may be formed by multiple layers connected or bonded together to form an airpath within the interior of the tube 9350. There may be at least one outer layer, which in one example may encompass the entire inferior tube portion 9363 in the manner of a sleeve 9364, as shown in FIGS. 31 and 32. In other examples, the outer sleeve 9364 may encompass the entire superior tube portion 9304, or the entire headgear tube (i.e., both the inferior tube portion 9363 and the superior tube portion 9304). In another example, separate outer layers provide a patient-contacting side of the tube 9350 and a non-patient-contacting side of the tube 9350.

The outer sleeve 9364 may comprise a textile and/or foam material and may replace the first outer layer 9371 and the second outer layer 9381. The textile material of the outer sleeve may be formed of the same materials and have the same structural arrangement as the first outer layer 9371 and second outer layer 9381 described herein. A foam outer sleeve material may be thermoformed to provide shape and/or rigidity. The outer sleeve may have a single longitudinal seam oriented away from the patient, or may be constructed in a substantially seamless manner. The outer sleeve 9364 may enhance comfort by protecting the patient from the seams 9352 of the inner layers which when in contact with the skin can cause irritation.

In some examples of the present technology, the non-patient contacting side of the inferior tube portion 9363 may include a layer of a more rigid material than the patient contacting side of the inferior tube portion 9363. The choice and amount of material used for the respective sides may depend on the desired performance characteristics. For example, the patient-contacting side of the inferior tube portion 9363 may be more elastic (i.e., contain a greater elastic content) than the non-patient contacting side, which may contain a greater number of layers, thicker layers, stiffer layers or be less elastic (i.e., have less elastic content) to confer some rigidity.

In certain of these examples, the outer layer forming the patient contacting side of the inferior tube portion 9363 may be contiguous or continuous with that of the superior tube portion 9304. This may alleviate the need for a seam or the like which could contact the patient's face in use and create a pressure point that may cause discomfort.

In some examples of the present technology, one of superior tube portion 9304 and the inferior tube portion 9363 may be constructed with an inner layer or inner portion (i.e., a layer or combination of layers other than the outer layer(s)) having a greater rigidity than the corresponding inner layer of the other tube portion. This may provide the tube portion having the more rigid inner layer with greater ability to stretch, a useful feature to allow the headgear of the present technology to be used with a wider range of differently shaped heads. In other examples, the outermost layer may have greater rigidity than a corresponding outermost layer of the other tube portion.

In some examples of the present technology, the greater rigidity of one of the superior tube portion 3304 and inferior tube portion 3363 relative to the other tube portion is achieved through the use of a material with a greater wall thickness. For example, referring to FIG. 17, the tubes portion may be configured of a first outer layer 9371 and a thermoplastic inner layer 9375 separated by a first adhesive layer 9372.

Together, these layers 9371, 9372, 9375 provide the overall wall thickness of the respective tube portions. One of the tube portions may be formed such that it has an overall wall thickness that is greater, or lesser as the case may be, than that of the other tube portion. This may confer the tube portion with the greater wall thickness with more rigidity relative to the other tube portion. Referring to FIG. 16, in another example, one of the tube portions may have an intermediate layer 3373, 3383 that is thicker than the intermediate layer in the other tube portion.

In another example, one of the superior 9304 and inferior tube portions 9363 may include additional layers that increase the overall wall thickness of the tube portion. For example, the superior tube portion 9304 may have a simple layered construction of FIG. 17 while the inferior tube portion 9363 may have the more complex, multilayered construction of FIG. 16. In other examples, this arrangement may be reversed; the inferior tube portion 9363 may be constructed with fewer layers than the superior tube portion 9304.

In yet another example of the present technology, the greater rigidity of one of the superior tube portion 9304 and inferior tube portion 9363 relative to the other tube portion is achieved through the use of a rigidising layer inserted into the layered construction of the tube portion required to have greater rigidity. For example, referring to FIG. 16, the intermediate layers 9373, 9383 of the non-patient contacting portion 9349 and patient contacting portion 9348 respectively may use a material that is more rigid in the inferior tube portion 9363 than the material used for the corresponding layers in the superior tube portion (or vice versa). For example, different materials (e.g., a material having greater rigidity than another material) may be used in the inferior tube portion than in the superior tube portion to attain greater rigidity in the inferior tube portion. In other examples, foam intermediate layers may have different thicknesses, different densities and/or may be thermoformed or otherwise treated to provide greater rigidity.

In other examples, the outer layers 9371, 9381 may be a layer of textile; for the inferior tube portion 9363, the textile used to construct these layers may comprise a woven structure that is different, and confers greater rigidity, than that of the corresponding layers of the superior tube portion 9304. In another example, yarn having a higher stiffness than the surrounding yarn may be provided in specific regions (e.g., inferior tube portion, superior tube portion, anterior side, posterior side, etc.) to form a rigidizer.

In another example, a yarn having a lower melt temperature than surrounding yarn may be provided to form a rigidizer portion (e.g., in the inferior tube portion, superior tube portion, anterior side of the tube, posterior side of the tube, etc.). For example, such yarn may be melted or fused to stiffen the yarn into a rigidising portion to provide rigidity to the gas delivery tube. In an example, the rigidising yarn includes polypropylene and the surrounding yarn includes nylon or other non-plastic materials such as cotton or wool.

In a further example of the present technology, the greater rigidity of one of the superior tube portion 9304 and inferior tube portion 9363 relative to the other tube portion is achieved through the use of materials being less extensible or less stretchable. For example, both the superior tube portion 9304 and inferior tube portion 9363 may be constructed with the same number of layers, such as shown in FIG. 16 or FIG. 17, such that they are similar in overall thickness, however the choice of materials may differ. For example, the superior tube portion 9304 may be comprised of layers having a greater elastic content and as such is more responsive to stretching forces being applied when the patient interface 9000 is being worn. For example, one or both of the outer layers 9371, 9381 of the inferior tube portion 9363 may comprise textile that is less elastic, less extensible or less stretchable than a textile material of one or both of the outer layers 9371, 9381 of the superior tube portion 9304 to provide the inferior tube portion with greater rigidity (or vice versa).

The respective inferior tube portion 9363 and superior tube portion 9304 may have inner portions thereof connected to each other at their common ends by, for example, stitching, bonding, thermoforming or ultrasonic welding. The headgear tube 9350 may then be covered with one or more outer layers, or alternatively a sleeve 9364 of textile material or the like, such that externally at least the headgear tube appears to be a unitary structure. The outermost layers in this example may be a textile material to provide the appearance and feel of bedclothes but in other examples the outermost layers may comprise a foam material. The innermost layer in this example is formed from a thermoplastic material or film to provide a medically suitable air path. In some examples, a foam layer or spacer fabric layer may also be provided between the textile layers and the thermoplastic layers on one or both of the patient-contacting side and non-patient-contacting sides of the air path, for extra resilience, comfort and/or compression response.

In some examples of the present technology, as shown in FIG. 31, the inferior tube portion 9363 may have an inner portion formed from two elongate lengths of material (first length of material) 9368 and second length of material 9366) joined at their edges along their length by thermoforming (or other suitable means such as ultrasonic welding) to form seams 9352. The inner portion may refer to any combination of layers (other than the outer layer(s)) of the non-patient contacting portion 9349 and/or the patient contacting portion 9348 as described in relation to FIGS. 16 and 17 (or the outermost layer(s) as described in any other embodiment). For instance, the inner portion may refer to the combination of the first inner layer 9375, the second adhesive layer 9374 and the intermediate layer 9373 of the non-patient contacting portion 9349 and the combination of the second inner layer 9385, second adhesive layer 9384 and the intermediate layer 9383 of the patient-contacting portion 9348, which may be further covered by an outer layer such as the first outer layer 9371 and the second outer layer, or alternately, the outer sleeve 9364.

The rigidity of the inner portion of the inferior tube portion 9363 may then be achieved through the design of the seams 9352. The headgear tube 9350 may have an anterior side 9354 and a posterior side 9355. The sides of the first length of material 9368 and the second length of material 9366 of inferior tube portion 9363 may be joined at seams 9352. One of the seams 9352 may be provided to the anterior/superior side of the inferior tube portion 9363 and the other of the seams 9352 may be provided to the posterior/inferior side of the inferior tube portion 9363 (as described above, in the inferior tube portion 9363, between the patient contacting side and non-patient contacting side, there is a side of the tube 9350 that is partially anterior- and partially superior-facing, and an opposite side that is partially posterior- and partially inferior-facing). This arrangement places the seams 9352 away from the patient-contacting side 9348 and avoids the creation of potential pressure points that may lead to patient discomfort. The outer layer may be in the form of a sleeve 9364 as shown in FIG. 31 but in other examples may be formed from two separate lengths of material as described in relation to FIGS. 16 and 17. One seam may impart greater stiffness/rigidity to the tube than the other seam.

In examples where the outer layer is formed from two or more separate lengths of material, such outer lengths of material may essentially correspond in location and/or orientation to the first length of material 9368 and second length of material 9366 of the inner portion, as described above. That is, for example, a first outer layer may be layered on top of the first length of material 9368 and a second outer layer may be layered on top of the second length of material 9366 such that the first and second outer layers are also joined along their lengths at seams 9352.

The seams 9352 themselves may be thermoformed or formed by ultrasonic welding. In further examples, the seams 9352 may be formed by gluing, stitching, over moulding, welding or by other suitable processes. The thickness of the seams 9352 may also contribute to the overall rigidity of the inferior tube portion 9363. Using the inner layers of the inferior tube portion 9363 as a means of providing rigidity may be preferred since the appearance of the seams 9352 is more easily hidden. Additionally, covering the seams 9352 with a sleeve 9364 may mitigate the risk of the seams 9352 creating pressure points leading to discomfort.

In further examples of the present technology, the seams 9352 may include or otherwise integrate rigidising elements 9358, such as lengths of metal wire or extrusions or alternatively, plastic rods or extrusions, into the inferior tube portion 9363, as best shown for example in FIG. 33-1. This may allow for the use of less dense materials for the inner layers of the headgear tube 9350 while still conferring the tube 9350 with rigidity. The rigidising elements 9358 may be embedded within or layered on top of the seam 9352. For example, the rigidising element may be embedded within any, all or any combination of the layers of the headgear tube. In an example, the rigidising elements 9358 may be embedded within the inner layers, outer layers and/or intermediate layers of the headgear tube. As shown in the example of FIG. 33-1, rigidising elements 9358 are embedded within an outer layer and intermediate layer of the patient contacting portion 9348 and also within an outer layer of the non-patient contacting portion 9349. In some of these examples, the rigidising element 9358 may be constructed with a face having concertina, corrugations, grooves, or similar structures transverse to its length dimension that act as controlled lines of weakness. This may enable, for example, flexibility in one axis but rigidity in a perpendicular axis achieving the advantageous stiffness and flexibility characteristics described above.

It is also noted that textile layers of the gas delivery tube may include at the seams yarn having a higher stiffness than surrounding yarn in order to form a rigidizing portion. It is further noted that yarn having a lower melt temperature than surrounding yarn (e.g., other yarn at the seam, or the yarn of the remaining tube) may be provided in the seams to form a rigidizer portion. For example, such yarn may be melted or fused (e.g., by thermoforming, welding, or otherwise heating) to stiffen the yarn into a rigidizing portion to provide rigidity to the gas delivery tube. In an example, the rigidising yarn includes polypropylene and the surrounding yarn includes nylon or other non-plastic materials such as cotton or wool.

Referring to FIGS. 32 and 33, in some examples of the present technology, the inner portion (e.g., of the inferior tube portion 9363 and/or the superior tube portion 9304) may comprise three or more (e.g., four, five, six or more) elongate lengths of material (e.g., first length of material 9368, second length of material 9366, and third length of material 9367), where each length is joined to adjacent lengths (e.g., along edges thereof) through the use of glues, stitching, thermoforming or ultrasonic welding, for example. The individual lengths of material may have densities and rigidities that differ from one another. For example, the first length of material 9368 may have a density, stiffness and/or rigidity that is different from a density, stiffness and/or rigidity of the second length of material 9366 and/or the third length of material 9367. Similarly, the second length of material 9366 may have a density, stiffness and/or rigidity that is different from a density, stiffness and/or rigidity of the first length of material 9368 and/or the third length of material 9367, and so on.

In an example, the first length of material 9368, which may correspond in location and thus form the patient-contacting portion 9348 of the inferior tube portion 9363, may be formed from one length of laminate material. This avoids placing the seams 9352 that join the first length of material 9368 to the neighbouring second length of material 9366 and third length of material 9367 centrally on the patient-contacting portion 9348. This avoids the seam 9352 bearing on the patient's face, particularly in examples where no sleeve 9364 is present. The non-patient contacting side 9349 may be formed from two lengths of material (second length of material 9366 and third length of material 9367) of lesser density than the first length of material 9368, such as foam or the like (or vice versa). Alternatively, the two lengths of material (second length of material 9366 and third length of material 9367) may be thicker than the first length of material 9368 (or vice versa). The lengths of material may be thermoformed, for example. For integrity of the air way within the headgear tube 9350, a gas-impermeable medically-approved material, such as a plastic film, may be provided to the inner-most layer.

Referring to FIG. 33 and the non-patient contacting portion 9349 of the headgear tube, it is noted that the second length of material 9366 may be positioned relatively posterior in use and the third length of material 9367 may be positioned relatively anterior in use.

It is noted that the entire headgear tube 9350, including the outer layers in examples without an outer sleeve, may be constructed from three or more lengths of material. In other words, each of the three lengths of material 9368, 9366, 9367 shown in the FIG. 33 embodiment may include the layered arrangement (including an outer layer(s)) as described in relation to the FIG. 16 and FIG. 17 embodiments. Such outer layers are joined to neighbouring lengths of material through seams 9352. The discussion herein relating to lengths of material of the inner portion or inner layers of the headgear tube may also refer to such embodiments including outer layers.

As can be seen in FIG. 33, the first length of material 9368 may have a concave shape to position the seams 9352 away from the patient's face (alternatively, the first length of material 9368 may have a substantially flat shape). To provide this configuration, the first length of material 9368 may be wider or have a greater circumferential extent than the second and/or third lengths of material 9366, 9367.

The use of three or more lengths of material to construct the inner layer(s) of the inferior tube portion 9363 may also provide for the use of differing materials for the inner layers corresponding to the anterior and posterior sides of the headgear tube 9350. In some examples, one of the inner layers is stiffer than the others, to provide sufficient rigidity to the shape of the headgear tube 9350, resisting occlusion of the tube 9350 during use and enabling efficient transfer of forces vectors to the seal-forming structure 9100. The other layers may be more flexible, for example to enable the headgear tubes 9350 to conform snuggly to the patient's head in use, which may mitigate against the effects of tube drag and provide for a stable patient interface 9000. Flexibility of the headgear tube 9350 may also provide the ability for the positioning and stabilising structure 9300 to better adapt to and securely fit a wider range of patient head shapes and sizes.

In some other examples of the present technology, the inner portions of the inferior tube portion 9363 and superior tube portion 9304 are formed from two asymmetrical lengths of material such that the connecting edges transition from the anterior and posterior sides of the headgear tube 9350 to the patient contacting and non-patient contacting sides of the headgear tube 9350. This may allow for greater rigidity in certain areas of the headgear tube 9350 as it transitions from the superior tube portion 9304 to the inferior tube portion 9363 while providing other areas with greater flexibility. Providing rigidity and flexibility to certain areas of the headgear tube 9350 also provides the positioning and stabilising structure 9300 with greater ability to adapt to a wider range of patients.

In some examples of the present technology, the cross-sectional profile of the headgear tube 9350, as it transitions from the superior tube portion to the inferior tube portion 9363, may change. In doing so, this may confer varying stiffness to the headgear tube 9350 along its length.

A change in cross-sectional profile may be achieved through the use of appropriately configured moulds during the thermoforming process. For example, FIG. 28 shows a cross-section of the inferior tube portion 9363 along line 28-28 in FIG. 26 and as can be seen, it comprises a domed profile in cross-section. This cross-section may also be considered trapezoidal. The patient-contacting portion 9348 is relatively flat (in comparison to the non-patient contacting portion 9349) for comfort when this portion of the tube bears against the patient's face. The long axis of this cross section provides greater resistance to bending caused by superior and inferior forces in use, to enable the headgear tube 9350 to transfer force vectors required for a stable and effective seal to the seal-forming structure 9100. The shorter axis of this cross section allows an appropriate level of flexibility in response to lateral and medial forces in use, enabling the headgear tube 9350 to conform to the shape of the patient's head.

FIG. 27 shows the cross-section of the superior tube portion 9304 along line 27-27, being proximate to the patient's crown in use. The superior tube portion 9304 comprises a more rectangular cross sectional profile than the inferior tube portion 9363. One of the long sides of the profile may correspond to the patient contacting portion 9348. The short sides of the cross section provide the superior tube portion 9304 with appropriate flexibility to conform to the patient's head in use. While the headgear tube 9350 is substantially self-supporting, it may conform to the superior and lateral surfaces of the patient's head in a manner similar to "draping" down over the patient's head.

In some examples, corners of a cross sectional profile of a headgear tube 9350 may be stiffened to provide the headgear tube with an appropriate level of stiffness. The headgear tubes 9350 of a patient interface 9000 according to the present technology may be stiffened by a cross section comprising one or more of: stiffer or thicker corners, a greater wall thickness, longer sides, additional layers, stiffer or thicker layers, wider or thicker seams, among other features, such as those discussed elsewhere herein.

In some examples of the present technology, the headgear tube 9350 of FIG. 26 may be formed from two or more separate tubes constructed in a manner as previously described, for example formed by multiple layers of material connected or bonded together to form an airpath within the interior of the tube, as described in respect of the headgear tube 9350 of FIGS. 14 to 17. At least one layer provides a patient-contacting portion of the tube and another layer provides a non-patient-contacting portion of the tube.

In one such example, the superior tube portion 9304 and the inferior tube portion 9363, are formed independently of each and then joined or connected to each other by thermo-forming, welding (e.g., ultrasonic welding), gluing, stitching or with removably connectable connectors. In these examples, one of the superior tube portion 9304 and the inferior tube portions 9363 may be formed to have a greater rigidity than the other tube portion.

In these examples, the superior tube portion 9304 has an inferior end that connects to a superior end of the inferior tube 9363. In one example, this connection between the respective portions is at the transition zone 9307 of the headgear tube 9350 between the patient's eye and ear in FIG. 26. However, in other examples, the connection may occur at a point above the patient's eye or below the ear.

The other ends of the superior tube portion 9304 and inferior tube portion 9363 may be connected to other components; for example the superior tube portion 9304 may have its first end 3305 connected to a crown connector. However, in some examples one or both of the superior tube portion 9304 and inferior tube portion 9363 may be connected to another length of tube.

Selecting particular lengths and properties of the separate superior tube portion 9304 and inferior tube portion 9363 may allow for the optimisation of the rigidity of certain parts of the headgear tube 3350. For example, the superior tube portion 9304 may substantially correspond to the portion of the patient's head between the eye and ear and a central location atop the head. This tube portion may be sufficiently flexible to drape down and conform to the curvature between the superior and lateral surfaces of the patient's head. This is also useful for providing the headgear with the ability to be used with a wider range of patients, irrespective of their head size. This may be emphasised by using more stretchable materials, relative to the inferior tube portion 9363, for forming the superior tube portion 9304. However, at the same time, the superior tube portion 9304 may be sufficiently rigid such that it is relatively unresponsive to minor anterior or posterior forces, such as may get applied to the elbow 9610 through drag of the air circuit.

Conversely, in the above example, the inferior tube portion 9363 is sufficiently rigid to allow for efficient transmittal and conversion of the forces from the superior and posterior portions of the headgear into suitable force vectors for sealing purposes. At the same time, the inferior tube portion may still retain sufficient flexibility, particularly in the anterior orientation so that it is able to conform to the front of the patient's face as the headgear tube transitions from running down the side of the head to running across the front of the face, towards the cushion module.

In one example, the superior tube portion 9304 is provided with the tab 9320 for use with a strap. However, in other examples, it may be the inferior tube portion 9363 that is provided with the tab 9320, depending on the respective lengths and rigidities of the superior and inferior tube portions.

The tabs may extend posteriorly from the non-face contacting and face contacting sides of the tubes respectively. In some examples of this technology, the tabs may be formed from the same layers of material used to construct the non-patient contacting portion 9349 and the patient-contacting portion 9348 of the superior tube portion and the inferior tube portion, i.e. the tabs are contiguous with the respective layers, as shown in FIG. 34. This may be advantageous since it allows the tab to be formed at the same time as cutting or forming of the material for the patient-contacting portions of the superior tube portion 9304 and the inferior tube portion 9363. Furthermore, by being contiguous with the layer of material used for the respective sides of the superior and inferior tube portions, there may no need for the stitching or welding that would otherwise be needed to affix a separate tab to the tubes. It will be appreciated that this aspect of the present technology may also be applied to the headgear tubes illustrated in FIGS. 20 to 23 and elsewhere in the disclosure.

In some examples, the tabs 9320 may be formed of a material that is relatively rigid and which confers some rigidity onto the tube portion to which it is attached. This may allow for the remaining length of the tube portion to be less rigid.

In some examples of the technology, the tabs 9320 may be configured to extend posteriorly around the patient's head from the left and right headgear tubes sufficiently such that they form a strap. The free ends of the respective tabs may be joined together by a clip or buckle or the like.

In some examples of the technology, and as previously described, the superior ends of the superior tube portion of each headgear tube 9350 may engage a crown tube portion, superior to the patient's head. This crown portion may be provided to the user in a variety of sizes and could optionally include appropriately configured connection port or decoupling structure on its non-patient contacting side, such as a swivel elbow, that engages with an air circuit 4170. In this example, the crown tube portion may comprise a crown connector 9360. However, in other examples, the crown tube portion may be integrally formed or permanently connected to a pair of headgear tubes 9350 (for example connecting the superior tube portions 9304 of respective headgear tubes 9350).

In other examples of the technology, the posterior ends of the inferior tube portion 9363 of each headgear tube may engage an anterior tube portion, configured to be located proximate an entrance to the patient's airways in use. This anterior tube portion may be provided to the user in a variety of sizes. In some examples, the anterior tube portion may include appropriately configured connections to engage with a cushion module 9150. In some examples, the anterior tube portion may comprise a seal-forming structure 9100 configured to provide a flow of gas at therapeutic pressure to the entrance of the patient's airways.

5.3.3.2.1.11 Crown Connector

As mentioned above, in some examples of the present technology the positioning and stabilising structure 9300 may comprise a pair of gas delivery tubes in the form of headgear tubes 9350 connecting to a cushion module 9150 or seal-forming structure 9100 in front of the patient's face and connecting to a crown connector 9360 atop the patient's head.

FIGS. 20-23 show a patient interface 9000 according to one example of the present technology comprising a crown connector 9360. FIG. 24 shows the crown connector 9360 and elbow 9610 in isolation. As illustrated, the patient interface 9000 comprises a pair of headgear tubes 9350, a crown connector 9360 and a cushion module 9150.

The cushion module 9150 in this example comprises a vent module opening 9410 configured to receive a vent module (not shown). The vent module may comprise one or more vent holes and may comprise a diffuser configured to diffuse the vent flow of gas.

The crown connector 9360 in this example receives a flow of pressurised gas from a respiratory pressure therapy device. The patient interface 9000 comprises a connection port 9600 configured to connect to and receive the flow of pressurised gas from a supply conduit of an air circuit 4170. In this example the connection port 9600 is provided on an elbow 9610 of the patient interface. The elbow 9610 is fluidly connected to the crown connector 9360 of the positioning and stabilising structure 9300. The crown connector 9360 comprises a hollow interior through which the flow of pressurised gas can flow from the elbow 9610 to the interior of each headgear tube. The elbow 9610 may connect to the crown connector 9360 through a snap fit mechanism. For example, one of the elbow and the crown connector (or the swivel ring 9614 when used) may include a protrusion and the other may include a corresponding recess. In the example of FIG. 35, the swivel ring 9614 may include a protrusion 9617 and the elbow may include a mating recess 9618.

In an example, the elbow 9610 is rotatably connected to the crown connector 9360. The ability of the elbow to rotate with respect to the crown connector provides a decoupling effect in order to decouple the crown connector and the positioning and stabilising structure 9300 from tube drag. The elbow 9610 also comprises a conduit connector 9612. The conduit connector 9612 is configured to connect to a supply conduit of the air circuit 4170, fluidly connecting the interior of the elbow 9610 to the supply conduit to enable the flow of pressurised gas to be conveyed from the supply conduit to the elbow and then on to the crown connector 9360 and headgear tubes 9350. In this example, the conduit connector 9612 is rotatable (e.g. swivelable) with respect to the elbow 9610. The supply conduit may form a friction fit to the conduit connector 9612 and may therefore not be able to rotate with respect to the conduit connector. Accordingly, the ability for the conduit connector 9612 to swivel provides a decoupling effect to reduce tube drag.

In one example, the crown connector 9360 is separable from each headgear tube 9350. FIG. 24 shows the crown connector 9360 and swivel elbow 9610 as an assembly in isolation and FIGS. 25 and 38 show the crown connector 9360 in isolation without the elbow 9610. The crown connector 9360 may be T-shaped. In this example, the crown connector 9360 comprises a fluid connection opening 9390 of the positioning and stabilising structure 9300. The fluid connection opening 9390 may be provided centrally in the crown connector 9360 and may open in a substantially superior direction in use and, depending on how the patient wears the patient interface 9000, may face a partially anterior or partially posterior direction in use. As best shown in FIGS. 25, 38 and 42, an upper wall 9510 of the crown connector may protrude upwardly to form a rim (e.g., a circular rim) defining the fluid connection opening 9390. The upper wall 9510 may include side portions that extend down and connect to a lower wall 9520 of the crown connector 9360 to form a hollow interior of the crown connector, as shown in FIGS. 25, 38, 39 and 42.

In one example, the crown connector 9360 comprises a pair of crown connector tube portions 9365. In use, the crown connector tube portions 9365 are configured to lie against a superior surface of the patient's head. The crown connector tube portions 9365 may extend away from the fluid connection opening 9390. Together the crown connector tube portions 9365 may form the hollow interior through which a flow of pressurised gas can flow from the fluid connection opening 9390 towards each of the headgear tubes 9350. The crown connector tube portions 9365 may each comprise the same or a similar cross-sectional shape to the headgear tubes 9350, providing a flat patient-contacting surface and a curved non-patient-contacting surface. As shown in FIGS. 25 and 39, the crown connector tube portions 9365 in this example comprise a trapezoidal or D-shaped cross section.

In one example, the crown connector 9360 is formed from silicone. In other examples, the crown connector 9360 is formed from another rubber, TPE, textile and/or foam materials.

The fluid connection opening 9390 is configured to receive the elbow 9610. FIG. 35 shows a cross sectional view through the centre (e.g. through the sagittal plane in use) of the crown connector 9360 according to an example. As shown, the elbow 9610 is received in the fluid connection opening 9390. In some examples, the elbow 9610 connects to a swivel ring 9614, as shown in FIG. 35. The swivel ring 9614 is received in the fluid connection opening 9390 and itself receives the elbow 9610. The swivel ring 9614 is configured to allow the elbow 9610 to rotate within the swivel ring 9614, decoupling the elbow 9610 and supply conduit from the crown connector 9360. The swivel ring 9614 may be formed from a rigid material such as polycarbonate, polypropylene or nylon, as examples. As shown in FIG. 35, the crown connector 9360 comprises a sealing flange 9362 configured to seal against the swivel ring 9614 to prevent leaks between the fluid connection opening 9390 and the swivel ring 9614. The sealing flange 9362 may extend at an angle (e.g., at an incline or slope) inwardly from the periphery of the fluid connection opening 9390 (e.g., the sealing flange may extend inwardly at an angle from the rim defining the fluid connection opening 9390 toward an interior of the crown connector). The sealing flange 9362 is advantageously moulded together with the crown connector 9360. This is advantageous because the body of the crown connector and the sealing flange 9362 can be formed together in the same operation, avoiding the need to overmould a resilient sealing flange to a rigid swivel ring as a separate operation. In other examples, however, the swivel ring 9614 may comprise a sealing flange, for example an outwardly extending flange moulded to the swivel ring.

In the FIG. 35 example, the sealing flange 9362 is provided to the periphery of the fluid connection opening 9390 although in an alternative example the sealing flange 9362 may be provided more internally to the crown connector 9360, in which case it may seal to a lower portion of the swivel ring 9614 rather than to the middle or top. The swivel ring 9614 may comprise a pair of flanges (e.g., U-shaped structure with opposing pair of flanges) within which to receive the periphery of the fluid connection opening 9390.

The swivel ring 9614 also has the advantage of providing rigidity to the fluid connection opening 9390, allowing the crown connector 9360 to be formed from a flexible material such as silicone or TPE.

In another example, the crown connector 9360 may include a lip seal 9560 (e.g., a flange) that extends radially inwardly of the fluid connection opening 9390 at a location within the hollow interior of the crown connector, as shown in FIG. 35. The lip seal 9560 may be arranged to engage and create a seal with a lower end of the elbow 9610 to prevent leaks between the elbow and the crown connector. The lip seal 9560 may be formed integrally (e.g., molded with) the crown connector.

As shown in FIGS. 38 and 40-42, an occlusion-preventer 9530 is disposed on an inner surface of the lower wall 9520 of crown connector 9360. The occlusion-preventer 9530 is structured to prevent the lower end of the elbow 9610 from engaging the inner surface of the lower wall 9520, which would reduce or cut off the flow of gas from the elbow. Occlusion-preventer 9530 protrudes upwardly from the inner surface of lower wall 9520 to a height above any other surface on the lower wall in the central portion of the crown connector below the fluid connection opening 9390. Should an external force push the elbow 9610 toward the lower wall 9520, the occlusion-preventer 9530 would prevent the lower end of the elbow from engaging the inner surface of the lower wall 9520 thereby maintaining a space between the lower end of the elbow and the lower wall 9520 of the crown connector, thus ensuring that the flow of gas would continue to flow through the crown connector and into the headgear tubes 9350.

The occlusion-preventer 9530 may extend from an anterior side to a posterior side of the crown connector 9360 at a central portion thereof below the fluid connection opening 9390. The occlusion-preventer may have an elongate configuration (e.g., a rib) extending from the anterior side to the posterior side of the crown connector, as shown in FIGS. 38 and 41-1. The inner surface of the lower wall 9520 may slope or be inclined (e.g., angled with respect to horizontal or to adjacent portions (e.g., portions near the crown connector ports 9361) of the inner surface) downwardly from each crown connector tube portion 9365 to the occlusion-preventer 9530. That is, the inner surface of the lower wall 9520 of the crown connector 9360 may include a pair of ramps 9532, 9534 disposed on respective sides of the occlusion-preventer. This arrangement enhances the distance between the top of the occlusion-preventer 9530 and the inner surface of the lower wall 9520 at the central portion of the crown connector. This in effect increases the space that would be maintained between the lower end of the elbow 9610 and the inner surface of the lower wall 9520 should the elbow be forced toward the lower wall, which in turn ensures that a greater flow rate through the crown connector is maintained.

The occlusion-preventer 9530 may have an "I" shape, as shown in FIGS. 38 and 41-1. Alternatively, the occlusion-preventer may have a linear elongate rib shape without the end portions of the "I" shape, as shown in FIG. 41-2. Additionally, the occlusion-preventer 9530 may extend in an interrupted manner. For example, a middle portion of the occlusion-preventer may be omitted such that a pair of protruding portions are disposed respectively at the anterior side and the posterior side of the crown connector 9360.

In the illustrated examples of FIGS. 38 and 40-42, a reinforcement 9550 extends along the inner surface of the lower wall 9520 at opposing anterior and posterior edges of the crown connector 9360 to stabilize the occlusion-preventer 9350. The reinforcement 9550 may be formed as a portion of the lower wall 9520 having increased thickness. That is, the anterior and posterior end portions of the occlusion-preventer 9530 are disposed in portions of the lower wall 9520 having increased thickness. The reinforcement 9550 helps to keep the occlusion-preventer upright when the elbow 9610 applies an external force thereon.

In the illustrated examples, the headgear tubes 9350 removably connect to the crown connector 9360. The headgear tubes may comprise male connectors at their ends. As shown in FIGS. 12A and 12B, each headgear tube 9350 comprises a connector 9351 at each end. The connectors 9351 may form a snap fit connection to a corresponding female connector portion in each of the crown connector 9360 and the cushion module 9150. Each of the headgear tubes 9350 may comprise a seal portion 9353 proximate each connector 9351. The seal portions 9353 may be formed from a compliant material (e.g. silicone) to form a good seal to the crown connector 9360 and cushion module 9150. The crown connector 9360 and cushion module 9150 may be formed from a resilient material such as silicone as well, or a harder material such as polycarbonate. It is noted that the end of the headgear tube connecting to the crown connector 9360 may be configured such that the connector 9351 and/or the seal portion 9353 has a shape (e.g., trapezoidal or D-shaped cross section) that is the same as or similar to the shape of the tube portions 9365 of the crown connector 9360.

Referring to FIGS. 36 to 37-2, in one example, a patient interface 9000 may comprise a pair of headgear tubes 9350, a cushion module 9150 and multiple (e.g., two, three, or more) crown connectors 9360-1, 9360-2, 9360-3. The multiple crown connectors may each comprise a different length (N). The patient may assemble the patient interface 9000 with any of the multiple crown connectors 9360-1, 9360-2, 9360-3 and, since each of the crown connectors comprises a different length (N), the patient can vary the length of the loop (L) formed by the pair of headgear tubes 9360, crown connector 9360 and cushion module 9150 to suit the size of their head and/or their preferences. For example, the patient can choose from a medium length crown connector 9360-2 which may correspond to an average head size, or the patient can use a longer (e.g. wider across the top of the patient's head) crown connector 9360-3 to achieve a greater circumference of the positioning and stabilising structure 9300 or a shorter crown connector 9360-1 to reduce the circumference (e.g. hoop/loop length) of the positioning and stabilising structure 9300.

The crown connector shown in FIGS. 24-25 may be considered a small-size crown connector 9360-1. In another example, a larger size crown connector 9360-2 (and an even larger size crown connector 9360-3) (FIGS. 37-1 and 37-2) may comprise a fluid connection opening 9390 of the same size as shown in FIGS. 24-25 but may comprise longer crown connector tube portions 9365. Such crown connectors 9360-2, 9360-3 would be used with the headgear tubes 9350 shown in FIGS. 20-23 and 36 in order to provide a positioning and stabilising structure 9300 having a larger circumference in order to fit to a larger head. By providing a range of crown connectors 9360-1, 9360-2, 9360-3 (e.g. two, three, or more), a large portion of the population can be accommodated.

The means of connecting the ends of the respective headgear tubes 9350 may be through the use of snap-fit headgear tube connectors 9351 such as those previously described in respect of FIGS. 12A and 12B. These allow for the respective components to be separated from each other for cleaning or to better customise the headgear 9300 to the patient. This may be by swapping existing gas delivery tubes for longer or shorter ones or alternatively by changing the cushion module 9150 and/or crown connector 9360.

FIG. 26 shows a headgear tube 9350 in isolation. The headgear tube in this example comprises a headgear tube connector 9351 at a superior end and another headgear tube connector 9351 at an inferior end of the headgear tube. The superior headgear tube connector 9351 is configured to connect to the crown connector 9360 and the inferior headgear tube connector 9351 is configured to connect to the cushion module 9150.

As discussed above, the headgear tubes 9350 may be formed from soft and/or resilient materials such as textiles, foams, spacer fabric, silicone and the like. The headgear tube connectors 9351 may be formed from a more rigid material, in some examples, such as from polycarbonate, nylon, polypropylene and the like. The more rigid material may facilitate a more reliable connection between the headgear tube connectors 9351 and the other components to which they connect (e.g. the crown connector 9360 and cushion module 9150).

In this example, the superior headgear tube connector 9351 is configured to connect to a crown connector port 9361 of the crown connector 9360. FIGS. 24-25 show the crown connector ports 9361 of the exemplary crown connector 9360. As illustrated, the crown connector 9360 comprises a pair of crown connector ports 9361. One crown connector port 9361 is located on each side of the fluid connection opening 9390 at a respective end of the crown connector tube portions 9365. Each crown connector port 9361 may be an opening in the crown connector 9360 into a hollow interior of the crown connector tube portions 9365. Air under pressure can flow from the interior of the crown connector 9360 through the crown connector ports 9361 and into the interior of the headgear tubes 9350.

As discussed above, the crown connector 9360 may be formed from a soft and/or resilient material such as silicone. The crown connector ports 9361 in some examples may comprise connectors corresponding (e.g. complementary) to the headgear tube connectors 9351 at the superior ends of the headgear tubes 9350. The connectors at the crown connector ports 9361 may be formed from a material more rigid than the material of the crown connector (e.g., more rigid than silicone), such as polycarbonate, polypropylene, semi-rigid or rigid plastic materials, and/or nylon, and the like, in order to facilitate a robust connection (e.g., a removable snap-fit connection) between the headgear tube 9350 and crown connector 9360. Such crown piece connectors 9502 may be female connectors disposed within and at the ends of the crown connector tube portions 9365, as shown in FIGS. 39 and 42. That is, the crown piece connectors 9502 may be disposed along an inner surface of the crown connector tube portions 9365. For example, the crown piece connectors 9502 may be disposed along the inner surface of the lower wall 9520, sides and/or upper wall 9510 of the crown connector. In the illustrated example of FIGS. 39 and 42, crown piece connector 9502 forms a ring or loop shape (e.g., matching the cross-sectional shape of the crown connector tube portion 9365) along the inner surface of the crown connector tube portion 9365 to form a female connector for connecting with a male connector (e.g., headgear tube connector 9351) on the headgear tube. Rigid inserts (such as rigid crown piece connectors 9502) disposed in the crown connector 9360 for facilitating connection to the headgear tubes 9350 also have the advantage of providing structural rigidity to the crown connector 9360 and the crown connector ports 9361. The lower portion of the crown piece connector 9502 may be wider than the upper portion of the crown piece connector as shown in FIG. 42, or vice versa, to alter rigidity of the crown connector or to accommodate the headgear tube connectors as desired. The crown piece connectors 9502 may be embedded or otherwise fixed within the material of the crown connector, for example by overmolding or other techniques.

In some examples, the superior end of each headgear tube 9350 may comprise a resilient material such as silicone to create a silicone-to-silicone interface between the headgear tube and the crown connector 9360. A silicone-to-silicone abutment may facilitate a reliable seal about the crown connector port 9361 and opening into the headgear tube 9350. In other examples, the superior end of the headgear tube 9350 may comprise a rigid portion configured to abut against the periphery of the crown connector port 9361. Where the crown connector 9360 is formed from a resilient material (e.g. silicone or TPE) a reliable seal may be achieved even if the end of the headgear tube 9350 at the headgear tube connector 9351 comprises a less resilient material.

In other examples, the crown connector 9360 may comprise male connectors at the crown connector ports 9361 and the superior ends of the headgear tubes 9350 may comprise corresponding (e.g. complementary) female connectors. In further examples, the crown connector 9360 may comprise a male connector at one of the two crown connector ports 9361 and a female connector at the other of the two crown connector ports 9361. Further still, in some examples the crown connector 9360 and headgear tubes 9350 may not comprise connectors and may instead be formed to connect to one another (e.g. via a friction fit) or via separate connectors used to bridge the gaps between the headgear tubes 9350 and the crown connector 9360.

In further examples, the crown connector 9360 may comprise a rigid ring proximate the crown connector ports 9361 configured to reinforce the crown connector tube portions 9365 (e.g., at the crown connector ports 9361). The rigid ring may be disposed within the crown connector tube portions 9365 or on the exterior of the crown connector 9360. The rigid rings may be provided to the crown connector tube portions 3365 proximate the ends of the crown connector tube portions 9365 (i.e., adjacent the crown connector ports 9361). The rigid rings may be separable from the crown connector 9360 or may be permanently attached, for example by overmoulding. These rigid rings may reinforce and provide rigidity to the otherwise flexible silicone crown connector 9360 and facilitate a friction fit connection to be made with the headgear tubes 9350.

In other examples of the present technology the crown connector 9360 and headgear tubes 9350 may not be separable and may instead be integrally formed or permanently connected.

The elbow 9610 also comprises a vent 9400-1, as shown in FIG. 20. The vent 9400-1 may comprise a plurality of micro vents. The micro vents may each have a diameter of less than 0.5 mm, less than 0.3 mm or 0.2 mm or less, in examples. The vent 9400-1 may comprise a vent module that is moulded separately and then attached to the elbow 9610 (e.g. by gluing or welding) or may be overmoulded to the elbow. In other examples, the vent 9400-1 may comprise a smaller number of larger holes or may comprise a mesh structure providing even small openings for a vent flow of gas to pass.

5.3.3.2.2 Headgear Straps

In certain forms of the present technology, the positioning and stabilising structure 9300 comprises at least one headgear strap acting in addition to the tubes 9350 to position and stabilise the seal-forming structure 9100 in sealing position at the entrance to the patient's airways. As shown in FIGS. 10 and 11, the patient interfaces 9000 each comprise a strap 9310 forming part of the positioning and stabilising structure 9300. The strap 9310 may be known as a back strap or a rear headgear strap, for example. In other examples of the present technology, one or more further straps may be provided. For example, a patient interface 9000 according to an example of the present technology having a full face or oro-nasal cushion module may have a second, lower, strap configured to overlie the back of the patient's neck.

5.3.3.2.2.1 Strap

In the example shown in FIGS. 10 and 11, strap 9310 of the positioning and stabilising structure 9300 is connected between the two tubes 9350 positioned on each side of the patient's head and passing around the back of the patient's head, for example overlying or lying inferior to the occipital bone of the patient's head in use. The strap 9310 connects to each tube above the patient's ears. In other embodiments, for example as part of an oro-nasal patient interface, the positioning and stabilising structure 9300 comprises an upper strap similar to strap 9310 and at least one additional lower headgear strap that connects between the tubes and/or cushion module and passes below the patient's ears and around the back of the patient's head. Such a lower headgear strap may also be connected to an upper strap (e.g. a similar to strap 9310).

In certain forms of the technology, the positioning and stabilising structure 9300 comprises a mechanism for connecting a headgear strap to the headgear tubes 9350. The headgear strap may be connected directly or indirectly to the headgear tubes 9350. In the case of the patient interfaces 9000 shown in FIGS. 10 and 11, for example, a tab 9320 configured to connect to strap 9310 projects away from each headgear tube 9350 in a generally posterior direction. The tabs 9320 have holes in them to receive the ends of strap 9310.

In some forms of the present technology, the strap 9310 is adjustable. For example, in the case of the patient interfaces 9000 shown in FIGS. 10 and 11, the strap 9310 is, in use, threaded through a hole in the form of a slit 9322 in each tab 9320. The length of the strap 9310 between the tabs 9320 may be adjusted by pulling more or less of the strap 9310 through one or both of the tabs 9320. The strap 9310 may be secured to itself after passing through the slits 9322 in the tabs 9320, for example, with hook-and-loop fastening means. The strap 9310 therefore is able to be adjusted to fit around different head sizes. In some forms of the technology the angle of the strap 9310 relative to the headgear tubes 9350 or patient's head is able to be adjusted to fit around the patient's head at different locations. This adjustability assists the positioning and stabilising structure 9300 to accommodate different head shapes and sizes.

In some forms of the technology, the strap 9310 exerts a force on the headgear tubes 9350 to pull them in an at least partially posterior (e.g. rearwards) direction at the locations of the tabs 9320. The strap 9310 may also exert a force on the headgear tubes 9350 to pull them in an at least partially inferior (e.g. downwards) direction. The magnitude of this force may be adjusted by altering the length of the strap 9310 between the tabs 9320.

In some forms of the technology, such as the example shown in FIGS. 10 and 11, the direction of the force applied to the headgear tubes 9350 by the strap 9310 may also be altered. This direction may be altered by adjusting the angle of the strap 9310 relative to the headgear tubes 9350 or patient's head. In some forms of the technology the location at which the strap 9310 exerts a force on the headgear tubes 9350 may be altered by adjusting the location at which the strap 9310 is secured to the headgear tubes 9350.

The adjustability of the magnitude and direction of the force applied to the headgear tubes 9350 by the strap 9310 may advantageously enable the positioning and stabilising structure 9300 to accommodate a range of head sizes and head shapes. The strap 9310 may balance forces in the headgear tubes 9350 which may assist the headgear to maintain its shape and an effective seal to the patient's face, while remaining comfortable.

In some forms of the technology, when worn by a patient, a point on the headgear tubes 9350 near the tab 9320 will receive a generally upward (e.g. superior) force from the upper portion of the headgear tubes 9350 due to tension in the headgear tubes 9350 and, in some examples, due to a biasing mechanism (described in further detail below) acting to keep the headgear secured to the patient's head. Additionally, the point on the headgear tubes 9350 near the tab 9320 may receive a generally forward (e.g. anterior) and downward (e.g. inferior) reaction force caused by a biasing mechanism acting to urge the seal-forming structure 9100 upwards and into the patient's nose. The directions and magnitudes of the forces required for a secure fit and effective seal may vary between patients based on the position of the positioning and stabilising structure 9300 on the head, which may vary due to, for example, differences in head shapes and sizes. In some forms of the technology, the adjustability of the rear headgear strap 9310 enables the forces to be balanced for a range of head shapes and sizes to hold the positioning and stabilising structure 9300 in a comfortable position while maintaining an effective seal.

For example, to provide a larger force acting in the posterior (e.g. rearward) direction on the portions of the headgear tubes 9350 proximate the tabs 9320, the strap 9310 may be adjusted by pulling more of the strap 9310 through the slits 9322 in the tabs 9320. Doing so will cause the strap 9310 to shorten in length and, especially if the strap 9310 is elastic, to apply a larger force on the headgear tubes 9350 in the posterior (e.g. rearward) direction. Similarly, the angle of the strap 9310 may be adjusted as required to balance both the vertical and horizontal components of the forces acting on the portions of the headgear tubes 9350 proximate the tabs 9320, across a range of head shapes and sizes.

The strap 9310 may comprise a rectangular cross-section along some or all of its length. Additionally, the strap 9310 may have a profile with one or more rounded edges to provide greater comfort and to reduce the risk of headgear straps marking or irritating the patient. In certain forms of the present technology, a positioning and stabilising structure 9300 comprises a strap 9310 that is bendable and e.g. non-rigid. An advantage of this aspect is that the strap 9310 is more comfortable for a patient to lie upon while the patient is sleeping.

In certain forms of the present technology, a positioning and stabilising structure 9300 comprises a strap 9310 that comprises two or more strap bands separated by a split. For example, as shown in FIGS. 10 and 11, the strap 9310 comprises a split 9313 configured in use to be located against the posterior of the patient's head. A split strap 9310 may anchor the patient interface 9000 on the patient's head in a particularly stable fashion in the case of some patient interface designs. The posterior of the patient's head may have complex geometry and the presence of a split 9313 in the strap 9310 may assist the strap to better conform to the back of the patient's head.

5.3.3.2.2.2 Eyelets

As noted above, each of the gas delivery tubes may comprise an eyelet or slit 9322 for connection with a strap. In some examples, the eyelet may be circular. In other examples, the eyelets may be elongate. Alternatively, the eyelets may have a round side and a straight side. The eyelets may be D-shaped, for example. The eyelets in the exemplary patient interfaces 9000 shown in FIGS. 10 and 11 are in the form of slits. In this example, the pair of gas delivery tubes 9350 provide a pair of slits 9322 to which a strap 9310 is able to be connected. That is, the strap 9310 may connect between the slits 9322. The strap 9310 may be constructed and arranged to contact, in use, a region of the patient's head inferior to or overlaying an occipital bone of the patient's head. In this example, the eyelets are formed by tabs 9320 connected to the tube walls of the tubes 9350.

The tabs 9320 and/or eyelets 9322 may be as described in U.S. Patent Application No. 62/764,995 (corresponding to PCT Application No. PCT/AU2019/050874, filed Aug. 20, 2019), the entire contents of each of which are incorporated herein by reference.

5.3.3.2.3 Headgear Architecture

In certain forms, the architecture of the patient interface 9000 is as shown in FIGS. 10 and 11, with a pair of gas delivery tubes 9350 for the left and right sides of the headgear 9300 engaging at their inferior ends to the cushion module 9150 and at their superior ends to the crown connector 9360, positioned superior of the patient's head.

In certain other forms, the architecture of the headgear 9300 may be as shown in FIGS. 18 and 19. Instead of separable gas delivery tubes 9350 for the left and right sides of the headgear, both sides may be produced together as a single thermoformed part. The positioning and stabilising structure 9300 in such an example may comprise a left headgear tube 9350 (e.g. a left arm or left portion), and a right headgear tube 9350 (e.g. a right arm or right portion). Between the left and right headgear tubes 9350 there may be a centre portion or joint that links the left and right headgear tubes 9350. An aperture is provided forming the fluid connection opening 9390 on the superior portion of the headgear, in this example at the joint between the left and right headgear tubes 9350. The inferior ends of the gas delivery tubes 9350 connect to the cushion module 9150 by a removable connection at a cushion module connection port 9357, for example a snap fit connection. In other examples, the connection may be permanent, such as by over moulding, welding or gluing. In these forms the inferior ends of the gas delivery tubes 9350 are provided with cushion module connection ports 9357 on their respective patient contacting sides. In this way, the connection of the headgear tube 9350 to the cushion module 9150 is hidden or otherwise obscured from view.

Alternatively, the inferior ends could engage with the cushion module using the snap-fit connections previously described with reference to FIGS. 12A and 12B. This could be either longitudinally from the inferior ends, i.e. the snap-fit connections extend from the ends or, alternatively, the snap-fit connections may be cylindrical in nature and thus could be perpendicular to the inferior ends. This latter arrangement may hide or otherwise obscure the visibility of the connection between the gas delivery tubes and the cushion module, for a more aesthetically pleasing appearance.

In the example shown in FIG. 18, the headgear tubes 9350 are connected to an elbow 9610 at a central point along the headgear tubes 9350 atop the patient's head. The elbow 9610 has only a 45 degree bend, rather than a 90 degree bend, and extends in a posterosuperior direction and connects to a short tube 9616. The short tube 9616 comprises a connection port 9600 at a distal end thereof. The short tube 9616 decouples the headgear tubes 9350 from the supply conduit, reducing tube drag.

The tabs 9320 of the positioning and stabilising structure 9300 of FIG. 18 are extended in length in comparison to the tabs 9320 of the positioning and stabilising structure 9300 of FIG. 20. The tabs 9320 extend to a point posterior to the patient's ears. Additionally, the slit to which the strap 9310 connects is located at a posterior location and is angled such the backstrap can connect from an inferior location which may advantageously prevent the strap 9310 from riding up in use.

In certain other forms, the architecture of the headgear 9300 may be reversed such that the left and right headgear tubes 9350 are joined at their inferior ends and are either permanently connected to a cushion module 9150 or are configured to receive the cushion module 9150 (e.g. by a removable connection such as a snap fit). In these forms, the superior ends of the gas delivery tubes 9350 may connect to the crown connector 9360. In some examples, the central portion of the headgear tubes 9350 which connects to the cushion module 9150 is formed to have shape corresponding to the curvature of the anterior portion of the cushion. That is, the central portion may be preformed. A preformed connection portion of the headgear tubes 9350 may advantageously enable easier fitting of the cushion to the headgear tubes 9350 by the user.

In some examples, the headgear tubes 9350 are manipulated into shape when fitted to a cushion module 9150.

In some examples in which the headgear tubes 9350 are inseparably joined at an inferior location (e.g. at the cushion module 9150), the headgear tubes 9350 may comprise a vent 9400 at a central anterior location, such as on the non-patient-contacting side of the headgear tubes 9350 opposite a cushion module 9150 on the patient-contacting side. The vent 9400 may be provided by a vent module received in a vent module opening 9410 proximate the cushion module 9150, as shown for example in FIGS. 20 and 23. The vent 9400 or vent module may be located directly anterior to the cushion module 9150 to minimise dead space and $CO_2$ build-up in use.

In some examples the vent module may be an over-moulded rigid part with vent holes formed therein. In other examples the vent module may be a removable rigid part. In further examples the vent module may be a diffuser module configured to provide venting while diffusing the vent flow of gas.

5.3.4 Vent

In one form, the patient interface 3000, 6000, 7000, 8000, 9000, 10000 includes at least one vent 3400, 6100, 9400, 9400-1 constructed and arranged to allow for the washout of exhaled gases, e.g. carbon dioxide.

In certain forms the vent is configured to allow a continuous vent flow from an interior of the plenum chamber to ambient whilst the pressure within the plenum chamber is positive with respect to ambient. The vent is configured such that the vent flow rate has a magnitude sufficient to reduce rebreathing of exhaled $CO_2$ by the patient while maintaining the therapeutic pressure in the plenum chamber in use. The vent may provide a continuous vent flow of gas from the interior of the plenum chamber to ambient throughout the patient's respiratory cycle.

One form of vent in accordance with the present technology comprises a plurality of holes, for example, about 20 to about 80 holes, or about 40 to about 60 holes, or about 45 to about 55 holes.

The vent 3400, 9400 may be located in the plenum chamber 3200, 9200. Alternatively, the vent 9400-1 is located in a decoupling structure, e.g., a swivel. In another example, the vent 6100 may be located along the tube, as shown in the FIG. 4R example. In other forms, the vent may be located throughout the tube such that a separate vent is not needed. In the examples shown in FIGS. 10, 11, 20 and 24, the patient interface 9000, 10000 may comprise at least one of the vents 9400, 9400-1. In an example, the patient interface 9000 comprises at least one vent 9400 in the plenum chamber 9200 and at least one vent 9400-1 in the elbow 9610. In another example, the plenum chamber 9200 comprises two vents 9400. Each vent 9400 on the plenum chamber 9200 comprises an array of holes. The vent 9400-1 on the elbow 9610 also may comprise an array of holes. The vent 9400 of the patient interface 9000 is sized and configured to provide sufficient gas washout throughout a range of therapeutic pressures.

The patient interface may comprise a diffuser configured to diffuse the flow of air though the vent to reduce vent noise and reduce jetting of air out of the vent holes. The diffuser may be provided to a cover over the vent holes. In some examples, the vent may comprise a vent module configured to be removed from the plenum chamber. The vent module may comprise a diffuser.

5.3.5 Decoupling Structure(s)

In one form the patient interface 3000, 6000, 7000, 8000, 9000, 10000 includes at least one decoupling structure, for example, a swivel or a ball and socket. The decoupling structure may be arranged at or proximate the connection port, hub or crown connector to permit the conduit of the air circuit 4170 to move relative to patient interface and reduce the risk of destabilising the seal of the seal-forming structure against the patient's face.

For example, the patient interface 9000, 10000 shown in FIGS. 10 and 11 comprises an elbow 9610 configured the swivel with respect to the positioning and stabilising structure 9300. In this example the elbow 9610 is configured to swivel about an axis concentric with a circular opening in the positioning and stabilising structure 9300. In some examples of the present technology, the elbow 9610 may form part of a ball and socket joint to the positioning and stabilising structure 9300. For example, a ring having a partially spherical inner surface may be provided to the positioning and stabilising structure 9300 and may be configured to receive the elbow 9610. The elbow 9610 may have partially spherical outer surface complimentary to the partially spherical inner surface of the ring, thereby enabling the elbow 9610 to swivel with respect to the ring in a plurality of axes.

5.3.6 Connection Port

Connection port 3600, 9600 allows for connection to the air circuit 4170. In the forms of the technology shown in FIGS. 4A-4D, for example, the connection port is positioned on top of the patient's head when the patient interface 3000 is being worn.

In the exemplary patient interface 9000, 10000 shown in FIGS. 10 and 11, the elbow 9610 forms part of the connection port 9600. The elbow 9610, as a decoupling structure, decouples movement of the air circuit 4170 from the positioning and stabilising structure 9300 in order to reduce tube drag on the positioning and stabilising structure 9300.

In other forms, the connection is configured to be positioned, in use, proximal a top, side, or rear portion of the patient's head. Patient interfaces in which the connection port is not positioned in front of the patient's face may be advantageous as some patient's find a conduit that connects to a patient interface in front of the face to be unsightly and obtrusive. For example, a conduit connecting to the patient interface in front of the face may be prone to being tangled up in bedclothes, particularly if the conduit extends downwardly from the patient interface in use.

5.3.7 Forehead Support

In one form, the patient interface 3000 includes a forehead support 3700. In other forms, the patient interface does not include a forehead support. Advantageously, the exemplary patient interface 3000, 6000, 7000, 8000, 9000, 10000, shown for example in FIGS. 4A, 4R, 4S, 4X, 10 and 11 comprises a positioning and stabilising structure that is able to hold the seal-forming structure in sealing position without connection to a forehead support or any frame or strap members that lie in front of the patient's face at eye level.

5.3.8 Anti-Asphyxia Valve

In one form, the patient interface 3000, 6000, 7000, 8000, 9000, 10000 includes an anti-asphyxia valve. In some examples, the patient interface includes a plurality of anti-asphyxia valves. For example, where airflow is provided to a seal-forming structure via two fluid connections, two anti-asphyxia valves may be provided to the patient interface, one at each fluid connection to the seal-forming structure.

5.3.9 Ports

In one form of the present technology, a patient interface 3000, 6000, 70000, 8000, 9000, 10000 includes one or more ports that allow access to the volume within the plenum chamber. In one form this allows a clinician to supply supplemental oxygen. In one form, this allows for the direct measurement of a property of gases within the plenum chamber, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014, as shown in FIG. 31A. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274, as shown in FIG. 31B.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

Referring to FIG. 31C, the RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a blower housing, such as in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.1.6 Clock

The RPT device 4000 may include a clock 4232 that is connected to the central controller 4230.

5.4.1.7 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

5.4.1.7.1 Display Driver

A display driver 4292 receives as an input the characters, symbols, or images intended for display on the display 4294, and converts them to commands that cause the display 4294 to display those characters, symbols, or images.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIGS. 32A and 32B) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 32A and FIG. 32B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.2 Humidifier Reservoir Dock

In one form, the humidifier 5000 may comprise a humidifier reservoir dock 5130 (as shown in FIG. 32B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.3 Water Level Indicator

The humidifier reservoir 5110 may comprise a water level indicator 5150 as shown in FIGS. 32A and 32B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(ii) Flattened: Having a rise followed by a relatively flat portion, followed by a fall.
(ii) M-shaped: Having two local peaks, one at the leading edge, and one at the trailing edge, and a relatively flat portion between the two peaks.
(9400) Chair-shaped: Having a single local peak, the peak being at the leading edge, followed by a relatively flat portion.
(9400) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(ii) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.7.4 Anatomy 5.7.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.7.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| | |
|---|---|
| 1000 | patient |
| 1100 | bed partner |
| 3000 | patient interface |
| 3100 | seal-forming structure |
| 3102 | sealing layer |
| 3104 | base |
| 3106 | naso-labial sulcus engagement area |
| 3107 | flanges |
| 3108 | first naris opening |
| 3109 | saddle region |
| 3110 | second naris opening |
| 3111 | height |
| 3112 | mold |
| 3114 | accommodating portion |
| 3116 | textile sheet |
| 3117 | pre-cut sheet |
| 3118 | membrane layer |
| 3120 | notches |
| 3122 | notch |
| 3124 | first flap |
| 3126 | second flap |
| 3150 | cushion assembly |
| 3152 | frame |
| 3154 | assembly connection port |
| 3155 | assembly connection port |
| 3200 | plenum chamber |
| 3300 | stabilizing structure |
| 3302 | left arm |
| 3304 | right arm |
| 3306 | end point |
| 3308 | first area |
| 3310 | second area |
| 3312 | joint |
| 3314 | arm support |
| 3322 | contacting layer |
| 3346 | tab |
| 3348 | air delivery tube |
| 3350 | tube |
| 3352 | inner layer |
| 3354 | outer layer |
| 3356 | interior surface |
| 3358 | interior surface |
| 3360 | textile sheet |
| 3362 | textile membrane |
| 3363 | tube |
| 3364 | tube sheet |
| 3366 | outer covering |
| 3368 | textile membrane |
| 3370 | textile membrane |
| 3372 | air passage |
| 3374 | exterior surface |
| 3376 | exterior surface |
| 3378 | outermost portion |
| 3380 | outermost portion |
| 3382 | laser |
| 3420 | head strap |
| 3422 | inner layer |
| 3424 | membrane layer |
| 3426 | outer layer |
| 3428 | first distance |
| 3430 | second distance |
| 3432 | head strap |
| 3434 | tube |
| 3436 | patient interface |
| 3437 | interior layer |
| 3438 | exterior layer |
| 3439 | strap |
| 3440 | strap |

-continued

| | |
|---|---|
| 3441 | strap |
| 3442 | strap |
| 3443 | pad |
| 3450 | tube |
| 3452 | inner textile layer |
| 3454 | outer textile layer |
| 3456 | foam layer |
| 3600 | connection port |
| 3602 | upper surface |
| 3604 | lower surface |
| 3606 | channel |
| 3608 | intake |
| 3700 | forehead support |
| 3701 | connection port |
| 3702 | inner portion |
| 3704 | outer portion |
| 3706 | support |
| 3800 | mold |
| 3802 | mold |
| 3804 | accommodating portion |
| 4000 | RPT device |
| 4010 | external housing |
| 4012 | upper portion |
| 4014 | lower portion |
| 4015 | panel |
| 4016 | chassis |
| 4018 | handle |
| 4020 | pneumatic block |
| 4100 | pneumatic components |
| 4110 | air filter |
| 4112 | inlet air filter |
| 4114 | outlet air filter |
| 4120 | muffler |
| 4122 | inlet muffler |
| 4124 | outlet muffler |
| 4140 | pressure generator |
| 4142 | controllable blower |
| 4144 | brushless DC motor |
| 4160 | anti-spillback valve |
| 4170 | air circuit |
| 4180 | supplemental oxygen |
| 4200 | electrical components |
| 4202 | printed circuit board assembly (PCBA) |
| 4210 | electrical power supply |
| 4220 | input devices |
| 4230 | central controller |
| 4232 | clock |
| 4240 | therapy device controller |
| 4250 | protection circuits |
| 4260 | memory |
| 4270 | transducers |
| 4272 | pressure sensors |
| 4274 | flow rate sensors |
| 4276 | Motor speed transducer |
| 4280 | data communication interface |
| 4282 | remote external communication network |
| 4284 | local external communication network |
| 4286 | remote external device |
| 4288 | local external device |
| 4290 | output devices |
| 4292 | display driver |
| 4294 | display |
| 4300 | algorithms |
| 5000 | humidifier |
| 5002 | humidifier inlet |
| 5004 | humidifier outlet |
| 5006 | humidifier base |
| 5110 | humidifier reservoir |
| 5120 | conductive portion |
| 5130 | humidifier reservoir dock |
| 5135 | locking lever |
| 5150 | water level indicator |
| 5240 | heating element |
| 6000 | patient interface |
| 6100 | vent |
| 6348 | air delivery tube |
| 7000 | patient interface |
| 7200 | hub |
| 7220 | elbow |

-continued

| | |
|---|---|
| 7230 | swivel connector |
| 7300 | positioning and stabilising structure |
| 7302 | left arm |
| 7303 | connector |
| 7304 | right arm |
| 7306 | notch |
| 7308 | chamfered edge |
| 7309 | slot |
| 7312 | upper connector |
| 7314 | lower connector |
| 7352 | inner layer |
| 7354 | outer layer |
| 7350 | tube |
| 7402 | outer covering |
| 7404 | adhesive layer |
| 7406 | outer cushioning layer |
| 7408 | adhesive layer |
| 7410 | textile membrane |
| 7222 | textile sheet |
| 7224 | adhesive layer |
| 7226 | inner cushioning layer |
| 7228 | adhesive layer |
| 7230 | textile membrane |
| 8000 | patient interface |
| 8300 | positioning and stabilising structure |
| 8302 | left arm |
| 8304 | right arm |
| 8350 | tube |
| 8362 | lower portion |
| 8364 | upper portion |
| 9000 | Patient interface |
| 9100 | Sealing or seal-forming structure |
| 9150 | Cushion module |
| 9200 | Plenum chamber |
| 9300 | Positioning and stabilising structure/headgear |
| 9304 | Superior tube portion |
| 9305 | First end of the superior tube portion |
| 9306 | Second end of the superior tube portion |
| 9310 | Strap |
| 9313 | Split |
| 9320 | Tab |
| 9322 | Slit |
| 9324 | Eyelet rigidiser portion |
| 9331 | Anterior edge |
| 9332 | Posterior edge |
| 9348 | Patient contacting portion |
| 9349 | Non-patient contacting portion |
| 9350 | Gas delivery tubes |
| 9351 | Headgear tube connector |
| 9352 | Seam |
| 9353 | Seal portion |
| 9357 | Cushion module connection port |
| 9358 | Rigidizing element |
| 9360 | Crown Connector |
| 9361 | Crown connector port |
| 9362 | Sealing flange |
| 9363 | Inferior tube portion |
| 9364 | Outer sleeve |
| 9365 | Crown connector tube portion |
| 9366 | Second length of material for inner portion of tube |
| 9367 | Third length of material for inner portion of tube |
| 9368 | First length of material for inner portion of tube |
| 9371 | First outer layer |
| 9372 | First adhesive layer of the non-patient contacting portion |
| 9373 | Intermediate layer of the non-patient contacting portion |
| 9374 | Second adhesive layer of the non-patient contacting portion |
| 9375 | First inner layer |
| 9381 | Second outer layer |
| 9382 | First adhesive layer of the patient contacting portion |
| 9383 | Intermediate layer of the patient contacting portion |
| 9384 | Second adhesive layer of the patient contacting portion |
| 9385 | Second inner layer |
| 9390 | Fluid connection opening |
| 9400 | Vent |
| 9400-1 | Vent |
| 9410 | Vent module opening |
| 9502 | Crown piece connector |
| 9510 | Upper wall of crown connector |
| 9520 | Lower wall of crown connector |

-continued

| | |
|---|---|
| 9530 | Occlusion-preventer |
| 9532 | Ramp |
| 9534 | Ramp |
| 9550 | Reinforcement |
| 9560 | Lip seal |
| 9600 | Connection port |
| 9610 | Elbow |
| 9612 | Conduit connector |
| 9614 | Swivel ring |
| 9616 | Short tube |
| 9617 | Protrusion |
| 9618 | Recess |
| 10000 | Patient interface |
| D1 | direction |
| D2 | direction |
| T | tensile force |
| V1 | first volume |
| V2 | second volume |
| W1 | first width |
| W2 | second width |
| X1 | zone |
| X2 | zone |
| X3 | zone |
| X4 | zone |

The invention claimed is:

1. A positioning and stabilising structure to provide a force to hold a seal-forming structure in a therapeutically effective position on a patient's head for positive pressure airway treatment of sleep disordered breathing, the positioning and stabilising structure comprising:
at least one gas delivery tube to deliver a flow of air to an entrance of the patient's airways via a seal-forming structure, each gas delivery tube being constructed and arranged to contact, in use, at least a region of the patient's head superior to an otobasion superior of the patient's head, each gas delivery tube comprising a tube wall defining a hollow interior through which air is able to flow to the seal-forming structure, each gas delivery tube comprising:
a superior tube portion configured to extend in use from a position on top of the patient's head to a position along the side of the patient's head or face, the superior tube portion comprising 1) a textile material and/or a foam material, and 2) an air-impermeable material provided to the textile material and/or the foam material to make the superior tube portion substantially air-impermeable; and
an inferior tube portion configured to extend from the position along the side of the patient's head or face to a position adjacent the entrance to the patient's airways, the inferior tube portion comprising 1) a textile material and/or a foam material, and 2) an air-impermeable material provided to the textile material and/or the foam material of the inferior tube portion to make the inferior tube portion substantially air-impermeable,
wherein one of the inferior tube portion and superior tube portion has a greater rigidity than the other of the inferior tube portion and superior tube portion, and
wherein each of the superior tube portion and the inferior tube portion comprises a plurality of layers adhered to one another including 1) at least one outer layer and 2) an inner portion with at least one inner layer, wherein the inner portion of one of the superior tube portion or the inferior tube portion has greater rigidity than the inner portion of the other of the superior tube portion or inferior tube portion.

2. The positioning and stabilising structure of claim 1, wherein the superior tube portion comprises a first end configured to lie against a superiorly-facing surface of the patient's head in use and a second end configured to lie against a laterally-facing surface of the patient's head in use.

3. The positioning and stabilising structure of claim 1, wherein the inferior tube portion comprises a first end configured to lie against a laterally-facing surface of the patient's head in use and a second end configured to connect with the seal-forming structure.

4. The positioning and stabilising structure of claim 1, wherein the inferior tube portion is configured to fluidly connect the superior tube portion with the seal-forming structure in use.

5. The positioning and stabilising structure of claim 1, wherein the superior tube portion is adapted to receive the flow of air from a source via a crown connector arranged to be positioned on top of the patient's head in use.

6. The positioning and stabilising structure of claim 1, further comprising a crown connector,
wherein the at least one gas delivery tube comprises a pair of gas delivery tubes, and the crown connector is configured to lie on top of the patient's head in use to fluidly connect between the pair of gas delivery tubes, and
wherein the crown connector comprises a hollow interior and a fluid connection opening configured to receive the flow of air into the hollow interior.

7. The positioning and stabilising structure of claim 1, wherein one of the inferior tube portion or the superior tube portion is configured with a first layer of material and a second layer of material, wherein the first layer of material is more rigid than the second layer of material.

8. The positioning and stabilising structure of claim 1, wherein the inferior tube portion and/or the superior tube portion is configured with a rigidising element to provide rigidity to the inferior tube portion and/or the superior tube portion.

9. The positioning and stabilising structure of claim 1, wherein the inferior tube portion and/or the superior tube portion is configured with a seam.

10. The positioning and stabilising structure of claim 1, wherein the inferior tube portion is formed as a first tube and the superior tube portion is formed as a second tube, wherein the first tube is joined to the second tube.

11. The positioning and stabilising structure of claim 10, wherein the first tube is joined to the second tube by thermoforming, ultrasonic welding, stitching, gluing or removably connectable connectors.

12. The positioning and stabilising structure of claim 1, wherein each gas delivery tube has a patient contacting portion configured to contact the patient in use and a non-patient contacting portion positioned away from the patient in use, and
wherein the patient contacting portion and/or the non-patient contacting portion comprises a plurality of layers.

13. The positioning and stabilising structure of claim 12, wherein the patient contacting portion includes a first outer later comprising a textile material or a foam material.

14. The positioning and stabilising structure of claim 12, wherein the non-patient contacting portion includes a second outer layer comprising a textile material or a foam material.

15. The positioning and stabilising structure of claim 12, wherein the patient contacting portion and/or the non-patient contacting portion includes an intermediate layer comprising a foam material or a spacer fabric material.

16. The positioning and stabilising structure of claim 1, wherein the inferior tube portion has greater rigidity than the superior tube portion.

17. The positioning and stabilising structure of claim 16, wherein the inferior tube portion has a wall thickness that is greater than a wall thickness of the superior tube portion to provide greater rigidity to the inferior tube portion.

18. The positioning and stabilising structure of claim 17, wherein the inferior tube portion comprises materials that are less extendible in length than materials of the superior tube portion, thereby providing greater rigidity to the inferior tube portion.

19. The positioning and stabilising structure of claim 16, wherein the inferior tube portion has at least one additional layer not provided to the superior tube portion to provide greater rigidity to the inferior tube portion.

20. The positioning and stabilising structure of claim 16, wherein a rigidising element is provided to one of the plurality of layers to provide greater rigidity to the inferior tube portion.

21. The positioning and stabilising structure of claim 16, wherein the inferior tube portion comprises a greater number of layers than the superior tube portion, thereby providing greater rigidity to the inferior tube portion.

22. The positioning and stabilising structure of claim 16, wherein the superior tube portion and inferior tube portion each comprises a textile layer, the textile layer in the inferior tube portion having a woven structure that is different than a woven structure of the textile layer in the superior tube portion,
wherein the woven structure of the inferior tube portion provides greater rigidity to the inferior tube portion as compared to the superior tube portion.

23. The positioning and stabilising structure of claim 1, wherein the inferior tube portion comprises a greater resistance to bending towards an inferior direction than towards a medial direction, in use.

24. The positioning and stabilising structure of claim 1, wherein the superior tube portion comprises a greater resistance to bending towards an anterior direction and/or a posterior direction than towards an inferior direction in use.

25. The positioning and stabilising structure of claim 1, wherein the superior tube portion has greater rigidity than the inferior tube portion.

26. The positioning and stabilising structure of claim 1, wherein the inner portion of the inferior tube portion includes a plurality of inner layers.

27. The positioning and stabilising structure of claim 26, wherein the inner portion of the superior tube portion includes a plurality of inner layers.

28. The positioning and stabilising structure of claim 1, wherein the at least one gas delivery tube comprises a pair of gas delivery tubes configured to, in use, extend along respective sides of the patient's head,
said positioning and stabilising structure further comprising a rear strap having first and second end portions respectively connected to the pair of gas delivery tubes, the rear strap being configured to engage a rear portion of the patient's head in use.

29. The positioning and stabilising structure of claim 28, wherein each gas delivery tube includes a strap connection portion having a slit formed therein to adjustably receive a respective one of the first and second end portions of the rear strap.

30. The positioning and stabilising structure of claim 29, wherein each gas delivery tube includes a transition zone between the superior tube portion and the inferior tube portion, the transition zone being in an area of the strap connection portion.

31. The positioning and stabilising structure of claim 30, wherein each strap connection portion forms a tab that extends from a respective one of the gas delivery tubes.

32. A patient interface comprising:
a seal-forming structure constructed and arranged to form a seal with a region of the patient's face surrounding an entrance to the patient's airways for sealed delivery of a flow of air at a therapeutic pressure of at least 6 cmH2O above ambient air pressure throughout the patient's respiratory cycle in use; and
the positioning and stabilising structure of claim 1 to provide a force to hold the seal-forming structure in a therapeutically effective position on the patient's head for positive pressure airway treatment of sleep disordered breathing.

33. The positioning and stabilising structure of claim 32, wherein the inferior tube portion has greater rigidity than the superior tube portion to allow for efficient transmittal and conversion of headgear forces into force vectors to facilitate sealing of the seal-forming structure with the patient's face.

* * * * *